United States Patent
Akioka et al.

(10) Patent No.: US 9,788,547 B2
(45) Date of Patent: *Oct. 17, 2017

(54) AROMATIC COMPOUND AND USES THEREOF

(71) Applicant: SUMITOMO CHEMICAL COMPANY, LIMITED, Tokyo (JP)

(72) Inventors: Yuki Akioka, Takarazuka (JP); Takayuki Shioda, Takarazuka (JP); Sadayuki Arimori, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/128,681

(22) PCT Filed: Mar. 23, 2015

(86) PCT No.: PCT/JP2015/059820
§ 371 (c)(1),
(2) Date: Sep. 23, 2016

(87) PCT Pub. No.: WO2015/147314
PCT Pub. Date: Oct. 1, 2015

(65) Prior Publication Data
US 2017/0105413 A1 Apr. 20, 2017

(30) Foreign Application Priority Data
Mar. 28, 2014 (JP) ................. 2014-067941

(51) Int. Cl.
A01N 47/20 (2006.01)
A01N 43/56 (2006.01)
C07D 231/16 (2006.01)
C07D 231/20 (2006.01)

(52) U.S. Cl.
CPC ............ A01N 43/56 (2013.01); A01N 47/20 (2013.01); C07D 231/16 (2013.01); C07D 231/20 (2013.01)

(58) Field of Classification Search
CPC .................................. A01N 43/653
See application file for complete search history.

(56) References Cited

U.S. PATENT DOCUMENTS

| 5,824,705 | A | 10/1998 | Mueller et al. |
| 5,861,359 | A | 1/1999 | Theodoridis |
| 5,948,819 | A | 9/1999 | Ohtsuka et al. |
| 6,252,083 | B1 | 6/2001 | Mueller et al. |
| 6,583,090 | B1 | 6/2003 | Gewehr et al. |
| 9,314,023 | B2 | 4/2016 | Arimori et al. |
| 2011/0183978 | A1 | 7/2011 | Sudau et al. |
| 2013/0129839 | A1 | 5/2013 | Long et al. |
| 2013/0281455 | A1 | 10/2013 | Sudau et al. |
| 2015/0203511 | A1 | 7/2015 | Arimori et al. |
| 2015/0305339 | A1 | 10/2015 | Long et al. |
| 2016/0081340 | A1 | 3/2016 | Arimori et al. |

FOREIGN PATENT DOCUMENTS

| JP | 7-502747 A | 3/1995 |
| JP | 2002-506060 A | 2/2002 |
| JP | 2003-12416 A | 1/2003 |
| JP | 2007-284384 A | 11/2007 |
| JP | 2011-1292 A | 1/2011 |
| JP | 2011-1294 A | 1/2011 |
| JP | 2013-507334 A | 3/2013 |
| JP | 2013-536866 A | 9/2013 |
| WO | WO 95/27693 A1 | 10/1995 |
| WO | WO 97/05115 A1 | 2/1997 |
| WO | WO 2014-051161 A1 | 4/2014 |
| WO | WO 2014/051165 A1 | 4/2014 |

(Continued)

OTHER PUBLICATIONS

International Search Report for PCT/JP2015/059820 dated May 19, 2015.
International Preliminary Report on Patentability and English translation of the Written Opinion of the International Searching Authority (forms PCT/IB/373 and PCT/ISA/237), dated Oct. 4, 2016, for International Application No. PCT/JP2015/059820.

(Continued)

Primary Examiner — Rebecca Anderson
Assistant Examiner — Karen Cheng
(74) Attorney, Agent, or Firm — Birch, Stewart, Kolasch & Birch, LLP

(57) ABSTRACT

A pest control agent comprising an aromatic compound represented by formula (1) wherein $R^1$ represents a halogen atom, etc.; $R^3$ represents a hydrogen atom, etc.; $R^7$ represents a C1-C3 alkyl group optionally having one or more halogen atoms, etc.; $Z^2$ represents a halogen atom, etc.; $Z^3$ represents a C1-C3 alkyl group optionally having one or more halogen atoms, etc.; and Q represents the following group Q1, Q2, or Q3 has excellent control activity.

(1)

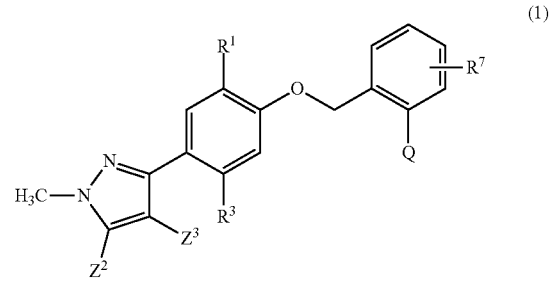

8 Claims, No Drawings

(56) References Cited

FOREIGN PATENT DOCUMENTS

WO  WO 2014/192953 A1  12/2014
WO  WO 2015/050039 A1  4/2015

OTHER PUBLICATIONS

International Preliminary Report on Patentability and English translation of the Written Opinion of the International Searching Authority (forms PCT/IB/373 and PCT/ISA/237), dated Oct. 4, 2016, for International Application No. PCT/JP2015/060404.
International Search Report (form PCT/ISA/210), dated Jun. 23, 2015, International Application No. PCT/JP2015/060404.

AROMATIC COMPOUND AND USES THEREOF

TECHNICAL FIELD

The present invention relates to an aromatic compound and uses thereof.

BACKGROUND ART

Heretofore, various chemicals have been developed so as to control pests and provided in practice use, but in some cases, these chemicals may not exert enough activity.

Meanwhile, there have been known, as compounds having an aromatic group, compounds represented by the following formula (X):

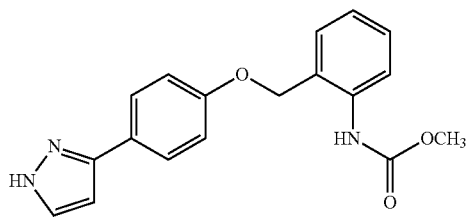
(X)

(see JPH07-502747-A)

The present invention provides a compound having excellent control activity against pests.

DISCLOSURE OF THE INVENTION

The present inventors have intensively studied so as to find compounds having excellent control activity against pests, and found that an aromatic compound represented by formula (1) shown below has excellent control activity against pests.

The present invention is as follows.

[1] An aromatic compound represented by formula (1):

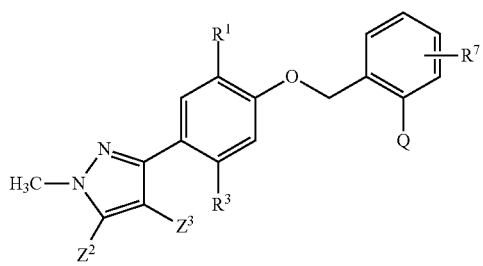
(1)

wherein $R^1$ represents a halogen atom or a C1-C4 alkyl group optionally having one or more halogen atoms;

$R^3$ represents a hydrogen atom or a C1-C4 alkyl group optionally having one or more halogen atoms;

$R^7$ represents a C1-C3 alkyl group optionally having one or more halogen atoms, a hydrogen atom, a halogen atom, a C1-C3 alkoxy group optionally having one or more halogen atoms, a C3-C4 cycloalkyl group optionally having one or more halogen atoms, or a C2-C4 alkenyl group optionally having one or more halogen atoms;

$Z^2$ represents a halogen atom, a C1-C3 alkoxy group, or a C1-C3 alkyl group;

$Z^3$ represents a C1-C3 alkyl group optionally having one or more halogen atoms, or a halogen atom;

Q represents the following group Q1, Q2, or Q3;

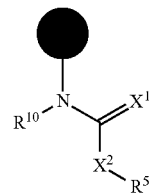
Q1

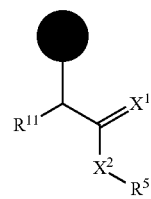
Q2

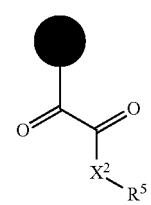
Q3

$R^5$ represents a C1-C3 alkyl group optionally having one or more halogen atoms;

$R^{10}$ (represents a hydrogen atom, a hydroxyl group, or a methyl group;

$R^{11}$ represents a hydrogen atom, a hydroxyl group, a methyl group, or a methoxy group;

$X^1$ represents an oxygen atom or a sulfur atom;

$X^2$ represents an oxygen atom, a sulfur atom, $NR^{12}$, or a direct bond;

and $R^{12}$ represents a C1-C3 alkyl group optionally having one or more halogen atoms, or a hydrogen atom.

[2] The aromatic compound according to [1], wherein $R^1$ is a methyl group, $R^3$ is a hydrogen atom, $R^{11}$ is a hydroxyl group, and $X^1$ is an oxygen atom.

[3] An aromatic compound represented by formula (2):

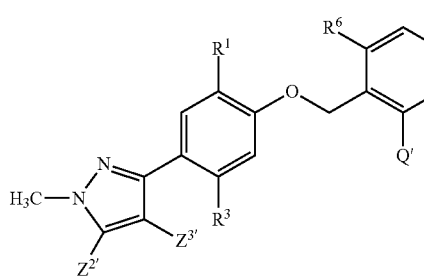
(2)

wherein $R^1$ and $R^3$ are the same as defined above;

$R^6$ represents a C1-C3 alkyl group optionally having one or more halogen atoms, a hydrogen atom, a halogen atom, a C1-C3 alkoxy group optionally having one or more halogen atoms, or a C3-C4 cycloalkyl group optionally having one or more halogen atoms;

$Z^{2'}$ represents a halogen atom or a C1-C3 alkoxy group;
$Z^{3'}$ represents a C1-C3 alkyl group or a halogen atom;
$Q'$ represents the following group $Q1'$, $Q2'$, or $Q3'$;

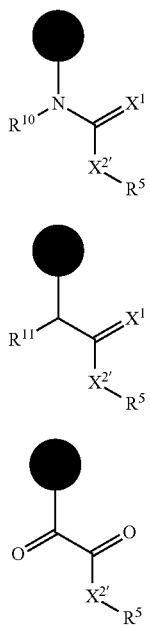

$R^5$, $R^{10}$, $R^{11}$, and $X^1$ are the same as defined above;
$X^{2'}$ represents an oxygen atom, $NR^{12}$, or a direct bond;
$R^{12}$ is the same as defined above.

[4] A pest control agent comprising the aromatic compound according to any one of [1], [2], or [3].

[5] A method for controlling pests, which comprises treating plants or soil with an effective amount of the aromatic compound according to [1], [2], or [3].

[6] Use of the aromatic compound according to [1], [2], or [3] for controlling pests.

According to the present invention, pests can be controlled.

MODE FOR CARRYING OUT THE INVENTION

In the present invention, a compound represented by formula (1) is referred to as the present compound, and a pest control agent containing the present compound is referred to as the present control agent.

Substituents as used herein will be mentioned below.

Examples of the halogen atom include a fluorine atom, a chlorine atom, a bromine atom, and an iodine atom.

Examples of the C1-C4 alkyl group optionally having one or more halogen atoms include a methyl group, an ethyl group, a propyl group, an isopropyl group, a butyl group, an isobutyl group, a sec-butyl group, a tert-butyl group, a fluoromethyl group, a chloromethyl group, a dichloromethyl group, a difluoromethyl group, a trifluoromethyl group, a trichloromethyl group, a 2-fluoro ethyl group, a 2,2,2-trifluoroethyl group, and a 1-trifluoromethyl-2,2,2-trifluoroethyl group.

Examples of the C3-C4 cycloalkyl group optionally having one or more halogen atoms include a cyclopropyl group, a cyclobutyl group, a 2,2-dichloro cyclopropyl group, and a 2,2-difluoro cyclopropyl group.

Examples of the C1-C3 alkyl group include a methyl group, an ethyl group, a propyl group, and an isopropyl group.

Examples of the C1-C3 alkyl group optionally having one or more halogen atoms include a methyl group, an ethyl group, a propyl group, an isopropyl group, a monofluoromethyl group, a monochloromethyl group, a monobromomethyl group, a difluoromethyl group, a trifluoromethyl group, a trichloromethyl group, a 2,2,2-trifluoroethyl group, a 2,2,2-trifluoro-1-trifluoromethylethyl group, a 1,2,2,2-tetrafluoro-1-trifluoromethylethyl group, and a 3-fluorobutyl group.

Examples of the C1-C3 alkoxy group include a methoxy group, an ethoxy group, a propyloxy group, and an isopropyloxy group.

Examples of the C1-C3 alkoxy group optionally having one or more halogen atoms include a methoxy group, an ethoxy group, a propyloxy group, an isopropyloxy group, a trifluoromethoxy group, a difluoromethoxy group, a 2-fluoroethoxy group, a 2,2,2-trifluoroethoxy group, and a 3-chloropropoxy group.

Examples of Aspect of the present compound include the following compounds.

A compound represented by formula (1) in which $X^1$ is an oxygen atom.
A compound represented by formula (1) in which $X^1$ is a sulfur atom.
A compound represented by formula (1) in which $X^1$ is an oxygen atom and $R^5$ is a methyl group.
A compound represented by formula (1) in which $X^1$ is a sulfur atom and $R^5$ is a methyl group.
A compound represented by formula (1) in which $X^1$ is an oxygen atom and $R^5$ is an ethyl group.
A compound represented by formula (1) in which $X^1$ is a sulfur atom and $R^5$ is an ethyl group.
A compound represented by formula (1) in which Q is Q1.
A compound represented by formula (1) in which Q is Q2.
A compound represented by formula (1) in which Q is Q3.
A compound represented by formula (1) in which $Z^2$ is a halogen atom.
A compound represented by formula (1) in which $Z^2$ is a C1-C3 alkoxy group.
A compound represented by formula (1) in which $Z^2$ is a C1-C3 alkyl group.
A compound represented by formula (1) in which $Z^3$ is a halogen atom.
A compound represented by formula (1) in which $Z^3$ is a C1-C3 alkyl group optionally having one or more halogen atoms.
A compound represented by formula (1) in which $Z^3$ is a C1-C3 alkyl group.
A compound represented by formula (1) in which $R^1$ is a halogen atom.
A compound represented by formula (1) in which $R^1$ is a C1-C4 alkyl group optionally having one or more halogen atoms.
A compound represented by formula (1) in which $R^3$ is a hydrogen atom.
A compound represented by formula (1) in which $R^3$ is a C1-C4 alkyl group optionally having one or more halogen atoms.
A compound represented by formula (1) in which $R^7$ is a C1-C3 alkyl group optionally having one or more halogen atoms.
A compound represented by formula (1) in which $R^7$ is a halogen atom.

A compound represented by formula (1) in which $R^7$ is a C1-C3 alkoxy group optionally having one or more halogen atoms.

A compound represented by formula (1) in which $R^7$ is a C3-C4 cycloalkyl group optionally having one or more halogen atoms.

A compound represented by formula (1) in which $R^7$ is a C2-C4 alkenyl group optionally having one or more halogen atoms.

A compound represented by formula (1) in which Q is Q1, $R^{10}$ is a hydrogen atom and $X^1$ is an oxygen atom.

A compound represented by formula (1) in which Q is Q1, $R^{10}$ is a hydrogen atom, and $X^1$ is a sulfur atom.

A compound represented by formula (1) in which Q is Q1, $R^{10}$ is a hydroxyl group, and $X^1$ is an oxygen atom.

A compound represented by formula (1) in which Q is Q1, $R^{10}$ is a hydroxyl group, and $X^1$ is a sulfur atom.

A compound represented by formula (1) in which Q is Q1, $R^{10}$ is a methyl group, and $X^1$ is an oxygen atom.

A compound represented by formula (1) in which Q is Q1, $R^{10}$ is a methyl group, and $X^1$ is a sulfur atom.

A compound represented by formula (1) in which Q is Q2, $R^{11}$ is a hydrogen atom, and $X^1$ is an oxygen atom.

A compound represented by formula (1) in which Q is Q2, $R^{11}$ is a hydrogen atom, and $X^1$ is a sulfur atom.

A compound represented by formula (1) in which Q is Q2, $R^{11}$ is a hydroxyl group, and $X^1$ is an oxygen atom.

A compound represented by formula (1) in which Q is Q2, $R^{11}$ is a hydroxyl group, and $X^1$ is a sulfur atom.

A compound represented by formula (1) in which Q is Q2, $R^{11}$ is a methyl group, and $X^1$ is an oxygen atom.

A compound represented by formula (1) in which Q is Q2, $R^{11}$ is a methyl group, and $X^1$ is a sulfur atom.

A compound represented by formula (1) in which Q is Q2, $R^{11}$ is a methoxy group, and $X^1$ is an oxygen atom.

A compound represented by formula (1) in which Q is Q2, $R^{11}$ is a methoxy group, and $X^1$ is a sulfur atom.

A compound represented by formula (1) in which Q is Q3 and $X^2$ is an oxygen atom.

A compound represented by formula (1) in which Q is Q3 and $X^2$ is $NR^{12}$.

A compound represented by formula (1) in which Q is Q3 and $X^2$ is a direct bond.

A compound represented by formula (1) in which $R^1$ is a C1-C4 alkyl group optionally having one or more halogen atoms, $R^3$ is a hydrogen atom, and $R^7$ is a C1-C3 alkyl group optionally having one or more halogen atoms, a hydrogen atom, a halogen atom, a C1-C3 alkoxy group optionally having one or more halogen atoms, a C3-C4 cycloalkyl group optionally having one or more halogen atoms, or a C2-C4 alkenyl group optionally having one or more halogen atoms.

A compound represented by formula (1) in which $R^1$ is a C1-C4 alkyl group optionally having one or more halogen atoms, $R^3$ is a hydrogen atom, and $R^7$ is a hydrogen atom or an alkyl group optionally having one or more halogen atoms.

A compound represented by formula (1) in which $R^1$ is a C1-C4 alkyl group optionally having one or more halogen atoms, $R^3$ is a hydrogen atom, $R^7$ is a C1-C3 alkyl group optionally having one or more halogen atoms, a hydrogen atom, a halogen atom, a C1-C3 alkoxy group optionally having one or more halogen atoms, a C3-C4 cycloalkyl group optionally having one or more halogen atoms, or a C2-C4 alkenyl group optionally having one or more halogen atoms, Q is Q1, $X^1$ is an oxygen atom, and $R^{12}$ is a C1-C3 alkyl group optionally having one or more halogen atoms.

A compound represented by formula (1) in which $R^1$ is a C1-C4 alkyl group optionally having one or more halogen atoms, $R^3$ is a hydrogen atom, $R^7$ is a hydrogen atom or an alkyl group optionally having one or more halogen atoms, Q is Q1, $X^1$ is an oxygen atom, and $R^{12}$ is a C1-C3 alkyl group optionally having one or more halogen atoms.

A compound represented by formula (1) in which $R^1$ is a C1-C4 alkyl group optionally having one or more halogen atoms, $R^3$ is a hydrogen atom, $R^7$ is an alkyl group optionally having one or more halogen atoms, Q is Q1, $X^1$ is an oxygen atom, and $R^{12}$ is a C1-C3 alkyl group optionally having one or more halogen atoms.

A compound represented by formula (1) in which Q is Q2, $Z^2$ is a halogen atom, and $Z^3$ is a C1-C3 alkyl group.

A compound represented by formula (1) in which Q is Q2, $Z^2$ is a halogen atom, $Z^3$ is a C1-C3 alkyl group, $R^1$ is a C1-C4 alkyl group optionally having one or more halogen atoms, $R^3$ is a hydrogen atom, and $R^7$ is a hydrogen atom.

A compound represented by formula (1) in which Q is Q2, $Z^2$ is a halogen atom, $Z^3$ is a C1-C3 alkyl group, $R^1$ is a C1-C4 alkyl group optionally having one or more halogen atoms, $R^3$ is a hydrogen atom, $R^7$ is a hydrogen atom, $X^1$ is an oxygen atom, $R^{11}$ is a hydroxyl group, and $X^2$ is $NR^{12}$.

A compound represented by formula (1) in which Q is Q3, $Z^2$ is a halogen atom, and $Z^3$ is a C1-C3 alkyl group.

A compound represented by formula (1) in which Q is Q3, $Z^2$ is a halogen atom, $Z^3$ is a C1-C3 alkyl group, $R^1$ is a C1-C4 alkyl group optionally having one or more halogen atoms, $R^3$ is a hydrogen atom, and $R^7$ is a hydrogen atom.

A compound represented by formula (1) in which Q is Q3, $Z^2$ is a halogen atom, $Z^3$ is a C1-C3 alkyl group, $R^1$ is a C1-C4 alkyl group optionally having one or more halogen atoms, $R^3$ is a hydrogen atom, $R^7$ is a hydrogen atom, and $X^2$ is an oxygen atom or $NR^{12}$.

A compound represented by formula (2) in which $X^1$ is an oxygen atom.

A compound represented by formula (2) in which $X^1$ is a sulfur atom.

A compound represented by formula (2) in which $X^1$ is an oxygen atom and $R^5$ is a methyl group.

A compound represented by formula (2) in which $X^1$ is a sulfur atom and $R^5$ is a methyl group.

A compound represented by formula (2) in which $X^1$ is an oxygen atom and $R^5$ is an ethyl group.

A compound represented by formula (2) in which $X^1$ is a sulfur atom and $R^5$ is an ethyl group.

A compound represented by formula (2) in which Q' is Q1'.

A compound represented by formula (2) in which Q' is Q2'.

A compound represented by formula (2) in which Q' is Q3'.

A compound represented by formula (2) in which $Z^{2'}$ is a halogen atom.

A compound represented by formula (2) in which $Z^{2'}$ is a C1-C3 alkoxy group.

A compound represented by formula (2) in which $Z^{3'}$ is a halogen atom.

A compound represented by formula (2) in which $Z^{3'}$ is a C1-C3 alkyl group.

A compound represented by formula (2) in which $R^1$ is a halogen atom.

A compound represented by formula (2) in which $R^1$ is a C1-C4 alkyl group optionally having one or more halogen atoms.

A compound represented by formula (2) in which $R^3$ is a hydrogen atom.
A compound represented by formula (2) in which $R^3$ is a C1-C4 alkyl group optionally having one or more halogen atoms.
A compound represented by formula (2) in which $R^6$ is a C1-C3 alkyl group optionally having one or more halogen atoms.
A compound represented by formula (2) in which $R^6$ is a halogen atom.
A compound represented by formula (2) in which $R^6$ is a C1-C3 alkoxy group optionally having one or more halogen atoms.
A compound represented by formula (2) in which $R^6$ is a C3-C4 cycloalkyl group optionally having one or more halogen atoms.
A compound represented by formula (2) in which Q' is Q1', $R^{10}$ is a hydrogen atom, and $X^1$ is an oxygen atom.
A compound represented by formula (2) in which Q' is Q1', $R^{10}$ is a hydrogen atom, and $X^1$ is a sulfur atom.
A compound represented by formula (2) in which Q' is Q1', $R^{10}$ is a hydroxyl group, and $X^1$ is an oxygen atom.
A compound represented by formula (2) in which Q' is Q1', $R^{10}$ is a hydroxyl group, and $X^1$ is a sulfur atom.
A compound represented by formula (2) in which Q is Q1, $R^{10}$ is a methyl group, and $X^1$ is an oxygen atom.
A compound represented by formula (2) in which Q' is Q1', $R^{10}$ is a methyl group, and $X^1$ is a sulfur atom.
A compound represented by formula (2) in which Q' is Q2', $R^{11}$ is a hydrogen atom, and $X^1$ is an oxygen atom.
A compound represented by formula (2) in which Q' is Q2', $R^{11}$ is a hydrogen atom, and $X^1$ is a sulfur atom.
A compound represented by formula (2) in which Q' is Q2', $R^{11}$ is a hydroxyl group, and $X^1$ is an oxygen atom.
A compound represented by formula (2) in which Q' is Q2', $R^{11}$ is a hydroxyl group, and $X^1$ is a sulfur atom.
A compound represented by formula (2) in which Q' is Q2', $R^{11}$ is a methyl group, and $X^1$ is an oxygen atom.
A compound represented by formula (2) in which Q' is Q2', $R^{11}$ is a methyl group, and $X^1$ is a sulfur atom.
A compound represented by formula (2) in which Q' is Q2', $R^{11}$ is a methoxy group, and $X^1$ is an oxygen atom.
A compound represented by formula (2) in which Q' is Q2', $R^{11}$ is a methoxy group, and $X^1$ is a sulfur atom.
A compound represented by formula (2) in which Q' is Q3' and $X^{2'}$ is an oxygen atom.
A compound represented by formula (2) in which Q' is Q3' and $X^{2'}$ is $NR^{12}$.
A compound represented by formula (2) in which Q' is Q3' and $X^{2'}$ is a direct bond.
A compound represented by formula (2) in which $R^1$ is a C1-C4 alkyl group optionally having one or more halogen atoms, $R^3$ is a hydrogen atom, and $R^6$ is a C1-C3 alkyl group optionally having one or more halogen atoms, a hydrogen atom, a halogen atom, a C1-C3 alkoxy group optionally having one or more halogen atoms, or a C3-C4 cycloalkyl group optionally having one or more halogen atoms. A compound represented by formula (2) in which $R^1$ is a C1-C4 alkyl group optionally having one or more halogen atoms, $R^3$ is a hydrogen atom, and $R^6$ is a hydrogen atom or an alkyl group optionally having one or more halogen atoms.
A compound represented by formula (2) in which $R^1$ is a C1-C4 alkyl group optionally having one or more halogen atoms, $R^3$ is a hydrogen atom, $R^6$ is a C1-C3 alkyl group optionally having one or more halogen atoms, a hydrogen atom, a halogen atom, a C1-C3 alkoxy group optionally having one or more halogen atoms, or a C3-C4 cycloalkyl group optionally having one or more halogen atoms, Q' is Q1', $X^1$ is an oxygen atom, and $R^{12}$ is a C1-C3 alkyl group optionally having one or more halogen atoms.
A compound represented by formula (2) in which $R^1$ is a C1-C4 alkyl group optionally having one or more halogen atoms, $R^3$ is a hydrogen atom, $R^6$ is a hydrogen atom or an alkyl group optionally having one or more halogen atoms, Q' is Q1', $X^1$ is an oxygen atom, and $R^{12}$ is a C1-C3 alkyl group optionally having one or more halogen atoms.
A compound represented by formula (2) in which Q' is Q2', $Z^{2'}$ is a halogen atom, and $Z^{3'}$ is a C1-C3 alkyl group.
A compound represented by formula (2) in which Q' is Q2', $Z^{2'}$ is a halogen atom, $Z^{3'}$ is a C1-C3 alkyl group, $R^1$ is a C1-C4 alkyl group optionally having one or more halogen atoms, $R^3$ is a hydrogen atom, and $R^6$ is a hydrogen atom.
A compound represented by formula (2) in which Q' is Q2', $Z^{2'}$ is a halogen atom, $Z^{3'}$ is a C1-C3 alkyl group, $R^1$ is a C1-C4 alkyl group optionally having one or more halogen atoms, $R^3$ is a hydrogen atom, $R^6$ is a hydrogen atom, $X^1$ is an oxygen atom, $R^{11}$ is a hydroxyl group, and $X^{2'}$ is $NR^{12}$.
A compound represented by formula (2) in which Q' is Q3', $Z^{2'}$ is a halogen atom, and $Z^{3'}$ is a C1-C3 alkyl group.
A compound represented by formula (2) in which Q' is Q3', $Z^{2'}$ is a halogen atom, $Z^{3'}$ is a C1-C3 alkyl group, $R^1$ is a C1-C4 alkyl group optionally having one or more halogen atoms, $R^3$ is a hydrogen atom, and $R^6$ is a hydrogen atom.
A compound represented by formula (2) in which Q' is Q3', $Z^{2'}$ is a halogen atom, $Z^{3'}$ is a C1-C3 alkyl group, $R^1$ is a C1-C4 alkyl group optionally having one or more halogen atoms, $R^3$ is a hydrogen atom, $R^6$ is a hydrogen atom, and $X^{2'}$ is an oxygen atom or $NR^{12}$.

Next, a process for producing the present compound will be described.

The present compound can be produced, for example, by the following Production Processes.

(Production Process A)

The present compound can be produced by reacting a compound represented by formula (A) (hereinafter referred to as the compound (A)) with a compound represented by formula (B) (hereinafter referred to as the compound (B)) in the presence of a base:

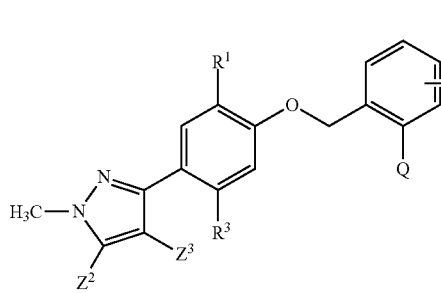

(1)

wherein $R^1$, $R^3$, $R^7$, $Z^2$, $Z^3$, and Q are the same as defined above, and A represents a leaving group such as a chlorine atom or a bromine atom.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; acid amides such as dimethylformamide (hereinafter referred to as DMF), 1, 3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water and mixtures thereof.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate and potassium hydrogen carbonate, and these compounds are usually used in the proportion within a range of 0.05 to 5 mols based on 1 mol of the compound (A).

In the reaction, the compound (B) is usually used in the proportion within a range of 1 to 10 mols based on 1 mol of the compound (A).

The reaction temperature of the reaction is usually within a range of −20 to 150° C. The reaction time of the reaction is usually within a range of 0.1 to 24 hours.

After completion of the reaction, the present compound can be isolated by performing post-treatment operations such as extraction of the reaction mixture with an organic solvent, and drying and concentration of the organic layer. The isolated present compound may be further purified by operations such as distillation, chromatography, and recrystallization.

(Production Process B)

Among the present compounds, a compound in which Q is Q1 (hereinafter referred to as the compound (1-1)) can be produced by reacting a compound represented by formula (C) (hereinafter referred to as the compound (C)) with a compound represented by formula (D) (hereinafter referred to as the compound (D)):

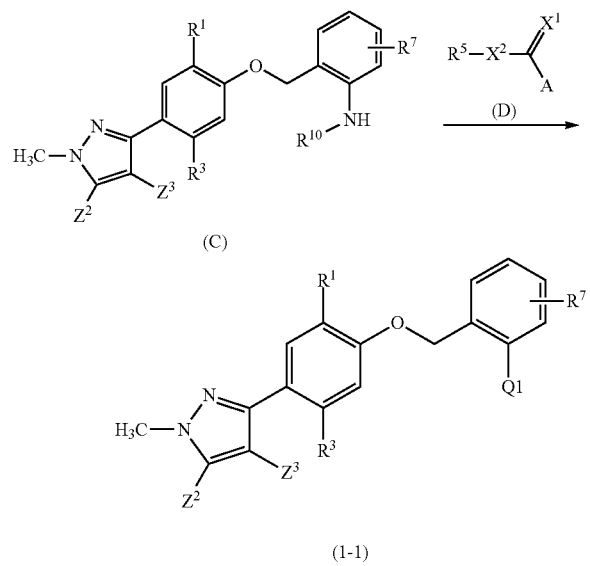

wherein symbols are the same as defined above.

Examples of the compound (D) to be used in the reaction include methyl chlorocarbonate, ethyl chlorocarbonate, acetyl chloride, propionyl chloride, dimethylcarbamoyl chloride, and the like, and commercially available products can be used.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; acid amides such as DMF, 1, 3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water and mixtures thereof.

In the reaction, the compound (D) is usually used in the proportion within a range of 1 to 10 mols based on 1 mol of the compound (C).

The reaction temperature of the reaction is usually within a range of −20 to 150° C. The reaction time of the reaction is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate and potassium hydrogen carbonate may be added, and these compounds are usually used in the proportion within a range of 0.05 to 5 mols based on 1 mol of the compound (C).

After completion of the reaction, the compound (1-1) can be isolated by performing post-treatment operations such as extraction of the reaction mixture with an organic solvent, and drying and concentration of the organic layer. The isolated compound may be further purified by operations such as distillation, chromatography, and recrystallization.

(Production Process C)

Among the present compounds, a compound represented by formula (1-S) in which Q is Q1 or Q2, and $X^1$ is a sulfur atom (hereinafter referred to as the compound (1-S)) can be produced by reacting a compound in which Q is Q1 or Q2, and $X^1$ is an oxygen atom (hereinafter referred to as the compound (1-O)) among the present compounds with a sulfurizing agent:

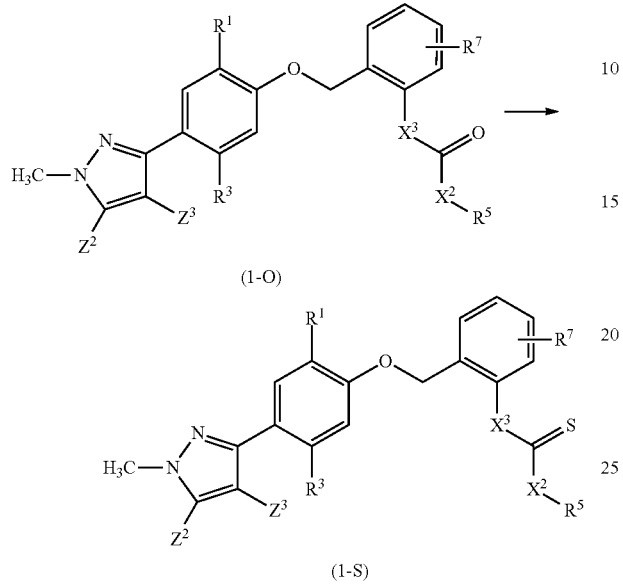

$X^3 = NR^{10}$ or $CHR^{11}$ wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; nitriles such as acetonitrile; and mixtures thereof.

Examples of the sulfurizing agent to be used in the reaction include phosphorous pentasulfide and Lawesson's reagent (2,4-bis (4-methoxyphenyl)-1, 3, 2, 4-dithiadiphosphetane 2,4-disulfide).

In the reaction, the sulfurizing agent is usually used in the proportion within a range of 0.5 to 1.5 mols based on 1 mol of the compound (1-O).

The reaction temperature of the reaction is usually within a range of −20 to 150° C. The reaction time of the reaction is usually within a range of 0.1 to 24 hours.

In the reaction, if necessary, organic bases such as pyridine and triethylamine; and inorganic bases such as alkali metal hydroxides and alkali metal carbonates may be added, and the amount of the base to be added is within a range of 0.5 to 1.5 mols, based on the compound (1-O).

After completion of the reaction, the compound (1-S) can be isolated by performing post-treatment operations such as extraction of the reaction mixture with an organic solvent, and drying and concentration of the organic layer. The isolated compound (1-S) can also be purified by chromatography, recrystallization, and the like.

(Production Process D)

Among the present compounds, a compound represented by formula (1-3) in which Q is Q1 and $R^{10}$ is a methyl group (hereinafter referred to as the compound (1-3)) can be produced by reacting a compound represented by formula (1-2) (hereinafter referred to as the compound (1-2)) with a methylating agent in the presence of a base:

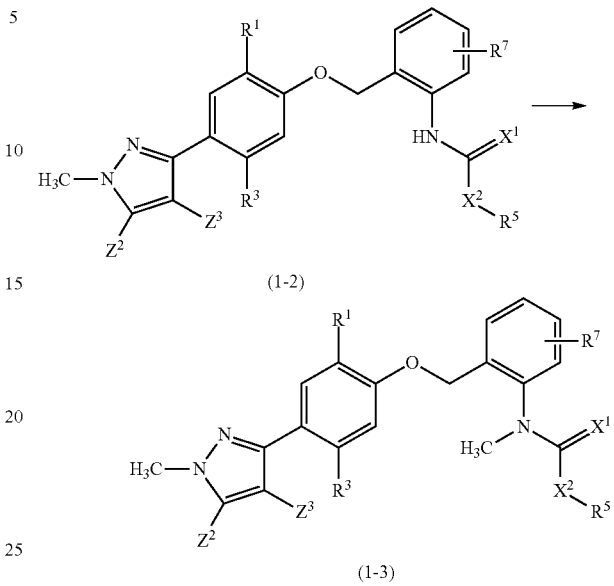

wherein symbols are the same as defined above.

The reaction is usually performed in a solvent.

Examples of the solvent to be used in the reaction include hydrocarbons such as n-hexane, cyclohexane, n-pentane, toluene, and xylene; ethers such as tetrahydrofuran, 1, 4-dioxane, ethylene glycol dimethyl ether, methyl tert-butyl ether, and diisopropyl ether; halogenated hydrocarbons such as chloroform, 1,2-dichloroetane, and chlorobenzene; sulfoxides such as methyl sulfoxide; nitriles such as acetonitrile; and mixtures thereof.

Commercially available products can be usually used as the methylating agent to be used in the reaction, and examples thereof include methyl bromide, methyl iodide, dimethyl sulfate, methyl p-toluenesulfonate, methyl methanesulfonate, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as sodium carbonate and potassium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal hydrides such as lithium hydride, sodium hydride, and potassium hydride; and alkali metal alkoxides such as sodium tert-butoxide and potassium tert-butoxide.

In the reaction, the methylating agent is usually used in the proportion within a range of 1 to 10 mols, and the base is usually used in the proportion within a range of 1 to 10 mols, based on 1 mol of the compound (1-2).

The reaction temperature of the reaction is usually within a range of −20 to 150° C. The reaction time of the reaction is usually within a range of 0.1 to 24 hours.

After completion of the reaction, the compound (1-3) can be isolated by performing post-treatment operations such as extraction of the reaction mixture with an organic solvent, and drying and concentration of the organic layer. The isolated compound (1-3) can also be purified by chromatography, recrystallization, and the like.

(Production Process E)

Among the present compounds, a compound represented by formula (1-4) in which Q is Q3 and $X^2$ is an oxygen atom (hereinafter referred to as the compound (1-4)) can be produced by reacting a compound represented by formula (E-1) (hereinafter referred to as the compound (E-1)) with a compound represented by formula (E-2) (hereinafter referred to as the compound (E-2)) in the presence of a Grignard reagent:

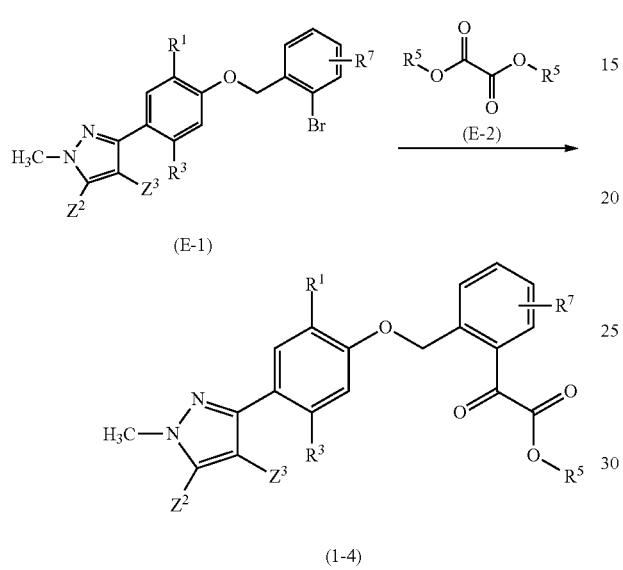

wherein symbols are the same as defined above.

The reaction is usually performed in a solvent.

Examples of the solvent to be used in the reaction include hydrocarbons such as n-hexane, cyclohexane, n-pentane, toluene, and xylene; ethers such as tetrahydrofuran, 1,4-dioxane, ethylene glycol dimethyl ether, methyl tert-butyl ether, and diisopropyl ether; and mixtures thereof.

Commercially available products can be usually used as the Grignard reagent to be used in the reaction, and examples thereof include methyl magnesium chloride, methyl magnesium bromide, isopropyl magnesium chloride, and isopropyl magnesium bromide.

In the reaction, the Grignard reagent is usually used in the proportion within a range of 1 to 2 mols, and the compound (E-2) is usually used in the proportion within a range of 1 to 10 mols, based on 1 mol of the compound (E-1).

The reaction temperature of the reaction is usually within a range of −90 to 100° C. The reaction time of the reaction is usually within a range of 0.1 to 24 hours.

After completion of the reaction, the compound (1-4) can be isolated by performing post-treatment operations such as extraction of the reaction mixture with an organic solvent, and drying and concentration of the organic layer. The isolated compound (1-4) can also be purified by chromatography, recrystallization, and the like.

(Production Process F)

Among the present compounds, a compound represented by formula (1-6) in which Q is Q3 and $X^2$ is $NR^{12}$ (hereinafter referred to as the compound (1-6)) can be produced by reacting the compound (1-4) with a compound represented by formula (F-1) (hereinafter referred to as the compound (F-1)):

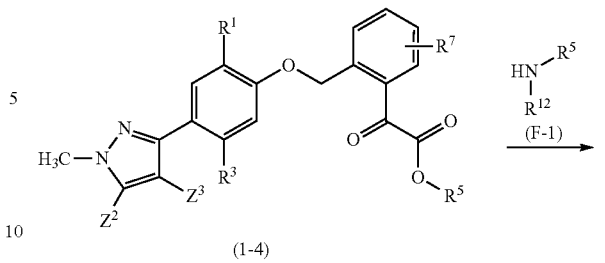

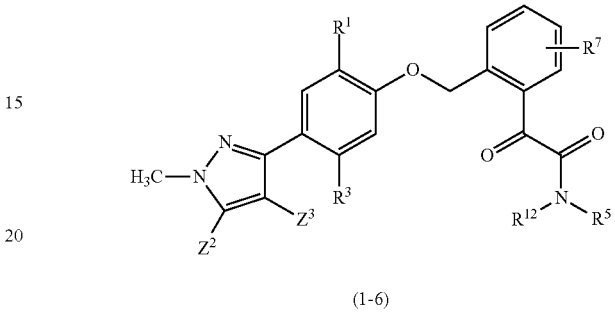

wherein symbols are the same as defined above.

The reaction is usually performed in a solvent.

Examples of the solvent to be used in the reaction include hydrocarbons such as n-hexane, cyclohexane, n-pentane, toluene, and xylene; ethers such as tetrahydrofuran, 1,4-dioxane, ethylene glycol dimethyl ether, methyl tert-butyl ether, and diisopropyl ether; alcohols such as methanol and ethanol; halogenated hydrocarbons such as chloroform, 1,2-dichloroetane, and chlorobenzene; sulfoxides such as methyl sulfoxide; nitriles such as acetonitrile; and mixtures thereof.

In the reaction, the compound (F-1) is usually used in the proportion within a range of 1 to 10 mols based on 1 mol of the compound (1-4).

The reaction temperature of the reaction is usually within a range of −20 to 150° C. The reaction time of the reaction is usually within a range of 0.1 to 24 hours.

After completion of the reaction, the compound (1-6) can be isolated by performing post-treatment operations such as extraction of the reaction mixture with an organic solvent, and drying and concentration of the organic layer. The isolated compound (1-6) can also be purified by chromatography, recrystallization, and the like.

(Production Process G)

Among the present compounds, a compound represented by formula (1-7) (hereinafter referred to as the compound (1-7)) can be produced by mixing the compound (1-4) with a reducing agent:

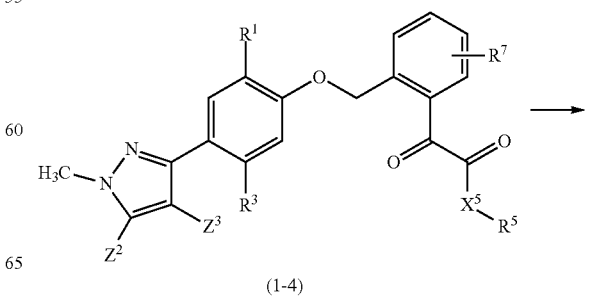

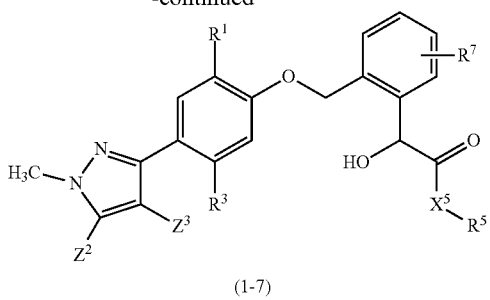

(1-7)

wherein symbols are the same as defined above.

The reaction is usually performed in a solvent.

Examples of the solvent to be used in the reaction include hydrocarbons such as n-hexane, cyclohexane, n-pentane, toluene, and xylene; ethers such as tetrahydrofuran, 1,4-dioxane, ethylene glycol dimethyl ether, methyl tert-butyl ether, and diisopropyl ether; alcohols such as methanol and ethanol; halogenated hydrocarbons such as chloroform, 1,2-dichloroetane, and chlorobenzene; sulfoxides such as methyl sulfoxide; nitriles such as acetonitrile; and mixtures thereof.

Examples of the reducing agent to be used in the reaction include sodium borohydride, sodium cyanoborohydride, and sodium triacetoxyborohydride.

In the reaction, the reducing agent is usually used in the proportion within a range of 1 to 10 mols based on 1 mol of the compound (1-4).

The reaction temperature of the reaction is usually within a range of −20 to 150° C. The reaction time of the reaction is usually within a range of 0.1 to 24 hours.

After completion of the reaction, the compound (1-7) can be isolated by performing post-treatment operations such as extraction of the reaction mixture with an organic solvent, and drying and concentration of the organic layer. The isolated compound (1-7) can also be purified by chromatography, recrystallization, and the like.

The present compound can be produced in accordance with reactions mentioned in aforementioned Production Processes A to G.

A method for synthesizing intermediate compounds will be shown below.

(Reference Production Process A)

The compound (A) can be produced by reacting a compound represented by formula (A1) (hereinafter referred to as the compound (A1)) with a halogenating agent:

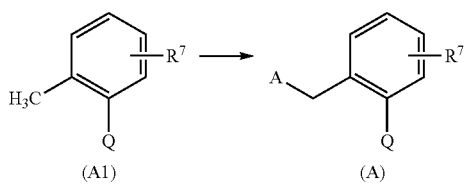

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of the halogenating agent to be used in the reaction include a chlorinating agent, a brominating agent, and an iodinating agent, for example, a chlorinating agent such as chlorine, sulfuryl chloride, N-chlorosuccinimide, or N-bromosuccinimide; a brominating agent such as bromine, 1,3-dibromo-5,5-dimethylhydantoin, or N-bromophthalimide; and an iodinating agent such as iodine or iodosuccinimide.

In the reaction, a radical initiator can also be used.

Examples of the radical initiator to be used in the reaction include benzoyl peroxide, azobisisobutyronitrile (AIBN), diacyl peroxide, dialkyl peroxydicarbonate, tert-alkyl peroxy ester, monoperoxy carbonate, di(tert-alkylperoxy) ketal, and ketone peroxide.

In the reaction, the halogenating agent is usually used in the proportion within a range of 1 to 10 mols, and the radical initiator is usually used in the proportion within a range of 0.01 to 5 mols, based on 1 mol of the compound (A1).

The reaction temperature of the reaction is usually within a range of −20 to 150° C. The reaction time of the reaction is usually within a range of 0.1 to 24 hours.

After completion of the reaction, the compound (A) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process B)

The compound (B) can be produced by reacting a compound represented by formula (YA1) (hereinafter referred to as the compound (YA1)) with an acid:

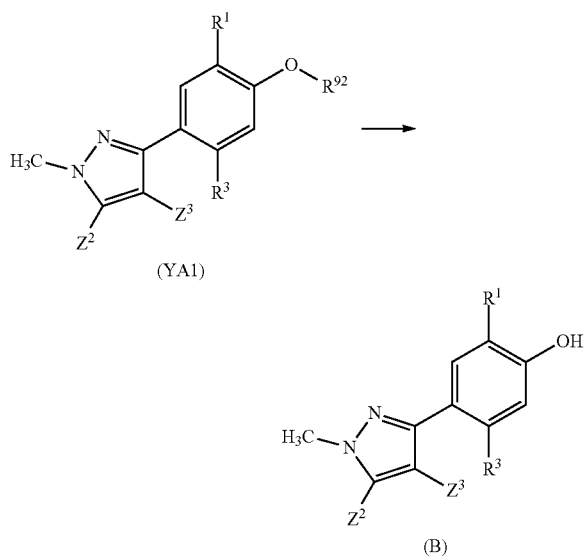

wherein $R^1$, $R^3$, $Z^2$, and $Z^3$ are the same as defined above, and $R^{92}$ represents a C1-C3 alkyl group.

The reaction is usually performed in a solvent.

Examples of the solvent to be used in the reaction include alcohols such as methanol, ethanol, propanol, and butanol; water, acetic acid, and mixtures thereof.

Examples of the acid to be used in the reaction include hydrochloric acid and hydrobromic acid, and aqueous solutions thereof can also be used as the solvent.

In the reaction, the acid is usually used in the proportion of large excess based on 1 mol of the compound (YA1).

The reaction temperature of the reaction is usually within a range of −20 to 150° C. The reaction time of the reaction is usually within a range of 0.1 to 100 hours.

After completion of the reaction, the compound (B) can be isolated by performing post-treatment operations such as extraction of the reaction mixture with an organic solvent, and drying and concentration of the organic layer. Alternatively, the compound (B) can be isolated by performing post-treatment operations such as concentration of the reaction mixture. The isolated compound can also be purified by chromatography, recrystallization, and the like.

(Reference Production Process C)

Among the compounds represented by formula (YA1), a compound represented by formula (YAB-2) in which $Z^3$ is a methyl group (hereinafter referred to as the compound (YAB-2)) can be produced by reacting a compound represented by formula (YAB-1) (hereinafter referred to as the compound (YAB-1)) with a reducing agent in the presence of an acid:

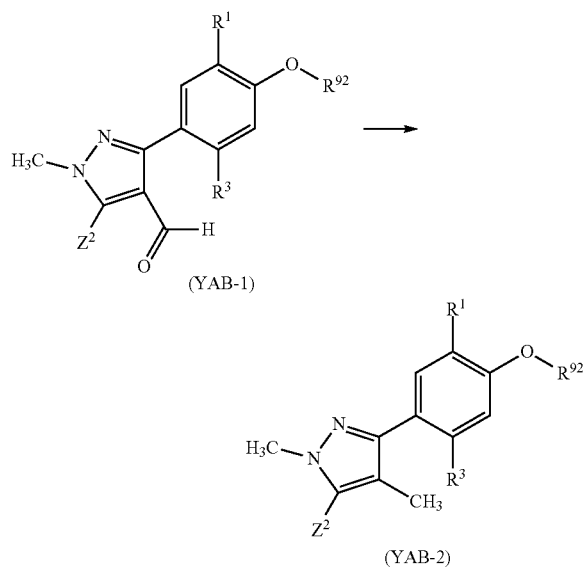

(YAB-1)

(YAB-2)

wherein symbols are the same as defined above.

The reaction is performed in a solvent or in the absence of a solvent.

Examples of the solvent to be used in the reaction include hydrocarbons such as n-hexane, cyclohexane, n-pentane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; esters such as ethyl acetate and methyl acetate; ketones such as acetone, methyl ethyl ketone, and methyl isobutyl ketone; sulfoxides such as methyl sulfoxide; nitriles such as acetonitrile; and mixtures thereof.

Examples of the acid to be used in the reaction include boron trifluoride, trifluoroacetic acid, and the like.

Examples of the reducing agent to be used in the reaction include metal boronate compounds such as lithium borohydride, sodium borohydride, and potassium borohydride; and trialkylsilane compounds such as triethylsilane.

In the reaction, the reducing agent is usually used in the proportion within a range of 1 to 10 mols, and the acid is usually in the proportion within a range of 1 to 10 mols, or in the proportion of large excess, based on 1 mol of the compound (YAB-1).

The reaction temperature of the reaction is usually within a range of −20 to 150° C. The reaction time of the reaction is usually within a range of 0.1 to 24 hours.

After completion of the reaction, the compound (YAB-2) can be isolated by performing post-treatment operations such as extraction of the reaction mixture with an organic solvent, and drying and concentration of the organic layer. The present compound represented by formula (YAB-2) can be isolated by performing post-treatment operations such as filtration and concentration of the reaction mixture. The isolated compound can also be purified by chromatography, recrystallization, and the like.

(Reference Production Process D)

The compound (YAB-1) can be produced by reacting a compound represented by formula (YAC-1) (hereinafter referred to as the compound (YAC-1)) with a compound represented by formula (U-2) (hereinafter referred to as the compound (U-2)) in the presence of a base:

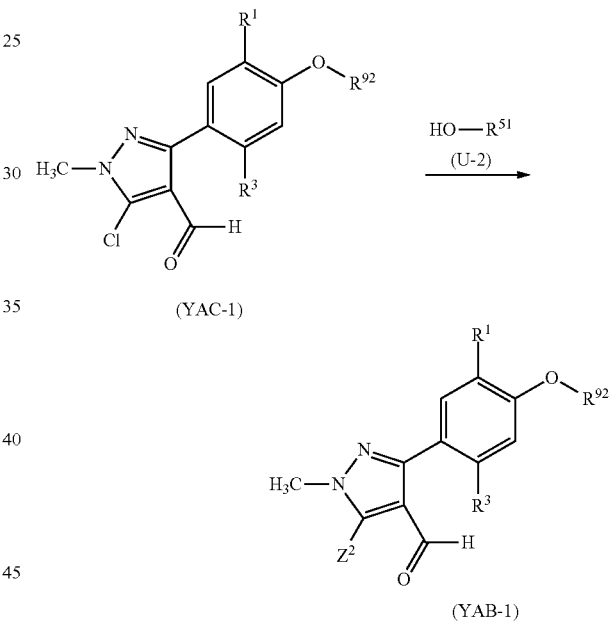

(YAC-1)

(YAB-1)

wherein $R^1$, $R^3$, $Z^2$, and $R^{92}$ are the same as defined above, and $R^{51}$ represents a C1-C3 alkyl group The reaction is usually performed in a solvent.

Examples of the solvent to be used in the reaction include hydrocarbons such as n-hexane, cyclohexane, n-pentane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; esters such as ethyl acetate and methyl acetate; ketones such as acetone, methyl ethyl ketone, and methyl isobutyl ketone; sulfoxides such as methyl sulfoxide; nitriles such as acetonitrile; and mixtures thereof.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate and potassium hydrogen carbonate; alkali metal hydroxides such as lithium hydroxide, sodium hydroxide, potassium hydroxide, and cesium hydroxide; alkali metal hydrides such as lithium hydride, sodium hydride, and potassium hydride; and alkali metal alkoxide such as sodium tert-butoxide and potassium tert-butoxide.

In the reaction, the compound (U-2) is usually used in the proportion within a range of 1 to 10 mols, and the base is usually used in the proportion within a range of 1 to 10 mols, based on 1 mol of the compound (YAC-1).

The reaction temperature of the reaction is usually within a range of −20 to 150° C. The reaction time of the reaction is usually within a range of 0.1 to 24 hours.

In the reaction, after preparing a metal salt in advance using the compound (U-2) and the base, the metal salt can also be used in the reaction. Examples of the metal salt include sodium methoxide, sodium ethoxide, sodium propoxide, sodium isopropoxide, potassium methoxide, potassium ethoxide, sodium thiomethoxide, and sodium thioethoxide.

In the reaction, the metal salt prepared from the compound (U-2) and the base is usually used in the proportion within a range of 1 to 10 mols based on 1 mol of the compound (YAC-1).

After completion of the reaction, the compound (YAB-1) can be isolated by performing post-treatment operations such as extraction of the reaction mixture with an organic solvent, and drying and concentration of the organic layer. Alternatively, the compound (YAB-1) can be isolated by performing post-treatment operations such as filtration and concentration of the reaction mixture. The isolated compound can also be purified by chromatography, recrystallization, and the like.

(Reference Production Process E)

The compound (YAC-1) can be produced by reacting a compound represented by formula (YAD-1) (hereinafter referred to as the compound (YAD-1)) with a mixture of DMF and phosphorus oxychloride, followed by a reaction with water:

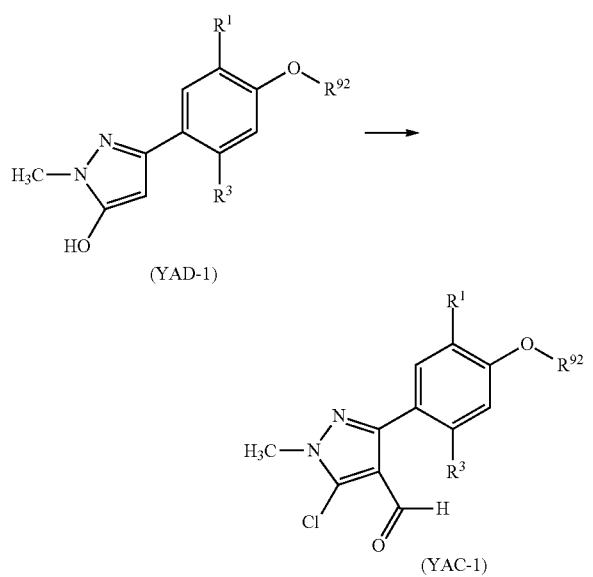

(YAD-1)

(YAC-1)

wherein symbols are the same as defined above.

The reaction is usually performed in a solvent.

Examples of the solvent to be used in the reaction include hydrocarbons such as n-hexane, cyclohexane, n-pentane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; esters such as ethyl acetate and methyl acetate; ketones such as acetone, methyl ethyl ketone, and methyl isobutyl ketone; sulfoxides such as methyl sulfoxide; nitriles such as acetonitrile; and mixtures thereof.

In the reaction, DMF is used in the proportion within a range of 1 to 10 mols, and water is used in the proportion within a range of 1 to 10 mols, based on 1 mol of the compound (YAD-1), and phosphorus oxychloride is used in the proportion within a range of 2 to 5 mols based on 1 mol of DMF.

The reaction temperature of the reaction is usually within a range of −20 to 150° C. The reaction time of the reaction is usually within a range of 0.1 to 24 hours.

After completion of the reaction, compound (YAC-1) can be isolated by usually performing post-treatment operations such as addition of 1 mol or more of water, extraction of the reaction mixture with an organic solvent, and drying and concentration of the organic layer. The isolated compound (YAC-1) can also be purified by chromatography, recrystallization, and the like.

(Reference Production Process F)

A compound represented by formula (YAE-2) (hereinafter referred to as the compound (YAE-2)) can be produced by reacting a compound represented by formula (YAE-1) (hereinafter referred to as the compound (YAE-1)) with a compound represented by formula (AE1) (hereinafter referred to as the compound (AE1)):

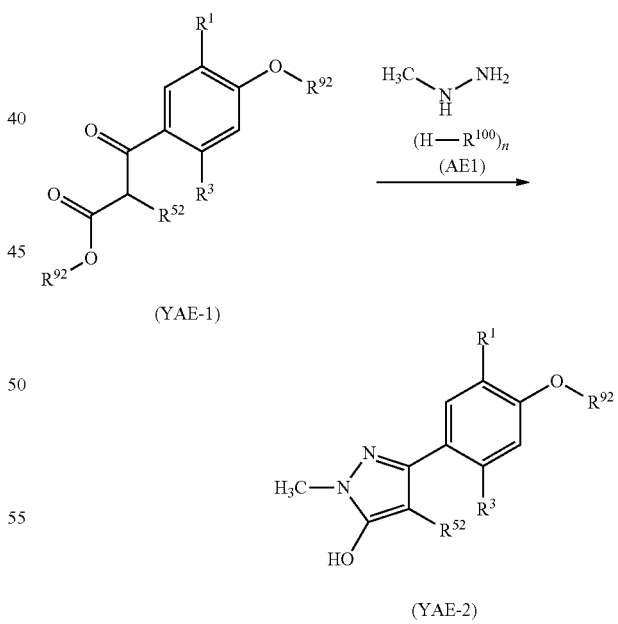

(YAE-1)

(YAE-2)

wherein $R^1$, $R^3$, $Z^1$, and $R^{92}$ are the same as defined above, $R^{52}$ represents a hydrogen atom or a C1-C3 alkyl group, $R^{100}$ represents a halogen atom, and n represents 0 or 1.

The reaction is performed in a solvent or in the absence of a solvent.

Examples of the solvent to be used in the reaction include hydrocarbons such as n-hexane, cyclohexane, n-pentane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; nitriles such as acetonitrile; and mixtures thereof.

In the reaction, an acid may be added, and examples of the acid to be used in the reaction include hydrochloric acid, sulfuric acid, acetic acid, hydrobromic acid, p-toluenesulfonic acid, and the like.

In the reaction, the compound (AE1) is usually used in the proportion within a range of 1 to 100 mols, and the acid is usually used in the proportion within a range of 1 to 100 mols, based on 1 mol of the compound (YAE-1).

The reaction temperature of the reaction is usually within a range of −20 to 150° C. The reaction time of the reaction is usually within a range of 0.1 to 24 hours.

After completion of the reaction, the compound (YAE-2) can be isolated by performing post-treatment operations such as concentration of the reaction mixture under reduced pressure, extraction of the reaction mixture with an organic solvent, and drying and concentration of the organic layer. The isolated compound (YAE-2) can also be purified by chromatography, recrystallization, and the like.

(Reference Production Process G)

The compound (YAE-1) can be produced by reacting a compound represented by formula (YAF-1) (hereinafter referred to as the compound (YAF-1)) with a compound represented by formula (AF1) (hereinafter referred to as the compound (AF1)) in the presence of a base:

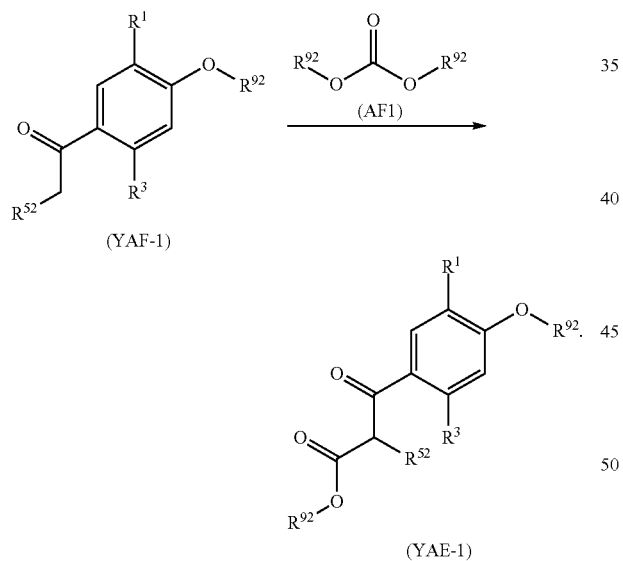

wherein symbols are the same as defined above.

The reaction is usually performed in a solvent.

Examples of the solvent to be used in the reaction include hydrocarbons such as n-hexane, cyclohexane, n-pentane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; esters such as ethyl acetate and methyl acetate; ketones such as acetone, methyl ethyl ketone, and methyl isobutyl ketone; sulfoxides such as methyl sulfoxide; nitriles such as acetonitrile; and mixtures thereof.

Examples of the base to be used in the reaction include alkali metal hydrides such as sodium hydride; and alkali metal alkoxides such as potassium tert-butoxide.

In the reaction, the compound (AF1) is usually used in the proportion within a range of 1 to 10 mols, and the base is usually used in the proportion within a range of 1 to 10 mols, based on 1 mol of the compound (YAF-1).

The reaction temperature of the reaction is usually within a range of −20 to 150° C. The reaction time of the reaction is usually within a range of 0.1 to 24 hours.

In the reaction, if necessary, additives may be added, and examples thereof include 18-crown-6-ether and dibenzo-18-crown-6-ether. These additive are usually used in the proportion within a range of 0.001 to 1.2 mols, based on 1 mol of the compound (YAF-1).

After completion of the reaction, the compound (YAE-1) can be isolated by performing post-treatment operations such as extraction of the reaction mixture with an organic solvent, and drying and concentration of the organic layer. The isolated compound (YAE-1) can also be purified by chromatography, recrystallization, and the like.

(Reference Production Process H)

The compound (YAF-1) can be produced by reacting a compound represented by formula (YAG-1) (hereinafter referred to as the compound (YAG-1)) with a compound represented by formula (AG1) (hereinafter referred to as the compound (AG1)) in the presence of a base:

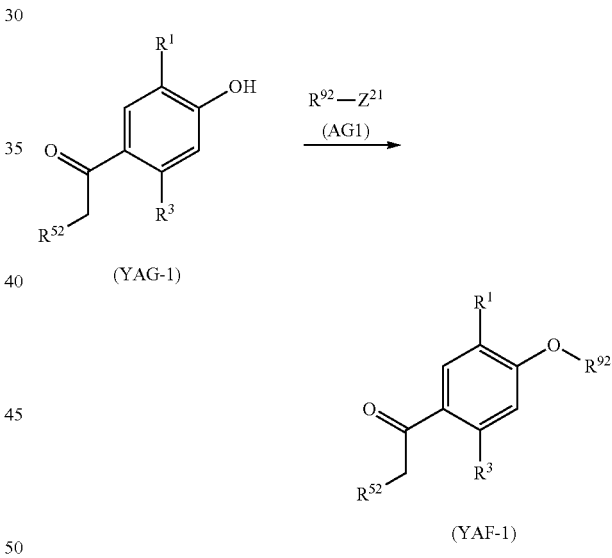

wherein $R^1$, $R^3$, $R^{52}$, $R^{92}$ and $Z^3$ are the same as defined above, $Z^{21}$ represents a leaving group such as a chlorine atom, a bromine atom, an iodine atom, a methanesulfonyloxy group, a trifluoromethanesulfonyloxy group, or a p-toluenesulfonyloxy group.

The reaction is usually performed in a solvent.

Examples of the solvent to be used in the reaction include hydrocarbons such as n-hexane, cyclohexane, n-pentane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; esters such as ethyl acetate and methyl acetate; ketones such as acetone, methyl ethyl ketone, and methyl isobutyl ketone; sulfoxides such as methyl sulfoxide; nitriles such as acetonitrile; and mixtures thereof.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate and potassium hydrogen carbonate; alkali metal hydroxides such as lithium hydroxide, sodium hydroxide, potassium hydroxide, and cesium hydroxide; and alkali metal alkoxides such as sodium tert-butoxide and potassium tert-butoxide.

In the reaction, the compound (AG1) is usually used in the proportion within a range of 1 to 10 mols, and the base is usually used in the proportion within a range of 1 to 10 mols, based on 1 mol of the compound (YAG-1).

The reaction temperature of the reaction is usually within a range of −20 to 150° C. The reaction time of the reaction is usually within a range of 0.1 to 24 hours.

After completion of the reaction, the compound (YAF-1) can be isolated by performing post-treatment operations such as extraction of the reaction mixture with an organic solvent, and drying and concentration of the organic layer. The isolated compound (YAF-1) can also be purified by chromatography, recrystallization, and the like.

(Reference Production Process I)

The compound (YAG-1) can be produced by reacting a compound represented by formula (YAH-1) (hereinafter referred to as the compound (YAH-1)) in the presence of an acid catalyst:

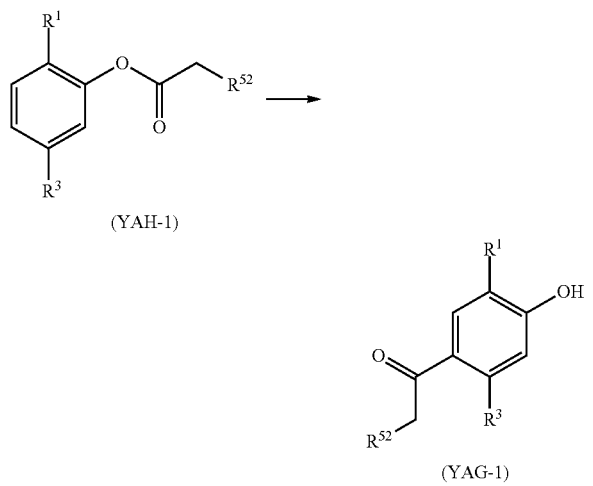

(YAH-1)

(YAG-1)

wherein symbols are the same as defined above.

The reaction is usually performed in a solvent.

Examples of the solvent to be used in the reaction include hydrocarbons such as n-hexane, cyclohexane, and n-pentane; halogenated hydrocarbons such as chloroform, dichloromethane, 1,2-dichloroetane, and chlorobenzene; nitriles such as nitromethane, acetonitrile, and propionitrile; and mixtures thereof.

Examples of the acid catalyst to be used in the reaction include aluminum trichloride, titanium tetrachloride, iron trichloride, hydrogen fluoride, hypochlorous acid, and polyphosphoric acid.

In the reaction, a rearrangement agent is usually used in the proportion within a range of 1 to 10 mols based on 1 mol of the compound (YAH-1).

The reaction temperature of the reaction is usually within a range of −20 to 150° C. The reaction time of the reaction is usually within a range of 0.1 to 72 hours.

After completion of the reaction, the compound (YAG-1) can be isolated by performing post-treatment operations such as extraction of the reaction mixture with an organic solvent, and drying and concentration of the organic layer. The isolated compound (YAG-1) can also be purified by chromatography, recrystallization, and the like.

(Reference Production Process J)

The compound (YAH-1) can be produced by reacting a compound represented by formula (YAI-1) (hereinafter referred to as the compound (YAI-1)) with a compound represented by formula (AI1) (hereinafter referred to as the compound (AI1)) in the presence of a base:

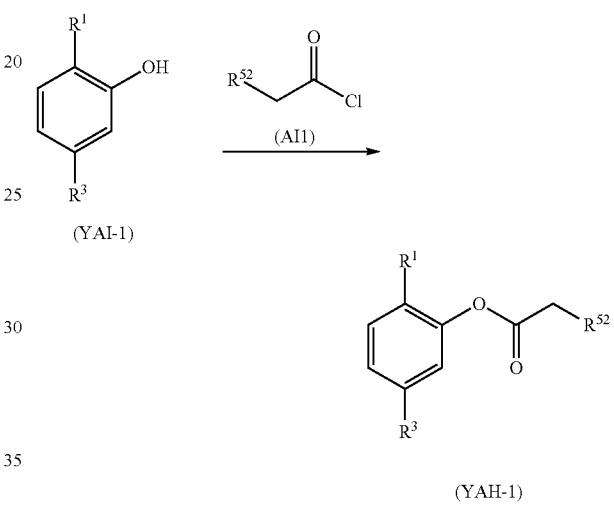

(YAI-1)

(YAH-1)

wherein symbols are the same as defined above.

The reaction is usually performed in a solvent.

Examples of the solvent to be used in the reaction include hydrocarbons such as n-hexane, cyclohexane, n-pentane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; esters such as ethyl acetate and methyl acetate; ketones such as acetone, methyl ethyl ketone, and methyl isobutyl ketone; sulfoxides such as methyl sulfoxide; nitriles such as acetonitrile; and mixtures thereof.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as sodium carbonate and potassium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal hydrides such as lithium hydride, sodium hydride, and potassium hydride; and alkali metal alkoxide such as sodium tert-butoxide and potassium tert-butoxide.

In the reaction, the compound (AI1) is usually used in the proportion within a range of 1 to 10 mols, and the base is usually used in the proportion within a range of 1 to 10 mols, based on 1 mol of the compound (YAI-1).

The reaction temperature of the reaction is usually within a range of −78 to 150° C. The reaction time of the reaction is usually within a range of 0.1 to 72 hours.

After completion of the reaction, the compound (YAH-1) can be isolated by performing post-treatment operations such as extraction of the reaction mixture with an organic solvent, and drying and concentration of the organic layer. The isolated compound (YAH-1) can also be purified by chromatography, recrystallization, and the like.

(Reference Production Process K)

Among compounds represented by formula (YA1), a compound represented by formula (YAJ-2) in which $Z^3$ is a halogen atom (hereinafter referred to as the compound (YAJ-2)) can be produced by reacting a compound represented by formula (YAJ-1) (hereinafter referred to as the compound (YAJ-1)) with a halogenating agent:

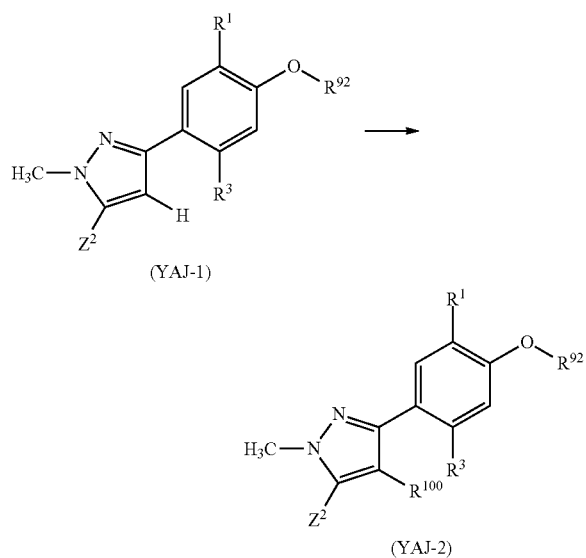

wherein symbols are the same as defined above.

The reaction is usually performed in a solvent.

Examples of the solvent to be used in the reaction include hydrocarbons such as n-hexane, cyclohexane, n-pentane, toluene, and xylene; ethers such as tetrahydrofuran, 1, 4-dioxane, ethylene glycol dimethyl ether, methyl tert-butyl ether, and diisopropyl ether; halogenated hydrocarbons such as chloroform, 1,2-dichloroetane, and chlorobenzene; esters such as ethyl acetate and methyl acetate; ketones such as acetone, methyl ethyl ketone, and methyl isobutyl ketone; sulfoxides such as methyl sulfoxide; nitriles such as acetonitrile; and mixtures thereof.

Examples of the halogenating agent to be used in the reaction include fluorine, chlorine, bromine, iodine, 1-chloromethyl-4-fluoro-1, 4-diazoniabicyclo [2, 2, 2] octane-bistetra fluoroborate, N-chlorosuccinimide, N-bromosuccinimide, N-iodosuccinimide, and sulfuryl chloride.

In the reaction, the halogenating agent is usually used in the proportion within a range of 1 to 10 mols based on 1 mol of the compound (YAJ-1).

The reaction temperature of the reaction is usually within a range of −20 to 150° C. The reaction time of the reaction is usually within a range of 0.1 to 24 hours.

After completion of the reaction, the compound (YAJ-2) can be isolated by performing post-treatment operations such as extraction of the reaction mixture with an organic solvent, and drying and concentration of the organic layer. The isolated compound (YAJ-2) may also be purified by operations such as chromatography and recrystallization.

(Reference Production Process L)

Among compounds represented by formula (YA1), a compound represented by formula (YAK-1) in which $Z^2$ is a C1-C3 alkoxy group and $Z^3$ is a hydrogen atom or a C1-C3 alkyl group (hereinafter referred to as the compound (YAK-1)) can be produced by reacting the compound (YAE-2) with an alkylating agent in the presence of a base:

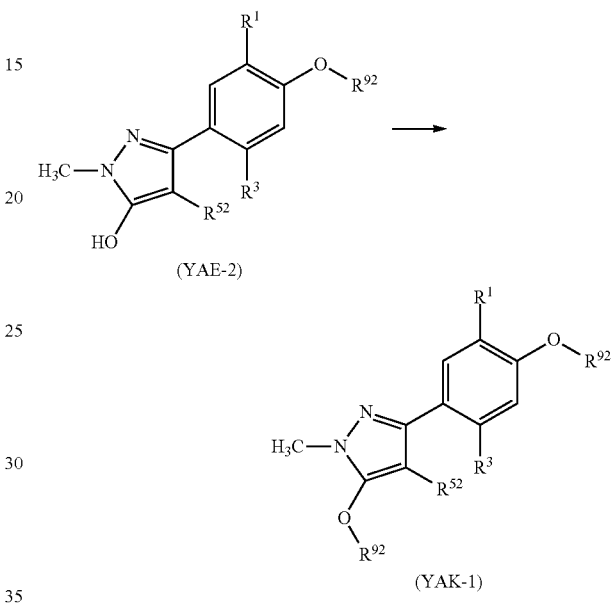

wherein symbols are the same as defined above.

The reaction is usually performed in a solvent.

Examples of the solvent to be used in the reaction include hydrocarbons such as n-hexane, cyclohexane, n-pentane, toluene, and xylene; ethers such as tetrahydrofuran, 1, 4-dioxane, ethylene glycol dimethyl ether, methyl tert-butyl ether, and diisopropyl ether; halogenated hydrocarbons such as chloroform, 1,2-dichloroetane, and chlorobenzene; sulfoxides such as methyl sulfoxide; nitriles such as acetonitrile; and mixtures thereof.

Commercially available products can be usually used as the alkylating agent to be used in the reaction, and examples thereof include methyl bromide, ethyl bromide, propyl bromide, methyl iodide, ethyl iodide, propyl iodide, isopropyl iodide, dimethyl sulfate, methyl p-toluenesulfonate, ethyl p-toluenesulfonate, propyl p-toluenesulfonate, methyl methanesulfonate, ethyl methanesulfonate, propyl methanesulfonate, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as sodium carbonate and potassium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal hydrides such as lithium hydride, sodium hydride, and potassium hydride; and alkali metal alkoxides such as sodium tert-butoxide, and potassium tert-butoxide.

In the reaction, the alkylating agent is usually in the proportion within a range of 1 to 10 mols, and the base is usually used in the proportion within a range of 1 to 10 mols, based on 1 mol of the compound (YE-2).

The reaction temperature of the reaction is usually within a range of −20 to 150° C. The reaction time of the reaction is usually within a range of 0.1 to 24 hours.

After completion of the reaction, the compound (YAK-1) can be isolated by performing post-treatment operations such as extraction of the reaction mixture with an organic solvent, and drying and concentration of the organic layer. The isolated compound (YAK-1) can also be purified by chromatography, recrystallization, and the like.

(Reference Production Process M)

A compound represented by formula (YAL-1) (hereinafter referred to as the compound (YAL-1)) can be produced by reacting the compound (YAE-2) with a halogenating agent:

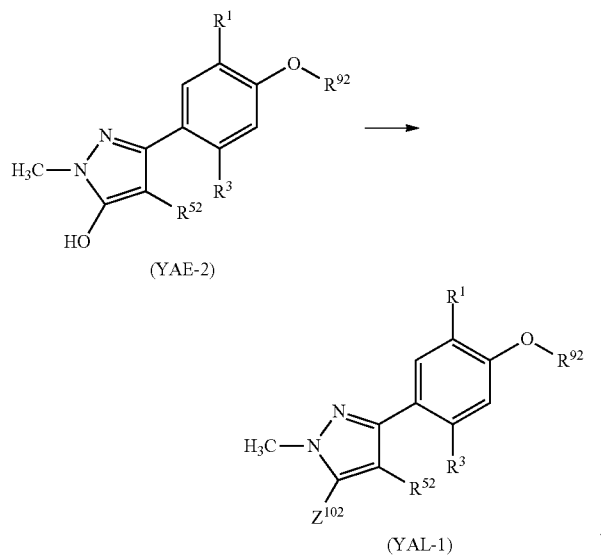

wherein $R^1$, $R^3$, $R^{52}$, and $R^{92}$ are the same as defined above, and $Z^{102}$ represents a chlorine atom or a bromine atom.

The reaction is usually performed in a solvent.

Examples of the solvent to be used in the reaction include hydrocarbons such as n-hexane, cyclohexane, n-pentane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; esters such as ethyl acetate and methyl acetate; ketones such as acetone, methyl ethyl ketone, and methyl isobutyl ketone; sulfoxides such as methyl sulfoxide; nitriles such as acetonitrile; and mixtures thereof.

Examples of the halogenating agent to be used in the reaction include phosphorus oxychloride, phosphorus oxybromide, and the like.

In the reaction, the halogenating agent is used in the proportion within a range of 1 to 10 mols based on 1 mol of the compound (YAE-2).

The reaction temperature of the reaction is usually within a range of −20 to 150° C. The reaction time of the reaction is usually within a range of 0.1 to 24 hours.

After completion of the reaction, the compound (YAL-1) can be isolated by usually performing post-treatment operations such as addition of water, extraction of the reaction mixture with an organic solvent, and drying and concentration of the organic layer. The isolated compound (YAL-1) can also be purified by chromatography, recrystallization, and the like.

(Reference Production Process N)

The compound (E-1) can be produced by reacting a compound represented by formula (YAM-1) (hereinafter referred to as the compound (YAM-1)) with the compound (B) in the presence of a base.

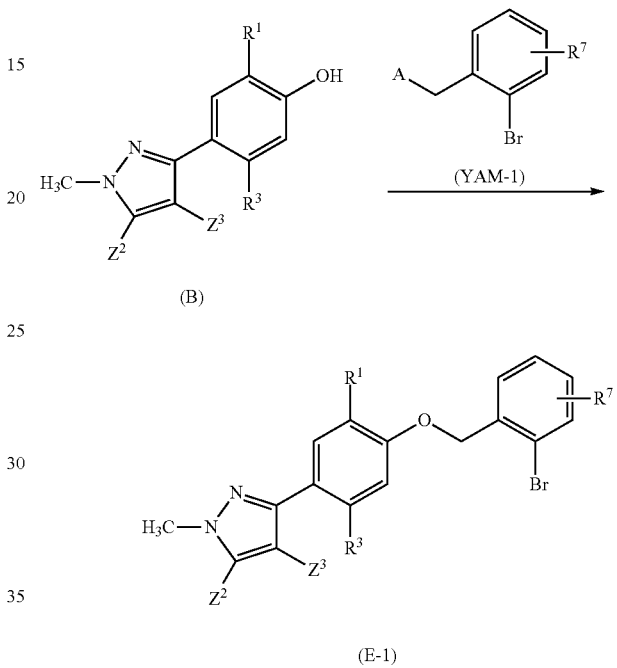

The reaction can be carried out in accordance with Production Process A.

(Reference Production Process O)

The compound (YAM-1) can be produced by reacting a compound represented by formula (YAN-1) (hereinafter referred to as the compound (YAN-1)) with a halogenating agent.

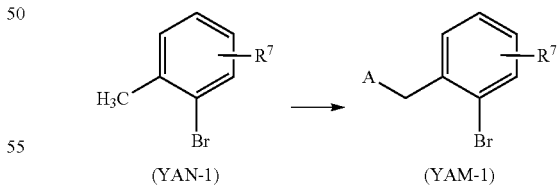

The reaction can be carried out in accordance with Reference Production Process A.

(Reference Production Process P)

A compound represented by formula (YAO-2) (hereinafter referred to as the compound (YAO-2)) can be produced by reacting a compound represented by formula (YAO-1) (hereinafter referred to as the compound (YAO-1)) with a methylating agent:

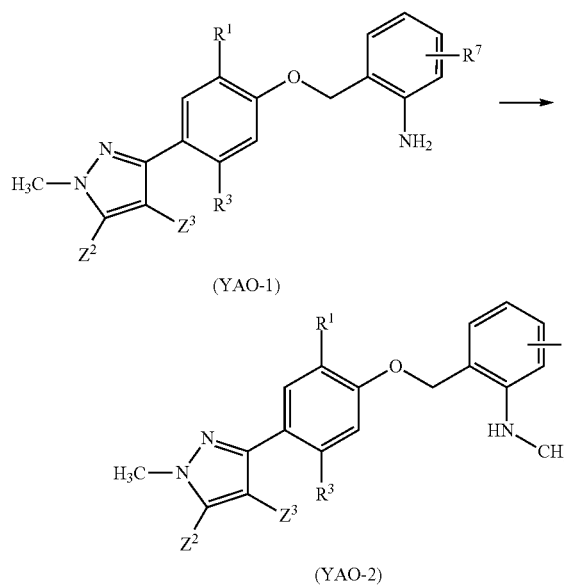

(YAO-1)

(YAO-2)

wherein symbols are the same as defined above.

The reaction is usually performed in a solvent.

Examples of the solvent to be used in the reaction include hydrocarbons such as n-hexane, cyclohexane, n-pentane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; sulfoxides such as methyl sulfoxide; nitriles such as acetonitrile; and mixtures thereof.

Commercially available products can be usually used as the methylating agent to be used in the reaction, and examples thereof include methyl bromide, methyl iodide, dimethyl sulfate, methyl p-toluenesulfonate, methyl methanesulfonate, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as sodium carbonate and potassium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal hydrides such as lithium hydride, sodium hydride, and potassium hydride; and alkali metal alkoxides such as sodium tert-butoxide and potassium tert-butoxide.

In the reaction, the methylating agent is usually used in the proportion within a range of 1 to 10 mols, and the base is usually used in the proportion within a range of 1 to 10 mols, based on 1 mol of the compound (YAO-1).

The reaction temperature of the reaction is usually within a range of –20 to 150° C. The reaction time of the reaction is usually within a range of 0.1 to 24 hours.

After completion of the reaction, the compound (YAO-2) can be isolated by performing post-treatment operations such as extraction of the reaction mixture with an organic solvent, and drying and concentration of the organic layer. The isolated compound (YAO-2) can also be purified by chromatography, recrystallization, and the like.

(Reference Production Process Q)

A compound represented by formula (YAP-2) (hereinafter referred to as the compound (YAP-2)) can be produced by reacting a compound represented by formula (YAP-1) (hereinafter referred to as the compound (YAP-1)) with hydrogen in the presence of a catalyst:

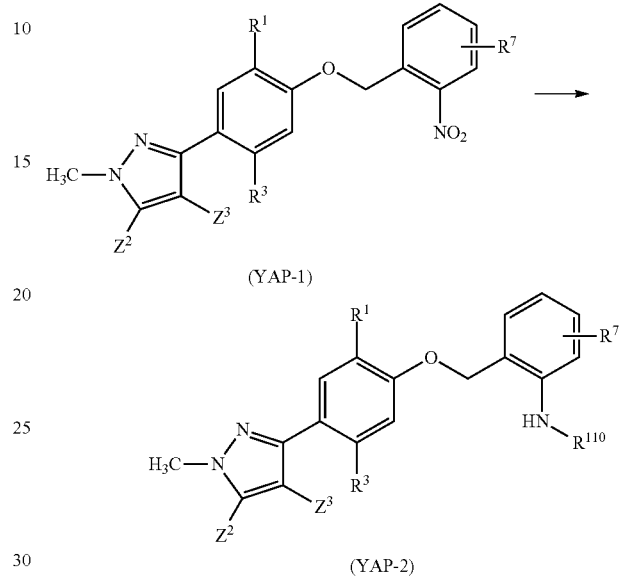

(YAP-1)

(YAP-2)

wherein $R^1$, $R^3$, $R^6$, $Z^2$ and $Z^3$ are the same as defined above, and $R^{110}$ represents a hydrogen atom or a hydroxyl group.

The reaction is usually performed in a solvent.

Examples of the solvent to be used in the reaction include alcohols such as methanol, ethanol, propanol, and butanol; esters such as ethyl acetate and butyl acetate; halogenated hydrocarbons such as carbon tetrachloride, chloroform, dichloromethane, 1,2-dichloroetane, tetrachloroethane, and chlorobenzene; ethers such as diethyl ether, tetrahydrofuran, 1,4-dioxane, ethylene glycol dimethyl ether, anisole, methyl tert-butyl ether, and diisopropyl ether; hydrocarbons such as n-heptane, n-hexane, cyclohexane, n-pentane, toluene, and xylene; water and mixtures thereof.

Examples of the catalyst to be used in the reaction include palladium-supported carbon (Pd/C), platinum-supported carbon (Pt/C), osmium-supported carbon (Os/C), ruthenium-supported carbon (Ru/C), rhodium-supported carbon (Rh/C), and Raney nickel.

The reaction temperature of the reaction is usually within a range of –20 to 150° C. The reaction time of the reaction is usually within a range of 0.1 to 24 hours.

After completion of the reaction, the compound (YAP-2) can be isolated by performing post-treatment operations such as filtration of the catalyst, followed by concentration of the filtrate. The isolated compound (YAP-2) can also be purified by chromatography, recrystallization, and the like.

(Reference Production Process R)

The compound (YAP-1) can be produced by reacting a compound represented by formula (YAQ-1) (hereinafter referred to as the compound (YAQ-1)) with the compound (B) in the presence of a base.

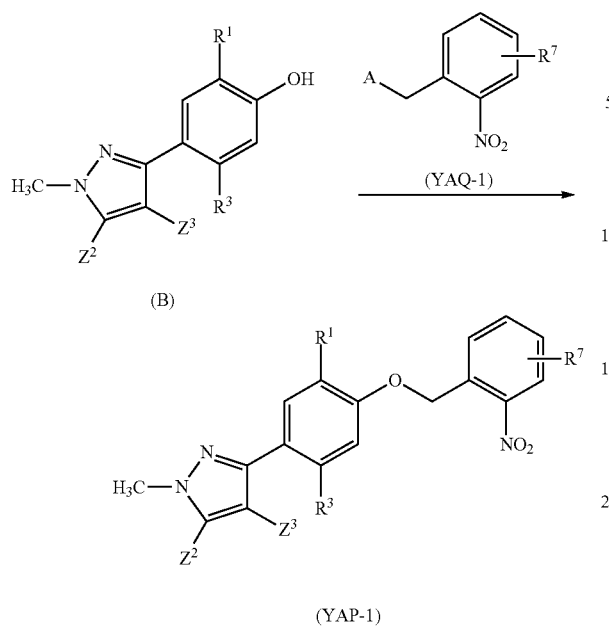

(B)

(YAP-1)

The reaction can be carried out in accordance with Production Process A.

(Reference Production Process S)

The compound (YAQ-1) can be produced by reacting a compound represented by formula (YAR-1) (hereinafter referred to as the compound (YAQ-1)) with a halogenating agent.

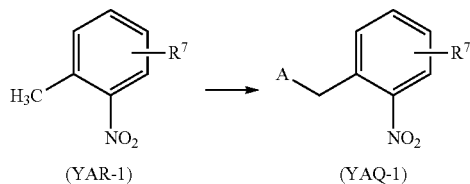

The reaction can be carried out in accordance with Reference Production Process A.

(Reference Production Process T)

A compound represented by formula (YAS-2) (hereinafter referred to as the compound (YAS-2)) can be produced by reacting a compound represented by formula (YAS-1) (hereinafter referred to as the compound (YAS-1)) with potassium fluoride:

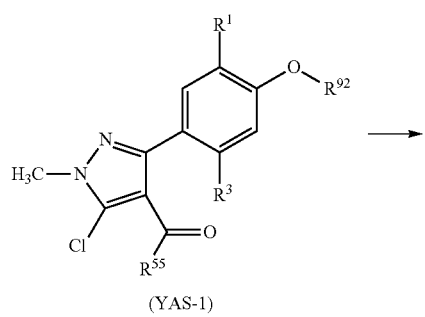

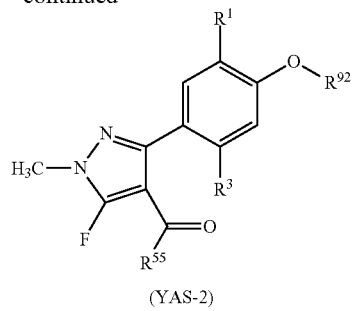

(YAS-2)

wherein $R^{55}$ represents a hydrogen atom, a halogen atom, or a hydroxy group, and other symbols are the same as defined above.

The reaction is usually performed in a solvent.

Examples of the solvent to be used in the reaction include hydrocarbons such as n-hexane, cyclohexane, n-pentane, toluene, and xylene; sulfoxides such as sulfolane and methyl sulfoxide; and mixtures thereof.

In the reaction, potassium fluoride is usually used in the proportion within a range of 1 to 10 mols based on 1 mol of the compound (YAS-1).

The reaction temperature of the reaction is usually within a range of 0° C. to 300° C. The reaction time of the reaction is usually within a range of 0.1 to 24 hours.

After completion of the reaction, the compound (YAS-2) can be obtained by usually performing post-treatment operations such as addition of 1 mol or more of water, extraction of the reaction mixture with an organic solvent, and drying and concentration of the organic layer. The isolated compound (YAS-2) can also be purified by chromatography, recrystallization, and the like.

Regarding a form of the present control agent, the present compound is usually used after mixing with solid carriers, liquid carriers, surfactants, and the like, and optionally adding auxiliary agents for formulation, such as stickers, dispersers, and stabilizers to formulate into wettable powders, water dispersible granules, flowables, granules, dry flowables, emulsifiable concentrates, aqueous solutions, oil solutions, smoking agents, aerosols, microcapsules, and the like. In these formulations, the present compound is usually contained within a range of 0.1 to 99%, and preferably 0.2 to 90% by weight.

Examples of the solid carriers include clays (for example, kaolin, diatomaceous earth, synthetic hydrated silicon dioxide, Fubasami clay, bentonite, and acid clay), talcs or other inorganic minerals (for example, sericite, quartz powder, sulfur powder, activated charcoal, calcium carbonate, and hydrated silica) in the form of fine powders or particulates, and examples of the liquid carries include water, alcohols (for example, methanol and ethanol), ketones (for example, acetone and methyl ethyl ketone), aromatic hydrocarbons (for example, benzene, toluene, xylene, ethylbenzene, and methyl naphthalene), aliphatic hydrocarbons (for example, n-hexane, cyclohexanone, and kerosene), esters (for example, ethyl acetate and butyl acetate), nitriles (for example, acetonitrile and isobutyronitrile), ethers (for example, dioxane and diisopropylether), acid amides (for example, DMF and dimethylacetamide), and halogenated hydrocarbons (for example, dichloroethane, trichloroethylene, and carbon tetrachloride).

Examples of the surfactants include alkyl sulfates, alkyl sulfonates, alkyl aryl sulfonates, alkyl aryl ethers, and polyoxyethylenated compounds thereof, polyoxyethylene glycol ethers, polyhydric alcohol esters, and sugar alcohol derivatives.

Examples of other auxiliary agents for formulation include stickers and dispersers, specifically casein, gelatin, polysaccharides (for example, starch, gum arabic, cellulose derivatives, and alginic acid), lignin derivatives, bentonite, sugars, water-soluble synthetic polymers (for example, polyvinyl alcohol, polyvinylpyrrolidone, and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids or esters thereof, and the like.

The method for applying the present compound is not particularly limited, as long as the applying form is a form by which the present compound may be applied substantially, and includes, for example, an application to plants such as a foliage application; an application to area for cultivating plants such as a submerged treatment; and an application to seeds such as seed disinfection.

The present compound may be used as a mixture with various oils, such as mineral oils or vegetable oils, or surfactants. Specific examples of oils or surfactants, which can be used as a mixture with various oils or surfactants, include Nimbus (registered trademark), Assist (registered trademark), Aureo (registered trademark), Iharol (registered trademark), Silwet L-77 (registered trademark), BreakThru (registered trademark), Sundancell (registered trademark), Induce (registered trademark), Penetrator (registered trademark), AgriDex (registered trademark), Lutensol A8 (registered trademark), NP-7 (registered trademark), Triton (registered trademark), Nufilm (registered trademark), Emulgator NP7 (registered trademark), Emulad (registered trademark), TRITON X 45 (registered trademark), AGRAL 90 (registered trademark), AGROTIN (registered trademark), ARPON (registered trademark), EnSpray N (registered trademark), BANOLE (registered trademark), and the like.

The present compound can also be used as a mixture with or together with known fungicides, insecticides, acaricides, nematicides, and plant growth regulators.

The application dose of the present compound varies depending on weather conditions, dosage forms, timing of application, methods of application, areas to be applied, target diseases, target plants, and the like, and the amount of the present compound is usually within a range of 1 to 500 g, and preferably 2 to 200 g, per 1,000 m$^2$ of the area to be applied. The emulsifiable concentrate, the wettable powder, or the suspension concentrate is usually applied by diluting with water. In this case, the concentration of the present compound after dilution is usually within a range of 0.0005 to 2% by weight, and preferably 0.005 to 1% by weight. The dust formulation or the granular formulation is usually applied, as itself without dilution. In the application to seeds, the amount of the present compound in the present control agent is usually within a range of 0.001 to 100 g, and preferably 0.01 to 50 g, per 1 kg of the seeds.

Also, in another embodiment, for example, the present compound or the present control agent can be administered to the inside (inside of the body) or the outside (body surface) of the below-mentioned vertebrate to thereby exterminate systemically or unsystemically the living things or parasites which are parasitic on the vertebrate. Examples of a method of the internal administration include oral administration, anal administration, transplantation, or administration via injection subcutaneously, intramuscularly, or intravenously. Examples of a method of the external administration include transdermal administration. Also, the present compound can be ingested to a livestock animal so as to exterminate sanitary insects which occur in the excrement of the animal.

When the present compound or the present control agent is applied to the animals such as the livestock animal and pets on which pests are parasitic, the dose varies depending on the administration method etc., and it is desirable in general to administer the present compound so that a dose of the present compound is within a range of 0.1 mg to 2,000 mg, and preferably 0.5 mg to 1,000 mg, per 1 kg of body weight of the animal.

The present compound or the present control agent can be used as an agent for controlling plant diseases in agricultural lands such as fields, paddy fields, lawns, and orchards. The present compound or the present control agent can control diseases occurred in the agricultural lands for cultivating the following plants.

Crops: corn, rice, wheat, barley, rye, triticale, oat, sorghum, cotton, soybean, peanut, French bean (kidney bean), lima bean, adzuki bean, cowpea, mung bean, black gram, scarlet runner bean, rice bean, moth bean, tepary bean, broad bean, pea, chickpea, lentil, lupine, gandule bean, buckwheat, beet, rapeseed, sunflower, sugar cane, tobacco, and the like; Vegetables: solanaceous vegetables (for example, eggplant, tomato, pimento, pepper, bell pepper, and potato), cucurbitaceous vegetables (for example, cucumber, pumpkin, zucchini, water melon, and melon), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, green onion, onion, garlic, and asparagus), umbelliferous vegetables (for example, carrot, parsley, celery, and parsnip), chenopodiaceous vegetables (for example, spinach and Swiss chard), lamiaceous vegetables (for example, *Perilla frutescens*, mint, basil, and lavender), strawberry, sweet potato, *Dioscorea japonica, colocasia*, and the like; Flowers; Ornamental foliage plants;

Fruits: pomaceous fruits (for example, apple, pear, Japanese pear, Chinese quince, and quince), stone fruits (for example, peach, plum, nectarine, *Prunus* mume, cherry fruit, apricot, and prune), citrus fruits (for example, Citrus unshiu, orange, lemon, lime, and grapefruit), nuts (for example, chestnut, walnuts, hazelnuts, almond, pistachio, cashew nuts, and macadamia nuts), berry fruits (for example, blueberry, cranberry, blackberry, and raspberry), grape, kaki persimmon, olive, Japanese plum, banana, coffee, date palm, coconuts, and the like;

Trees other than fruit trees: tea, mulberry, flowering plant, roadside trees (for example, ash, birch, dogwood, *Eucalyptus, Ginkgo biloba*, lilac, maple, *Quercus*, poplar, Judas tree, *Liquidambar formosana*, plane tree, *zelkova*, Japanese arborvitae, fir wood, hemlock, juniper, *Pinus, Picea*, and *Taxus* cuspidate); and the like.

Lawn: lawn grasses (zoysiagrass, Korean lawn grass, etc.), Bermuda glasses (*cynodon dactylon*, etc.), bentgrasses (redtop grass, creeping bentgrass, colonial bentgrass, etc.), bluegrasses (Kentucky bluegrass, rough bluegrass, etc.), fescue grasses (tall fescue, chewings fescue, creeping red fescue, etc.), perennial ryegrasses, (Italian ryegrass, perennial flax, etc.), orchard grass, timothy, etc.

The above-mentioned plants include genetically modified crops.

The pests which can be controlled by the present compound or the present control agent include plant pathogens such as filamentous fungus, as well as harmful arthropods such as harmful insects and harmful mites, and nathelminth such as nematodes, and specifically include the following examples, but are not limited thereto.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*); Wheat diseases: powdery mildew (*Erysiphe graminis*), fusarium blight (*Fusarium graminearum, F. avenaceum, F. culmorum, Microdochium nivale*), rust (*Puccinia striiformis, P. graminis, P. recondita*), snow mould (*Micronectriella nivale, M. majus*), typhula snow blight (*Typhula* sp.), loose smut (*Ustilago tritici*), stinking smut (*Tilletia caries, T. controversa*), eyespot (*Pseudocercosporella herpotrichoides*), leaf blotch (*Septoria tritici*), glume blotch (*Stagonospora nodorum*), tan spot (*Pyrenophora tritici-repentis*), damping-off by *Rhizoctonia* (*Rhizoctonia solani*), and take all disease (*Gaeumannomyces graminis*); Barley diseases: powdery mildew (*Erysiphe graminis*), fusarium blight (*Fusarium gaminearum, F. avenaceum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramularia leaf spot (Ramularia collo-*cygni*), and damping-off by *Rhizoctonia* (*Rhizoctonia solani*); Corn diseases: rust (*Puccinia sorghi*), southern rust (*Puccinia polysora*), northern leaf blight (*Setosphaeria turcica*), tropical rust (*Physopella zeae*), southern leaf blight (*Cochliobolus heterostrophus*), anthracnose (*Colletotrichum graminicola*), gray leaf spot (*Cercospora zeae-maydis*), eyespot (*Kabatiella zeae*), and *phaeosphaeria* leaf spot (*Phaeosphaeria maydis*);

Cotton diseases: anthracnose (*Colletotrichum gossypii*), grey mildew (Ramularia areola), *alternaria* leaf spot (*Alternaria macrospora, A. gossypii*), and Black root rot by *Thielaviopsis*. (*Thielaviopsis basicola*); Coffee diseases: rust (*Hemileia vastatrix*) and *Cercospora* leaf spot (*Cercospora coffeicola*); Rape seed diseases: *sclerotinia* rot (*Sclerotinia sclerotiorum*), black spot (*Alternaria brassicae*), and black leg (*Phoma lingam*); Sugarcane diseases: sugarcane rust (*Puccinia melanocephaela, Puccinia kuehnii*), sugarcane smut (*Ustilago scitaminea*); Sunflower diseases: sunflower rust (*Puccinia helianthi*), downy mildew (*Plasmopara halstedii*); Citrus diseases: melanose (*Diaporthe citri*), scab (*Elsinoe fawcetti*), fruit rot (*Penicillium digitatum, P. italicum*), and *Phytophthora* rot (*Phytophthora parasitica, Phytophthora citrophthora*); Apple diseases: blossom blight (*Monilinia mali*), canker (*Valsa ceratosperma*), powdery mildew (*Podosphaera leucotricha*), *alternaria* leaf spot (*Alternaria alternata* apple pathotype), scab (*Venturia inaequalis*), bitter rot (*Glomerella cingulata*), brown spot (*Diplocarpon mali*), ring spot (*Botryosphaeria berengeriana*), and crown rot (*Phytophtora cactorum*); Pear diseases: scab (*Venturia nashicola, V. pirina*), black spot (*Alternaria alternata* Japanese pear pathotype), and rust (*Gymnosporangium haraeanum*); Peach diseases: brown rot (*Monilinia fructicola*), scab (*Cladosporium carpophilum*), and *Phomopsis* rot (*Phomopsis* sp.); Grapes diseases: anthracnose (*Elsinoe ampelina*), ripe rot (*Glomerella cingulata*), powdery mildew (Uncinula necator), rust (*Phakopsora ampelopsidis*), black rot (*Guignardia bidwellii*), and downy mildew (*Plasmopara viticola*); Japanese persimmon diseases: anthracnose (Gloeosporium kaki) and leaf spot (*Cercospora kaki, Mycosphaerella nawae*); Diseases of gourd family: anthracnose (*Colletotrichum lagenarium*), powdery mildew (*Sphaerotheca fuliginea*), gummy stem blight (*Didymella bryoniae*), target spot (*Corynespora cassiicola*), fusarium wilt (*Fusarium oxysporum*), downy mildew (*Pseudoperonospora cubensis*), phytophthora rot (*Phytophthora* sp.), and damping-off (*Pythium* sp.); Tomato diseases: early blight (*Alternaria solani*), leaf mold (*Cladosporium fulvum*), leaf mold (*Pseudocercospora fuligena*), late blight (*Phytophthora infestans*), and powdery mildew (*Leveillula taurica*); Eggplant diseases: brown spot (*Phomopsis vexans*) and powdery mildew (*Erysiphe cichoracearum*);

Cruciferous vegetables diseases: *alternaria* leaf spot (*Alternaria japonica*), white spot (*Cercosporella brassicae*), clubroot (*Plasmodiophora brassicae*), and downy mildew (*Peronospora parasitica*); Welsh onion diseases: rust (*Puccinia allii*); Soybean diseases: purple stain (*Cercospora kikuchii*), *sphaceloma* scad (*Elsinoe* glycines), pod and stem blight (*Diaporthe phaseolorum* var. *sojae*), rust (*Phakopsora pachyrhizi*), target spot (*Corynespora cassiicola*), anthracnose (*Colletotrichum* glycines, *C. truncatum*), Rhizoctonia aerial blight (*Rhizoctonia solani*), septoria brown spot (*Septoria glycines*), and frog eye leaf spot (*Cercospora sojina*), *Sclerotinia* rot (*Sclerotinia sclerotiorum*), powdery mildew (*Microsphaera diffusa*), brown stem rot (*Phytophthora sojae*), and downy mildew (*Peronospora manshurica*); Kidney bean diseases: *sclerotinia* rot (*Sclerotinia sclerotiorum*), sclerotinia rot (*Sclerotinia sclerotiorum*), rust (*Uromyces appendiculatus*), Angular leaf spot (*Phaeoisariopsis griseola*), and anthracnose (*Colletotrichum lindemuthianum*); Peanut diseases: early leaf spot (*Cercospora personata*), late leaf spot (*Cercospora arachidicola*), and southern blight (*Sclerotium rolfsii*); Garden pea diseases: powdery mildew (*Erysiphe pisi*); Potato diseases: early blight (*Alternaria solani*), late blight (*Phytophthora infestans*), pink rot (*Phytophthora erythroseptica*), powdery scab (*Spongospora subterranea* f. sp. *subterranea*), and *verticillium* wilt (*Verticillium albo-atrum, V. dahliae, V. nigrescens*); Strawberry diseases: powdery mildew (*Sphaerotheca humuli*); Tea diseases: net blister blight (*Exobasidium reticulatum*), white scab (*Elsinoe leucospila*), gray blight (*Pestalotiopsis* sp.), and anthracnose (*Colletotrichum* theae-*sinensis*); Tobacco diseases: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*); Sugar beet diseases: *cercospora* leaf spot (*Cercospora beticola*), leaf blight (*Thanatephorus cucumeris*), root rot (*Thanatephorus cucumeris*), and *aphanomyces* root rot (*Aphanomyces cochlioides*); Rose diseases: black spot (*Diplocarpon rosae*) and powdery mildew (*Sphaerotheca pannosa*); Chrysanthemum diseases: leaf blight (*Septoria chrysanthemi*-indici) and white rust (*Puccinia horiana*); Onion diseases: *botrytis* leaf blight (*Botrytis cinerea, B. byssoidea, B. squamosa*), graymold neck rot (*Botrytis alli*), and small sclerotial rot (*Botrytis squamosa*); various crops diseases: gray mold (*Botrytis cinerea*) and *sclerotinia* rot (*Sclerotinia sclerotiorum*); Japanese radish diseases: *alternaria* leaf spot (*Alternaria brassicicola*); Turfgrass diseases: dollar spot (*Sclerotinia homoeocarpa*) and brown patch and large patch (*Rhizoctonia solani*); and Banana diseases: Sigatoka disease (*Mycosphaerella fijiensis, Mycosphaerella musicola*).

Seed diseases or diseases in the initial stage of growth of various crops caused by *Aspergillus* spp., *Penicillium* spp., *Fusarium* spp., *Gibberella* spp., *Tricoderma* spp., *Thielaviopsis* spp., *Rhizopus* spp., *Mucor* spp., *Corticium* spp., *Rhoma* spp., *Rhizoctonia* spp., *Diplodia* spp., and the like; Virus diseases of various crops mediated by *Polymixa* spp., *Olpidium* spp., or the like.

Rice diseases: rice seedling blight (*Burkholderia plantarii*); Cucumber diseases: cucumber leaf spot (*Pseudomonas syringae* pv. *Lachrymans*); Eggplant diseases: eggplant wilting (*Ralstonia solanacearum*); Asiatic citrus diseases: citrus canker (*Xanthomonas citiri*); and Chinese cabbage diseases: soft rot (*Erwinia carotovora*).

Hemiptera: planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*) and green rice leafhopper (*Nephotettix virescens*); aphids (Aphididae) such as cotton aphid (*Aphis gossypii*), green peach aphid (*Myzus persicae*), cabbage aphid (*Brevicoryne brassicae*), potato aphid (*Macrosiphum euphorbiae*), foxglove aphid (*Aulacorthum solani*), oat bird-cherry aphid (*Rhopalosiphum padi*), and tropical citrus aphid (*Toxoptera citricidus*); stink bugs (Pentatomidae) such as green stink bug (*Nezara antennata*), bean bug (Riptortus clavetus), rice bug (*Leptocorisa chinensis*), white spotted spined bug (*Eysarcoris parvus*), stink bug (*Halyomorpha mista*), and tarnished plant bug (*Lygus lineolaris*); whiteflies (Aleyrodidae) such as greenhouse whitefly (*Trialeurodes vaporariorum*) and silverleaf whitefly (*Bemisia argentifolii*); scales (Coccidae) such as California red scale (Aonidiellaaurantii), San Jose scale (*Comstockaspis perniciosa*), citrus north scale (*Unaspis citri*), red wax scale (*Ceroplastes rubens*), and cottony cushion scale (*Icerya purchasi*); lace bugs (Tingidae); jumping plant lices (Homoptera, Psylloidea).

Lepidoptera: pyralid moths (Pyralidae) such as rice stem borer (*Chilo suppressalis*), yellow rice borer (Tryporyza incertulas), rice leafroller (*Cnaphalocrocis medinalis*), cotton leafroller (Notarcha derogata), Indian meal moth (Plodia interpunctella), oriental corn borer (*Ostrinia furnacalis*), cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (Plusia nigrisigna), *Thoricoplusia* spp., *Heliothis* spp., and *Helicoverpa* spp.; white butterflies (Pieridae) such as common white (*Pieris rapae*); tortricid moths (Tortricidae) such as *Adoxophyes* spp., oriental fruit moth (*Grapholita molesta*), soybean pod borer (Leguminivora glycinivorella), azuki bean podworm (Matsumuraeses azukivora), summer fruit *tortrix* (*Adoxophyes orana fasciata*), smaller tea *tortrix* (*Adoxophyes* sp.), oriental tea *tortrix* (Homona magnanima), apple *tortrix* (*Archips fuscocupreanus*), and codling moth (*Cydia pomonella*); leafblotch miners (Gracillariidae) such as tea leafroller (Caloptilia theivora), and apple leafminer (Phyllonorycter ringoneella); codling moths (Carposimidae) such as peach fruit moth (Carposina niponensis); lyonetiid moths (Lyonetiidae) such as *Lyonetia* spp.; tussock moths (Lymantriidae) such as *Lymantria* spp. and *Euproctis* spp.; yponomeutid moths (Yponomeutidae) such as diamondback (*Plutella xylostella*); gelechild moths (Gelechiidae) such as pink bollworm (*Pectinophora gossypiella*) and potato tubeworm (*Phthorimaea operculella*); tiger moths and allies (Arctiidae) such as fall webworm (*Hyphantria cunea*); and tineid moths (Tineidae) such as casemaking clothes moth (*Tinea translucens*), and webbing clothes moth (*Tineola bisselliella*).

Thysanoptera: yellow citrus *thrips* (*Frankliniella occidentalis*), melon *thrips* (*Thrips palmi*), yellow tea *thrips* (*Scirtothrips dorsalis*), onion *thrips* (*Thrips tabaci*), flower *thrips* (*Frankliniella intonsa*), and tobacco *thrips* (*Frankliniella fusca*).

Diptera: houseflies (*Musca domestica*), common mosquito (*Culex pipiens pallens*), horsefly (*Tabanus trigonus*), onion maggot (*Hylemya antiqua*), seedcorn maggot (*Hylemya platura*), *Anopheles sinensis*, rice leafminer (*Agromyza oryzae*), rice leafminer (Hydrellia griseola), rice stem maggot (*Chlorops oryzae*), melon fly (Dacus cucurbitae), Mediterranean fruit fly (*Ceratitis capitata*), and legume leafminer (*Liriomyza trifolii*).

Coleoptera: twenty-eight-spotted ladybirds (*Epilachna vigintioctopunctata*), cucurbit leaf beetle (*Aulacophora femoralis*), yellow striped flea beetle (*Phyllotreta striolata*), rice leaf beetle (*Oulema oryzae*), rice curculio (Echinocnemus squameus), riced water weevil (*Lissorhoptrus oryzophilus*), boll weevil (*Anthonomus grandis*), azuki bean weevil (*Callosobruchus chinensis*), hunting billbug (Sphenophorus venatus), Japanese beetle (*Popillia japonica*), cupreous chafer (*Anomala cuprea*), corn root worms (*Diabrotica* spp.), Colorado beetle (*Leptinotarsa decemlineata*), click beetles (*Agriotes* spp.), cigarette beetle (Lasioderma serricorne), varied carper beetle (*Anthrenus verbasci*), red flour beetle (Tribolium castaneum), powder post beetle (*Lyctus brunneus*), white-spotted longicorn beetle (*Anoplophora malasiaca*), and pine shoot beetle (Tomicus piniperda).

Orthoptera: asiatic locusts (*Locusta migratoria*), African mole cricket (*Gryllotalpa africana*), rice grasshopper (*Oxya yezoensis*), and rice grasshopper (*Oxya japonica*).

Hymenoptera: cabbage sawflies (*Athalia rosae*), leaf-cutting ant (*Acromyrmex* spp.), and fire ant (*Solenopsis* spp.).

Nematodes: white-tip nematode (*Aphelenchoides besseyi*), strawberry bud nematode (*Nothotylenchus acris*), soybean cyst nematode (*Heterodera glycines*), southern root-knot nematode (*Meloidogyne incognita*), cobb's root-lesion nematode (*Pratylenchus penetrans*), and false root-knot nematode (*Nacobbus aberrans*).

Blattariae: German cockroach (*Blattella germanica*), smoky-brown cockroach (*Periplaneta fuliginosa*), American cockroach (*Periplaneta americana*), brown cockroach (*Periplaneta brunnea*), and oriental cockroach (*Blatta orientalis*).

Acarina: Tetranychidae (for example, two-spotted spider mite (*Tetranychus urticae*), citrus red mite (*Panonychus citri*), and *Oligonychus* spp.); Eriophyidae (for example, pink citrus rust mite (Aculopspelekassi)); Tarsonemidae (for example, broad mite (*Polyphagotarsonemus latus*)); Tenuipalpidae; Tuckerellidae; Tuckerellidae Acaridae (for example, common grain mite (Tyrophagus putrescentiae)); Pyroglyphidae (for example, American house dust mite (*Dermatophagoides farinae*) and house dust mite (*Dermatophagoides* pteroenyssinus)); Cheyletidae (for example, cheyletid mite (*Cheyletus eruditus*), *Cheyletus malaccensis*, and *Cheyletus moorei*; and Dermanyssidae.

The present control agent comprising the present compound can be used in the field relating to a treatment of livestock diseases or livestock industry, and can exterminate the living things or parasites which are parasitic on the inside and/or the outside of vertebrates such as human being, cow, sheep, pig, poultry, dog, cat, and fish, so as to maintain public health. Examples of the pests include ticks (*Ixodes* spp.) (for example, *Ixodes scapularis*), *Boophilus* spp. (for example, cattle tick (*Boophilus microplus*)), *Amblyomma* spp., *Hyalomma* spp., *Rhipicephalus* spp. (for example, kennel tick (*Rhipicephalus sanguineus*)), *Haemaphysalis* spp. (for example, *Haemaphysalis longicornis*), *Ddermacentor* spp., *Ornithodoros* spp. (for example, *Ornithodoros moubata*), red mite (*Dermanyssus gallinae*), ghost ant (*Ornithonyssus sylviarum*), *Sarcoptes* spp. (for example, *Sarcoptes scabiei*), *Psoroptes* spp., *Chorioptes* spp., *Demodex* spp., *Eutrombicula* spp., *Ades* spp. (for example, Asian tiger mosquito (*Aedes albopictus*)), *Anopheles* spp., *Culex* spp., *Culicoides* spp., *Musca* spp., *Hypoderma* spp., *Gasterophilus* spp., *Haematobia* spp., *Tabanus* spp., *Simulium* spp., *Triatoma* spp., lice (Phthiraptera) (for example, *Damalinia* spp.), *Linognathus* spp., *Haematopinus* spp., *Ctenocephalides* spp. (for example, cat flea (*Ctenocephalides felis*)) *Xenopsylla* spp., Pharaoh's ant (Monomoriumpharaonis) and nematodes [for example, hairworm (for example, *Nippostrongylus brasiliensis, Trichostrongylus axei, Trichostrongylus colubriformis*), *Trichinella* spp. (for example, *Trichinella spiralis*), barber pole worm (*Haemonchus contortus*), *Nematodirus* spp. (for example, *Nematodirus battus*), *Ostertagia circumcincta, Cooperia* spp., *Hymenolepis nana*, and the like.

The present control agent containing at least one selected from the group consisting of the above-mentioned known fungicides, insecticide, acaricides, nematicides, and plant growth regulators may be directly applied to a plant body to be protected from pests, or may be applied to soil for fix planting of the plant body, and seeds.

At least one selected from the group consisting of the above-mentioned known fungicides, insecticide, acaricides, nematicides, and plant growth regulators may be applied to the plant body, simultaneously or separately, when using together with the present control agent. When applying separately, an application date may be different and a different dosage form may be used.

It is possible to combine an application of the present control agent to seeds of the plant with an application of at least one selected from the group consisting of the above-mentioned known fungicides, insecticide, acaricides, nematicides, and plant growth regulators to the plant, or soil for fix planting of the plant. It is also possible to combine an application of at least one selected from the group consisting of the above-mentioned known fungicides, insecticide, acaricides, nematicides, and plant growth regulators to seeds of the plant with an application of the present control agent to the plant, or soil for fix planting of the plant. An application to the plant, or soil for fix planting of the plant may be performed before, on, or after fix planting.

This application method is preferably applied to cultivation of corn, wheat, and rice.

It is possible to combine an application of the present control agent to a plant body, or soil on which the plant body is cultivated or to be cultivated (for example, soil of paddy fields, crop fields, orchards, or non-cultivated lands) with an application of at least one selected from known herbicides to the soil. The pest control agent of the present invention and herbicides can be applied simultaneously or separately. When applying separately, the application may be performed on the same or different day.

Examples of the herbicide, which can be used together with the present control agent, include glyphosate, salts of glyphosate, glufosinate, salts of glyphosate, 2,4-D, salts of 2,4-D, dicamba, salts of dicamba, and flumioxazin.

EXAMPLES

The present invention will be described in more detail below by way of Production Examples, Formulation Examples, and Test Examples, but the present invention is not limited to these Examples.

First, Production Examples of the present compound will be described.

Production Example 1

A mixture of 0.50 g of the intermediate (1A) mentioned in Reference Production Example 1, 0.48 g of the intermediate (17A) mentioned in Reference Production Example 17, 0.57 g of potassium carbonate, and 10 ml of acetonitrile was stirred with heating under reflux for 4 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.09 g of a compound represented by formula shown below (hereinafter referred to as the present compound 1).

Present Compound 1

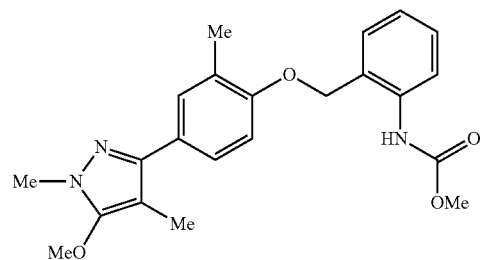 [SMILES: COC(=O)Nc1ccccc1COc1ccc(-c2nn(C)c(OC)c2C)cc1C]

$^1$H-NMR (CDCl$_3$) δ: 8.01 (1H, s), 7.74 (1H, s), 7.47 (1H, s), 7.41-7.36 (2H, m), 7.30 (1H, d, J=7.6 Hz), 7.12-7.05 (1H, m), 6.98 (1H, d, J=8.5 Hz), 5.11 (2H, s), 3.94 (3H, s), 3.76 (3H, s), 3.71 (3H, s), 2.29 (3H, s), 2.14 (3H, s).

In accordance with the reaction mentioned in Production Example 1, the present compounds 2 to 3 were synthesized.

Structure formulas and $^1$H-NMR data thereof are shown below.

Present Compound 2 Present Compound 3

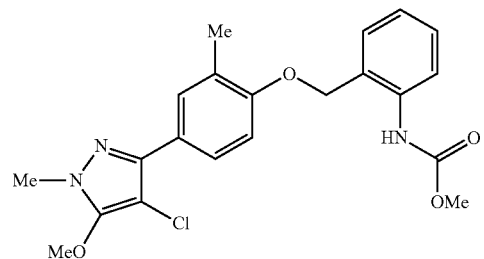

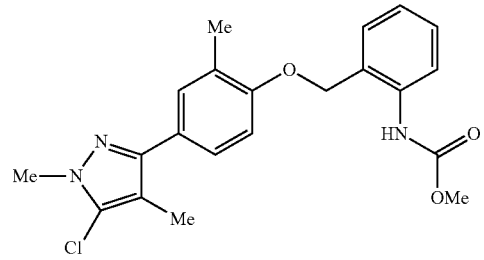

Present Compound 2

¹H-NMR (CDCl₃) δ: 8.00 (1H, s), 7.71 (1H, s), 7.68-7.59 (2H, m), 7.41-7.36 (1H, m), 7.31 (1H, dd, J=7.5, 1.4 Hz), 7.12-7.06 (1H, m), 7.00 (1H, d, J=8.2 Hz), 5.11 (2H, s), 4.11 (3H, s), 3.76 (3H, s), 3.71 (3H, s), 2.29 (3H, s).

Present Compound 3

¹H-NMR (CDCl₃) δ: 8.00 (1H, s), 7.72 (1H, s), 7.48-7.46 (1H, m), 7.43-7.36 (2H, m), 7.31 (1H, dd, J=7.7, 1.5 Hz), 7.12-7.07 (1H, m), 6.99 (1H, d, J=8.5 Hz), 5.12 (2H, s), 3.86 (3H, s), 3.76 (3H, s), 2.29 (3H, s), 2.15 (3H, s).

Production Example 2

A mixture of 1.42 g of the intermediate (10A) mentioned in Reference Production Example 10, 0.38 g of methyl chlorocarbonate, 1.0 ml of triethylamine, and 15 ml of DMF was stirred at room temperature for 8 hours. Water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.58 g of a compound represented by formula shown below (hereinafter referred to as the present compound 4).

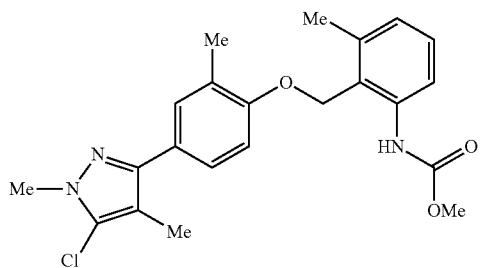 [SMILES: COC(=O)Nc1cccc(C)c1COc1ccc(-c2nn(C)c(Cl)c2C)cc1C]

¹H-NMR (CDCl₃) δ: 7.79 (1H, br s), 7.59-7.52 (1H, m), 7.49-7.46 (1H, m), 7.46-7.42 (1H, m), 7.30-7.25 (1H, m), 7.03 (1H, d, J=8.5 Hz), 6.98 (1H, d, J=7.6 Hz), 5.12 (2H, s), 3.86 (3H, s), 3.74 (3H, s), 2.41 (3H, s), 2.26 (3H, s), 2.16 (3H, s).

Compounds produced in accordance with the method mentioned in Production Example 2, and physical properties thereof are shown below.

Compounds represented by formula (a):

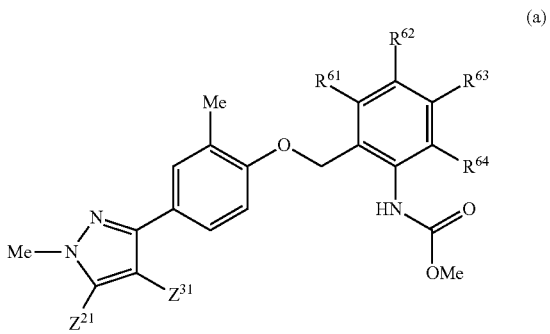

wherein $Z^{21}$, $Z^{31}$, $R^{61}$, $R^{62}$, $R^{63}$, and $R^{64}$ are shown in [Table 1] (as used herein, F represents fluoro, Cl represents chloro, Br represents bromo, Me represents methyl, Et represents ethyl, OMe represents methoxy, OEt represents ethoxy, CF2H represents difluoromethyl, CF3 represents trifluoromethyl, Cyclopropyl represents cyclopropyl, and Propen-2-yl represents propen-2-yl).

TABLE 1

| | $Z^{21}$ | $Z^{31}$ | $R^{61}$ | $R^{62}$ | $R^{63}$ | $R^{64}$ |
|---|---|---|---|---|---|---|
| Present Compound 11 | F | Me | Me | H | H | H |
| Present Compound 15 | Cl | Me | Br | H | H | H |
| Present Compound 16 | Cl | Me | F | H | H | H |
| Present Compound 17 | Cl | Me | Cl | H | H | H |
| Present Compound 18 | Cl | Me | OEt | H | H | H |
| Present Compound 19 | Cl | Me | Cyclopropyl | H | H | H |
| Present Compound 20 | F | Me | Cyclopropyl | H | H | H |
| Present Compound 21 | F | Me | H | H | H | H |
| Present Compound 22 | F | Me | OMe | H | H | H |
| Present Compound 23 | Cl | Me | Propen-2-yl | H | H | H |
| Present Compound 24 | Cl | Me | H | H | H | Me |
| Present Compound 25 | F | Me | H | H | H | Br |
| Present Compound 26 | Cl | Me | H | H | H | F |
| Present Compound 27 | Cl | Me | H | Me | H | H |
| Present Compound 28 | Cl | Me | H | H | Me | H |
| Present Compound 29 | F | Me | H | Me | H | H |
| Present Compound 30 | F | Me | H | H | Me | H |
| Present Compound 31 | F | Me | H | H | H | Me |
| Present Compound 32 | Cl | CF₂H | Me | H | H | H |
| Present Compound 33 | F | CF₂H | Me | H | H | H |
| Present Compound 34 | Me | Me | Me | H | H | H |
| Present Compound 35 | Me | Me | OMe | H | H | H |
| Present Compound 39 | Cl | Me | H | H | H | Et |
| Present Compound 43 | F | Me | H | H | H | Et |

¹H-NMR (CDCl₃) δ: 7.84-7.75 (1H, m), 7.62-7.53 (1H, m), 7.51-7.49 (1H, m), 7.46-7.44 (1H, m), 7.31-7.26 (1H, m), 7.03 (1H, d, J=8.5 Hz), 6.99 (1H, d, J=7.6 Hz), 5.13 (2H, s), 3.76 (3H, s), 3.75 (3H, s), 2.42 (3H, s), 2.27 (3H, s), 2.12 (3H, s).

Present Compound 15

¹H-NMR (CDCl₃) δ: 8.02-7.99 (2H, m), 7.47 (1H, s), 7.44-7.41 (1H, m), 7.35-7.32 (1H, m), 7.21 (1H, t, J=8.1 Hz), 7.06 (1H, d, J=8.5 Hz), 5.40 (2H, s), 3.86 (3H, s), 3.77 (3H, s), 2.30 (3H, s), 2.16 (3H, s).

Present Compound 16

¹H-NMR (CDCl₃) δ: 7.93 (1H, s), 7.87 (1H, d, J=8.4 Hz), 7.47 (1H, s), 7.41 (1H, dd, J=8.4, 2.3 Hz), 7.33-7.30 (1H, m), 7.04 (1H, d, J=8.6 Hz), 6.85-6.80 (1H, m), 5.27 (2H, s), 3.85 (3H, s), 3.78 (3H, s), 2.30 (3H, s), 2.15 (3H, s).

Present Compound 17

¹H-NMR (CDCl₃) δ: 8.02 (1H, s), 7.97 (1H, d, J=8.4 Hz), 7.47 (1H, s), 7.42 (1H, dd, J=8.4, 2.3 Hz), 7.28 (1H, t, J=8.2 Hz), 7.15 (1H, dd, J=7.9, 1.1 Hz), 7.06 (1H, d, J=8.4 Hz), 5.39 (2H, s), 3.86 (3H, s), 3.77 (3H, s), 2.30 (3H, s), 2.15 (3H, s).

Present Compound 18

¹H-NMR (CDCl₃) δ: 7.97 (1H, s), 7.64 (1H, d, J=8.2 Hz), 7.43 (1H, s), 7.38 (1H, dd, J=8.5, 2.3 Hz), 7.28-7.25 (1H, m), 7.12 (1H, d, J=8.5 Hz), 6.64 (1H, d, J=8.2 Hz), 5.34 (2H, s), 4.09 (2H, q, J=7.0 Hz), 3.85 (3H, s), 3.76 (3H, s), 2.30 (3H, s), 2.15 (3H, s), 1.45 (3H, t, J=7.0 Hz).

Present Compound 19

¹H-NMR (CDCl₃) δ: 7.81 (1H, s), 7.63 (1H, s), 7.48-7.44 (2H, m), 7.30-7.28 (1H, m), 7.09 (1H, d, J=8.4 Hz), 6.93 (1H, d, J=7.7 Hz), 5.39 (2H, s), 3.87 (3H, s), 3.75 (3H, s), 2.27 (3H, s), 2.17 (3H, s), 2.00-1.98 (1H, m), 0.93-0.90 (2H, m), 0.68-0.66 (2H, m).

Present Compound 20

¹H-NMR (CDCl₃) δ: 7.80 (1H, s), 7.63 (1H, s), 7.50 (1H, d, J=0.0 Hz), 7.45 (1H, dd, J=8.4, 2.3 Hz), 7.29 (1H, t, J=7.9 Hz), 7.09 (1H, d, J=8.4 Hz), 6.93 (1H, d, J=7.7 Hz), 5.38

(2H, s), 3.76 (3H, s), 3.75 (3H, s), 2.27 (3H, s), 2.11 (3H, s), 1.99-1.97 (1H, m), 0.93-0.91 (2H, m), 0.67-0.66 (2H, m).

Present Compound 21

¹H-NMR (CDCl₃) δ: 8.01 (1H, s), 7.72 (1H, s), 7.49 (1H, s), 7.43-7.36 (2H, m), 7.31 (1H, dd, J=7.6, 1.4 Hz), 7.10-7.08 (1H, m), 6.99 (1H, d, J=8.5 Hz), 5.11 (2H, s), 3.76 (3H, s), 3.75 (3H, s), 2.29 (3H, s), 2.10 (3H, s).

Present Compound 22

¹H-NMR (CDCl₃) δ: 7.95 (1H, s), 7.66 (1H, d, J=8.0 Hz), 7.45 (1H, s), 7.39 (1H, dd, J=8.5, 1.8 Hz), 7.29 (1H, t, J=8.4 Hz), 7.08 (1H, d, J=8.5 Hz), 6.66 (1H, d, J=7.6 Hz), 5.31 (2H, s), 3.87 (3H, s), 3.76 (3H, s), 3.74 (3H, s), 2.29 (3H, s), 2.09 (3H, s).

Present Compound 23

¹H-NMR (CDCl₃) δ: 7.89 (1H, s), 7.65 (1H, s), 7.47 (1H, d, J=0.0 Hz), 7.43 (1H, dd, J=8.7, 2.1 Hz), 7.35 (1H, t, J=7.9 Hz), 7.01 (1H, d, J=8.5 Hz), 6.98 (1H, dd, J=7.8, 1.1 Hz), 5.23-5.21 (1H, m), 5.12 (2H, s), 4.88-4.87 (1H, m), 3.86 (3H, s), 3.75 (3H, s), 2.27 (3H, s), 2.17 (3H, s), 2.03 (3H, s).

Present Compound 24

¹H-NMR (CDCl₃) δ: 7.46 (1H, s), 7.39 (1H, d, J=8.2 Hz), 7.30-7.29 (1H, m), 7.24-7.22 (2H, m), 6.95 (1H, d, J=8.5 Hz), 6.64 (1H, s), 5.09 (2H, s), 3.86 (3H, s), 3.75 (3H, s), 2.32 (3H, s), 2.29 (3H, s), 2.15 (3H, s).

Present Compound 25

¹H-NMR (CDCl₃) δ: 7.59-7.56 (2H, m), 7.49-7.46 (1H, m), 7.36 (1H, dd, J=8.4, 2.3 Hz), 7.19 (1H, t, J=7.8 Hz), 6.84 (1H, d, J=8.4 Hz), 6.53 (1H, s), 5.16 (2H, s), 3.80 (3H, s), 3.75 (3H, s), 2.32 (3H, s), 2.09 (3H, s).

Present Compound 26

¹H-NMR (CDCl₃) δ: 7.46 (1H, s), 7.38 (1H, d, J=8.5 Hz), 7.30-7.25 (2H, m), 7.12 (1H, t, J=8.9 Hz), 6.90 (1H, d, J=8.5 Hz), 6.54 (1H, s), 5.12 (2H, s), 3.86 (3H, s), 3.78 (3H, s), 2.30 (3H, s), 2.15 (3H, s).

Present Compound 27

¹H-NMR (CDCl₃) δ: 7.85 (1H, s), 7.56 (1H, s), 7.48-7.46 (1H, m), 7.42 (1H, dd, J=8.5, 1.9 Hz), 7.19 (1H, d, J=8.4 Hz), 7.12 (1H, s), 6.99 (1H, d, J=8.4 Hz), 5.07 (2H, s), 3.86 (3H, s), 3.75 (3H, s), 2.33 (3H, s), 2.29 (3H, s), 2.16 (3H, s).

Present Compound 28

¹H-NMR (CDCl₃) δ: 7.85 (1H, s), 7.67 (1H, s), 7.48-7.46 (1H, m), 7.41 (1H, dd, J=8.4, 1.8 Hz), 7.18 (1H, d, J=7.7 Hz), 6.99 (1H, d, J=8.6 Hz), 6.90 (1H, d, J=6.6 Hz), 5.08 (2H, s), 3.86 (3H, s), 3.76 (3H, s), 2.38 (3H, s), 2.28 (3H, s), 2.15 (3H, s).

Present Compound 29

¹H-NMR (CDCl₃) δ: 7.84 (1H, s), 7.56 (1H, s), 7.49-7.47 (1H, m), 7.42 (1H, dd, J=8.2, 2.0 Hz), 7.18 (1H, d, J=8.2 Hz), 7.12 (1H, s), 6.98 (1H, d, J=8.4 Hz), 5.07 (2H, s), 3.75 (6H, s), 2.33 (3H, s), 2.29 (3H, s), 2.10 (3H, s).

Present Compound 30

¹H-NMR (CDCl₃) δ: 7.85 (1H, s), 7.66 (1H, s), 7.48 (1H, s), 7.41 (1H, d, J=9.1 Hz), 7.18 (1H, d, J=7.5 Hz), 6.98 (1H, d, J=8.4 Hz), 6.90 (1H, d, J=7.7 Hz), 5.08 (2H, s), 3.76 (3H, s), 3.75 (3H, s), 2.37 (3H, s), 2.28 (3H, s), 2.09 (3H, s).

Present Compound 31

¹H-NMR (CDCl₃) δ: 7.49-7.46 (1H, m), 7.40-7.32 (2H, m), 7.24-7.20 (2H, m), 6.94 (1H, d, J=8.5 Hz), 6.64 (1H, s), 5.08 (2H, s), 3.75 (3H, s), 3.75 (3H, s), 2.32 (3H, s), 2.29 (3H, s), 2.09 (3H, s).

Present Compound 32

¹H-NMR (CDCl₃) δ: 7.78 (1H, s), 7.51-7.50 (3H, m), 7.30-7.28 (1H, m), 7.05 (1H, d, J=9.1 Hz), 6.99 (1H, d, J=7.5 Hz), 6.67 (1H, t, J=53.9 Hz), 5.14 (2H, s), 3.91 (3H, s), 3.75 (3H, s), 2.42 (3H, s), 2.26 (3H, s).

Present Compound 33

¹H-NMR (CDCl₃) δ: 7.77 (1H, s), 7.51-7.46 (3H, m), 7.28 (1H, t, J=7.9 Hz), 7.05 (1H, d, J=8.4 Hz), 6.99 (1H, d, J=7.7 Hz), 6.64 (1H, t, J=54.3 Hz), 5.14 (2H, s), 3.81 (3H, s), 3.75 (3H, s), 2.42 (3H, s), 2.26 (3H, s).

Present Compound 34

¹H-NMR (CDCl₃) δ: 7.79 (1H, s), 7.61 (1H, s), 7.48 (1H, s), 7.44 (1H, dd, J=8.4, 2.3 Hz), 7.27 (1H, t, J=7.7 Hz), 7.02 (1H, d, J=8.4 Hz), 6.98 (1H, d, J=7.7 Hz), 5.12 (2H, s), 3.82 (3H, s), 3.75 (3H, s), 2.41 (3H, s), 2.26 (3H, s), 2.22 (3H, s), 2.13 (3H, s).

Present Compound 35

¹H-NMR (CDCl₃) δ: 7.99 (1H, s), 7.66 (1H, d, J=8.2 Hz), 7.45 (1H, s), 7.39 (1H, dd, J=8.4, 2.0 Hz), 7.29 (1H, t, J=8.4 Hz), 7.07 (1H, d, J=8.4 Hz), 6.66 (1H, d, J=8.4 Hz), 5.30 (2H, s), 3.87 (3H, s), 3.80 (3H, s), 3.76 (3H, s), 2.29 (3H, s), 2.21 (3H, s), 2.11 (3H, s).

Present Compound 39

¹H-NMR (CDCl₃) δ: 7.46 (1H, s), 7.41-7.36 (2H, m), 7.30-7.27 (2H, m), 6.93 (1H, d, J=8.4 Hz), 6.48 (1H, s), 5.10 (2H, s), 3.86 (3H, s), 3.75 (3H, s), 2.68 (2H, q, J=7.6 Hz), 2.30 (3H, s), 2.15 (3H, s), 1.24 (3H, t, J=7.6 Hz).

Present Compound 43

¹H-NMR (CDCl₃) δ: 7.47 (1H, s), 7.38 (2H, d, J=7.7 Hz), 7.29-7.28 (2H, m), 6.92 (1H, d, J=8.4 Hz), 6.47 (1H, s), 5.09 (2H, s), 3.75 (6H, s), 2.68 (2H, q, J=7.6 Hz), 2.30 (3H, s), 2.09 (3H, s), 1.24 (3H, t, J=7.6 Hz).

Production Example 3

A mixture of 0.74 g of the intermediate (9A) mentioned in Reference Production Example 9, 0.19 g of methyl chlorocarbonate, 0.34 g of sodium hydrogen carbonate, and 8 ml of tetrahydrofuran was stirred at room temperature for 4 hours. The reaction solution was concentrated under reduced pressure. The residue thus obtained was subjected to silica gel column chromatography to obtain 0.37 g of a compound represented by formula shown below (hereinafter referred to as the present compound 5).

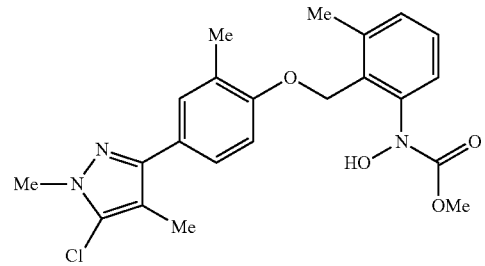

¹H-NMR (CDCl₃) δ: 7.44-7.41 (2H, m), 7.38-7.32 (1H, m), 7.31-7.25 (2H, m), 7.03-7.01 (1H, m), 6.91-6.89 (1H, m), 5.11 (2H, s), 3.86 (3H, s), 3.75 (3H, s), 2.45 (3H, s), 2.20 (3H, s), 2.16 (3H, s).

Compounds produced in accordance with the method mentioned in Production Example 3, and physical properties thereof are shown below.

Compounds represented by formula (b):

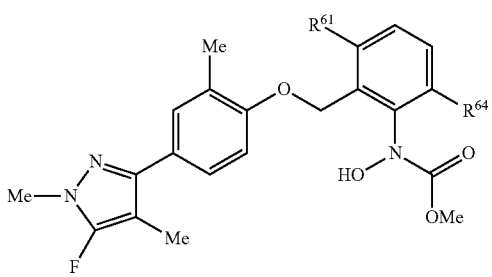

wherein $Z^{21}$, $Z^{31}$, $R^{61}$, $R^{62}$, $R^{63}$, and $R^{64}$ are shown in [Table 2].

TABLE 2

| | $R^{61}$ | $R^{64}$ |
|---|---|---|
| Present Compound 36 | Me | H |
| Present Compound 37 | OMe | H |
| Present Compound 38 | H | Me |

Present Compound 36
$^1$H-NMR (CDCl$_3$) δ: 7.99 (1H, s), 7.43-7.40 (1H, m), 7.39-7.37 (1H, m), 7.33-7.31 (1H, m), 7.25-7.23 (2H, m), 6.95 (1H, d, J=8.4 Hz), 5.06 (2H, s), 3.72 (3H, s), 3.71 (3H, s), 2.44 (3H, s), 2.17 (3H, s), 2.08 (3H, s).

Present Compound 37
$^1$H-NMR (CDCl$_3$) δ: 7.57-7.56 (1H, m), 7.41-7.38 (3H, m), 7.04-7.02 (2H, m), 6.98 (1H, d, J=7.7 Hz), 5.21 (2H, s), 3.87 (3H, s), 3.74 (3H, s), 3.73 (3H, s), 2.19 (3H, s), 2.08 (3H, s).

Present Compound 38
$^1$H-NMR (CDCl$_3$) δ: 8.51 (1H, s), 7.42 (2H, s), 7.33-7.23 (3H, m), 6.77 (1H, s), 5.17-5.13 (1H, m), 4.97 (1H, s), 3.75-3.73 (6H, m), 2.32 (3H, s), 2.25 (3H, s), 2.05 (3H, s).

Production Example 4

A mixture of 0.36 g of the intermediate (10A), 0.09 g of propionic acid chloride, 0.5 ml of triethylamine, and 5 ml of toluene was stirred at room temperature for 8 hours. Water was added and the mixture was extracted with ethyl acetate. The organic layer was washed with water, dried over anhydrous magnesium sulfate, and then concentrated under reduced pressure. The residue thus obtained was subjected to silica gel column chromatography to obtain 0.12 g of a compound represented by formula shown below (hereinafter referred to as the present compound 6).

Present Compound 6

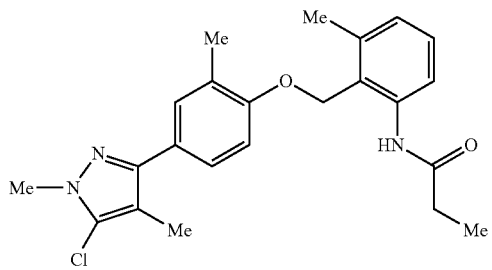

$^1$H-NMR (CDCl$_3$) δ: 8.06 (1H, br s), 7.86 (1H, d, J=8.2 Hz), 7.49 (1H, s), 7.45 (1H, dd, J=8.4, 2.2 Hz), 7.31-7.26 (1H, m), 7.06-7.00 (2H, m), 5.12 (2H, s), 3.86 (3H, s), 2.41 (3H, s), 2.34 (2H, q, J=7.6 Hz), 2.26 (3H, s), 2.17 (3H, s), 1.16 (3H, t, J=7.6 Hz).

In accordance with the reaction mentioned in Production Example 4, the present compounds 7 to 8 were synthesized.

Structure formulas and $^1$H-NMR data thereof are shown below. t,?

Present Compound 7   Present Compound 8

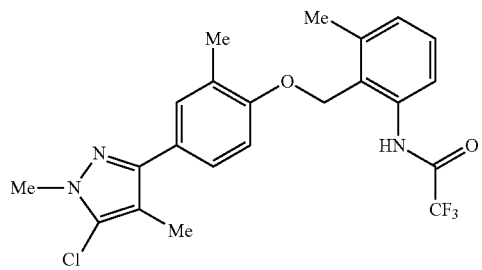

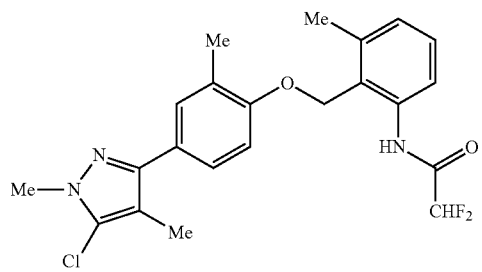

Present Compound 7
$^1$H-NMR (CDCl$_3$) δ: 9.36 (1H, s), 7.95 (1H, d, J=8.2 Hz), 7.50-7.48 (1H, m), 7.45-7.42 (1H, m), 7.36-7.31 (1H, m), 7.13 (1H, d, J=7.3 Hz), 6.99 (1H, d, J=8.5 Hz), 5.21 (2H, s), 3.86 (3H, s), 2.45 (3H, s), 2.26 (3H, s), 2.16 (3H, s).

Present Compound 8
$^1$H-NMR (CDCl$_3$) δ: 9.21 (1H, s), 7.95 (1H, d, J=8.2 Hz), 7.50-7.47 (1H, m), 7.44-7.41 (1H, m), 7.35-7.30 (1H, m), 7.11 (1H, d, J=7.6 Hz), 7.00 (1H, d, J=8.5 Hz), 5.98 (1H, t, J=54.4 Hz), 5.18 (2H, s), 3.86 (3H, s), 2.45 (3H, s), 2.26 (3H, s), 2.16 (3H, s).

Production Example 5

To a mixture of 0.02 g of sodium hydride and 2 ml of tetrahydrofuran, 0.24 g of the present compound 5 was added, followed by stirring at room temperature for 0.5 hour. To this mixture, 0.08 g of iodomethane was added, followed by stirring at room temperature for 2 hours. The reaction solution was concentrated under reduced pressure and the residue thus obtained was subjected to silica gel column chromatography to obtain 0.20 g of a compound represented by formula shown below (hereinafter referred to as the present compound 9).

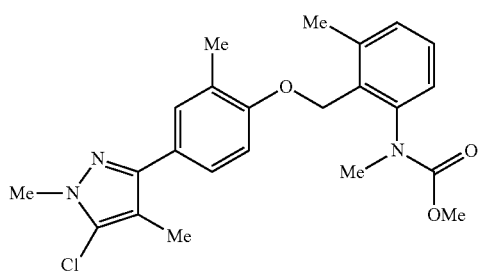 [SMILES: COC(=O)N(O)c1cccc(C)c1COc1ccc(-c2nn(C)c(Cl)c2C)cc1C]

$^1$H-NMR (CDCl$_3$) δ: 7.46-7.41 (2H, m), 7.32 (1H, t, J=7.8 Hz), 7.25-7.21 (1H, m), 7.06 (1H, d, J=7.8 Hz), 7.01 (1H, d, J=8.2 Hz), 5.00-4.92 (2H, m), 3.86 (3H, s), 3.61 (3H, s), 3.22 (3H, s), 2.45 (3H, s), 2.19 (3H, s), 2.17 (3H, s).

Production Example 6

To a mixture of 0.04 g of sodium hydride and 2 ml of DMF, 0.36 g of the intermediate (10A) was added, followed by stirring at room temperature for 0.5 hour. To this mixture, 0.11 g of dimethylcarbamoyl chloride was added, followed by stirring at room temperature for 2 hours.

The reaction solution was concentrated under reduced pressure and the residue thus obtained was subjected to silica gel column chromatography to obtain 0.08 g of a compound represented by formula shown below (hereinafter referred to as the present compound 10).

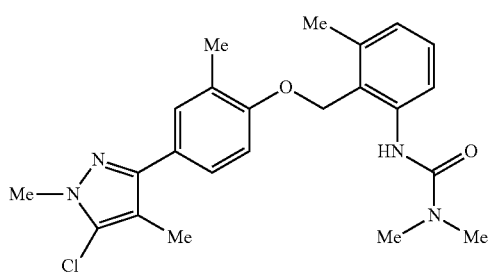 [SMILES: Cc1cc(-c2nn(C)c(Cl)c2C)ccc1OCc1c(C)cccc1NC(=O)N(C)C]

$^1$H-NMR (CDCl$_3$) δ: 7.77 (1H, d, J=8.0 Hz), 7.48-7.47 (1H, m), 7.47-7.43 (1H, m), 7.30-7.25 (2H, m), 7.07 (1H, d, J=8.2 Hz), 6.95 (1H, d, J=7.3 Hz), 5.11 (2H, s), 3.87 (3H, s), 2.88 (3H, s), 2.80 (3H, s), 2.40 (3H, s), 2.23 (3H, s), 2.17 (3H, s).

Production Example 7

A mixture of 13.0 g of the intermediate (21A) mentioned in Reference Production Example 21 and 32 ml of tetrahydrofuran was cooled to −78° C., and then 27 ml of an isopropyl magnesium chloride-lithium chloride complex tetrahydrofuran solution (1.3 mol/L) was added dropwise thereto, followed by stirring at −78° C. for 1 hour. This reaction solution was added dropwise to a mixture of 14.0 ml of diethyl oxalate cooled to −78° C. and 32 ml of tetrahydrofuran, and then the temperature was raised to room temperature while stirring. To the reaction solution, 200 ml of an aqueous saturation ammonium chloride solution was added and then the mixture was extracted with chloroform. The organic layer was washed with water, dried over anhydrous magnesium sulfate, and then concentrated under reduced pressure. The residue thus obtained was subjected to silica gel column chromatography to obtain 0.27 g of a compound represented by formula shown below (hereinafter referred to as the present compound 14).

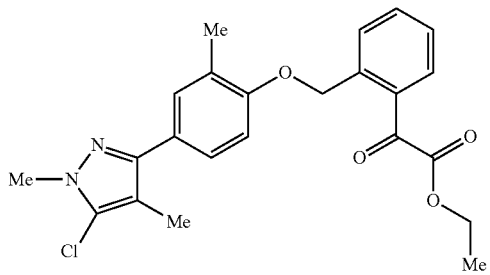 [SMILES: CCOC(=O)C(=O)c1ccccc1COc1ccc(-c2nn(C)c(Cl)c2C)cc1C]

$^1$H-NMR (CDCl$_3$) δ: 7.84-7.80 (2H, m), 7.70-7.64 (1H, m), 7.51-7.45 (2H, m), 7.41-7.38 (1H, m), 6.93 (1H, d, J=8.5 Hz), 5.45 (2H, s), 4.31 (2H, q, J=7.2 Hz), 3.87 (3H, s), 2.35 (3H, s), 2.16 (3H, s), 1.32 (3H, t, J=7.2 Hz).

Production Example 8

To a mixture of 0.27 g of the present compound 14 and 1.2 ml of methanol, 1.2 ml of a 40% dimethylamine methanol solution was added, followed by stirring at room temperature for 2 hours. This reaction solution was concentrated under reduced pressure and the residue thus obtained was subjected to silica gel column chromatography to obtain 0.20 g of a compound represented by formula shown below (hereinafter referred to as the present compound 12).

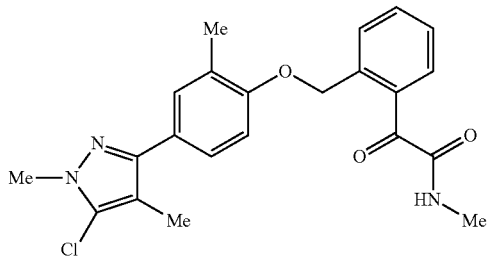 [SMILES: CNC(=O)C(=O)c1ccccc1COc1ccc(-c2nn(C)c(Cl)c2C)cc1C]

$^1$H-NMR (CDCl$_3$) δ: 7.59-7.55 (1H, m), 7.48-7.37 (4H, m), 7.36-7.32 (1H, m), 7.06 (1H, dd, J=7.4, 1.5 Hz), 6.83 (1H, d, J=8.5 Hz), 3.86 (3H, s), 2.88 (3H, d, J=5.3 Hz), 2.22 (3H, s), 2.14 (3H, s).

Production Example 9

To a mixture of 0.18 g of the present compound 12 and 2 ml of methanol, 0.03 g of sodium borohydride was added, followed by stirring at room temperature for 2 hours. To the reaction solution, water was added and the mixture was extracted with chloroform. The organic layer was washed with water, dried over anhydrous magnesium sulfate, and then concentrated under reduced pressure. The residue thus obtained was subjected to silica gel column chromatography to obtain 0.14 g of a compound represented by formula shown below (hereinafter referred to as the present compound 13).

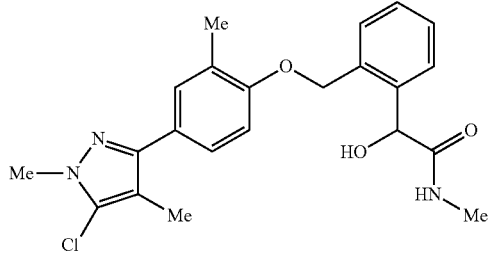 [SMILES: CNC(=O)C(O)c1ccccc1COc1ccc(-c2nn(C)c(Cl)c2C)cc1C]

$^1$H-NMR (CDCl$_3$) δ: 7.52-7.30 (7H, m), 7.13-7.08 (1H, m), 7.05 (1H, d, J=8.5 Hz), 5.34-5.17 (2H, m), 4.36 (1H, s), 3.87 (3H, s), 2.83 (3H, d, J=4.8 Hz), 2.40 (3H, s), 2.26 (3H, s).

Production Example 10

A mixed solution of 0.10 g of the present compound 15, 0.02 g of ethylboronic acid, 0.01 g of a 1,1'-bis(diphenylphosphino)ferrocene-palladium(II) dichloride-dichloromethane complex, 0.2 g of cesium carbonate, and 1 ml of dioxane was heated under reflux for 2 hours. The reaction solution was filtered with Celite (registered trademark) and the filtrate was concentrated under reduced pressure. The residue thus obtained was subjected to silica gel column chromatography to obtain 0.08 g of a compound represented by formula shown below (hereinafter referred to as the present compound 40).

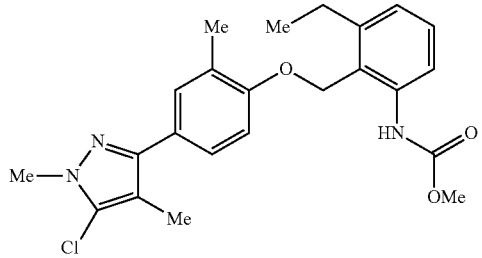 [SMILES: CCc1cccc(NC(=O)OC)c1COc1ccc(-c2nn(C)c(Cl)c2C)cc1C]

$^1$H-NMR (CDCl$_3$) δ: 7.79 (1H, s), 7.51-7.46 (3H, m), 7.32 (1H, t, J=7.9 Hz), 7.06 (1H, d, J=8.5 Hz), 7.01 (1H, d, J=7.8 Hz), 5.12 (2H, s), 3.87 (3H, s), 3.74 (3H, s), 2.74 (2H, q, J=7.6 Hz), 2.25 (3H, s), 2.17 (3H, s), 1.19 (3H, t, J=7.4 Hz).

Production Example 11

A mixed solution of 0.36 g of the intermediate (53A) mentioned in Reference Production Example 29, 0.24 ml of pyridine, and 4 ml of chloroform was ice-cooled and 0.09 ml of S-methyl chlorothioformate was added dropwise, followed by stirring at the same temperature for 3 minutes. The reaction solution was concentrated under reduced pressure and the residue thus obtained was subjected to silica gel column chromatography to obtain 0.42 g of a compound represented by formula shown below (hereinafter referred to as the present compound 44).

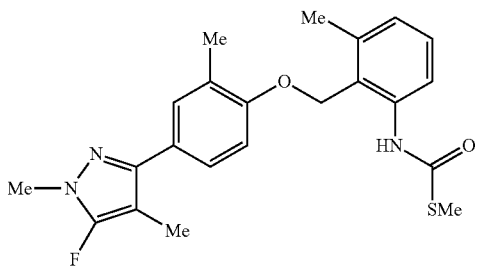 [SMILES: CSC(=O)Nc1cccc(C)c1COc1ccc(-c2nn(C)c(F)c2C)cc1C]

$^1$H-NMR (CDCl$_3$) δ: 8.11 (1H, s), 7.77 (1H, d, J=7.9 Hz), 7.50 (1H, s), 7.44 (1H, dd, J=8.4, 2.3 Hz), 7.27 (3H, t, J=7.8 Hz), 7.04-7.02 (2H, m), 5.14 (2H, s), 3.75 (3H, s), 2.42 (3H, s), 2.39 (3H, s), 2.29 (3H, s), 2.11 (3H, s).

Production Example 12

A mixture of 0.36 g of the intermediate (10A), 0.11 g of ethyl chlorocarbonate, 0.16 ml of pyridine, and 4 ml of chloroform was stirred at room temperature for 8 hours. Water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.30 g of the present compound 42.

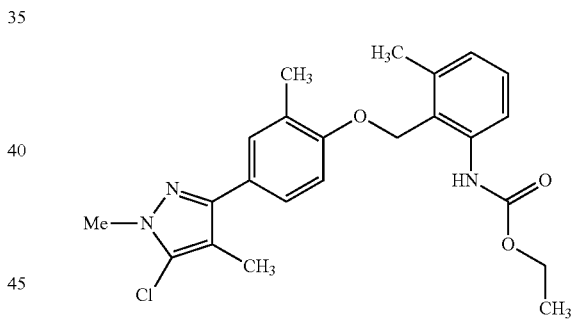

$^1$H-NMR (CDCl$_3$) δ: 7.82-7.80 (1H, m), 7.55-7.52 (1H, m), 7.50-7.47 (1H, m), 7.47-7.43 (1H, m), 7.30-7.24 (1H, m), 7.04 (1H, d, J=8.5 Hz), 6.98 (1H, d, J=7.8 Hz), 5.14 (2H, s), 4.20 (2H, q, J=7.1 Hz), 3.87 (3H, s), 2.41 (3H, s), 2.27 (3H, s), 2.17 (3H, s), 1.28 (3H, t, J=7.1 Hz).

Production Example 13

To a mixture of 0.36 g of the intermediate (10A), 0.14 ml of triethylamine, and 2 ml of tetrahydrofuran, 0.30 g of triphosgene was added under ice cooling, followed by stirring at room temperature for 2 hours. To the reaction solution, methylamine (7% tetrahydrofuran solution) was added, followed by stirring at room temperature for 2 hours. The reaction solution was concentrated under reduced pressure, and then the residue thus obtained was subjected to silica gel column chromatography to obtain 0.02 g of the present compound 41.

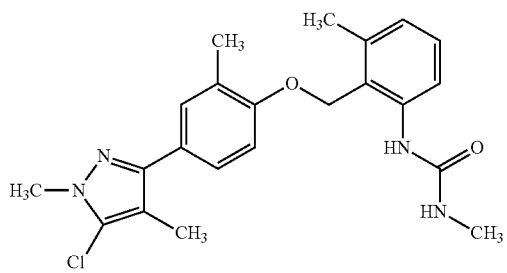

¹H-NMR (CDCl₃) δ: 9.24 (1H, br s), 7.64 (1H, d, J=8.0 Hz), 7.53 (1H, br s), 7.48-7.41 (2H, m), 7.33-7.28 (1H, m), 7.09-7.03 (2H, m), 5.11 (2H, s), 3.86 (3H, s), 2.81 (3H, d, J=4.6 Hz), 2.42 (3H, s), 2.22 (3H, s), 2.16 (3H, s).

With respect to intermediates for the production of the above-mentioned present compounds, Reference Production Examples are shown below.

Reference Production Example 1

A mixture of 10.0 g of o-tolyl isocyanate, 5.4 g of benzoyl peroxide, 14.3 g of N-bromosuccinimide, and 150 ml of chloroform was stirred with heating under reflux for 5 hours. After cooling, the reaction solution was concentrated under reduced pressure. To the residue thus obtained, 100 ml of chloroform and 50 ml of methanol were added, followed by stirring at room temperature for 15 hours. To the reaction solution, water was added and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 4.0 g of a compound represented by formula shown below (hereinafter referred to as the intermediate (1A)).

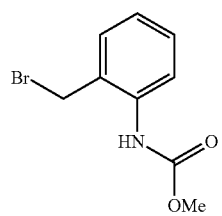

¹H-NMR (CDCl₃) δ: 7.82 (1H, s), 7.38-7.34 (1H, m), 7.30 (1H, dd, J=7.7, 1.4 Hz), 7.12-7.07 (1H, m), 6.86 (1H, s), 4.50 (2H, s), 3.81 (3H, s).

Reference Production Example 2

To a mixture of 5.0 g of 4-methoxy-3-methylbenzoic acid and 100 ml of tetrahydrofuran, 4.0 g of oxalyl chloride and 0.2 ml of DMF were added at room temperature, followed by stirring for 2.5 hours and further concentration under reduced pressure. To this mixture, 150 ml of chloroform, 3.5 g of N,O-dimethylhydroxylamine hydrochloride, and 9.3 g of diisopropylethylamine were added at room temperature, followed by stirring for 4 hours. Water was added and the mixture was extracted with chloroform, and the organic layer was washed with water, dried over anhydrous magnesium sulfate, and then concentrated under reduced pressure. The residue was subjected to column chromatography to obtain 6.1 g of a compound represented by formula shown below (hereinafter referred to as the intermediate (2A)).

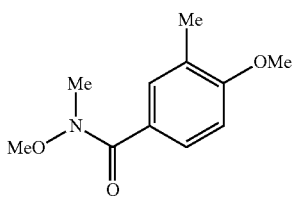 [SMILES: COc1ccc(C(=O)N(C)OC)cc1C]

¹H-NMR (CDCl₃) δ: 7.61-7.58 (1H, m), 7.54 (1H, dd, J=2.1, 0.6 Hz), 6.81 (1H, d, J=8.5 Hz), 3.87 (3H, s), 3.57 (3H, s), 3.35 (3H, s), 2.23 (3H, s).

Reference Production Example 3

A mixture of 5.7 g of the intermediate (2A), 100 ml of tetrahydrofuran, and 43 ml of a 0.95 mol/L ethyl magnesium bromide-tetrahydrofuran solution was stirred with heating under reflux for 6 hours. An aqueous saturation ammonium chloride solution was added at room temperature and the mixture was extracted with ethyl acetate. The organic layer was washed with water, dried over anhydrous magnesium sulfate, and then concentrated under reduced pressure. The residue was subjected to column chromatography to obtain 4.6 g of a compound represented by formula shown below (hereinafter referred to as the intermediate (3A)).

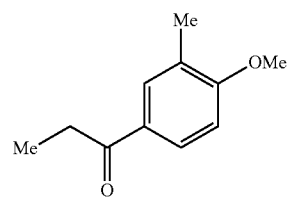 [SMILES: CCC(=O)c1ccc(OC)c(C)c1]

¹H-NMR (CDCl₃) δ: 7.83 (1H, dd, J=8.6, 2.3 Hz), 7.79-7.78 (1H, m), 6.84 (1H, d, J=8.7 Hz), 3.89 (3H, s), 2.95 (2H, q, J=7.2 Hz), 2.25 (3H, s), 1.21 (3H, t, J=7.2 Hz).

Reference Production Example 4

A mixture of 5.2 g of the intermediate (3A), 100 ml of tetrahydrofuran, 4.1 g of potassium tert-butoxide, and 3.6 g of diethyl carbonate was stirred with heating under reflux for 5.5 hours. After adding 20 ml of 6N hydrochloric acid at room temperature, the mixture was extracted with ethyl acetate. The organic layer was washed with water, dried over anhydrous magnesium sulfate, and then concentrated under reduced pressure. The residue was subjected to column chromatography to obtain 3.5 g of a compound represented by formula shown below (hereinafter referred to as the intermediate (4A)).

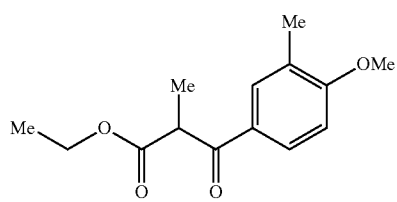 [SMILES: CCOC(=O)C(C)C(=O)c1ccc(OC)c(C)c1]

$^1$H-NMR (CDCl$_3$) δ: 7.86 (1H, dd, J=8.6, 2.3 Hz), 7.80 (1H, d, J=2.2 Hz), 6.86 (1H, d, J=8.7 Hz), 4.19-4.10 (3H, m), 3.90 (3H, s), 2.25 (3H, s), 1.47 (3H, d, J=7.2 Hz), 1.19 (3H, t, J=7.1 Hz).

Reference Production Example 5

A mixture of 3.5 g of the intermediate (4A), 100 ml of toluene, and 7.4 g of methylhydrazine was stirred with heating under reflux for 18 hours. Toluene was distilled off and 3N hydrochloric acid was added, and then the precipitate was filtered and washed with hexane to obtain 1.4 g of a compound represented by formula shown below (hereinafter referred to as the intermediate (5A)).

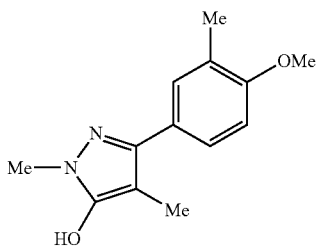 [SMILES: COc1ccc(-c2nn(C)c(O)c2C)cc1C]

$^1$H-NMR (DMSO-D$_6$) δ: 7.47-7.44 (2H, m), 7.07 (1H, d, J=8.2 Hz), 3.84 (3H, s), 3.66 (3H, s), 2.20 (3H, s), 2.05 (3H, s).

Reference Production Example 6

A mixture of 1.4 g of the intermediate (5A) and 31.8 g of phosphorus oxychloride was stirred at 100° C. for 11 hours. After concentration under reduced pressure and extraction with ethyl acetate, the organic layer was washed with water, dried over anhydrous magnesium sulfate, and then concentrated under reduced pressure. The residue was subjected to column chromatography to obtain 0.4 g of a compound represented by formula shown below (hereinafter referred to as the intermediate (6A)).

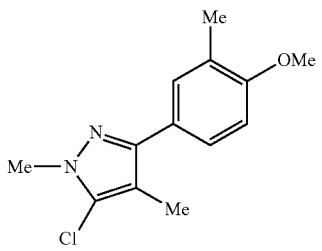 [SMILES: COc1ccc(-c2nn(C)c(Cl)c2C)cc1C]

$^1$H-NMR (DMSO-D$_6$) δ: 7.42-7.40 (2H, m), 6.98 (1H, d, J=9.2 Hz), 3.81 (3H, s), 3.80 (3H, s), 2.19 (3H, s), 2.11 (3H, s).

Reference Production Example 7

A mixture of 0.4 g of the intermediate (6A), 3 ml of 47% hydrobromic acid, and 3 ml of acetic acid was stirred with heating under reflux for 15 hours. The reaction solution was concentrated under reduced pressure, and then 20 ml of ethyl acetate was added to the residue, followed by stirring at room temperature for 1 hour. The precipitate was filtered, washed with hexane, and then dried under reduced pressure to obtain 0.3 g of a compound represented by formula shown below (hereinafter referred to as the intermediate (7A)).

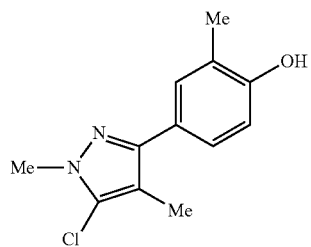 [SMILES: Cc1cc(-c2nn(C)c(Cl)c2C)ccc1O]

$^1$H-NMR (DMSO-D$_6$) δ: 7.33 (1H, s), 7.24 (1H, d, J=8.2 Hz), 6.83 (1H, d, J=8.2 Hz), 3.78 (3H, s), 2.15 (3H, s), 2.09 (3H, s).

Reference Production Example 8

A mixture of 4.73 g of the intermediate (7A), 4.60 g of 2-(bromomethyl)-3-methyl-1-nitrobenzene, 5.53 g of potassium carbonate, and 80 ml of acetonitrile was stirred with heating under reflux for 4 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 7.50 g of a compound represented by formula shown below (hereinafter referred to as the intermediate (8A)).

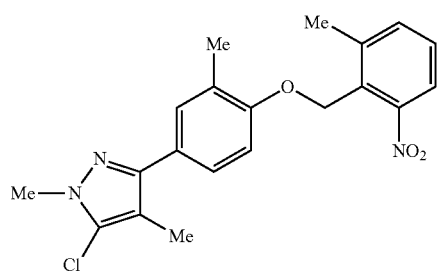 [SMILES: Cc1cc(-c2nn(C)c(Cl)c2C)ccc1OCc1c(C)cccc1[N+](=O)[O-]]

$^1$H-NMR (CDCl$_3$) δ: 7.69-7.64 (1H, m), 7.48 (1H, d, J=7.1 Hz), 7.45-7.38 (3H, m), 6.96 (1H, d, J=8.2 Hz), 5.26 (2H, s), 3.86 (3H, s), 2.53 (3H, s), 2.19 (3H, s), 2.16 (3H, s).

Compounds produced in accordance with Reference Production Example 8 and physical properties thereof are shown below. Compounds represented by formula (aA):

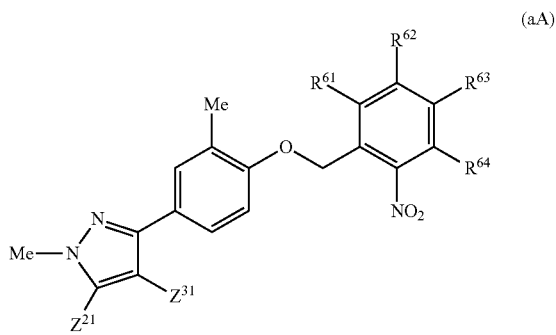

wherein $Z^{21}$, $Z^{31}$, $R^{61}$, $R^{62}$, $R^{63}$, and $R^{64}$ are shown in [Table 3].

TABLE 3

| | $Z^{21}$ | $Z^{31}$ | $R^{61}$ | $R^{62}$ | $R^{63}$ | $R^{64}$ |
|---|---|---|---|---|---|---|
| Intermediate (25A) | Cl | Me | Br | H | H | H |
| Intermediate (26A) | Cl | Me | F | H | H | H |
| Intermediate (27A) | Cl | Me | Cl | H | H | H |
| Intermediate (28A) | Cl | Me | OEt | H | H | H |
| Intermediate (29A) | F | Me | H | H | H | H |
| Intermediate (30A) | F | Me | Me | H | H | H |
| Intermediate (31A) | F | Me | OMe | H | H | H |
| Intermediate (32A) | Cl | Me | H | H | H | Me |
| Intermediate (33A) | F | Me | H | H | H | Br |
| Intermediate (34A) | Cl | Me | H | H | H | F |
| Intermediate (35A) | Cl | Me | H | Me | H | H |
| Intermediate (36A) | Cl | Me | H | H | Me | H |
| Intermediate (37A) | F | Me | H | Me | H | H |
| Intermediate (38A) | F | Me | H | H | Me | H |
| Intermediate (39A) | F | Me | H | H | H | Me |
| Intermediate (40A) | Cl | CHO | Me | H | H | H |
| Intermediate (41A) | F | CHO | Me | H | H | H |
| Intermediate (42A) | Me | Me | Me | H | H | H |
| Intermediate (43A) | Me | Me | OMe | H | H | H |
| Intermediate (44A) | F | Me | Br | H | H | H |
| Intermediate (75A) | Cl | Me | H | H | H | Br |

Intermediate (25A)

$^1$H-NMR (CDCl$_3$) δ: 7.86 (1H, dd, J=8.2, 1.1 Hz), 7.76 (1H, dd, J=8.0, 1.1 Hz), 7.40-7.38 (3H, m), 6.95 (1H, d, J=8.4 Hz), 5.47 (2H, s), 3.85 (3H, s), 2.18 (3H, s), 2.15 (3H, s).

Intermediate (26A)

$^1$H-NMR (CDCl$_3$) δ: 7.73 (1H, d, J=8.0 Hz), 7.52-7.50 (1H, m), 7.41-7.39 (3H, m), 6.97 (1H, d, J=8.0 Hz), 5.42 (2H, s), 3.85 (3H, s), 2.15 (6H, s).

Intermediate (27A)

$^1$H-NMR (CDCl$_3$) δ: 7.73 (1H, dd, J=8.0, 1.1 Hz), 7.68 (1H, dd, J=8.1, 1.3 Hz), 7.46 (1H, t, J=8.0 Hz), 7.42-7.38 (2H, m), 6.95 (1H, d, J=8.2 Hz), 5.47 (2H, s), 3.85 (3H, s), 2.17 (3H, s), 2.15 (3H, s).

Intermediate (28A)

$^1$H-NMR (CDCl$_3$) δ: 7.43-7.36 (4H, m), 7.12 (1H, dd, J=7.3, 2.1 Hz), 6.99 (1H, d, J=8.2 Hz), 5.42 (2H, s), 4.15 (2H, q, J=7.0 Hz), 3.85 (3H, s), 2.16 (3H, s), 2.15 (3H, s), 1.47 (3H, t, J=7.0 Hz).

Intermediate (30A)

$^1$H-NMR (CDCl$_3$) δ: 7.66 (1H, d, J=7.9 Hz), 7.48-7.38 (4H, m), 6.95 (1H, d, J=8.4 Hz), 5.25 (2H, s), 3.75 (3H, s), 2.53 (3H, s), 2.18 (3H, s), 2.10 (3H, s).

Intermediate (31A)

$^1$H-NMR (CDCl$_3$) δ: 7.46-7.37 (4H, m), 7.15 (1H, dd, J=7.8, 1.5 Hz), 6.96 (1H, d, J=8.4 Hz), 5.40 (2H, s), 3.94 (3H, s), 3.74 (3H, s), 2.15 (3H, s), 2.09 (3H, s).

Intermediate (32A)

$^1$H-NMR (CDCl$_3$) δ: 7.52 (1H, d, J=7.6 Hz), 7.47-7.42 (2H, m), 7.40-7.36 (1H, m), 7.31 (1H, d, J=7.1 Hz), 6.86 (1H, d, J=8.5 Hz), 5.17 (2H, s), 3.87 (3H, s), 2.42 (3H, s), 2.31 (3H, s), 2.16 (3H, s).

Intermediate (33A)

$^1$H-NMR (CDCl$_3$) δ: 7.67 (1H, dd, J=8.0, 1.1 Hz), 7.64-7.63 (1H, m), 7.49-7.46 (1H, m), 7.41-7.37 (2H, m), 6.81 (1H, d, J=8.5 Hz), 5.13 (2H, s), 3.74 (3H, s), 2.30 (3H, s), 2.08 (3H, s).

Intermediate (34A)

$^1$H-NMR (CDCl$_3$) δ: 7.59-7.49 (2H, m), 7.48-7.46 (1H, m), 7.38 (1H, dd, J=8.5, 2.2 Hz), 7.30-7.24 (1H, m), 6.85 (1H, d, J=8.5 Hz), 5.25 (2H, s), 3.86 (3H, s), 2.30 (3H, s), 2.15 (3H, s).

Intermediate (35A)

$^1$H-NMR (CDCl$_3$) δ: 8.11 (1H, d, J=8.2 Hz), 7.72 (1H, s), 7.50 (1H, s), 7.39 (1H, dd, J=8.7, 2.1 Hz), 7.30-7.27 (1H, m), 6.92 (1H, d, J=8.5 Hz), 5.51 (2H, s), 3.86 (3H, s), 2.48 (3H, s), 2.39 (3H, s), 2.16 (3H, s).

Intermediate (36A)

$^1$H-NMR (CDCl$_3$) δ: 7.99 (1H, s), 7.78 (1H, d, J=8.0 Hz), 7.50-7.48 (2H, m), 7.38 (1H, d, J=8.5 Hz), 6.90 (1H, d, J=8.5 Hz), 5.49 (2H, s), 3.86 (3H, s), 2.47 (3H, s), 2.37 (3H, s), 2.15 (3H, s).

Intermediate (37A)

$^1$H-NMR (CDCl$_3$) δ: 8.11 (1H, d, J=8.2 Hz), 7.71 (1H, s), 7.52-7.50 (1H, m), 7.39 (1H, dd, J=8.5, 1.8 Hz), 7.28-7.26 (1H, m), 6.91 (1H, d, J=8.2 Hz), 5.51 (2H, s), 3.75 (3H, s), 2.47 (3H, s), 2.39 (3H, s), 2.10 (3H, s).

Intermediate (38A)

$^1$H-NMR (CDCl$_3$) δ: 7.99 (1H, s), 7.78 (1H, d, J=8.0 Hz), 7.50-7.49 (2H, m), 7.38 (1H, dd, J=8.1, 1.9 Hz), 6.89 (1H, d, J=8.5 Hz), 5.48 (2H, s), 3.75 (3H, s), 2.46 (3H, s), 2.37 (3H, s), 2.09 (3H, s).

Intermediate (39A)

$^1$H-NMR (CDCl$_3$) δ: 7.51-7.47 (2H, m), 7.42 (1H, t, J=7.6 Hz), 7.37 (1H, dd, J=8.4, 2.3 Hz), 7.30 (1H, d, J=7.7 Hz), 6.84 (1H, d, J=8.6 Hz), 5.15 (2H, s), 3.74 (3H, s), 2.40 (3H, s), 2.29 (3H, s), 2.09 (3H, s).

Intermediate (40A)

$^1$H-NMR (CDCl$_3$) δ: 9.94 (1H, s), 7.69-7.66 (1H, m), 7.58 (1H, dd, J=8.4, 2.3 Hz), 7.51-7.49 (2H, m), 7.41 (1H, t, J=7.8 Hz), 7.00 (1H, d, J=8.4 Hz), 5.28 (2H, s), 3.93 (3H, s), 2.53 (3H, s), 2.19 (3H, s).

Intermediate (41A)

$^1$H-NMR (CDCl$_3$) δ: 9.85 (1H, s), 7.68 (1H, d, J=7.2 Hz), 7.58 (1H, dd, J=8.4, 2.3 Hz), 7.55-7.52 (1H, m), 7.50-7.47 (1H, m), 7.41 (1H, t, J=7.8 Hz), 7.00 (1H, d, J=8.4 Hz), 5.28 (2H, s), 3.82 (3H, s), 2.53 (3H, s), 2.19 (3H, s).

Intermediate (42A)

$^1$H-NMR (CDCl$_3$) δ: 7.66 (1H, d, J=7.9 Hz), 7.44-7.40 (4H, m), 6.95 (1H, d, J=8.2 Hz), 5.25 (2H, s), 3.80 (3H, s), 2.53 (3H, s), 2.21 (3H, s), 2.18 (3H, s), 2.12 (3H, s).

Intermediate (43A)

$^1$H-NMR (CDCl$_3$) δ: 7.46-7.36 (4H, m), 7.15 (1H, dd, J=7.9, 1.6 Hz), 6.96 (1H, d, J=8.4 Hz), 5.40 (2H, s), 3.94 (3H, s), 3.80 (3H, s), 2.21 (3H, s), 2.15 (3H, s), 2.10 (3H, s).

Intermediate (44A)

$^1$H-NMR (CDCl$_3$) δ: 7.86 (1H, dd, J=8.2, 1.1 Hz), 7.76 (1H, dd, J=8.2, 1.1 Hz), 7.42-7.38 (3H, m), 6.94 (1H, d, J=8.4 Hz), 5.46 (2H, s), 3.75 (3H, s), 2.17 (3H, s), 2.09 (3H, s).

Intermediate (75A)

$^1$H-NMR (CDCl$_3$) δ: 7.67 (1H, dd, J=8.1, 1.3 Hz), 7.64-7.62 (1H, m), 7.48-7.45 (1H, m), 7.41-7.37 (2H, m), 6.81 (1H, d, J=8.5 Hz), 5.13 (2H, s), 3.86 (3H, s), 2.30 (3H, s), 2.14 (3H, s).

Reference Production Example 9

To a mixture of 6.88 g of the intermediate (8A) and 100 ml of ethyl acetate, 0.40 g of a 5% carbon-supported platinum catalyst was added, followed by stirring under 1 atm hydrogen atmosphere at room temperature for 12 hours. The reaction solution was filtered with Celite (registered trademark) and then the filtrate was concentrated under reduced pressure to obtain 6.14 g of an intermediate (9A).

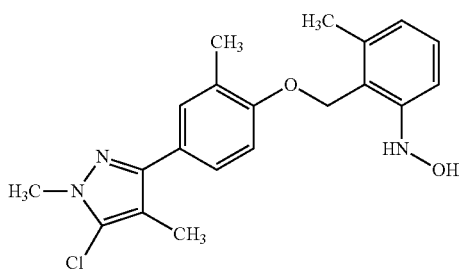 [SMILES: Cc1cc(-c2nn(C)c(Cl)c2C)ccc1OCc1c(C)cccc1NO]

$^1$H-NMR (CDCl$_3$) δ: 7.49-7.44 (3H, m), 7.30-7.28 (1H, m), 7.06 (1H, d, J=8.2 Hz), 6.88 (1H, t, J=4.4 Hz), 5.08 (2H, s), 5.02 (1H, br s), 3.89 (3H, s), 2.41 (3H, s), 2.25 (3H, s), 2.19 (3H, s).

Reference Production Example 10

To a mixture of 6.88 g of the intermediate (9A) and 100 ml of ethyl acetate, 0.27 g of a 5% carbon-supported platinum catalyst was added, followed by stirring under 1 atm hydrogen atmosphere at 40° C. for 8 hours. The reaction solution was filtered with Celite (registered trademark) and then the filtrate was concentrated under reduced pressure to obtain 4.24 g of an intermediate (10A).

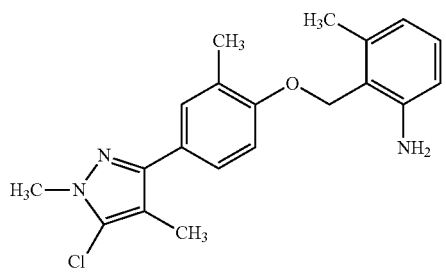 [SMILES: Cc1cc(-c2nn(C)c(Cl)c2C)ccc1OCc1c(C)cccc1N]

$^1$H-NMR (CDCl$_3$) δ: 7.47-7.42 (2H, m), 7.10-7.05 (2H, m), 6.66 (1H, d, J=7.3 Hz), 6.63 (1H, d, J=8.0 Hz), 5.10 (2H, s), 4.03 (2H, br s), 3.87 (3H, s), 2.37 (3H, s), 2.24 (3H, s), 2.17 (3H, s).

Reference Production Example 11

A mixture of 10 g of 1-(4-hydroxy-3-methylphenyl) ethanone, 13.6 g of isopropyl iodide, 18.4 g of potassium carbonate, and 250 ml of acetone was stirred with heating under reflux for 12 hours. The reaction mixture was filtered and then the filtrate was concentrated under reduced pressure. The residue thus obtained was subjected to silica gel column chromatography to obtain 9.5 g of a compound represented by formula shown below (hereinafter referred to as the intermediate (11A)).

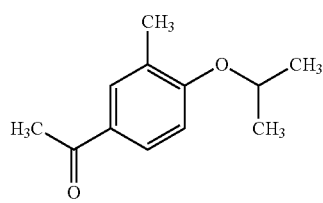

$^1$H-NMR (CDCl$_3$) δ: 7.80-7.78 (2H, m), 6.84 (1H, d, J=8.2 Hz), 4.69-4.60 (1H, m), 2.54 (3H, s), 2.23 (3H, s), 1.37 (6H, d, J=6.0 Hz).

Reference Production Example 12

To a mixture of 9.4 g of the intermediate (11A) and 150 ml of tetrahydrofuran, 11.6 g of diethyl carbonate, 4.5 g of 55% sodium hydride, 0.04 g of dibenzo-18-crown-6, and 3 ml of ethanol were added at room temperature, followed by stirring with heating under reflux for 9 hours. To the reaction mixture, water was added and an aqueous 10% hydrochloric solution was added to thereby acidify the solution, which was extracted with ethyl acetate. The organic layer was washed with water, dried over anhydrous magnesium sulfate, and then concentrated under reduced pressure. The residue thus obtained was subjected to silica gel column chromatography to obtain 12.1 g of a compound represented by formula shown below (hereinafter referred to as the intermediate (12A)).

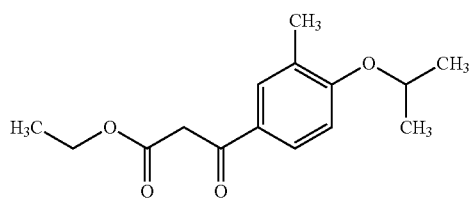 [SMILES: CCOC(=O)CC(=O)c1ccc(OC(C)C)c(C)c1]

$^1$H-NMR (CDCl$_3$) δ: 7.79-7.76 (2H, m), 6.85-6.83 (1H, m), 4.68-4.62 (1H, m), 4.21 (2H, q, J=7.2 Hz), 3.93 (2H, s), 2.22 (3H, s), 1.37 (6H, d, J=6.0 Hz), 1.26 (3H, t, J=7.1 Hz).

Reference Production Example 13

To a mixture of 12.1 g of the intermediate (12A) and 100 ml of toluene, 21 g of methylhydrazine was added at room temperature, followed by stirring for 12 hours. After toluene was distilled off under reduced pressure, 100 ml of water was added to the reaction mixture at room temperature and 10% hydrochloric acid was added to thereby acidify the solution, followed by stirring for 3 hours. The precipitate was filtered, washed with 400 ml of water and 500 ml of ethyl acetate, and then dried under reduced pressure to obtain 9.5 g of a compound represented by formula shown below (hereinafter referred to as the intermediate (13A)).

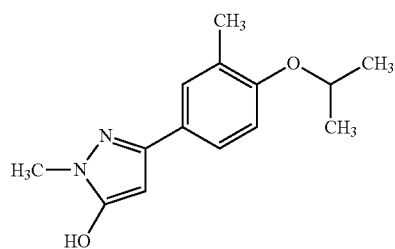 [SMILES: Cc1cc(-c2cc(O)n(C)n2)ccc1OC(C)C]

$^1$H-NMR (DMSO-D$_6$) δ: 7.58-7.54 (2H, m), 7.01-6.98 (1H, m), 5.95 (1H, s), 4.66-4.60 (1H, m), 3.62 (3H, s), 2.16 (3H, s), 1.28 (6H, d, J=5.1 Hz).

Reference Production Example 14

To 150 g of phosphorus oxychloride, 10.9 g of DMF was added at 0° C. and, after stirring for 0.5 hour, 28 g the intermediate (13A) was added. The mixture was stirred at 100° C. for 10 hours and then concentrated under reduced pressure. To the reaction mixture, 100 ml of iced water was added and the mixture was extracted with ethyl acetate. The organic layer was washed with water, dried over anhydrous magnesium sulfate, and then concentrated under reduced pressure. The residue thus obtained was subjected to silica gel column chromatography to obtain 21 g of a compound represented by formula shown below (hereinafter referred to as the intermediate (14A)).

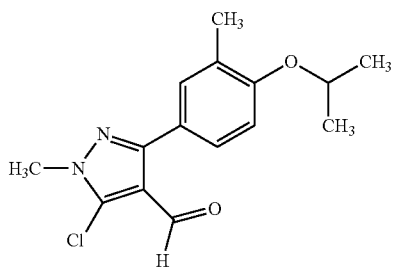 [SMILES: Cc1cc(-c2nn(C)c(Cl)c2C=O)ccc1OC(C)C]

$^1$H-NMR (CDCl$_3$) δ: 9.93 (1H, s), 7.52-7.50 (2H, m), 6.91-6.89 (1H, m), 4.63-4.54 (1H, m), 3.92 (3H, s), 2.25 (3H, s), 1.36 (6H, d, J=6.0 Hz).

Reference Production Example 15

To a mixture of 4.8 g of the intermediate (14A) and 100 ml of tetrahydrofuran, 0.6 g of methanol and 0.8 g of 55% sodium hydride were added at room temperature, followed by stirring for 3 hours. To the reaction mixture, 50 ml of water was added and the mixture was extracted with ethyl acetate. The organic layer was washed with water, dried over anhydrous magnesium sulfate, and then concentrated under reduced pressure. The residue thus obtained was subjected to silica gel column chromatography to obtain 4.5 g of a compound represented by formula shown below (hereinafter referred to as the intermediate (15A)).

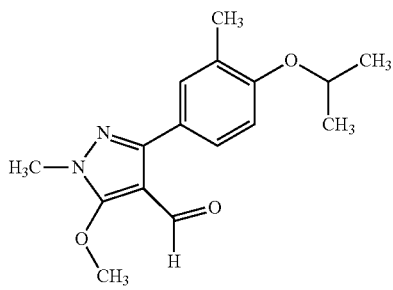 [SMILES: COc1c(C=O)c(-c2ccc(OC(C)C)c(C)c2)nn1C]

$^1$H-NMR (CDCl$_3$) δ: 9.75 (1H, s), 7.39 (1H, d, J=1.9 Hz), 7.35 (1H, dd, J=8.3, 2.3 Hz), 6.90 (1H, d, J=8.5 Hz), 4.63-4.54 (1H, m), 4.30 (3H, s), 3.71 (3H, s), 2.24 (3H, s), 1.36 (6H, d, J=6.0 Hz).

Reference Production Example 16

To a mixture of 4.2 g of the intermediate (15A) and 20 ml of trifluoroacetic acid, 4.2 g of triethylsilane was added at 0° C. After stirring at room temperature for 6 hours and concentration under reduced pressure, 10 ml of water was added and the mixture was extracted with ethyl acetate. The organic layer was washed with water, dried over anhydrous magnesium sulfate, and then concentrated under reduced pressure. The residue thus obtained was subjected to silica gel column chromatography to obtain 3.8 g of a compound represented by formula shown below (hereinafter referred to as the intermediate (16A)).

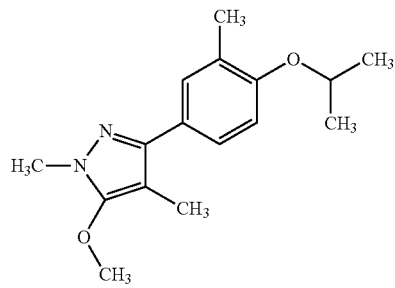 [SMILES: COc1c(C)c(-c2ccc(OC(C)C)c(C)c2)nn1C]

$^1$H-NMR (CDCl$_3$) δ: 7.43 (1H, dd, J=2.1, 0.7 Hz), 7.37-7.34 (1H, m), 6.86 (1H, d, J=8.5 Hz), 4.57-4.51 (1H, m), 3.93 (3H, s), 3.71 (3H, s), 2.24 (3H, s), 2.14 (3H, s), 1.35 (6H, d, J=6.0 Hz).

Reference Production Example 17

A mixture of 7.4 g of the intermediate (16A) and 100 ml of an aqueous 30% sulfuric acid solution was stirred with heating under reflux for 15 hours. The mixture was cooled to 0° C. and the precipitate was filtered, and then the precipitate washed with iced water, and then filtered to obtain a solid.

(Operation 1) The filtrate was concentrated under reduced pressure and cooled to 0° C., and the precipitate thus obtained was filtered and the precipitate was washed with iced water and then filtered to obtain a solid.

The above-mentioned (operation 1) was performed three times and the entire solid thus obtained was dried under reduced pressure to obtain 6.4 g of a compound represented by formula shown below (hereinafter referred to as the intermediate (17A)).

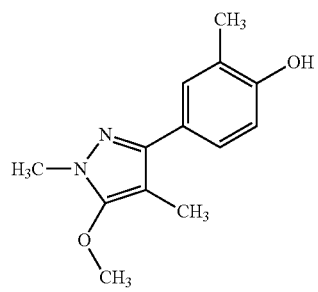 [SMILES: COc1c(C)c(-c2ccc(O)c(C)c2)nn1C]

$^1$H-NMR (DMSO-D$_6$) δ: 9.33 (1H, s), 7.29 (1H, s), 7.20 (1H, d, J=8.2 Hz), 6.79 (1H, d, J=8.2 Hz), 3.87 (3H, s), 3.60 (3H, s), 2.14 (3H, s), 2.04 (3H, s).

Reference Production Example 18

To a mixture of 9.5 g of the intermediate (13A) and 70 ml of DMF, 2.5 g of 55% sodium hydride was added at room temperature, followed by stirring for 1 hour. To the reaction mixture, 9.7 g of dimethyl sulfate was added, followed by stirring at 100° C. for 12 hours. To the reaction mixture, 100 ml of water was added and the mixture was extracted with ethyl acetate. The organic layer was washed with water, dried over anhydrous magnesium sulfate, and then concentrated under reduced pressure. The residue thus obtained was subjected to silica gel column chromatography to obtain 5.8 g of a compound represented by formula shown below (hereinafter referred to as the intermediate (18A)).

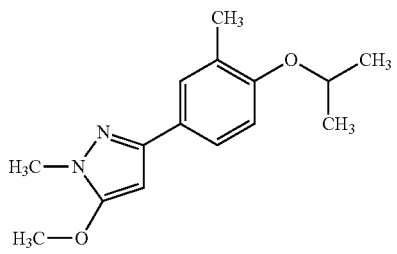 [SMILES: COc1cc(-c2ccc(OC(C)C)c(C)c2)nn1C]

$^1$H-NMR (CDCl$_3$) δ: 7.55 (1H, dd, J=2.3, 0.7 Hz), 7.49-7.47 (1H, m), 6.84 (1H, d, J=8.5 Hz), 5.75 (1H, s), 4.56-4.50 (1H, m), 3.92 (3H, s), 3.66 (3H, s), 2.23 (3H, s), 1.35 (3H, s), 1.33 (3H, s).

Reference Production Example 19

A mixture of 5.8 g of the intermediate (18A), 70 ml of chloroform, and 3.3 g of N-chlorosuccinimide was stirred at room temperature for 11 hours. To the reaction mixture, 100 ml of water was added and the mixture was extracted with chloroform. The organic layer was washed with water, dried over anhydrous magnesium sulfate, and then concentrated under reduced pressure. The residue thus obtained was subjected to silica gel column chromatography to obtain 5.6 g of a compound represented by formula shown below (hereinafter referred to as the intermediate (19A)).

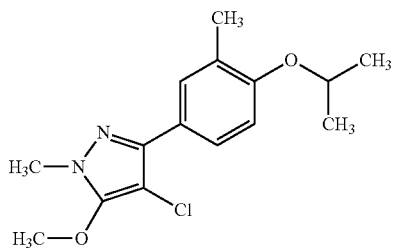 [SMILES: COc1c(Cl)c(-c2ccc(OC(C)C)c(C)c2)nn1C]

$^1$H-NMR (CDCl$_3$) δ: 7.62-7.59 (2H, m), 6.87 (1H, d, J=9.1 Hz), 4.59-4.53 (1H, m), 4.11 (3H, s), 3.70 (3H, s), 2.24 (3H, s), 1.36 (3H, s), 1.34 (3H, s).

Reference Production Example 20

A mixture of 5.6 g of the intermediate (19A) and 120 ml of an aqueous 30% sulfuric acid solution was stirred with heating under reflux for 20 hours. To the reaction mixture, 100 ml of water was added and the mixture was extracted with ethyl acetate. The organic layer was washed with water, dried over anhydrous magnesium sulfate, and then concentrated under reduced pressure. The residue thus obtained was subjected to silica gel column chromatography to obtain 1.2 g of a compound represented by formula shown below (hereinafter referred to as the intermediate (20A)).

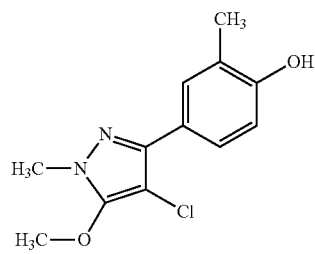 [SMILES: COc1c(Cl)c(-c2ccc(O)c(C)c2)nn1C]

$^1$H-NMR (CDCl$_3$) δ: 7.59 (1H, d, J=2.0 Hz), 7.55 (1H, dd, J=8.4, 2.0 Hz), 6.80 (1H, d, J=8.5 Hz), 5.06 (1H, s), 4.11 (3H, s), 3.70 (3H, s), 2.28 (3H, s).

Reference Production Example 21

A mixture of 7.70 g of the intermediate (7A), 8.20 g of 1-bromo-2-(bromomethyl)benzene, 9.07 g of potassium carbonate, and 130 ml of acetonitrile was stirred with heating under reflux for 4 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 13.0 g of a compound represented by formula shown below (hereinafter referred to as the intermediate (21A)).

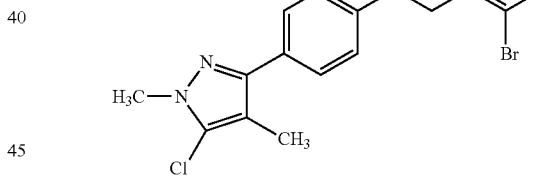

$^1$H-NMR (CDCl$_3$) δ: 7.62-7.57 (2H, m), 7.50-7.47 (1H, m), 7.41-7.32 (2H, m), 7.23-7.17 (1H, m), 6.92 (1H, d, J=8.5 Hz), 5.17 (2H, s), 3.86 (3H, s), 2.37 (3H, s), 2.16 (3H, s).

Reference Production Example 22

A mixture of 28.5 g of the intermediate (14A), 28.0 g of potassium fluoride, 125 ml of sulfolane, and 120 ml of toluene was stirred with heating at 120° C. to thereby distill off toluene, followed by stirring at 220° C. for 2 hours. To the reaction mixture, 200 ml of water was added and the mixture was extracted with ethyl acetate. The organic layer was washed with water, dried over anhydrous magnesium sulfate, and then concentrated under reduced pressure. The residue thus obtained was subjected to silica gel column chromatography to obtain 23.4 g of a compound represented by formula shown below (hereinafter referred to as the intermediate (22A)).

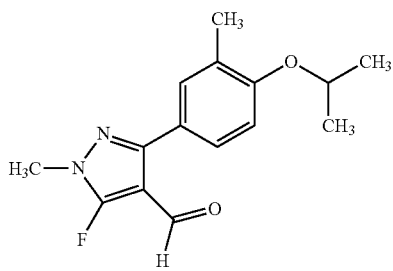 [SMILES: Cc1cc(-c2nn(C)c(F)c2C=O)ccc1OC(C)C]

¹H-NMR (CDCl₃) δ: 9.85 (1H, s), 7.53-7.50 (2H, m), 6.90 (1H, d, J=9.1 Hz), 4.67-4.50 (1H, m), 3.81 (3H, d, J=1.6 Hz), 2.25 (3H, s), 1.37 (3H, s), 1.36 (3H, s).

Reference Production Example 23

To a mixture of 23.4 g of the intermediate (22A) and 100 ml of trifluoroacetic acid, 24.7 g of triethylsilane was added at 0° C. After stirring at room temperature for 6 hours and concentration under reduced pressure, 75 ml of water was added and the mixture was extracted with ethyl acetate. The organic layer was washed with water, dried over anhydrous magnesium sulfate, and then concentrated under reduced pressure. The residue thus obtained was subjected to silica gel column chromatography to obtain 17.8 g of a compound represented by formula shown below (hereinafter referred to as the intermediate (23A)).

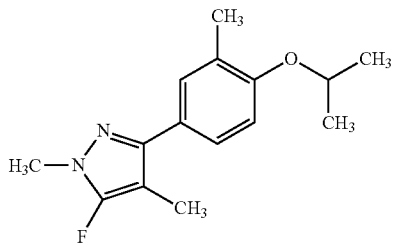 [SMILES: Cc1cc(-c2nn(C)c(F)c2C)ccc1OC(C)C]

¹H-NMR (CDCl₃) δ: 7.45-7.43 (1H, m), 7.38-7.36 (1H, m), 6.87 (1H, d, J=8.4 Hz), 4.59-4.52 (1H, m), 3.75 (3H, d, J=1.1 Hz), 2.24 (3H, s), 2.10 (3H, d, J=0.9 Hz), 1.35 (6H, d, J=6.1 Hz).

Reference Production Example 24

A mixture of 17.8 g of the intermediate (23A) and 170 ml of an aqueous 30% sulfuric acid solution was stirred with heating under reflux for 24 hours. The mixture was cooled to 0° C. and 100 ml of water was added, followed by neutralization with an aqueous sodium carbonate solution so as to adjust the pH to 7. After extraction with ethyl acetate, the organic layer was washed with water, dried over anhydrous magnesium sulfate, and then concentrated under reduced pressure. The residue thus obtained was subjected to silica gel column chromatography to obtain 6.78 g of a compound represented by formula shown below (hereinafter referred to as the intermediate (24A)).

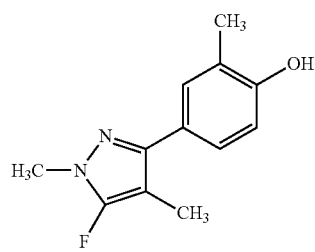 [SMILES: Cc1cc(-c2nn(C)c(F)c2C)ccc1O]

¹H-NMR (CDCl₃) δ: 7.44-7.42 (1H, m), 7.34-7.29 (1H, m), 6.79 (1H, d, J=8.2 Hz), 5.12 (1H, s), 3.75 (3H, d, J=1.1 Hz), 2.29 (3H, s), 2.10-2.08 (3H, m).

Reference Production Example 25

A mixed solution of 0.55 g of the intermediate (40A), 14 ml of chloroform, and 0.54 ml of N,N-diethylaminosulfur trifluoride was stirred at room temperature for 20 hours. The mixture was cooled to 0° C. and 100 ml of water was added, and the mixture was extracted with ethyl acetate. The organic layer was dried over anhydrous magnesium sulfate, and then concentrated under reduced pressure. The residue thus obtained was subjected to silica gel column chromatography to obtain 0.30 g of a compound represented by formula shown below (hereinafter referred to as the intermediate (67A)).

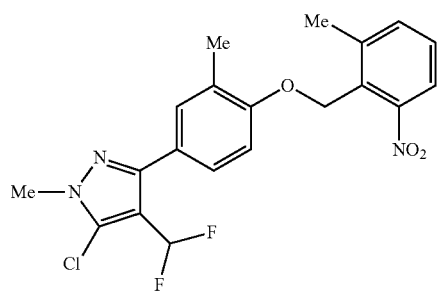 [SMILES: Cc1cc(-c2nn(C)c(Cl)c2C(F)F)ccc1OCc1c(C)cccc1[N+](=O)[O-]]

¹H-NMR (CDCl₃) δ: 7.67 (1H, d, J=7.9 Hz), 7.49-7.39 (4H, m), 6.97 (1H, d, J=8.4 Hz), 6.66 (1H, t, J=53.9 Hz), 5.26 (2H, s), 3.90 (3H, s), 2.53 (3H, s), 2.18 (3H, s).

In accordance with the reaction mentioned in Reference Production Example 25, a compound represented by formula shown below (hereinafter referred to as the intermediate (68A)) was synthesized.

Structural formula and ¹H-NMR data thereof are shown below.

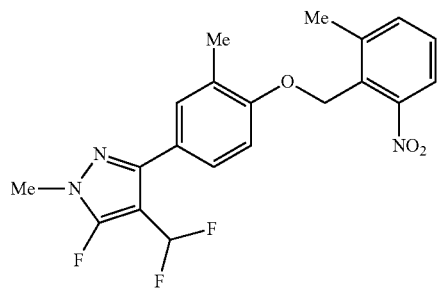 [SMILES: Cc1cc(-c2nn(C)c(F)c2C(F)F)ccc1OCc1c(C)cccc1[N+](=O)[O-]]

$^1$H-NMR (CDCl$_3$) δ: 7.67 (1H, d, J=7.9 Hz), 7.49-7.39 (4H, m), 6.98-6.96 (1H, m), 6.63 (1H, t, J=54.3 Hz), 5.26 (2H, s), 3.80 (3H, s), 2.53 (3H, s), 2.18 (3H, s).

Reference Production Example 26

A mixture of 0.45 g of the intermediate (25A), 0.19 g of cyclopropylboronic acid, 2.2 g of cesium carbonate, 0.02 g of a 1,1'-bis(diphenylphosphino)ferrocene-palladium(II) dichloride-dichloromethane complex, and 4.5 ml of 1,2-dimethoxyethane was stirred with heating under reflux for 2 hours. The reaction solution was filtered with Celite (registered trademark) and then the filtrate was concentrated under reduced pressure. The residue thus obtained was subjected to silica gel column chromatography to obtain 0.40 g of a compound represented by formula shown below (hereinafter referred to as the intermediate (69A)).

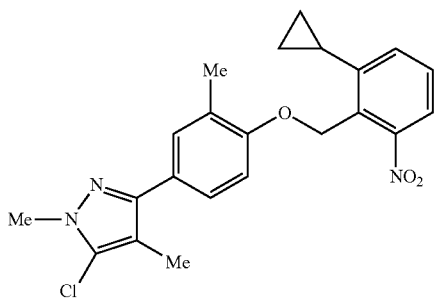 [SMILES: Cc1cc(-c2nn(C)c(Cl)c2C)ccc1OCc1c(C2CC2)cccc1[N+](=O)[O-]]

$^1$H-NMR (CDCl$_3$) δ: 7.64 (1H, dd, J=7.9, 1.4 Hz), 7.43-7.34 (4H, m), 7.00 (1H, d, J=8.2 Hz), 5.48 (2H, s), 3.86 (3H, s), 2.18 (3H, s), 2.16 (3H, s), 2.14-2.11 (1H, m), 1.06-1.03 (2H, m), 0.77-0.75 (2H, m).

In accordance with the reaction mentioned in Reference Production Example 26, an intermediate (70A) and an intermediate (71A) represented by formulas shown below were synthesized.

Structural formulas and $^1$H-NMR data thereof are shown below.

Intermediate (70A)    Intermediate (71A)

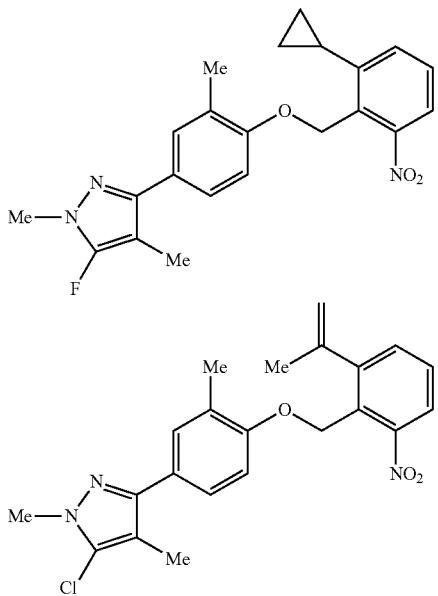

Intermediate (70A)
$^1$H-NMR (CDCl$_3$) δ: 7.65-7.63 (1H, m), 7.44-7.33 (4H, m), 6.99 (1H, d, J=8.4 Hz), 5.48 (2H, s), 3.75 (3H, s), 2.18 (3H, s), 2.15-2.12 (1H, m), 2.10 (3H, s), 1.06-1.03 (2H, m), 0.77-0.75 (2H, m).

Intermediate (71A)
$^1$H-NMR (CDCl$_3$) δ: 7.77-7.74 (1H, m), 7.47-7.44 (2H, m), 7.40-7.37 (2H, m), 6.89 (1H, d, J=8.4 Hz), 5.35-5.35 (1H, m), 5.31 (2H, s), 5.00-4.97 (1H, m), 3.85 (3H, s), 2.15 (6H, s), 2.10 (3H, s).

Reference Production Example 27

A mixed solution of 0.43 g of the intermediate (75A), 1.4 ml of diethylzinc (1.09M hexane solution), 0.02 g of a 1,1'-bis (diphenylphosphino) ferrocene-palladium(II) dichloride-dichloromethane complex, and 9 ml of 1, 2-dimethoxyethane was stirred with heating at 60° C. for 5 hours. The reaction solution was filtered with Celite (registered trademark) and then the filtrate was concentrated under reduced pressure. The residue thus obtained was subjected to silica gel column chromatography to obtain 0.08 g of a compound represented by formula shown below (hereinafter referred to as the intermediate (76A)).

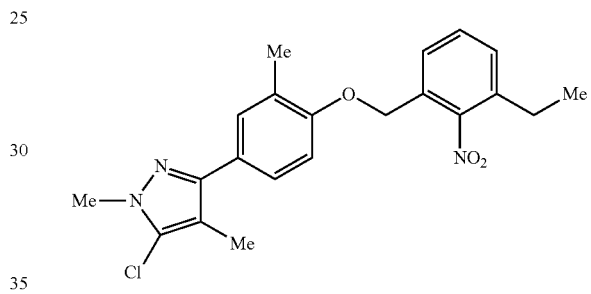

$^1$H-NMR (CDCl$_3$) δ: 7.51-7.46 (3H, m), 7.37-7.34 (2H, m), 6.85 (1H, d, J=8.4 Hz), 5.13 (2H, s), 3.86 (3H, s), 2.69 (2H, q, J=7.6 Hz), 2.30 (3H, s), 2.15 (3H, s), 1.29 (3H, d, J=7.6 Hz).

In accordance with the reaction mentioned in Production Example 27, an intermediate (79A) represented by formula shown below was synthesized.

Structural formula and $^1$H-NMR data thereof are shown below.

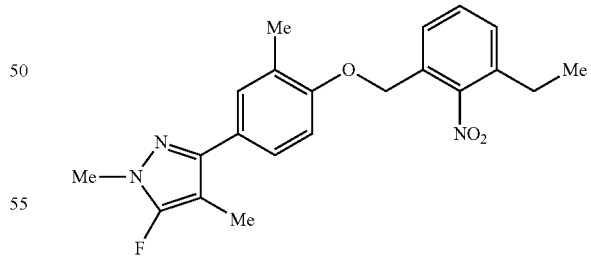

$^1$H-NMR (CDCl$_3$) δ: 7.52-7.44 (3H, m), 7.37-7.34 (2H, m), 6.85 (1H, d, J=8.4 Hz), 5.13 (2H, s), 3.74 (3H, s), 2.69 (2H, q, J=7.6 Hz), 2.30 (3H, s), 2.09 (3H, s), 1.28 (3H, t, J=7.6 Hz).

Reference Production Example 28

A mixed solution of 1.0 g of the intermediate (30A), 12 ml of 2-propanol, 0.18 g of ammonium chloride, and 4.5 ml of water was ice-cooled and 0.88 g of zinc was added, followed by stirring at the same temperature for 4 hours. The reaction solution was filtered with Celite (registered trademark) and an aqueous saturated sodium hydrogen carbonate solution was added to the filtrate, followed by concentration under reduced pressure. The residue thus obtained was subjected to silica gel column chromatography to obtain 0.5 g of a compound represented by formula shown below (hereinafter referred to as the intermediate (45A)).

Compounds produced in accordance with Reference Production Example 28 and physical properties thereof are shown below. Compounds represented by formula (bA):

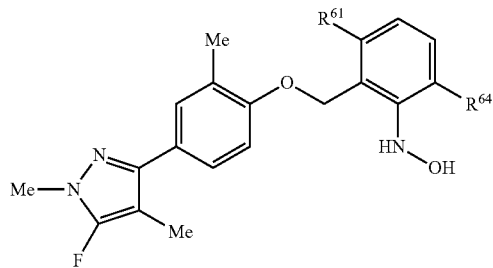

(bA)

wherein $R^{61}$, and $R^{64}$ are shown in [Table 4].

TABLE 4

|  | $R^{61}$ | $R^{64}$ |
| --- | --- | --- |
| Intermediate (45A) | Me | H |
| Intermediate (46A) | OMe | H |
| Intermediate (47A) | H | Me |

Intermediate (46A)
$^1$H-NMR (CDCl$_3$) δ: 7.61 (1H, s), 7.41-7.38 (2H, m), 7.29-7.26 (1H, m), 7.06 (1H, d, J=8.4 Hz), 7.00 (1H, d, J=8.2 Hz), 6.54 (1H, d, J=8.4 Hz), 5.79 (1H, s), 5.19 (2H, s), 3.85 (3H, s), 3.74 (3H, s), 2.23 (3H, s), 2.08 (3H, s).

Reference Production Example 29

To a mixture of 1.0 g of the intermediate (25A), 0.66 g of copper(I) chloride, and 22 ml of methanol, 0.80 g of potassium borohydride was added under ice cooling, followed by stirring under ice cooling for 30 minutes. The reaction solution was filtered with Celite (registered trademark) and then the filtrate was concentrated under reduced pressure. To the residue, ethyl acetate was added, followed by washing with an aqueous saturated sodium hydrogen carbonate solution. The organic layer was dried over anhydrous magnesium sulfate and concentrated under reduced pressure to obtain 0.80 g of the intermediate (48A) shown below.

Compounds produced in accordance with Reference Production Example 29 and physical properties thereof are shown below. Compounds represented by formula (cA):

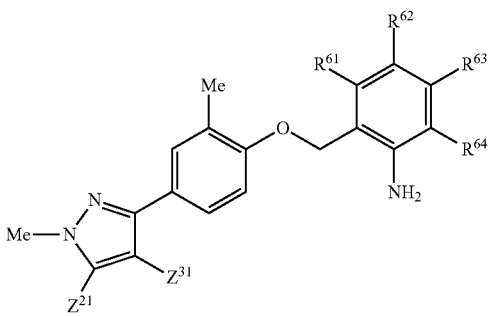

(cA)

wherein $Z^{21}$, $Z^{31}$, $R^{61}$, $R^{62}$, $R^{63}$, and $R^{64}$ are shown in [Table 5].

TABLE 5

|  | $Z^{21}$ | $Z^{31}$ | $R^{61}$ | $R^{62}$ | $R^{63}$ | $R^{64}$ |
| --- | --- | --- | --- | --- | --- | --- |
| Intermediate (48A) | Cl | Me | Br | H | H | H |
| Intermediate (49A) | Cl | Me | F | H | H | H |
| Intermediate (50A) | Cl | Me | Cl | H | H | H |
| Intermediate (51A) | Cl | Me | OEt | H | H | H |
| Intermediate (52A) | F | Me | H | H | H | H |
| Intermediate (53A) | F | Me | Me | H | H | H |
| Intermediate (54A) | F | Me | OMe | H | H | H |
| Intermediate (55A) | Cl | Me | H | H | H | Me |
| Intermediate (56A) | F | Me | H | H | H | Br |
| Intermediate (57A) | Cl | Me | H | H | H | F |
| Intermediate (58A) | Cl | Me | H | Me | H | H |
| Intermediate (59A) | Cl | Me | H | H | Me | H |
| Intermediate (60A) | F | Me | H | Me | H | H |
| Intermediate (61A) | F | Me | H | H | Me | H |
| Intermediate (62A) | F | Me | H | H | H | Me |
| Intermediate (63A) | Cl | CF$_2$H | Me | H | H | H |
| Intermediate (64A) | F | CF$_2$H | Me | H | H | H |
| Intermediate (65A) | Me | Me | Me | H | H | H |
| Intermediate (66A) | Me | Me | OMe | H | H | H |
| Intermediate (72A) | F | Me | Cyclopropyl | H | H | H |
| Intermediate (73A) | Cl | Me | Propen-2-yl | H | H | H |
| Intermediate (74A) | Cl | Me | H | H | H | Et |
| Intermediate (77A) | Cl | Me | Cyclopropyl | H | H | H |
| Intermediate (78A) | F | Me | H | H | H | Et |

Intermediate (49A)
$^1$H-NMR (CDCl$_3$) δ: 7.44 (1H, s), 7.41 (1H, dd, J=8.4, 2.0 Hz), 7.11-7.06 (2H, m), 6.51-6.46 (2H, m), 5.21 (2H, s), 4.30 (2H, s), 3.85 (3H, s), 2.25 (3H, s), 2.15 (3H, s).
Intermediate (50A)
$^1$H-NMR (CDCl$_3$) δ: 7.45 (1H, s), 7.42-7.41 (1H, m), 7.09-7.05 (2H, m), 6.82 (1H, d, J=7.9 Hz), 6.61 (1H, d, J=7.9 Hz), 5.33 (2H, s), 4.31 (2H, s), 3.86 (3H, s), 2.26 (3H, s), 2.16 (3H, s).
Intermediate (51A)
$^1$H-NMR (CDCl$_3$) δ: 7.41-7.37 (2H, m), 7.17 (1H, d, J=8.4 Hz), 7.06 (1H, t, J=8.2 Hz), 6.34-6.32 (2H, m), 5.29 (2H, s), 4.21 (2H, s), 4.06 (2H, q, J=6.9 Hz), 3.85 (3H, s), 2.25 (3H, s), 2.15 (3H, s), 1.43 (3H, t, J=6.9 Hz).
Intermediate (52A)
$^1$H-NMR (CDCl$_3$) δ: 7.48-7.45 (1H, m), 7.41 (1H, dd, J=8.5, 2.4 Hz), 7.21-7.18 (2H, m), 7.01 (1H, d, J=8.4 Hz), 6.78-6.74 (2H, m), 5.06 (2H, s), 4.11 (2H, s), 3.74 (3H, s), 2.26 (3H, s), 2.09 (3H, s).
Intermediate (53A)
$^1$H-NMR (CDCl$_3$) δ: 7.46-7.43 (2H, m), 7.08-7.06 (2H, m), 6.66 (1H, d, J=7.5 Hz), 6.62 (1H, d, J=8.2 Hz), 5.09 (2H, s), 4.03 (2H, s), 3.76 (3H, s), 2.37 (3H, s), 2.23 (3H, s), 2.11 (3H, s).

Intermediate (54A)

¹H-NMR (CDCl₃) δ: 7.43 (1H, s), 7.39 (1H, dd, J=8.4, 2.3H), 7.13-7.07 (2H, m), 6.36 (2H, dd, J=8.2, 1.6 Hz), 5.26 (2H, s), 4.20 (2H, s), 3.84 (3H, s), 3.74 (3H, s), 2.25 (3H, s), 2.09 (3H, s).

Intermediate (55A)

¹H-NMR (CDCl₃) δ: 7.47 (1H, s), 7.42 (1H, d, J=8.5 Hz), 7.15-7.08 (2H, m), 7.05 (1H, d, J=8.5 Hz), 6.75-6.69 (1H, m), 5.10 (2H, s), 4.13 (2H, br s), 3.87 (3H, s), 2.28 (3H, s), 2.23 (3H, s), 2.17 (3H, s).

Intermediate (56A)

¹H-NMR (CDCl₃) δ: 7.47-7.40 (3H, m), 7.17 (1H, dd, J=7.5, 1.4 Hz), 6.99 (1H, d, J=8.4 Hz), 6.64 (1H, t, J=7.8 Hz), 5.07 (2H, s), 4.63 (2H, s), 3.75 (3H, s), 2.26 (3H, s), 2.09 (3H, s).

Intermediate (57A)

¹H-NMR (CDCl₃) δ: 7.46 (1H, s), 7.41 (1H, d, J=8.5 Hz), 7.06-6.98 (3H, m), 6.73-6.66 (1H, m), 5.10 (2H, s), 4.18 (2H, br s), 3.86 (3H, s), 2.27 (3H, s), 2.16 (3H, s).

Intermediate (58A)

¹H-NMR (CDCl₃) δ: 7.45-7.40 (2H, m), 7.02-7.00 (3H, m), 6.66 (1H, d, J=7.9 Hz), 5.03 (2H, s), 3.97 (2H, s), 3.86 (3H, s), 2.27 (3H, s), 2.26 (3H, s), 2.16 (3H, s).

Intermediate (59A)

¹H-NMR (CDCl₃) δ: 7.44 (1H, s), 7.41-7.40 (1H, m), 7.10 (1H, d, J=7.7 Hz), 7.02 (1H, d, J=8.4 Hz), 6.59-6.58 (2H, m), 5.03 (2H, s), 4.05 (2H, s), 3.86 (3H, s), 2.28 (3H, s), 2.25 (3H, s), 2.15 (3H, s).

Intermediate (60A)

¹H-NMR (CDCl₃) δ: 7.45 (1H, s), 7.41 (1H, t, J=5.2 Hz), 7.02-6.99 (3H, m), 6.66 (1H, d, J=8.0 Hz), 5.03 (2H, s), 3.75 (3H, s), 2.26 (3H, s), 2.26 (3H, s), 2.09 (3H, s).

Intermediate (61A)

¹H-NMR (CDCl₃) δ: 7.45 (1H, s), 7.40 (1H, dd, J=8.4, 2.3 Hz), 7.10 (1H, d, J=7.5 Hz), 7.01 (1H, d, J=8.6 Hz), 6.59-6.58 (2H, m), 5.03 (2H, s), 4.04 (2H, s), 3.74 (3H, s), 2.28 (3H, s), 2.25 (3H, s), 2.09 (3H, s).

Intermediate (62A)

¹H-NMR (CDCl₃) δ: 7.46 (1H, s), 7.41 (1H, dd, J=8.5, 2.3 Hz), 7.11-7.09 (2H, m), 7.03 (1H, d, J=8.2 Hz), 6.71 (1H, t, J=7.6 Hz), 5.08 (2H, s), 4.11 (2H, s), 3.75 (3H, s), 2.26 (3H, s), 2.22 (3H, s), 2.09 (3H, s).

Intermediate (63A)

¹H-NMR (CDCl₃) δ: 7.49-7.48 (2H, m), 7.08-7.07 (2H, m), 6.80-6.53 (3H, m), 5.10 (2H, s), 4.02 (2H, s), 3.91 (3H, s), 2.37 (3H, s), 2.23 (3H, s).

Intermediate (64A)

¹H-NMR (CDCl₃) δ: 7.46-7.44 (2H, m), 7.10-7.06 (2H, m), 6.77-6.50 (3H, m), 5.10 (2H, s), 4.01 (2H, s), 3.80 (3H, s), 2.37 (3H, s), 2.23 (3H, s).

Intermediate (65A)

¹H-NMR (CDCl₃) δ: 7.45-7.43 (2H, m), 7.08-7.06 (2H, m), 6.65-6.62 (2H, m), 5.09 (2H, s), 4.04 (2H, s), 3.81 (3H, s), 2.37 (3H, s), 2.23 (3H, s), 2.21 (3H, s), 2.12 (3H, s).

Intermediate (72A)

¹H-NMR (CDCl₃) δ: 7.46-7.43 (2H, m), 7.12-7.07 (2H, m), 6.62 (1H, d, J=8.0 Hz), 6.59 (1H, d, J=7.8 Hz), 5.34 (2H, s), 4.05 (2H, s), 3.75 (3H, s), 2.24 (3H, s), 2.11 (3H, s), 2.00-1.96 (1H, m), 0.89-0.87 (2H, m), 0.67-0.65 (2H, m).

Intermediate (73A)

¹H-NMR (CDCl₃) δ: 7.44-7.41 (2H, m), 7.14 (1H, t, J=7.8 Hz), 7.03 (1H, d, J=8.4 Hz), 6.68 (1H, d, J=3.4 Hz), 6.66 (1H, d, J=2.9 Hz), 5.18-5.17 (1H, m), 5.08 (2H, s), 4.90-4.90 (1H, m), 3.86 (3H, s), 2.24 (3H, s), 2.16 (3H, s), 2.04 (3H, s).

Intermediate (74A)

¹H-NMR (CDCl₃) δ: 7.45 (1H, s), 7.41 (1H, d, J=8.2 Hz), 7.11 (2H, d, J=7.6 Hz), 7.04 (1H, d, J=8.2 Hz), 6.76 (1H, t, J=7.6 Hz), 5.09 (2H, s), 4.15 (2H, s), 3.86 (3H, s), 2.57 (2H, q, J=7.6 Hz), 2.26 (3H, s), 2.16 (3H, s), 1.28 (3H, t, J=7.6 Hz).

Intermediate (78A)

¹H-NMR (CDCl₃) δ: 7.46 (1H, s), 7.42-7.41 (1H, m), 7.12 (2H, d, J=7.9 Hz), 7.04 (1H, d, J=8.4 Hz), 6.76 (1H, t, J=7.5 Hz), 5.09 (2H, s), 4.15 (2H, s), 3.75 (3H, s), 2.57 (2H, q, J=7.6 Hz), 2.26 (3H, s), 2.10 (3H, s), 1.28 (3H, t, J=7.6 Hz).

In accordance with the process mentioned above, it is possible to obtain compounds HA1001-0001 to HW1084-0094.

The compounds HA1001-0001 to HW1084-0094 (hereinafter referred to as the present compounds A) represent aromatic compounds shown below [wherein E represents any one of the following substituent numbers 0001 to 0070]. In [substituent number; E] mentioned below, PYR3 represents a pyrazol-3-yl group.

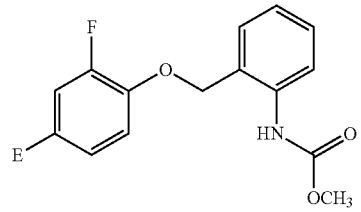
(HA1001)

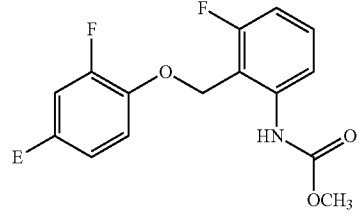
(HA1002)

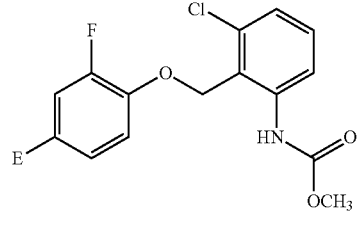
(HA1003)

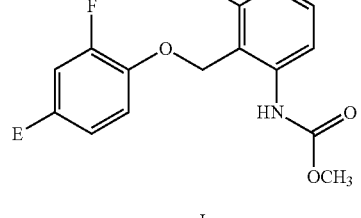
(HA1004)

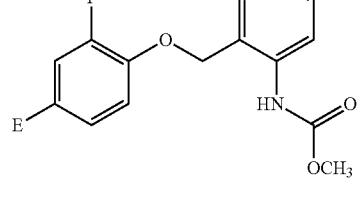
(HA1005)

-continued
(HA1006)
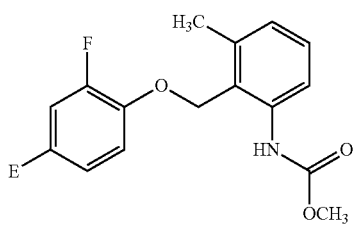
(HA1007)
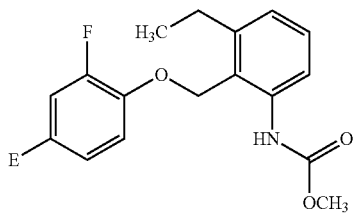
(HA1008)
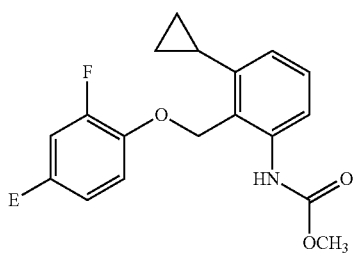
(HA1009)
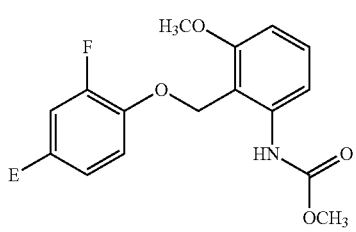
(HA1010)
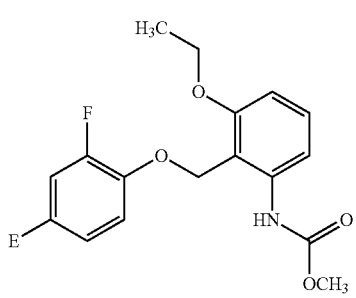
(HA1011)
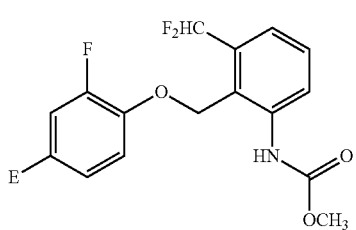
-continued
(HA1012)
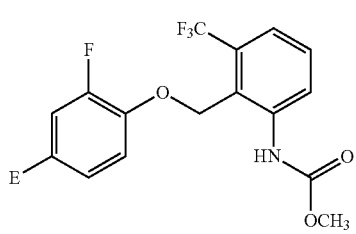
(HA1025)
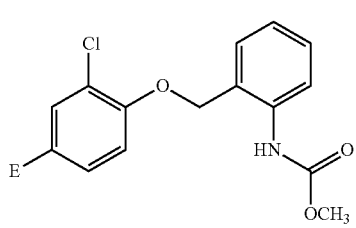
(HA1026)
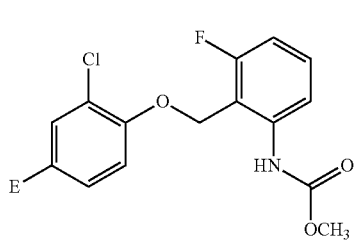
(HA1027)
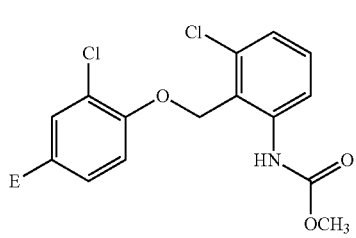
(HA1028)
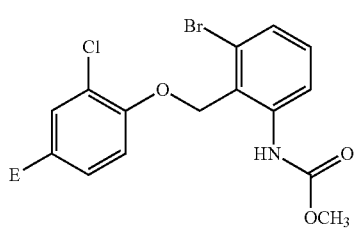
(HA1029)
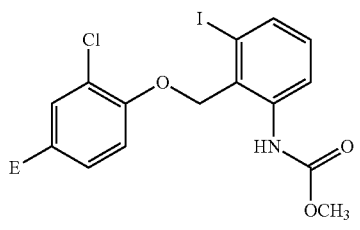
(HA1030)
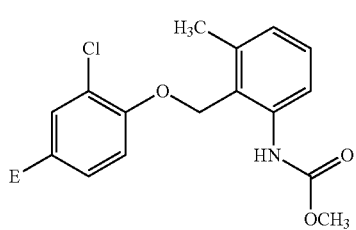

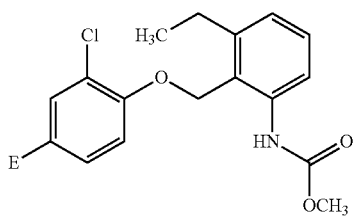
(HA1031)
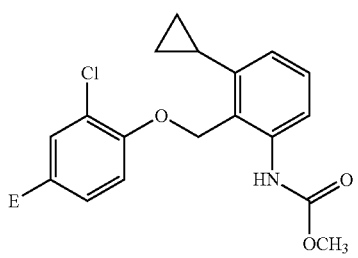
(HA1032)
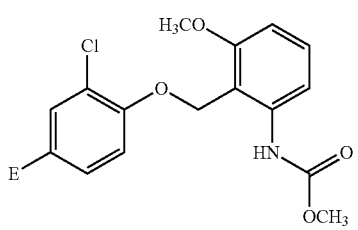
(HA1033)
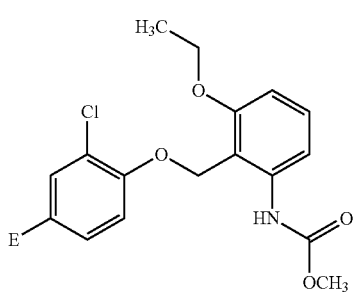
(HA1034)
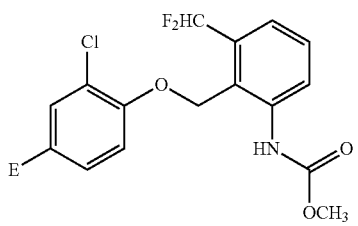
(HA1035)
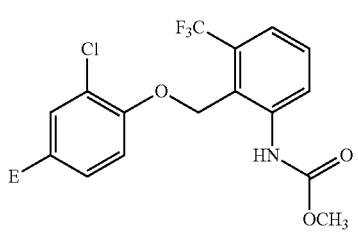
(HA1036)
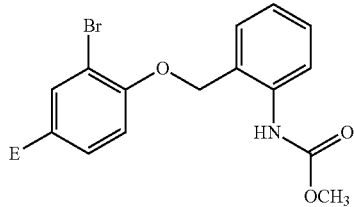
(HA1037)
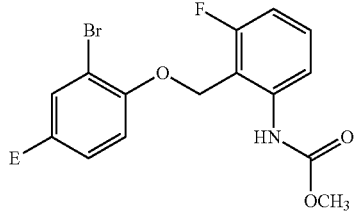
(HA1038)
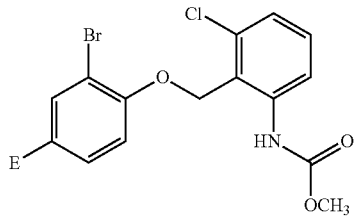
(HA1039)
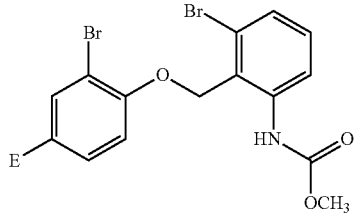
(HA1040)
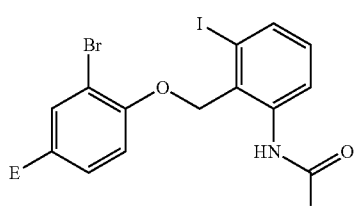
(HA1041)
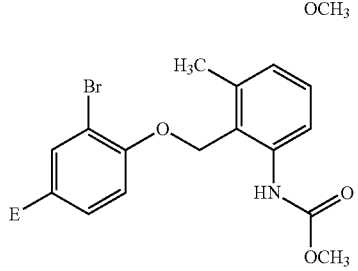
(HA1042)
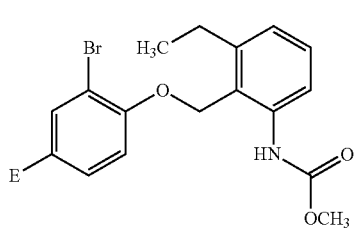
(HA1043)

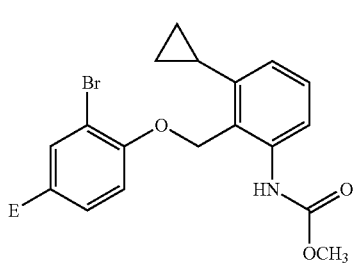
(HA1044)
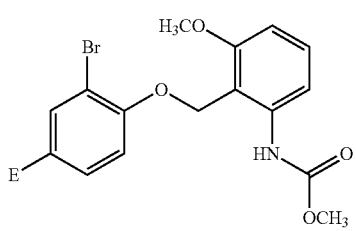
(HA1045)
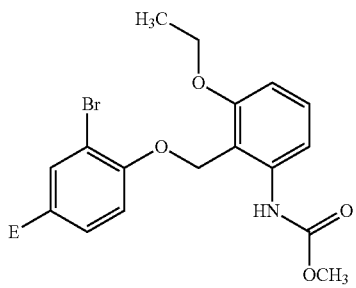
(HA1046)
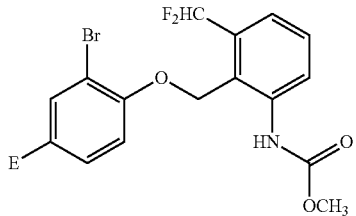
(HA1047)
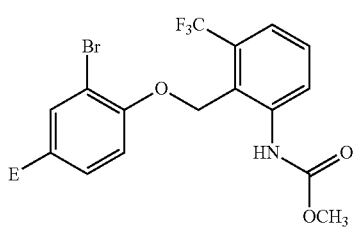
(HA1048)
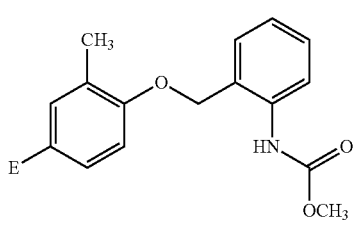
(HA1049)
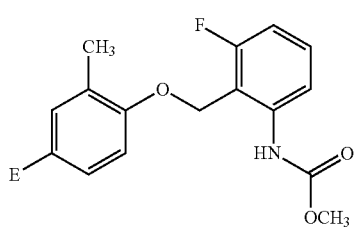
(HA1050)
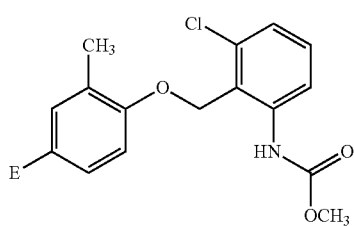
(HA1051)
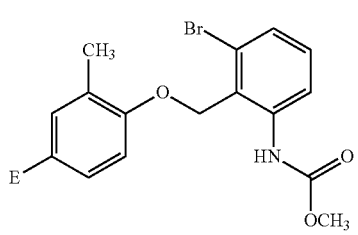
(HA1052)
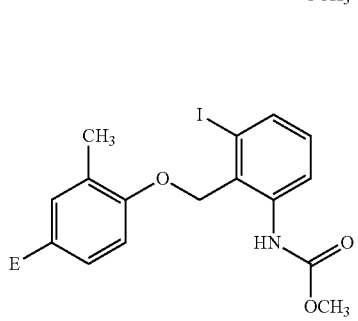
(HA1053)
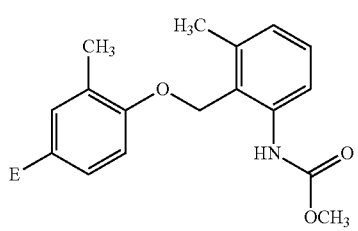
(HA1054)
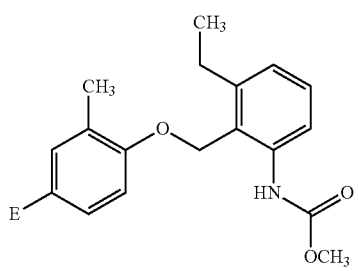
(HA1055)

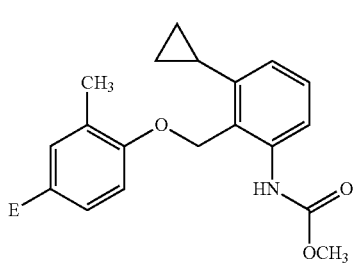
(HA1056)
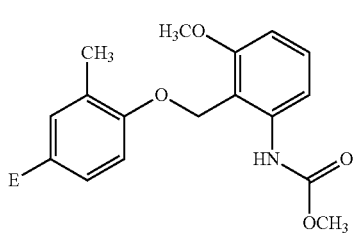
(HA1057)
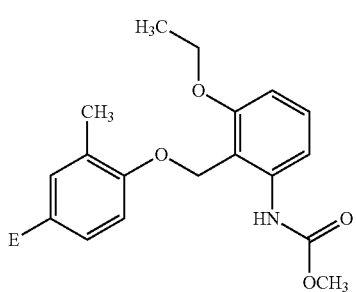
(HA1058)
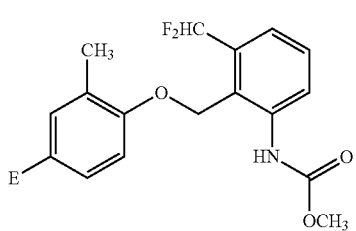
(HA1059)
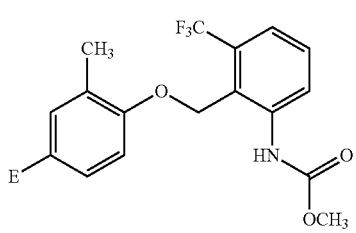
(HA1060)
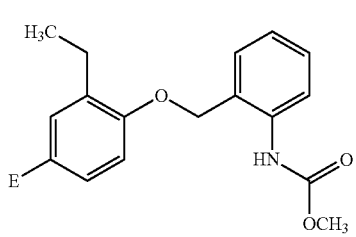
(HA1061)
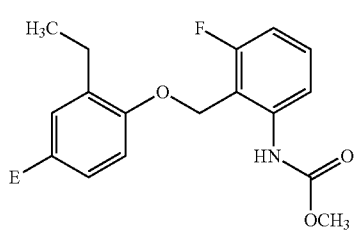
(HA1062)
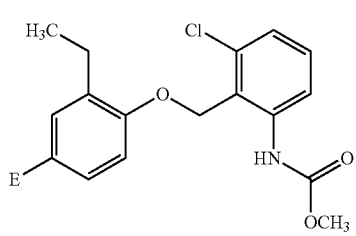
(HA1063)
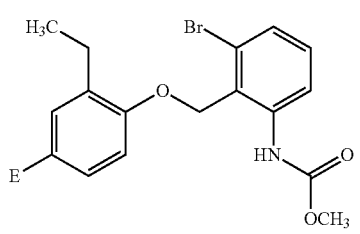
(HA1064)
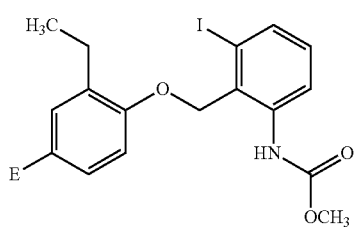
(HA1065)
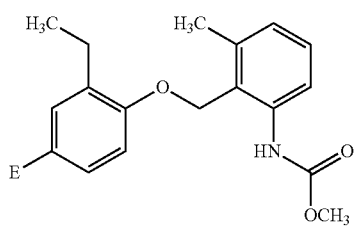
(HA1066)
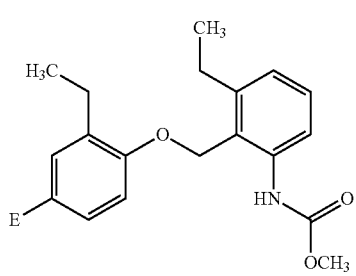
(HA1067)

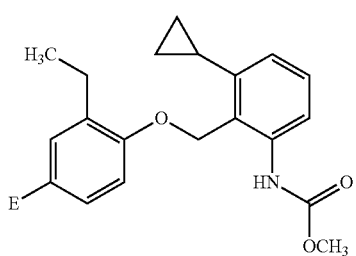
(HA1068)
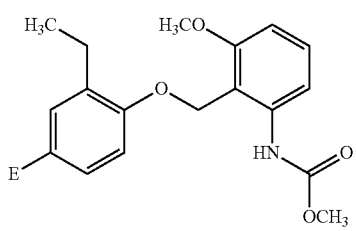
(HA1069)
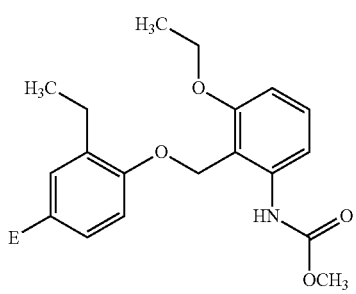
(HA1070)
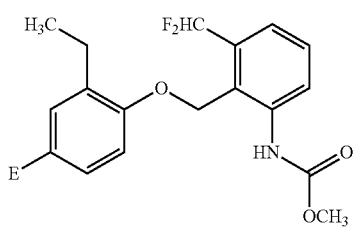
(HA1071)
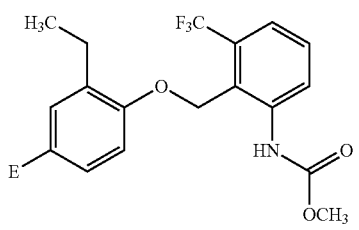
(HA1072)
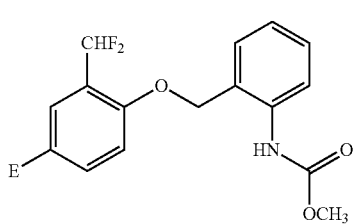
(HA1073)
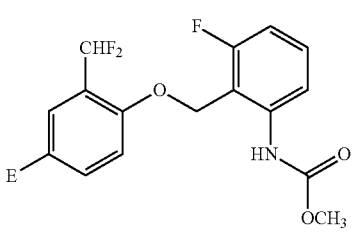
(HA1074)
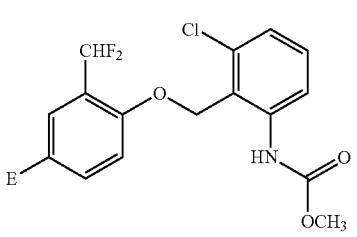
(HA1075)
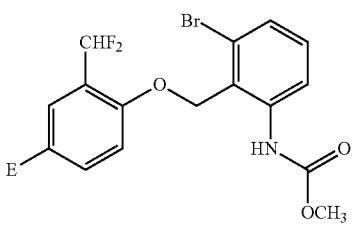
(HA1076)
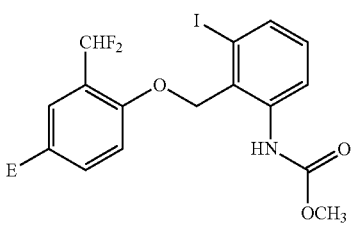
(HA1077)
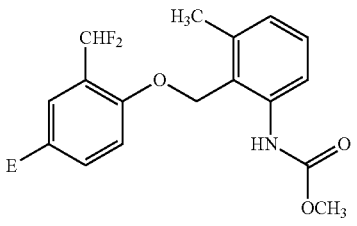
(HA1078)
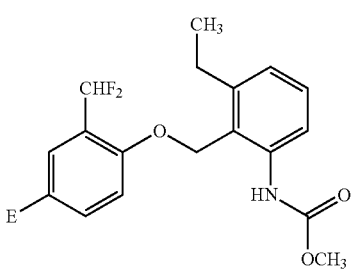
(HA1079)

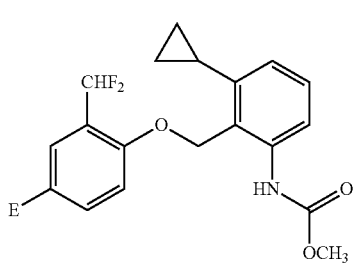
(HA1080)
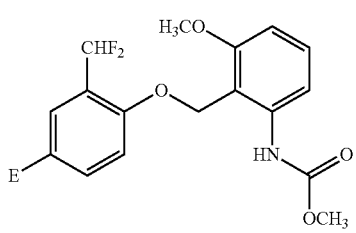
(HA1081)
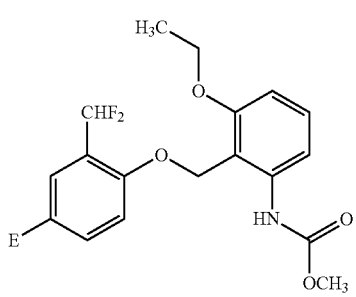
(HA1082)
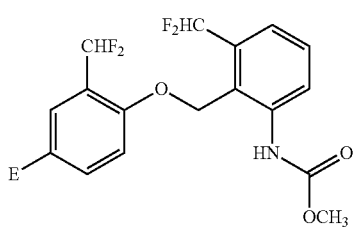
(HA1083)
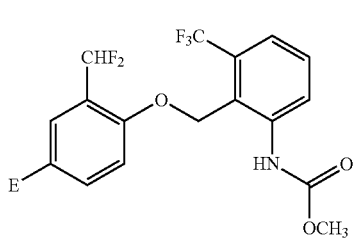
(HA1084)
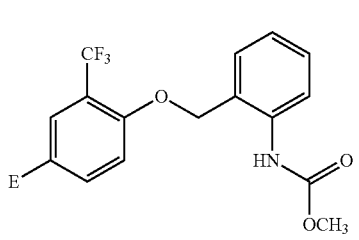
(HA1085)
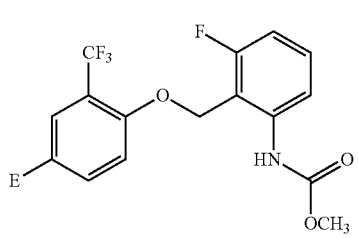
(HA1086)
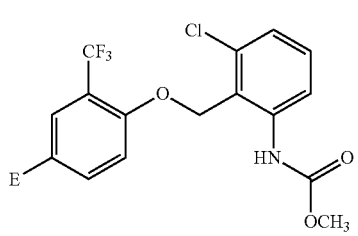
(HA1087)
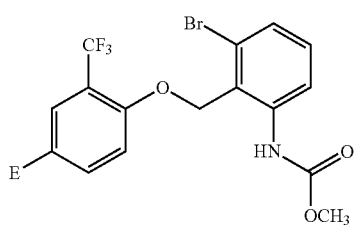
(HA1088)
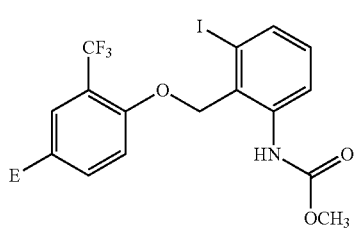
(HA1089)
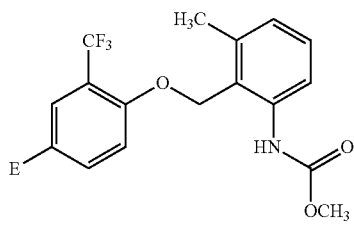
(HA1090)
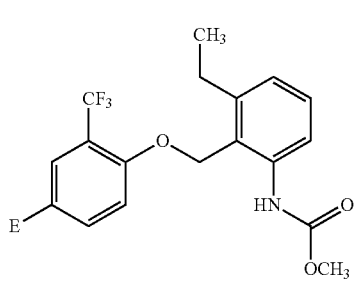
(HA1091)

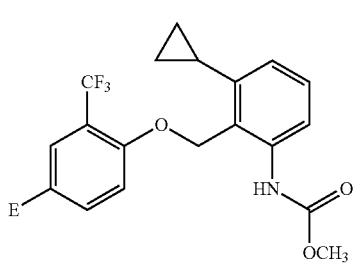
(HA1092)
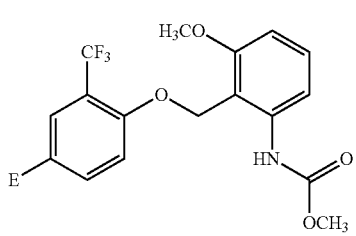
(HA1093)
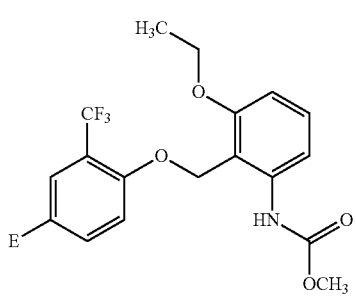
(HA1094)
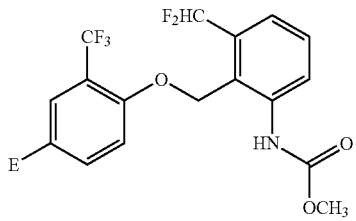
(HA1095)
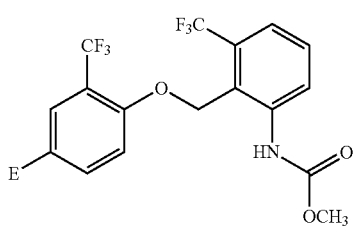
(HA1096)
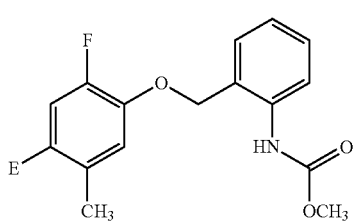
(HA4013)
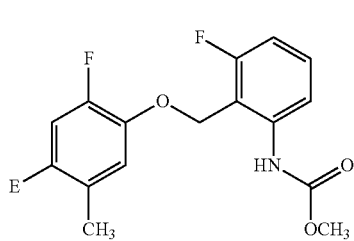
(HA4014)
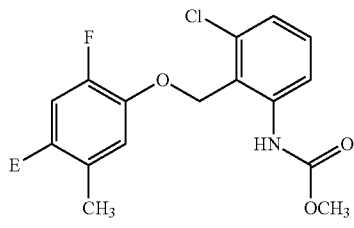
(HA4015)
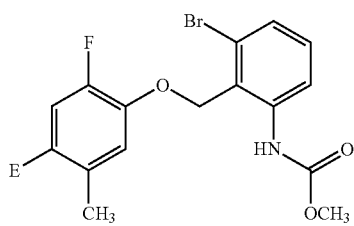
(HA4016)
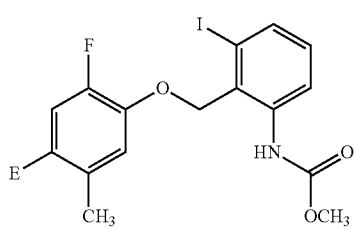
(HA4017)
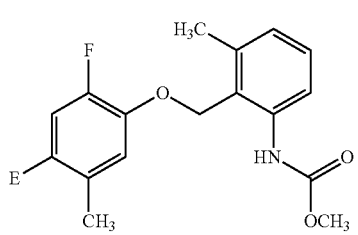
(HA4018)
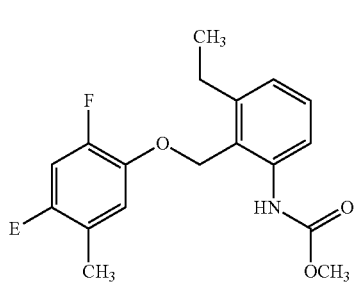
(HA4019)

(HA4020)
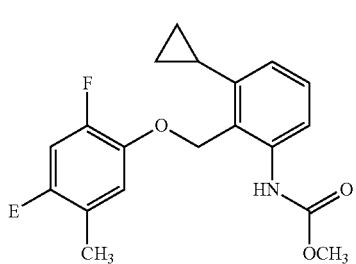
(HA4021)
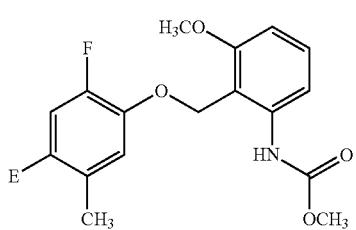
(HA4022)
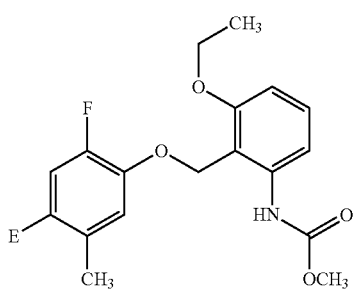
(HA4023)
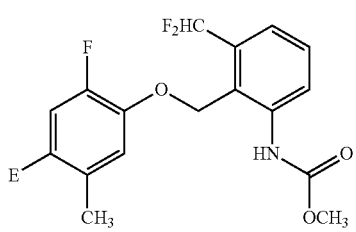
(HA4024)
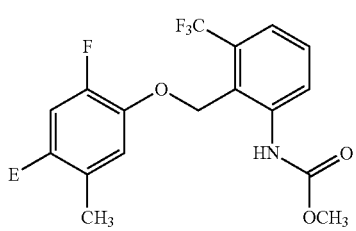
(HA4025)
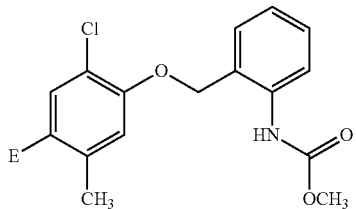
(HA4026)
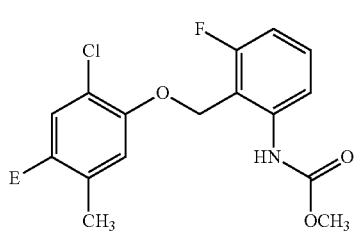
(HA4027)
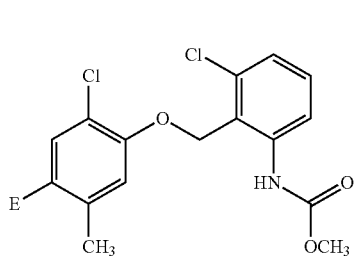
(HA4028)
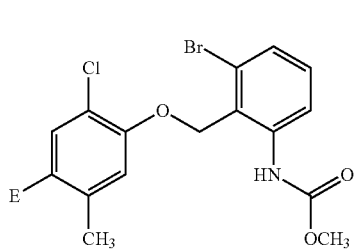
(HA4029)
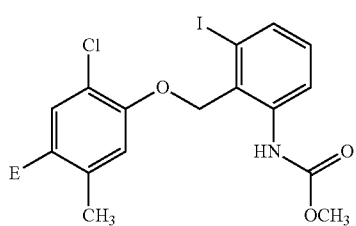
(HA4030)
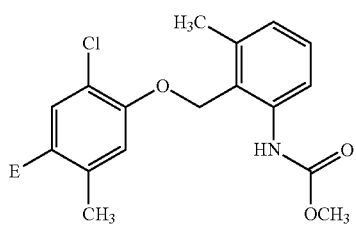
(HA4031)
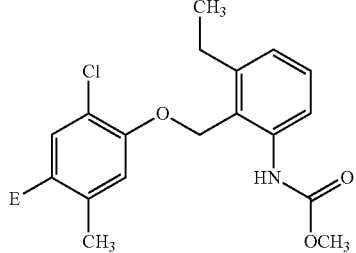

(HA4032) 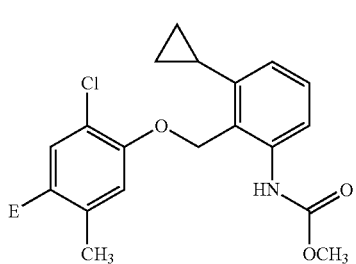
(HA4033) 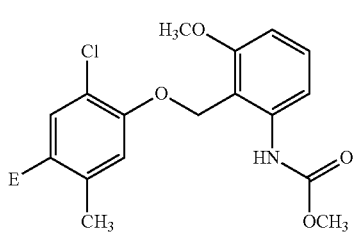
(HA4034) 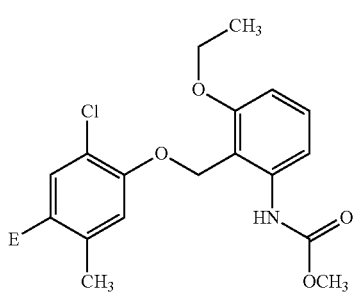
(HA4035) 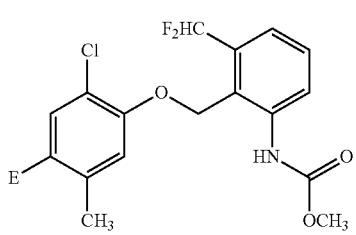
(HA4036) 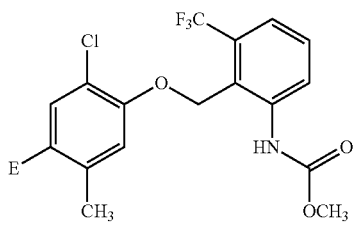
(HA4037) 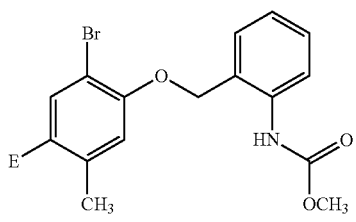
(HA4038) 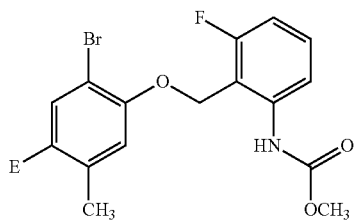
(HA4039) 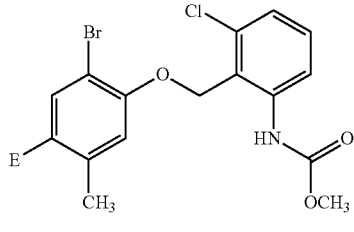
(HA4040) 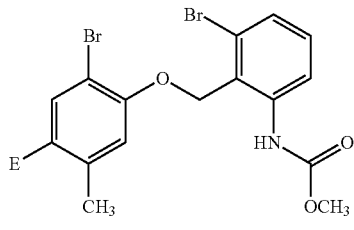
(HA4041) 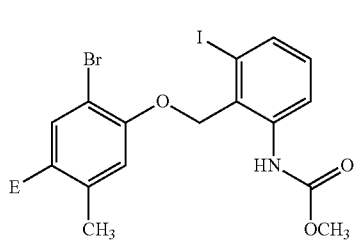
(HA4042) 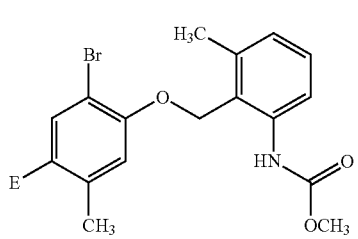
(HA4043) 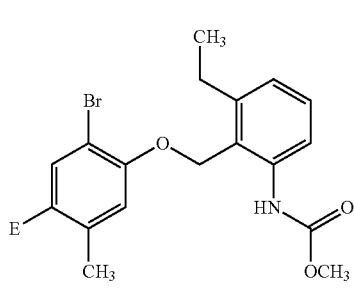

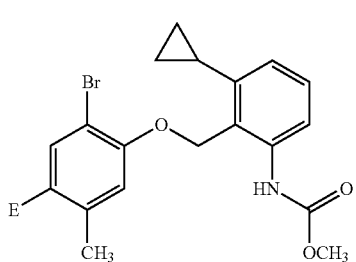
(HA4044)
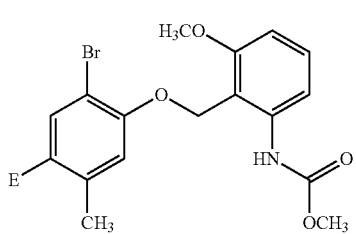
(HA4045)
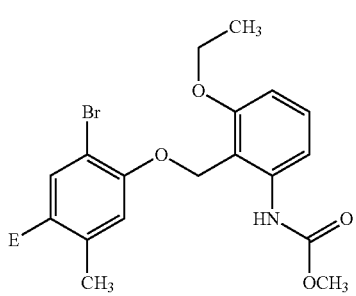
(HA4046)
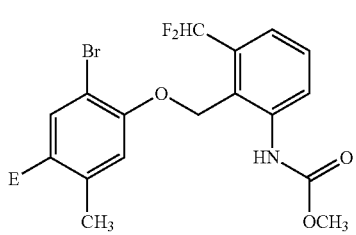
(HA4047)
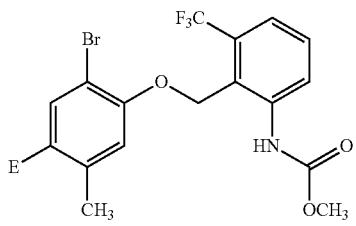
(HA4048)
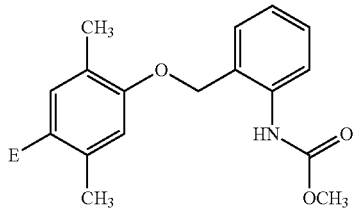
(HA4049)
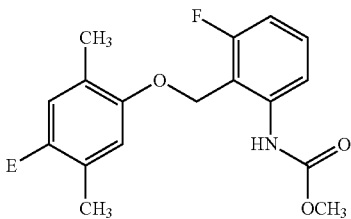
(HA4050)
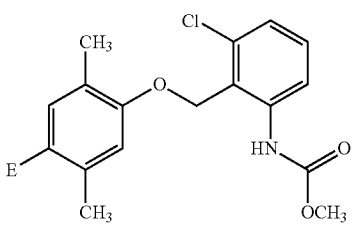
(HA4051)
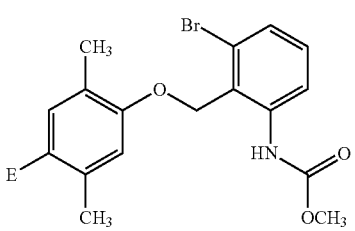
(HA4052)
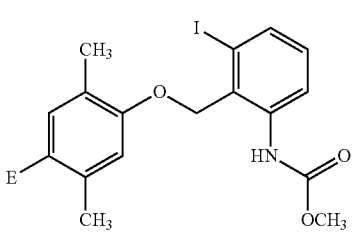
(HA4053)
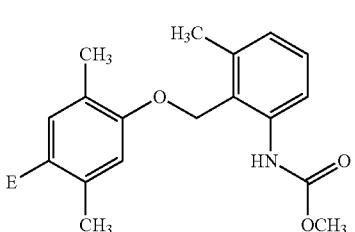
(HA4054)
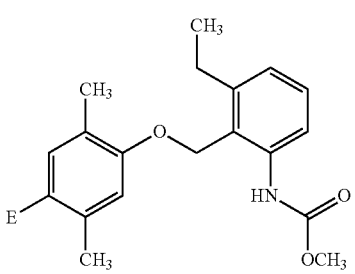
(HA4055)

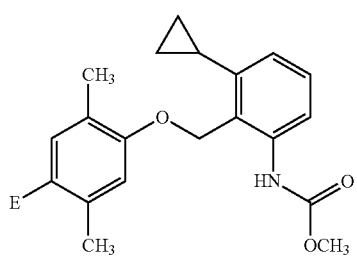
(HA4056)
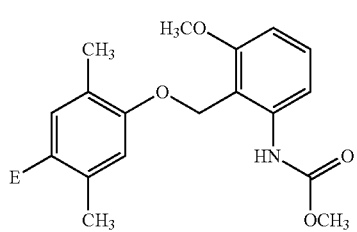
(HA4057)
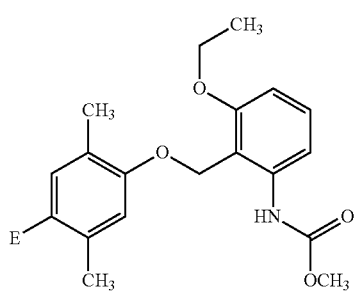
(HA4058)
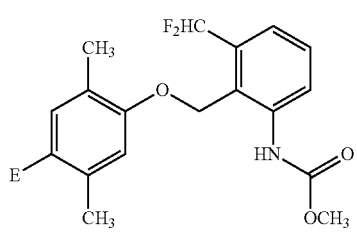
(HA4059)
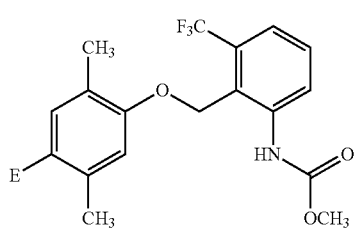
(HA4060)
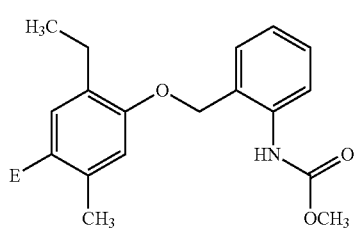
(HA4061)
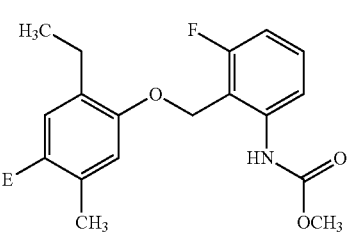
(HA4062)
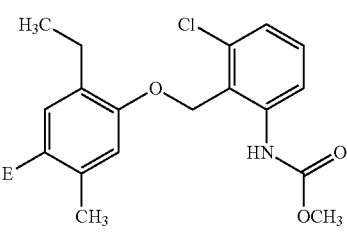
(HA4063)
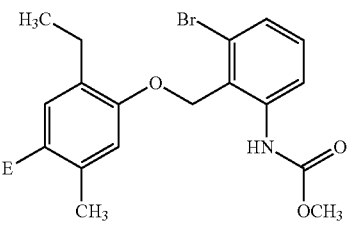
(HA4064)
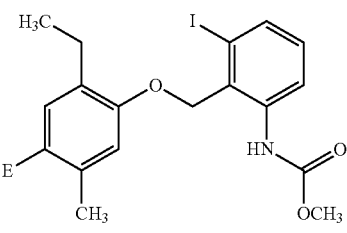
(HA4065)
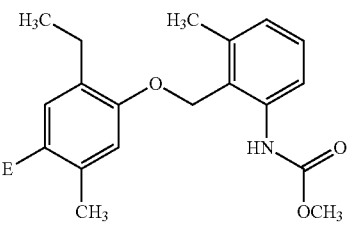
(HA4066)
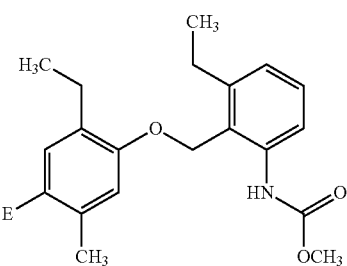
(HA4067)

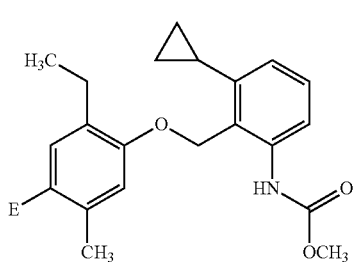
(HA4068)
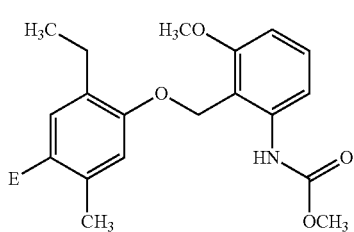
(HA4069)
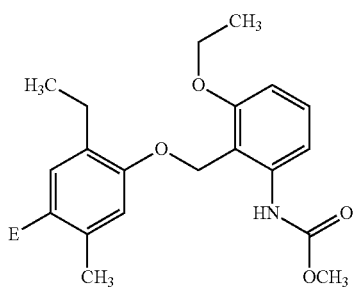
(HA4070)
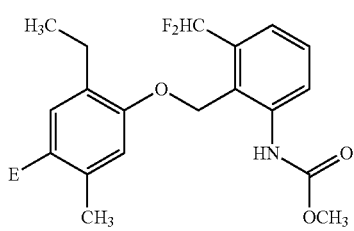
(HA4071)
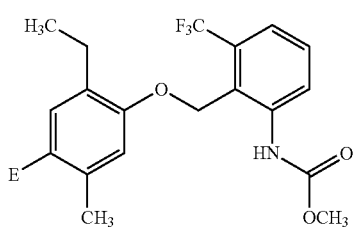
(HA4072)
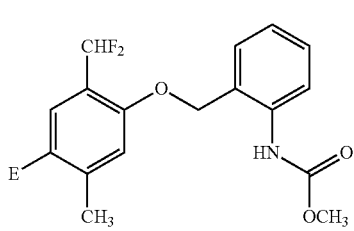
(HA4073)
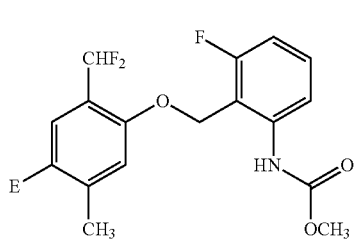
(HA4074)
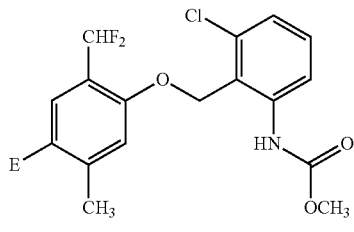
(HA4075)
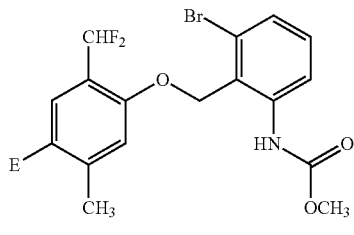
(HA4076)
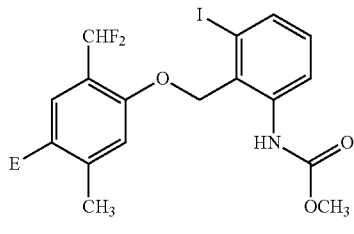
(HA4077)
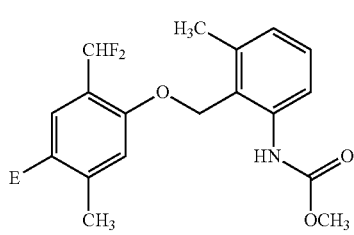
(HA4078)
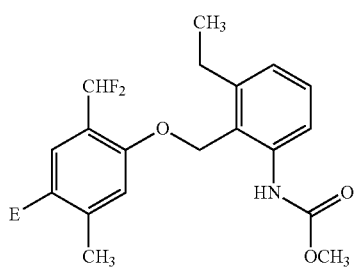
(HA4079)

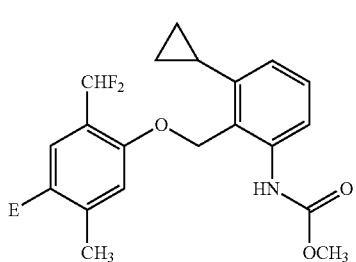
(HA4080)
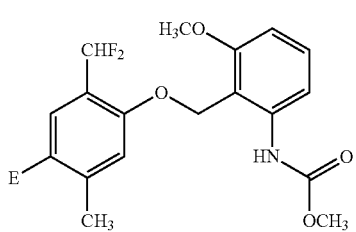
(HA4081)
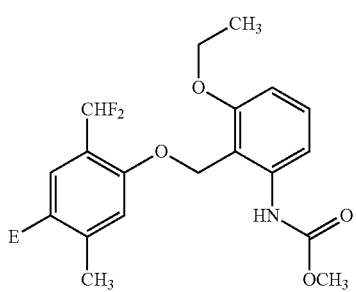
(HA4082)
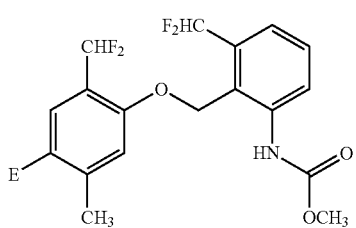
(HA4083)
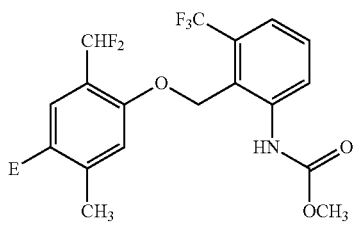
(HA4084)
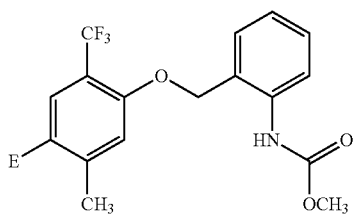
(HA4085)
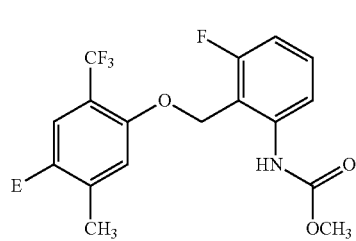
(HA4086)
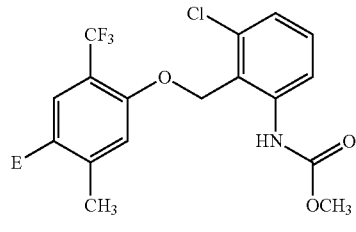
(HA4087)
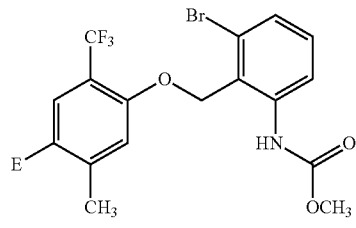
(HA4088)
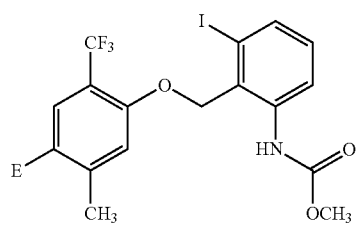
(HA4089)
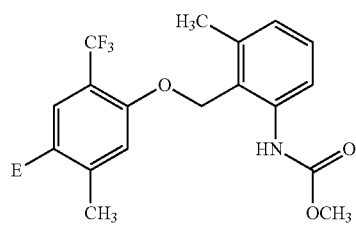
(HA4090)
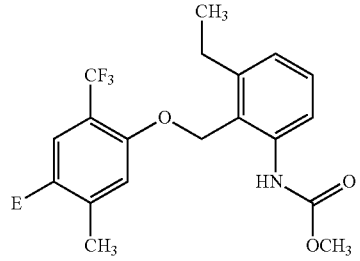
(HA4091)

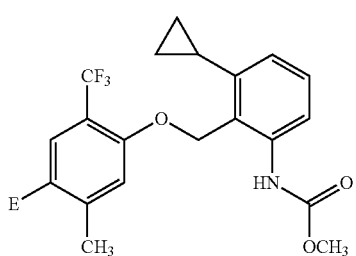
(HA4092)
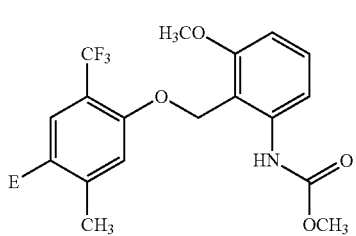
(HA4093)
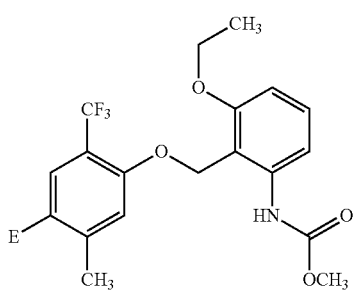
(HA4094)
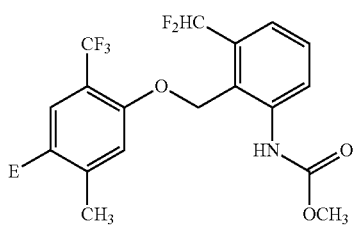
(HA4095)
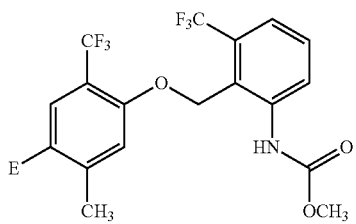
(HA4096)
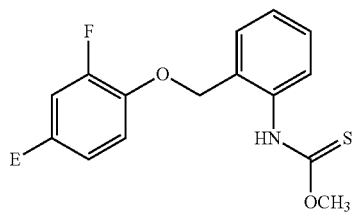
(HB1013)
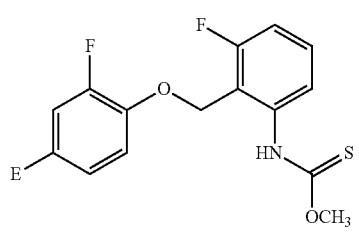
(HB1014)
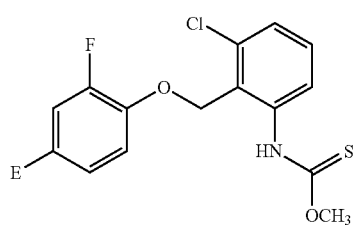
(HB1015)
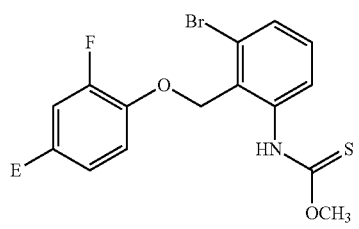
(HB1016)
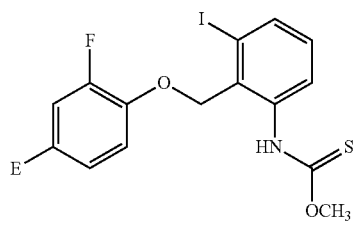
(HB1017)
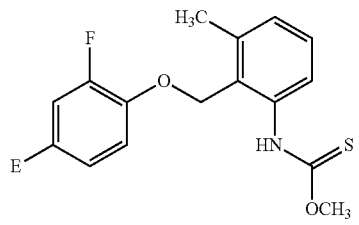
(HB1018)
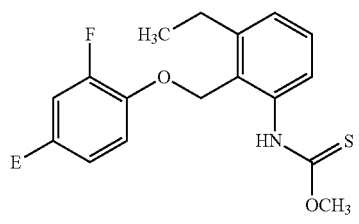
(HB1019)
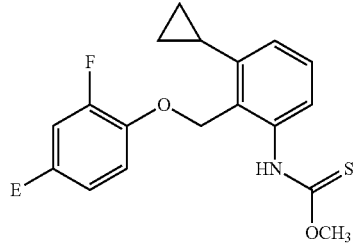
(HB1020)

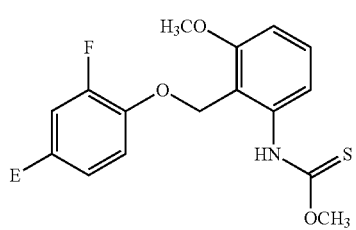
(HB1021)
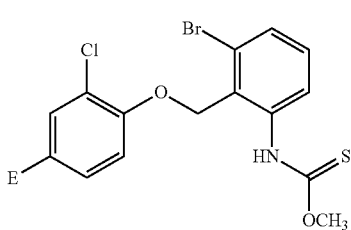
(HB1028)
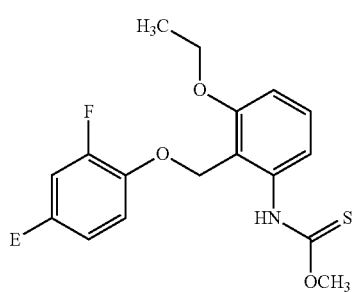
(HB1022)
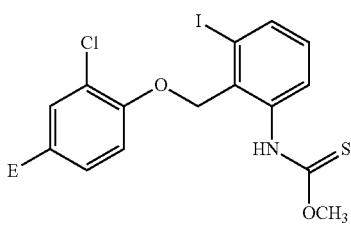
(HB1029)
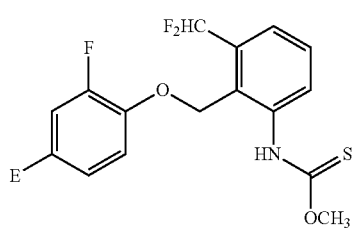
(HB1023)
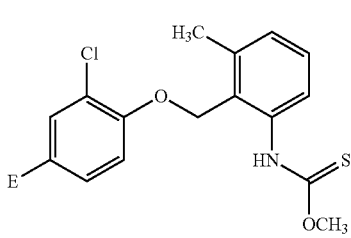
(HB1030)
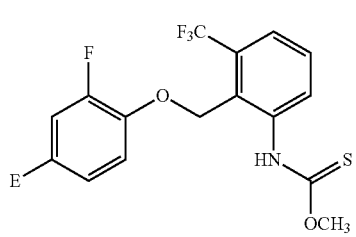
(HB1024)
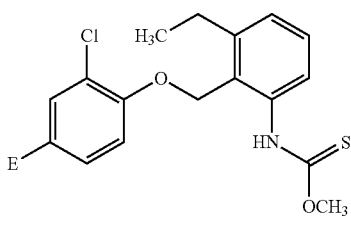
(HB1031)
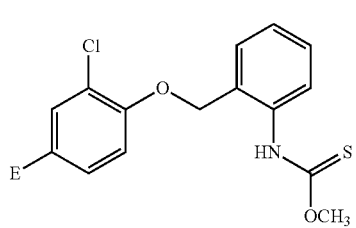
(HB1025)
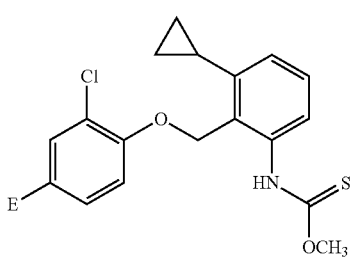
(HB1032)
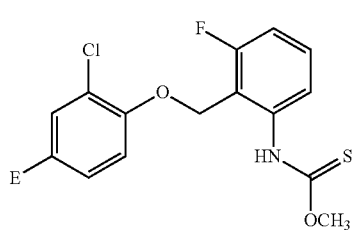
(HB1026)
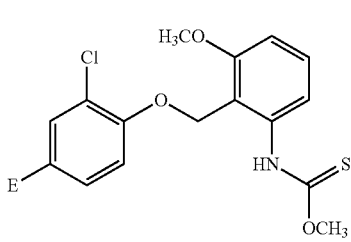
(HB1033)
(HB1027)

(HB1034) 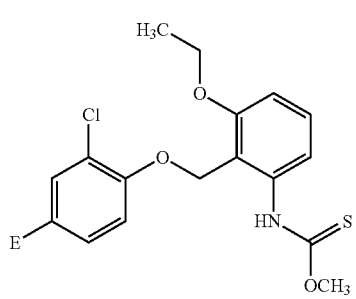
(HB1035) 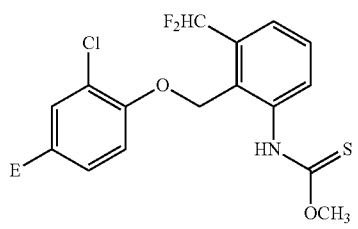
(HB1036) 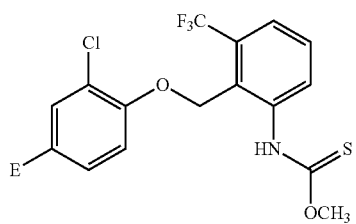
(HB1037) 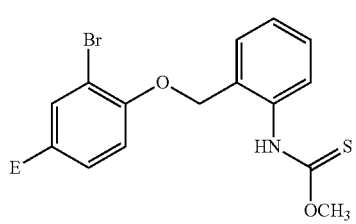
(HB1038) 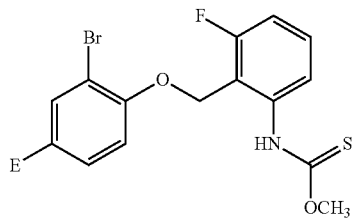
(HB1039) 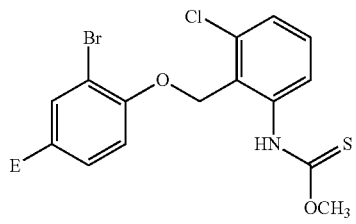
(HB1040) 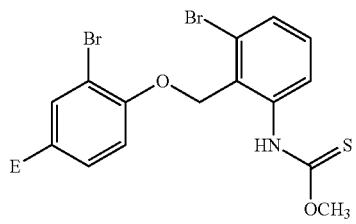
(HB1041) 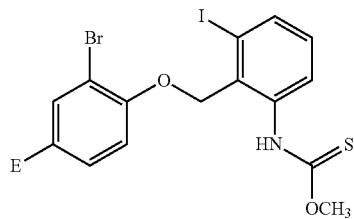
(HB1042) 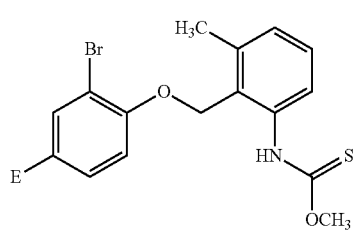
(HB1043) 
(HB1044) 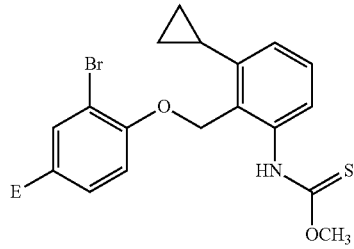
(HB1045) 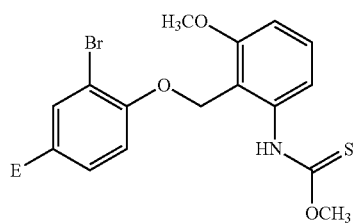
(HB1046) 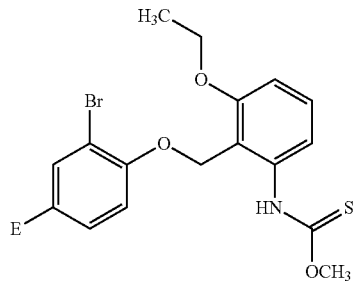

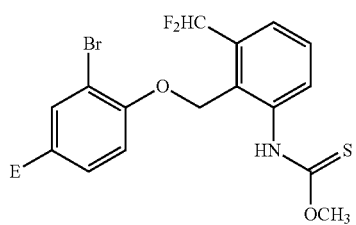
(HB1047)
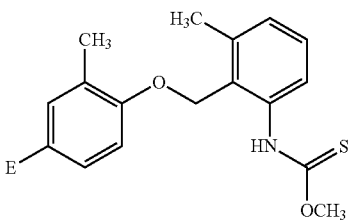
(HB1054)
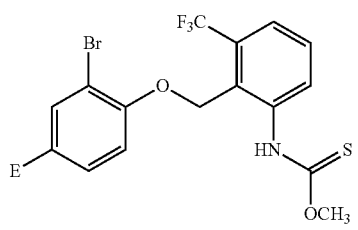
(HB1048)
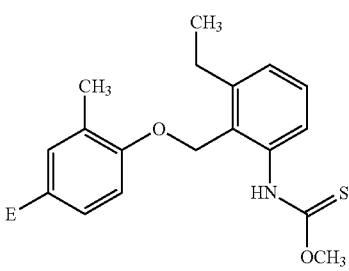
(HB1055)
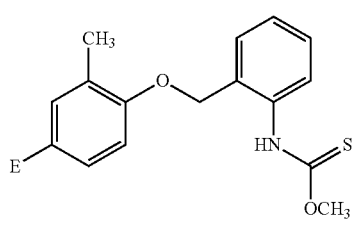
(HB1049)
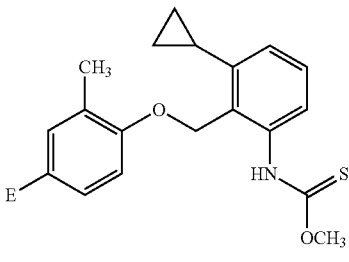
(HB1056)
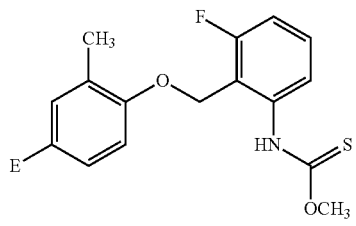
(HB1050)
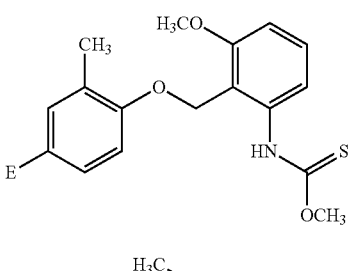
(HB1057)
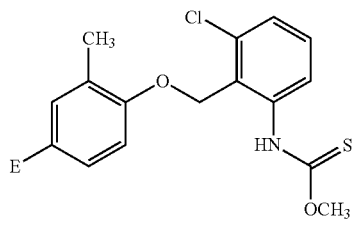
(HB1051)
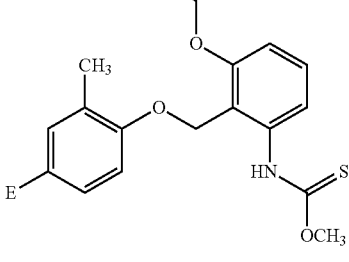
(HB1058)
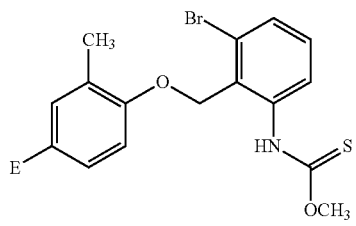
(HB1052)
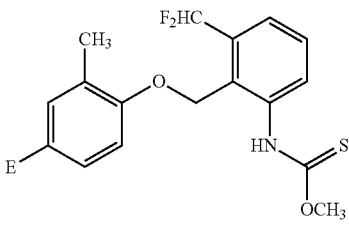
(HB1059)
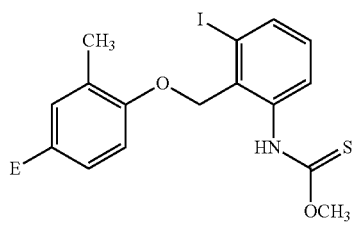
(HB1053)

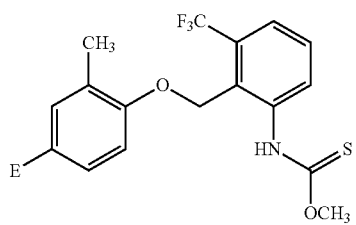 (HB1060)
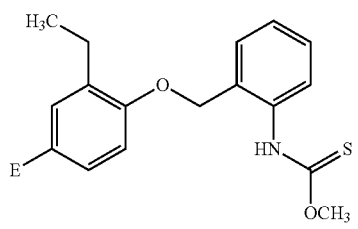 (HB1061)
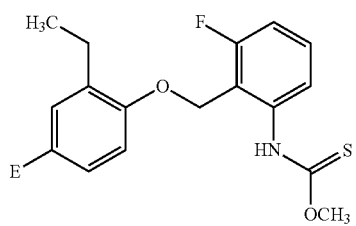 (HB1062)
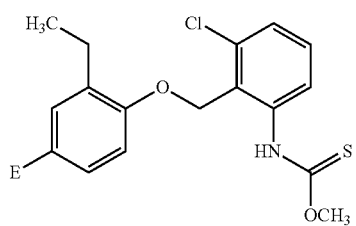 (HB1063)
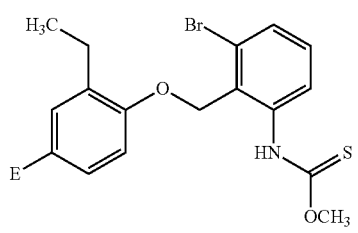 (HB1064)
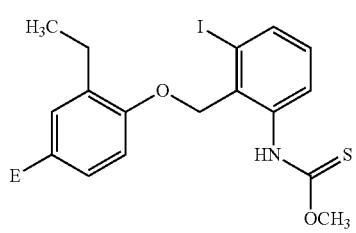 (HB1065)
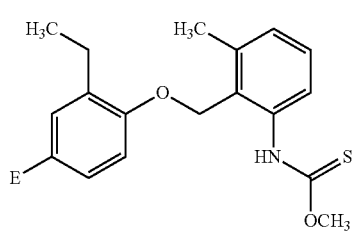 (HB1066)
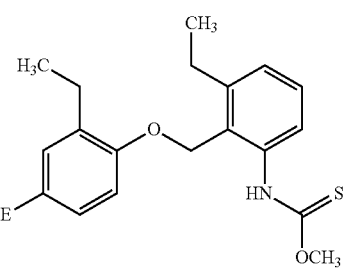 (HB1067)
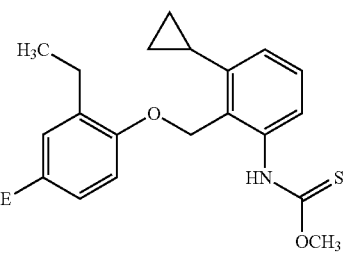 (HB1068)
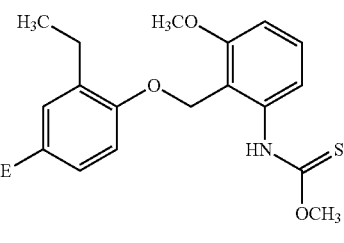 (HB1069)
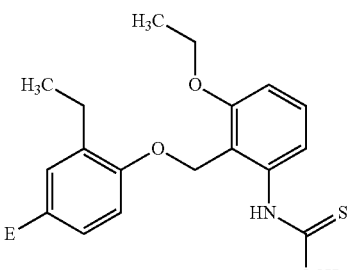 (HB1070)
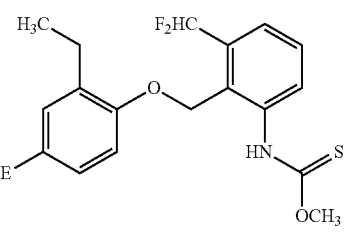 (HB1071)
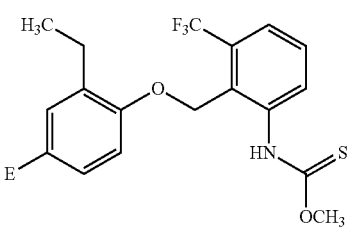 (HB1072)

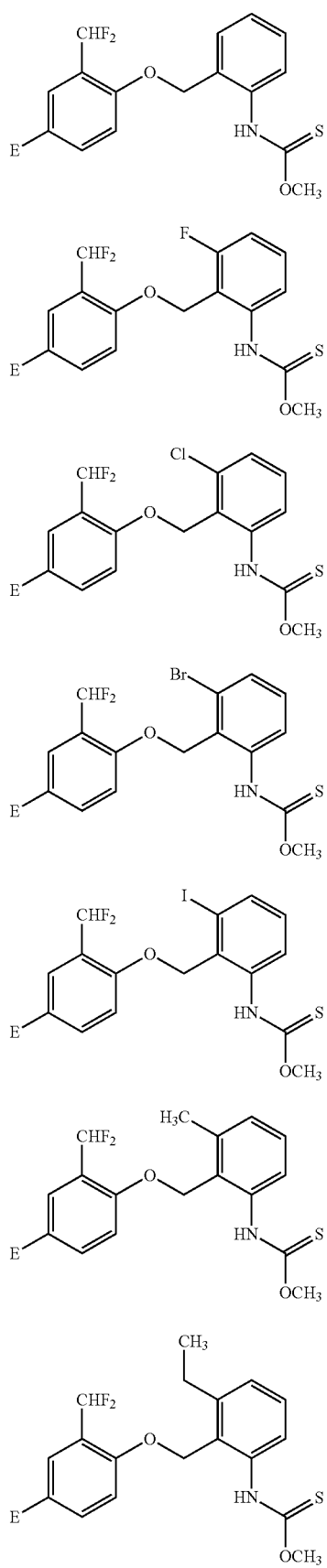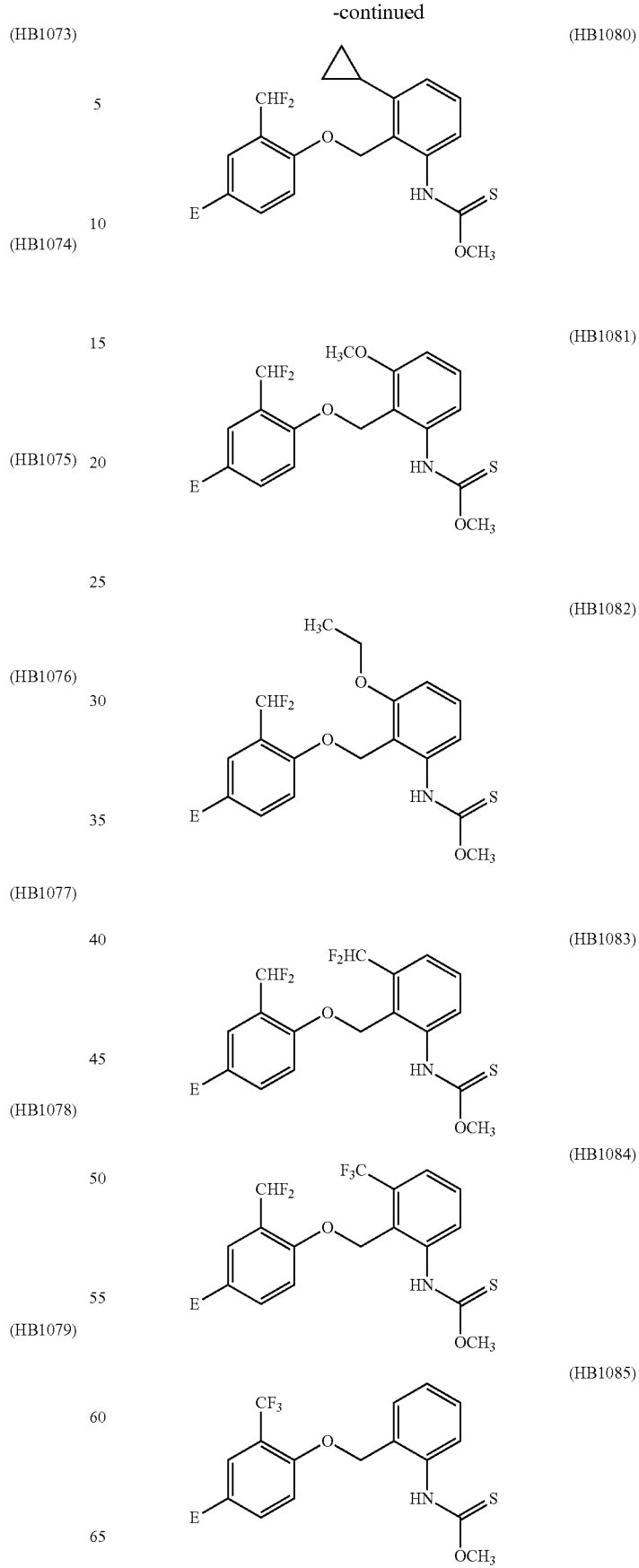

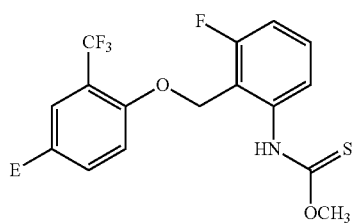 (HB1086)
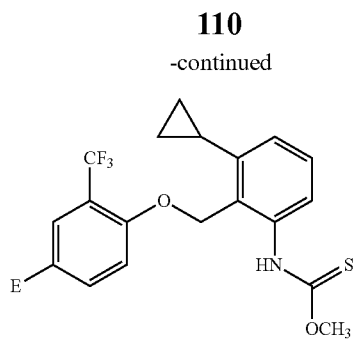 (HB1092)
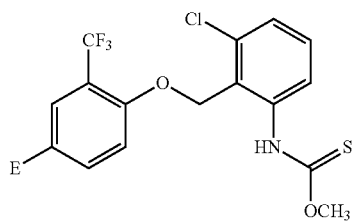 (HB1087)
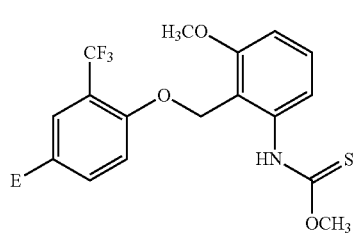 (HB1093)
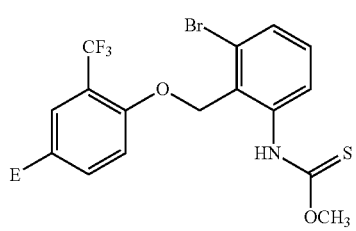 (HB1088)
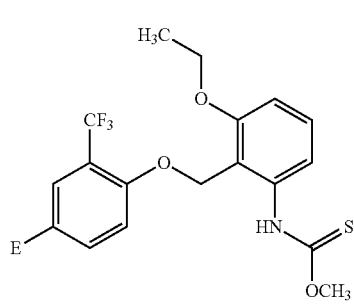 (HB1094)
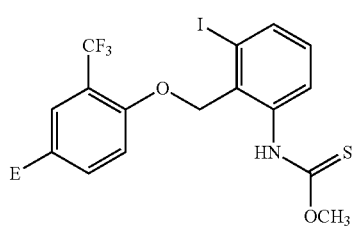 (HB1089)
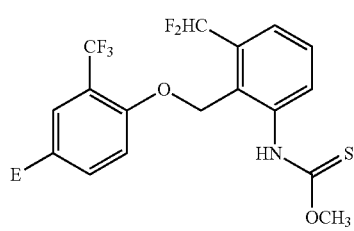 (HB1095)
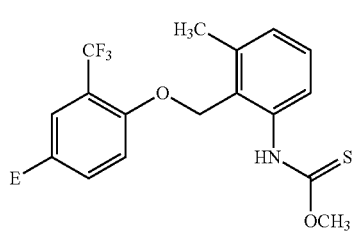 (HB1090)
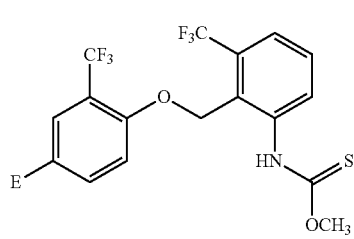 (HB1096)
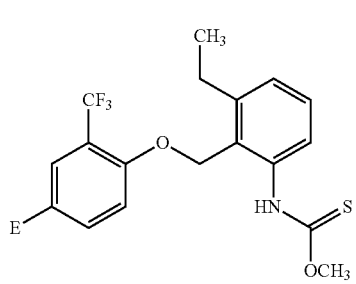 (HB1091)
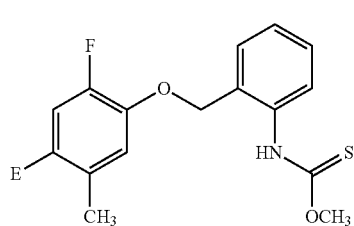 (HB4013)

-continued
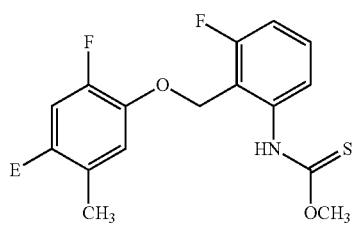 (HB4014)
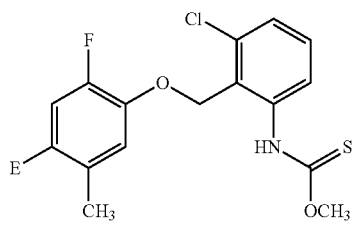 (HB4015)
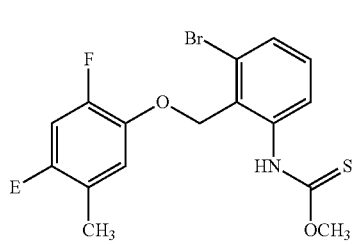 (HB4016)
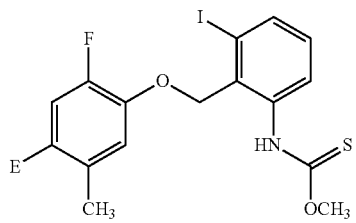 (HB4017)
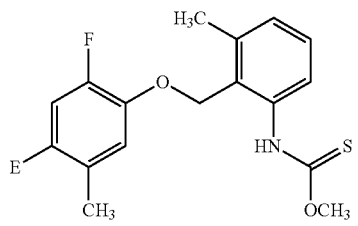 (HB4018)
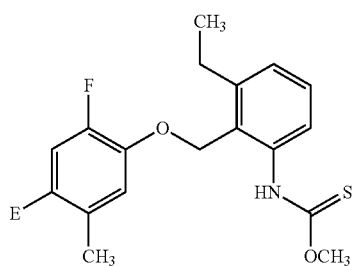 (HB4019)
-continued
 (HB4020)
 (HB4021)
 (HB4022)
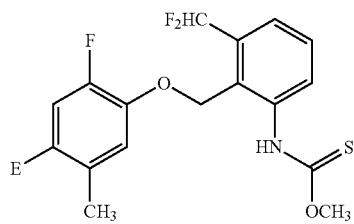 (HB4023)
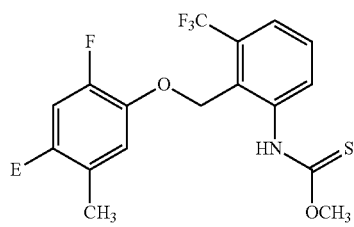 (HB4024)
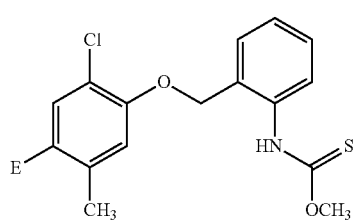 (HB4025)

(HB4026)
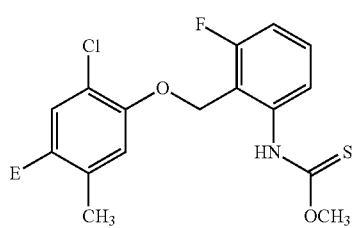
(HB4027)
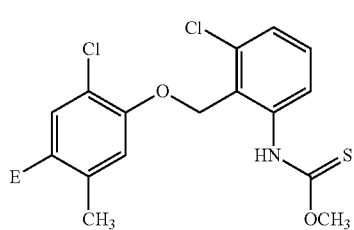
(HB4028)
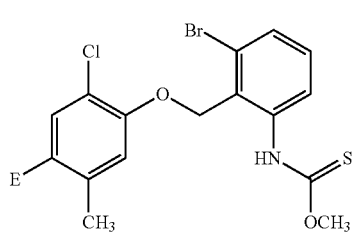
(HB4029)
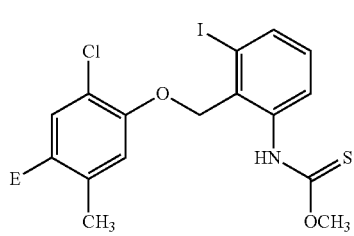
(HB4030)
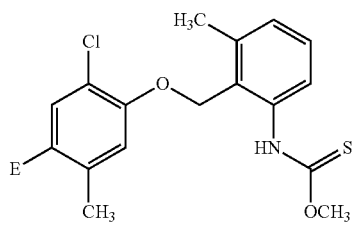
(HB4031)
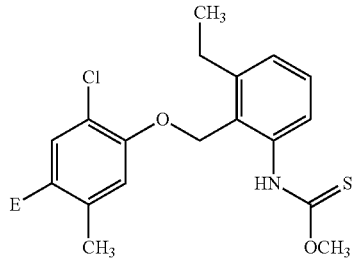
(HB4032)
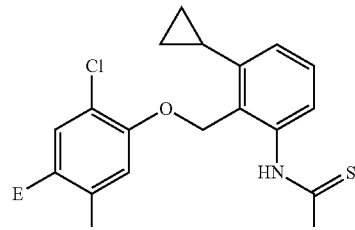
(HB4033)
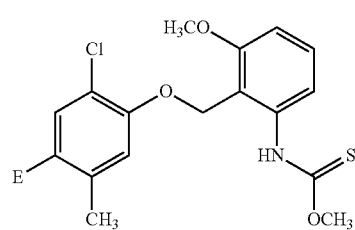
(HB4034)
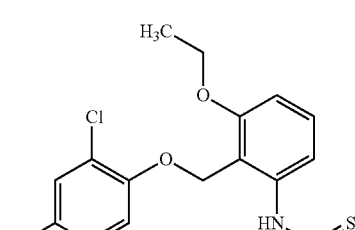
(HB4035)
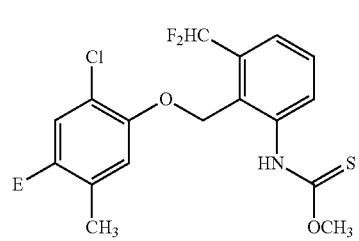
(HB4036)
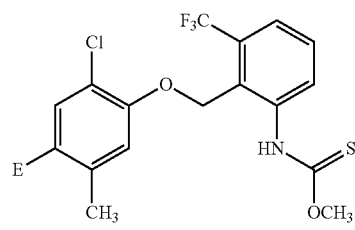
(HB4037)
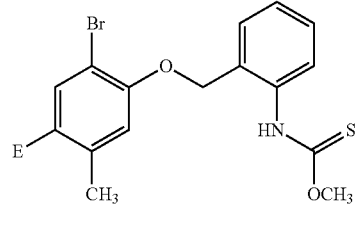

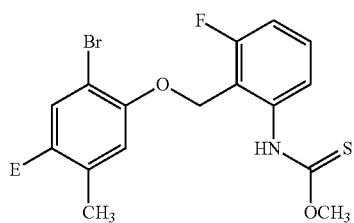
(HB4038)
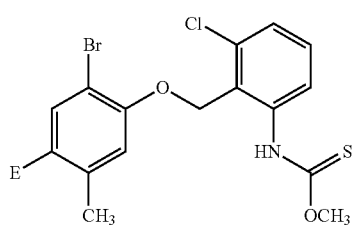
(HB4039)
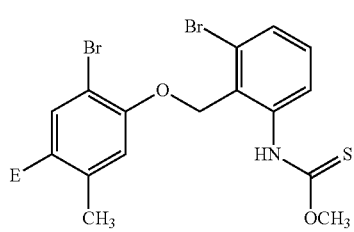
(HB4040)
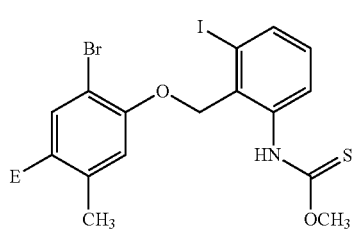
(HB4041)
(HB4042)
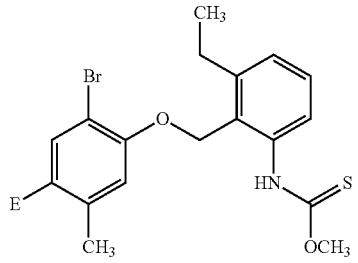
(HB4043)
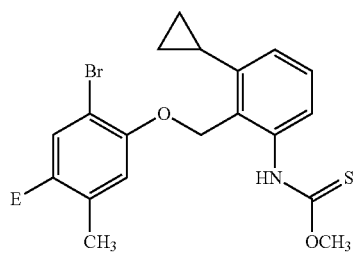
(HB4044)
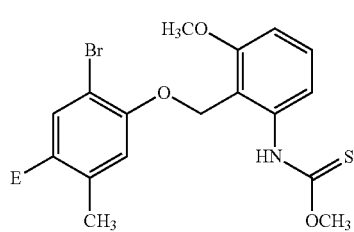
(HB4045)
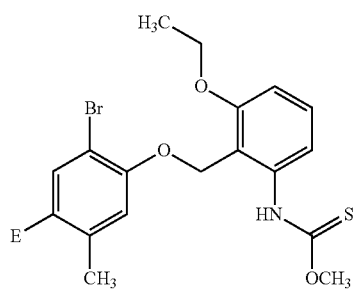
(HB4046)
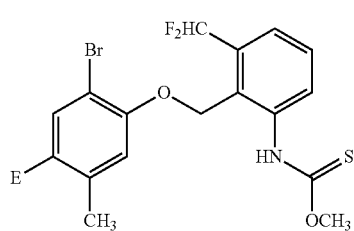
(HB4047)
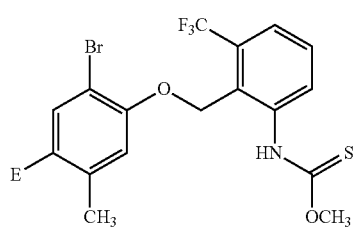
(HB4048)
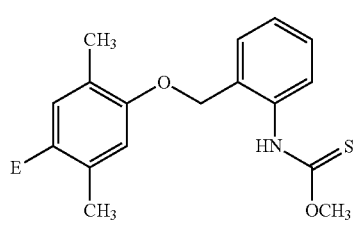
(HB4049)

(HB4050)
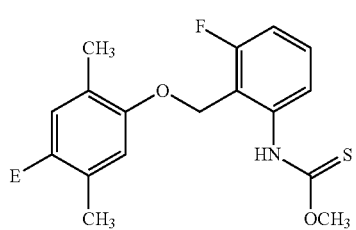
(HB4051)
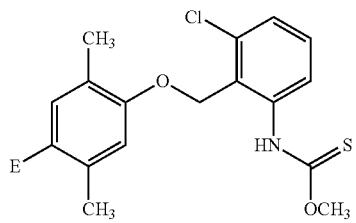
(HB4052)
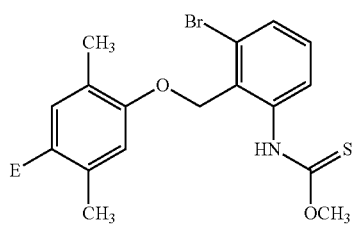
(HB4053)
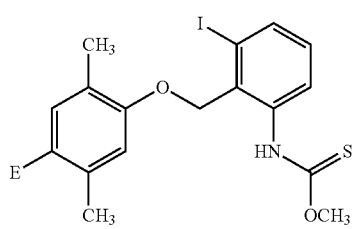
(HB4054)
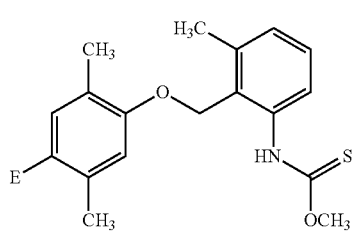
(HB4055)
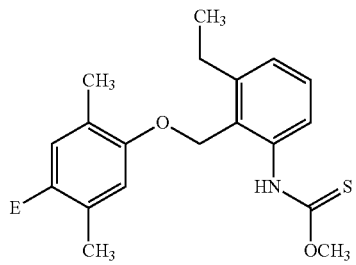
(HB4056)
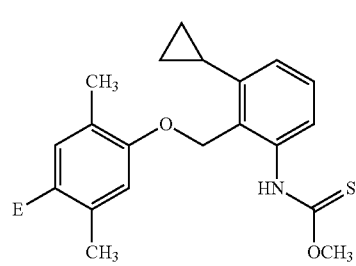
(HB4057)
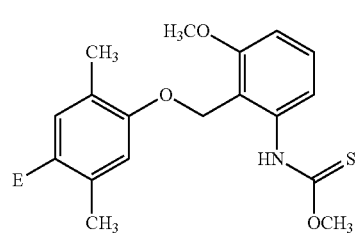
(HB4058)
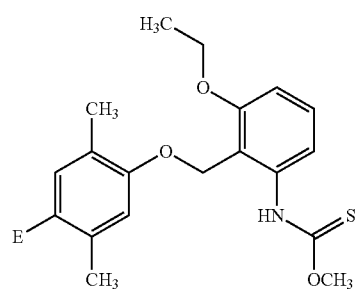
(HB4059)
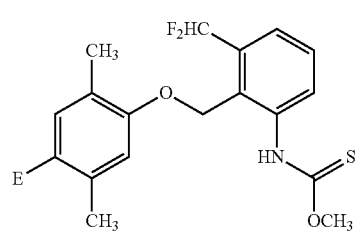
(HB4060)
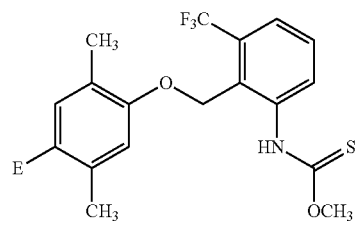
(HB4061)
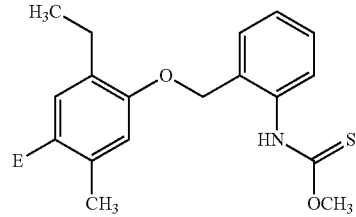

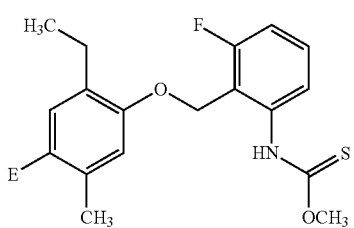 (HB4062)
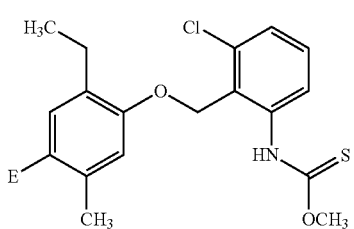 (HB4063)
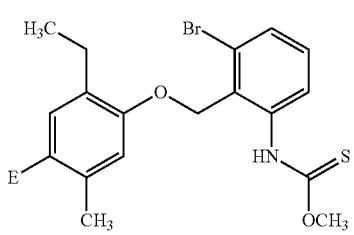 (HB4064)
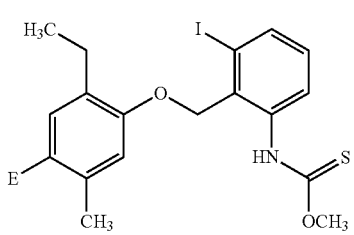 (HB4065)
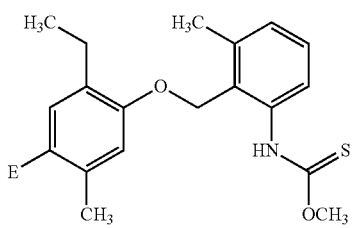 (HB4066)
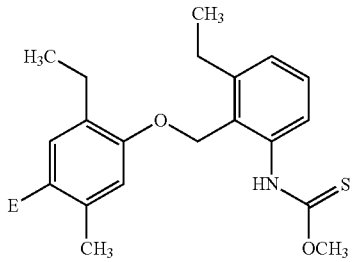 (HB4067)
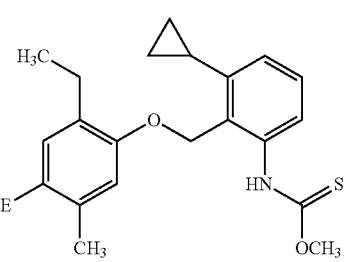 (HB4068)
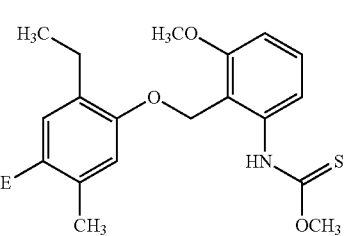 (HB4069)
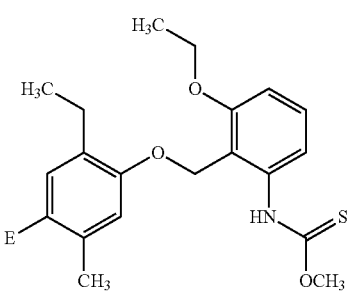 (HB4070)
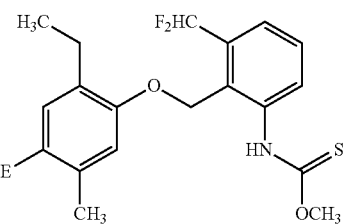 (HB4071)
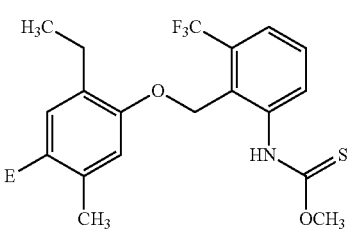 (HB4072)
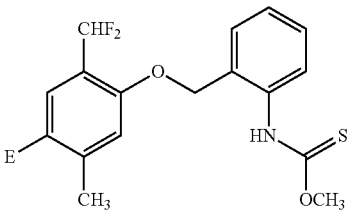 (HB4073)

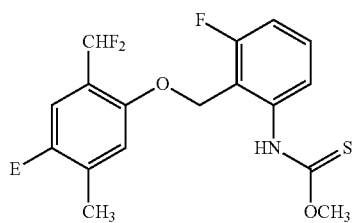
(HB4074)
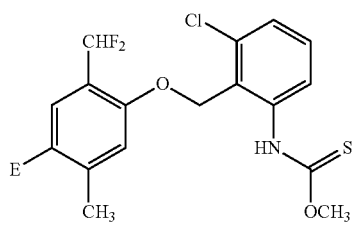
(HB4075)
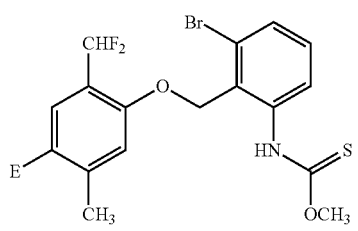
(HB4076)
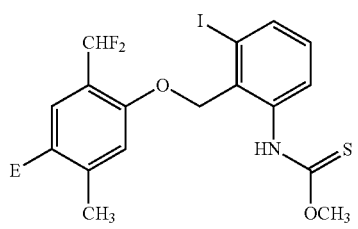
(HB4077)
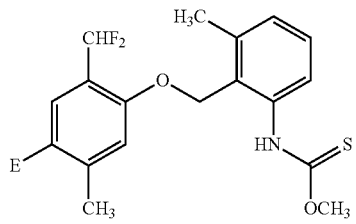
(HB4078)
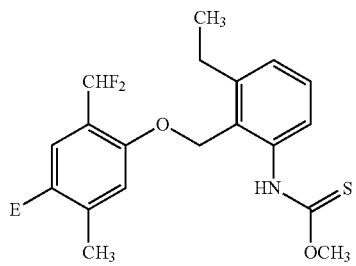
(HB4079)
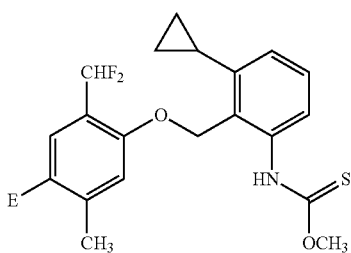
(HB4080)
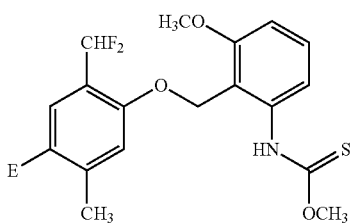
(HB4081)
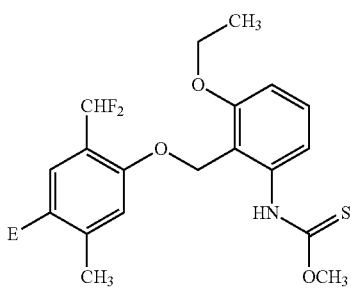
(HB4082)
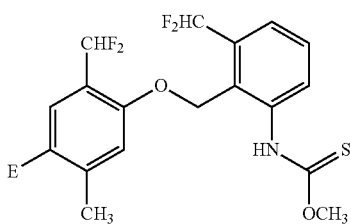
(HB4083)
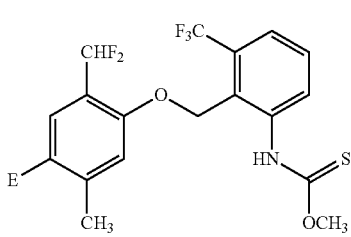
(HB4084)
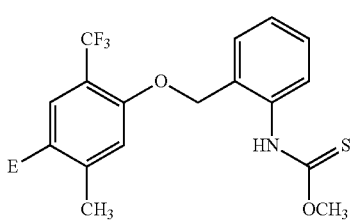
(HB4085)

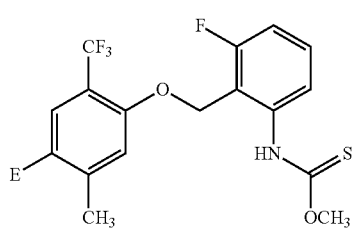
(HB4086)
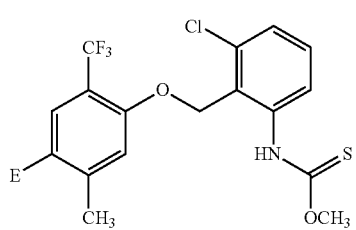
(HB4087)
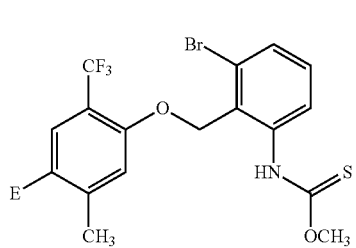
(HB4088)
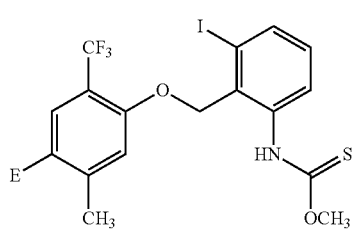
(HB4089)
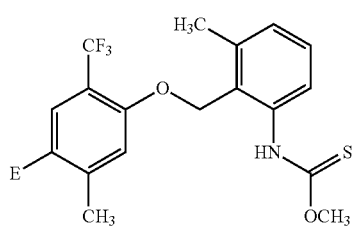
(HB4090)
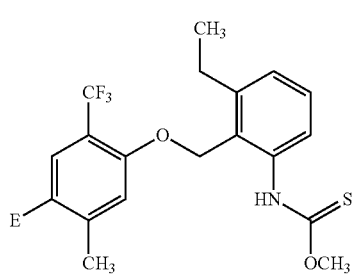
(HB4091)
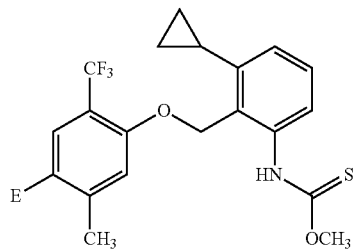
(HB4092)
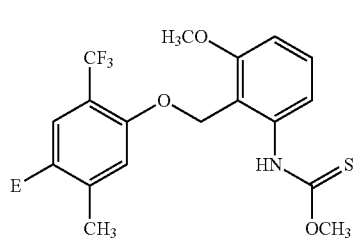
(HB4093)
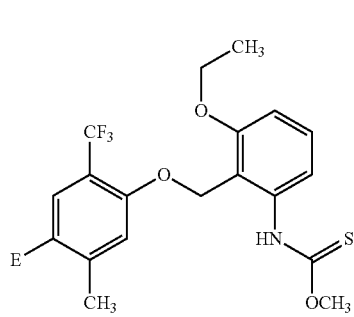
(HB4094)
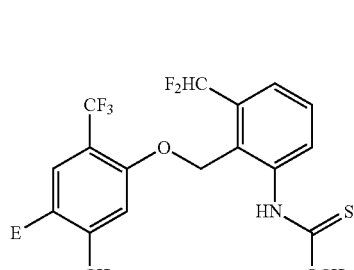
(HB4095)
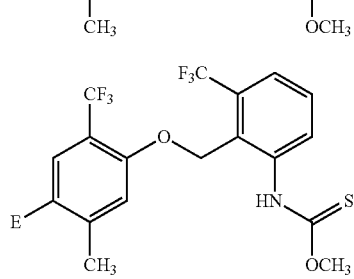
(HB4096)
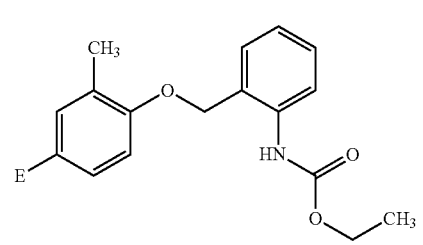
(HC1001)

-continued
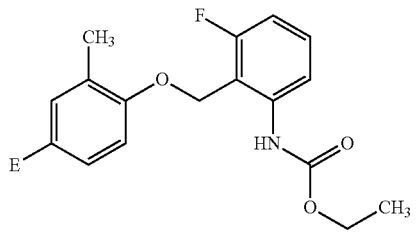 (HC1002)
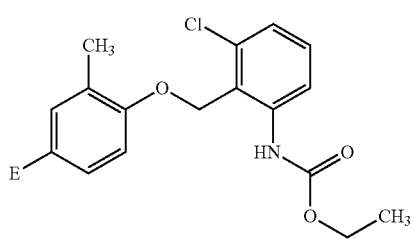 (HC1003)
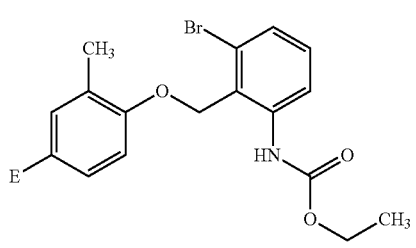 (HC1004)
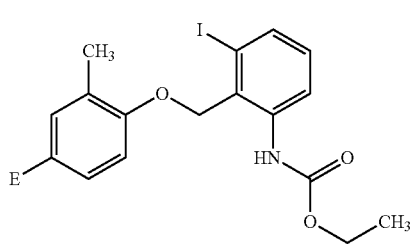 (HC1005)
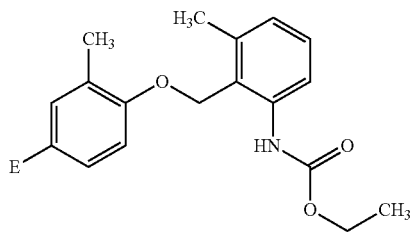 (HC1006)
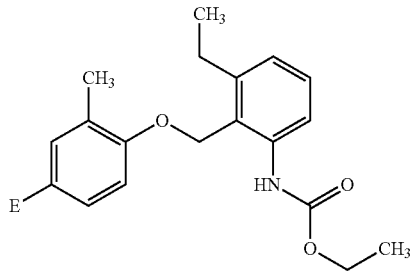 (HC1007)
-continued
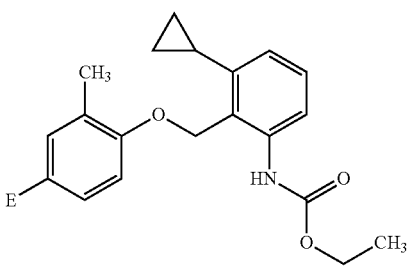 (HC1008)
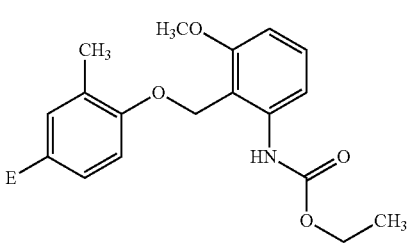 (HC1009)
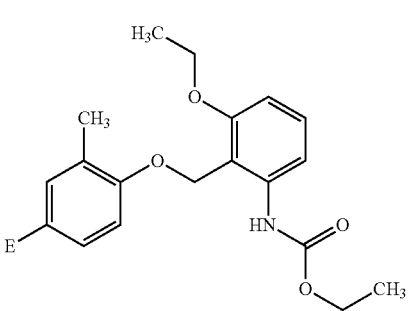 (HC1010)
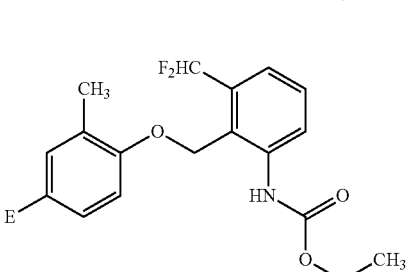 (HC1011)
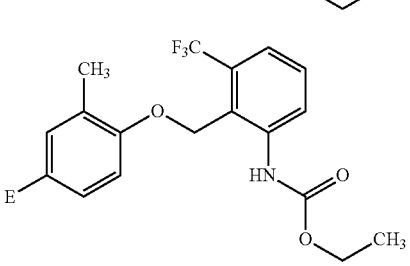 (HC1012)
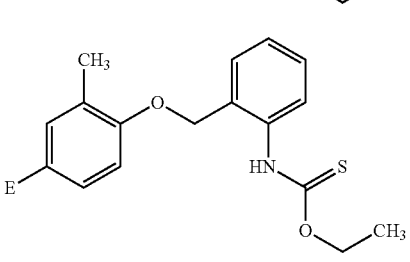 (HC1013)

-continued
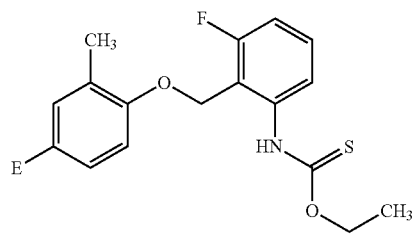 (HC1014)
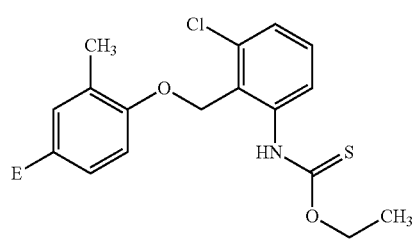 (HC1015)
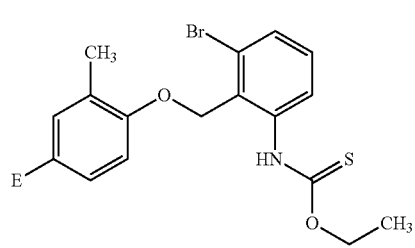 (HC1016)
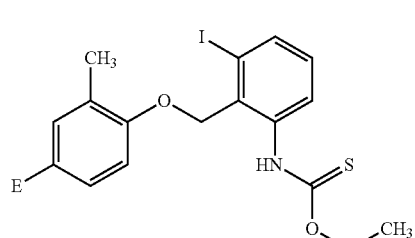 (HC1017)
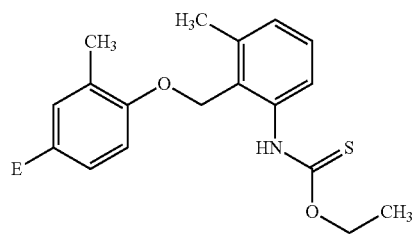 (HC1018)
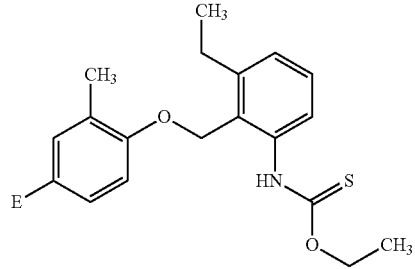 (HC1019)
-continued
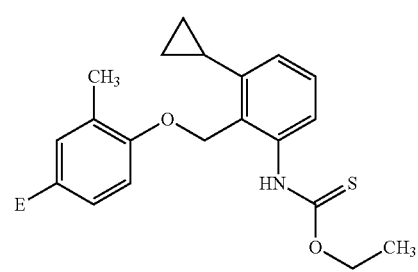 (HC1020)
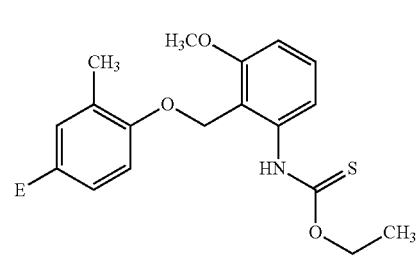 (HC1021)
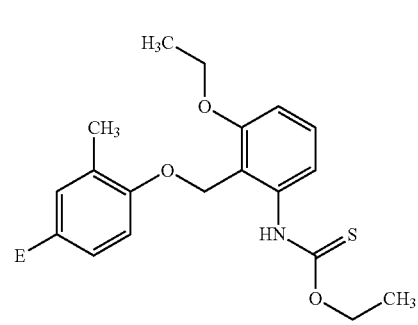 (HC1022)
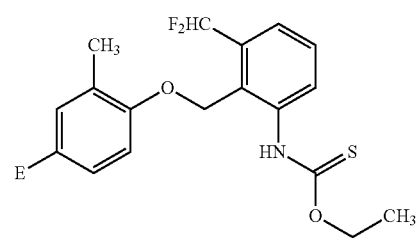 (HC1023)
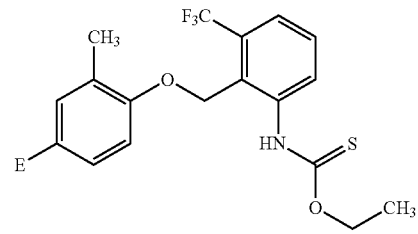 (HC1024)
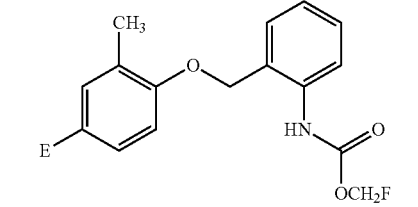 (HC1025)

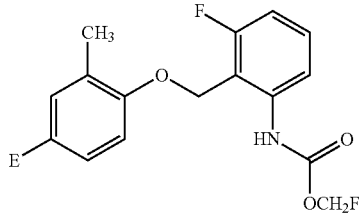
(HC1026)
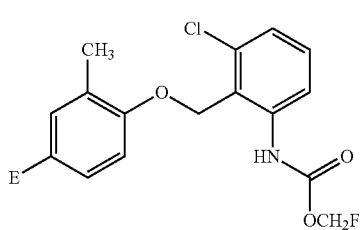
(HC1027)
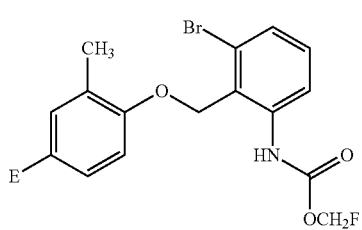
(HC1028)
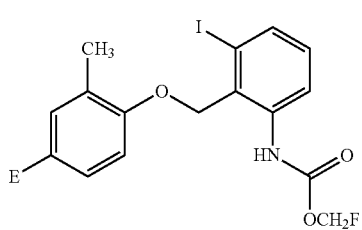
(HC1029)
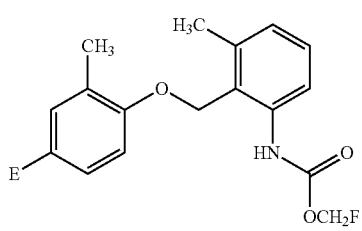
(HC1030)
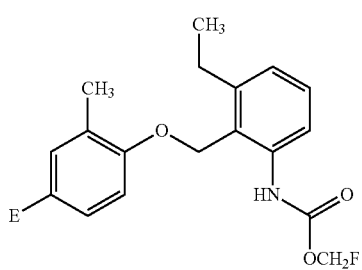
(HC1031)
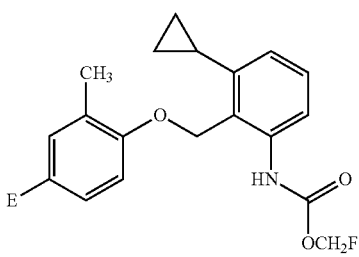
(HC1032)
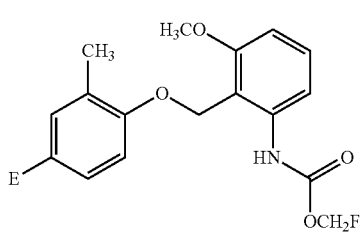
(HC1033)
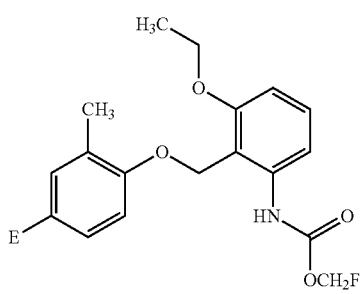
(HC1034)
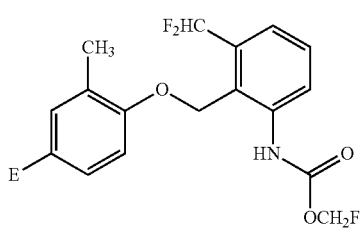
(HC1035)
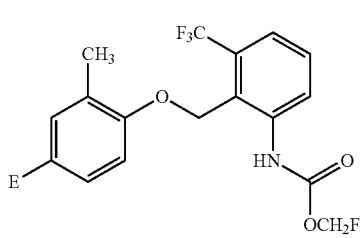
(HC1036)
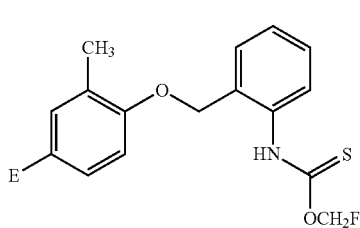
(HC1037)

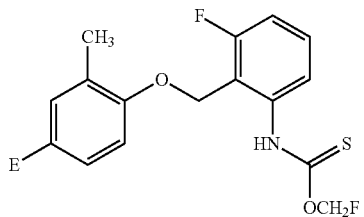 (HC1038)
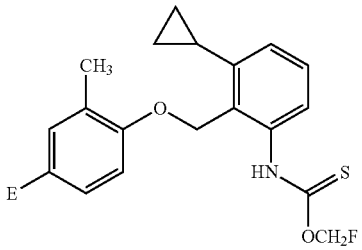 (HC1044)
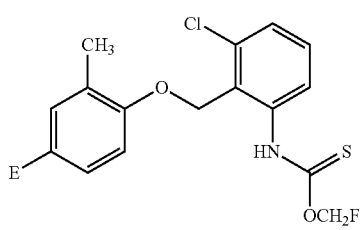 (HC1039)
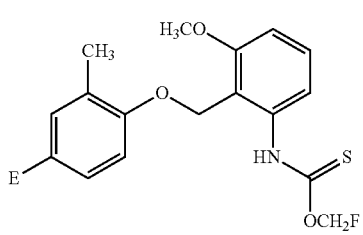 (HC1045)
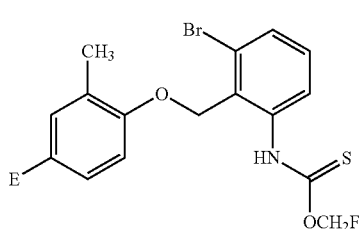 (HC1040)
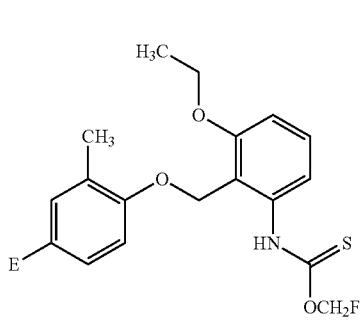 (HC1046)
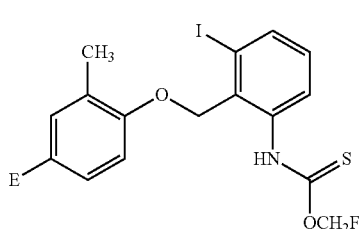 (HC1041)
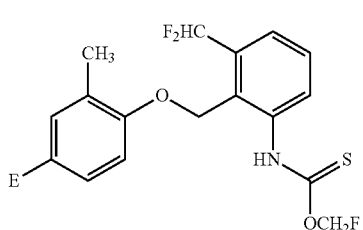 (HC1047)
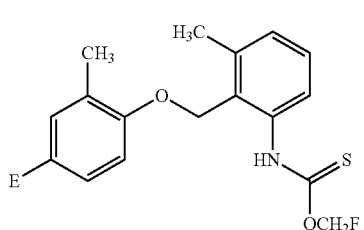 (HC1042)
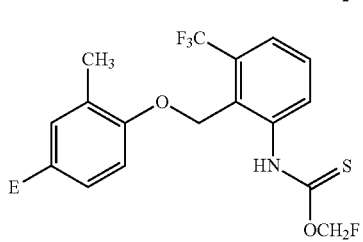 (HC1048)
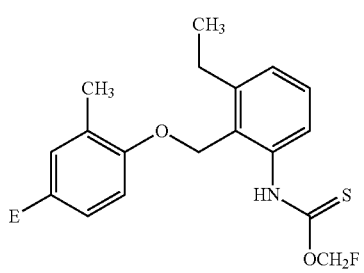 (HC1043)
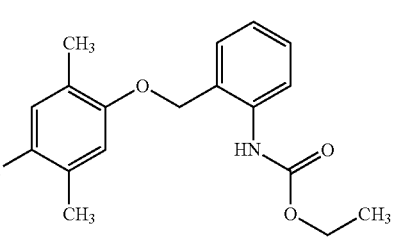 (HC2001)

(HC2002) 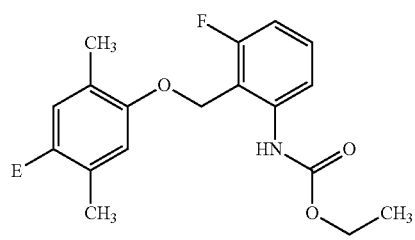
(HC2003) 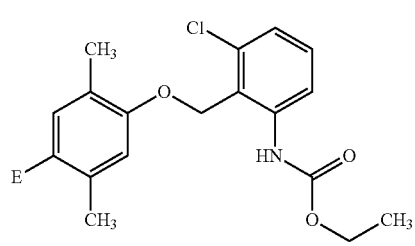
(HC2004) 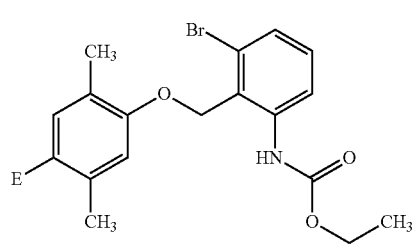
(HC2005) 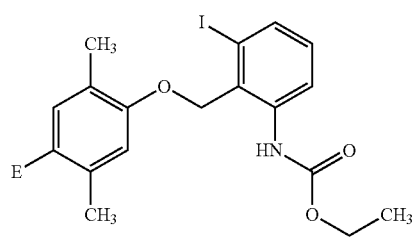
(HC2006) 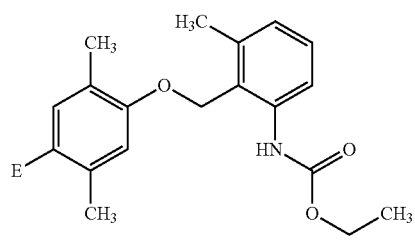
(HC2007) 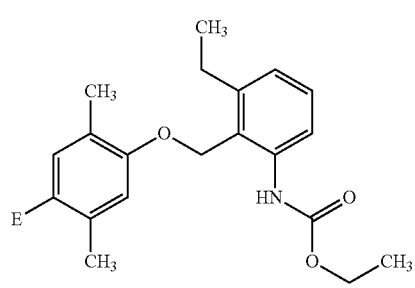
(HC2008) 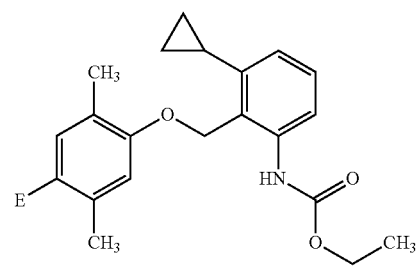
(HC2009) 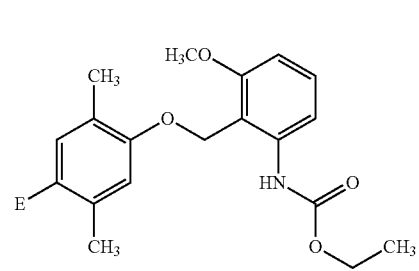
(HC2010) 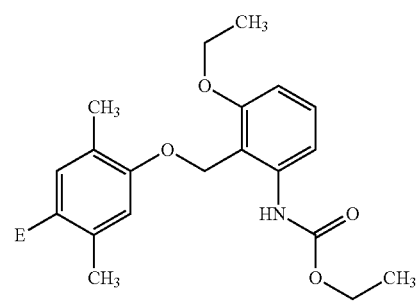
(HC2011) 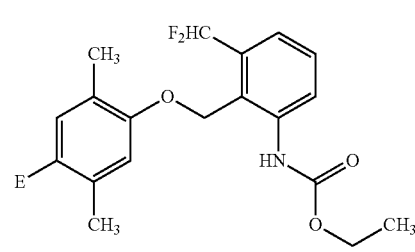
(HC2012) 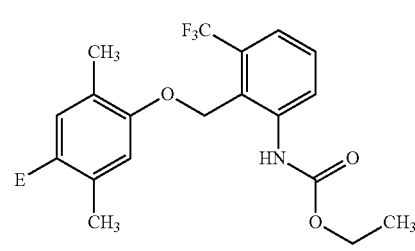
(HC2013) 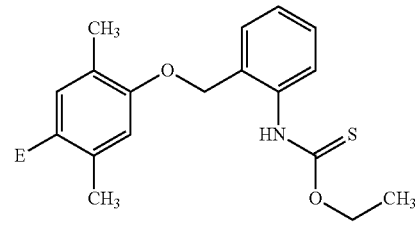

(HC2014) 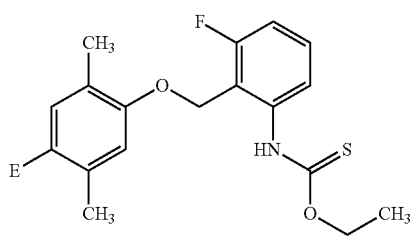
(HC2015) 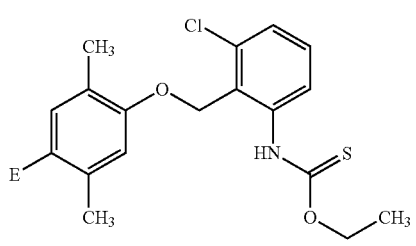
(HC2016) 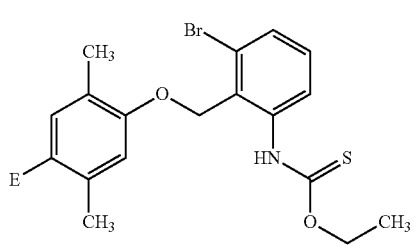
(HC2017) 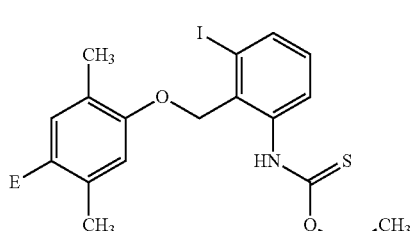
(HC2018) 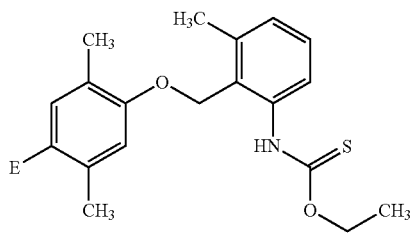
(HC2019) 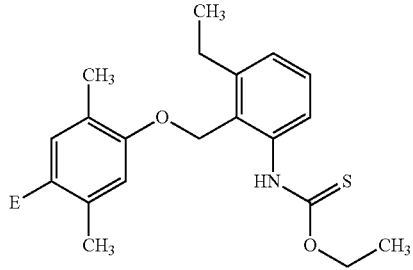
(HC2020) 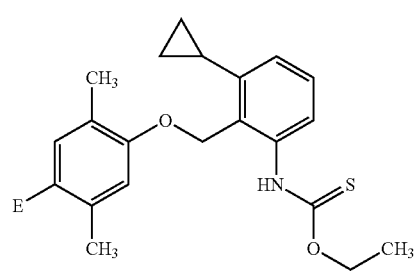
(HC2021) 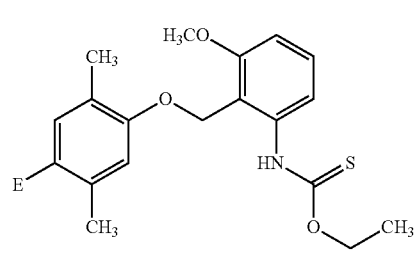
(HC2022) 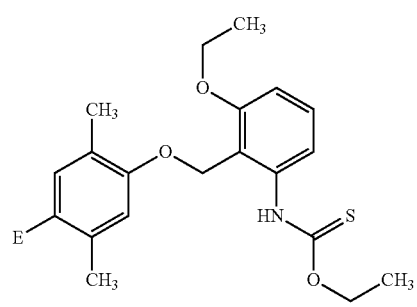
(HC2023) 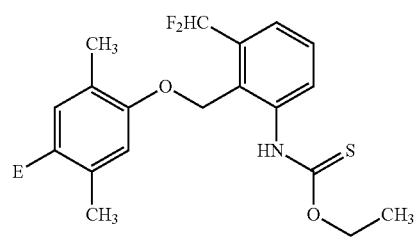
(HC2024) 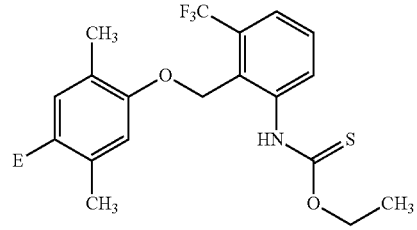
(HC2025) 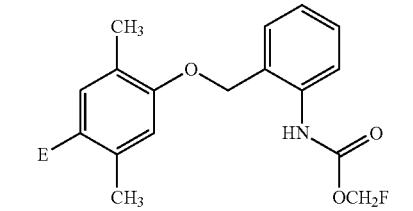

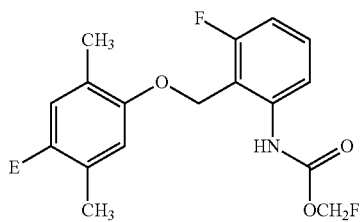
(HC2026)
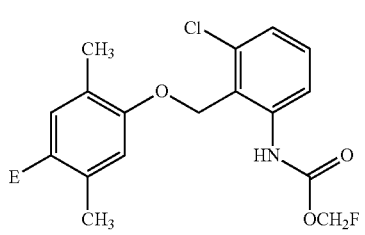
(HC2027)
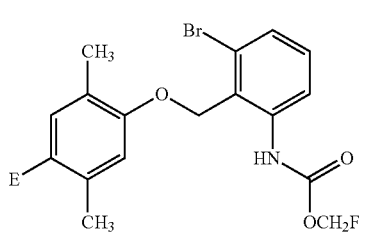
(HC2028)
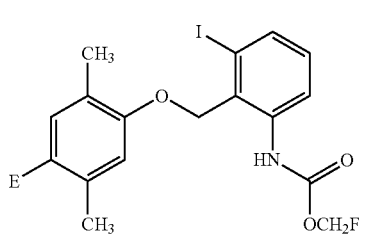
(HC2029)
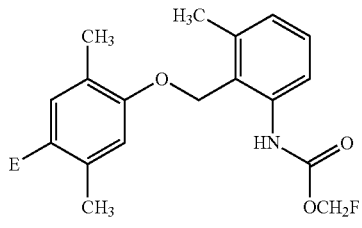
(HC2030)
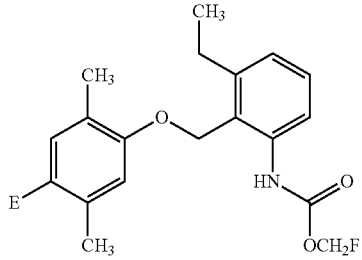
(HC2031)
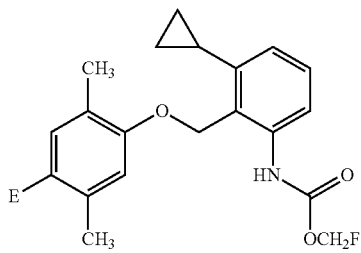
(HC2032)
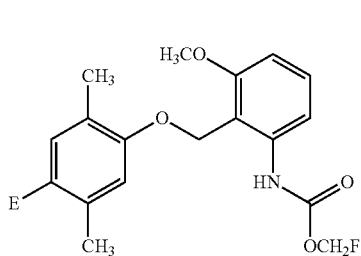
(HC2033)
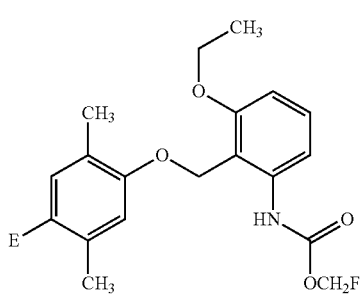
(HC2034)
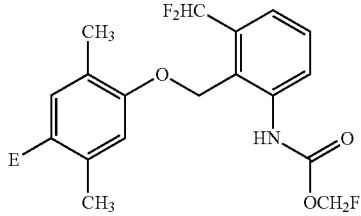
(HC2035)
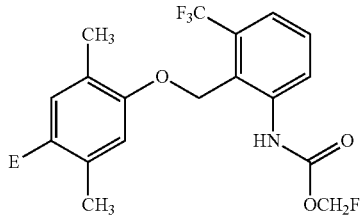
(HC2036)
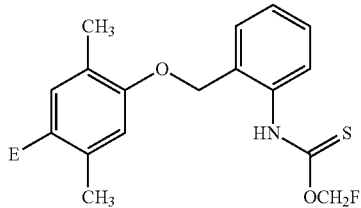
(HC2037)

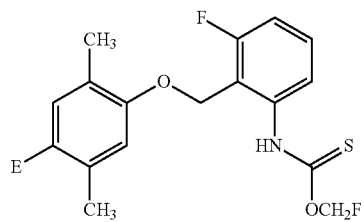
(HC2038)
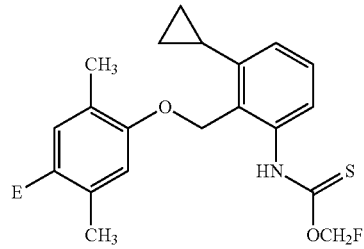
(HC2044)
(HC2039)
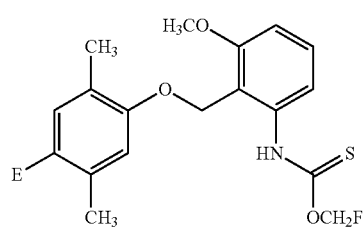
(HC2045)
(HC2040)
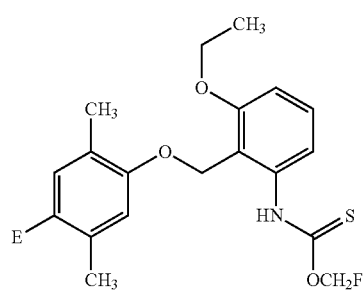
(HC2046)
(HC2041)
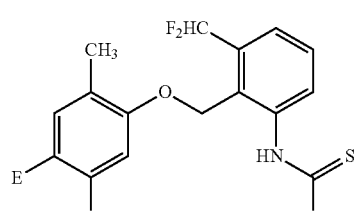
(HC2047)
(HC2042)
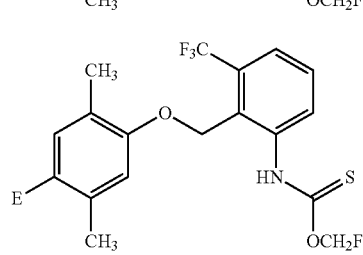
(HC2048)
(HC2043)
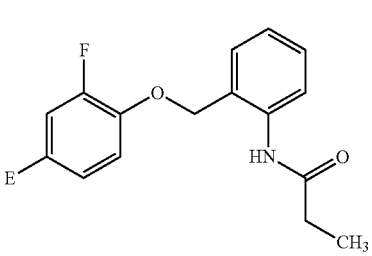
(HD1001)

-continued
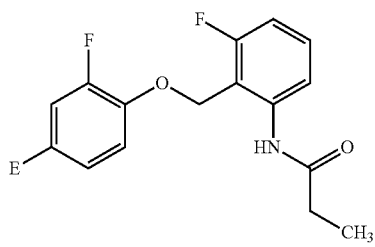
(HD1002)
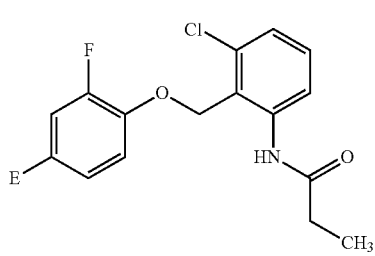
(HD1003)
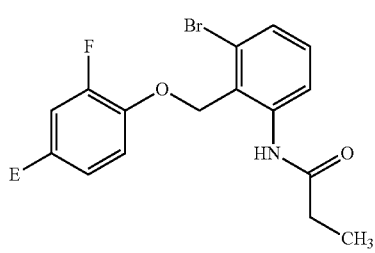
(HD1004)
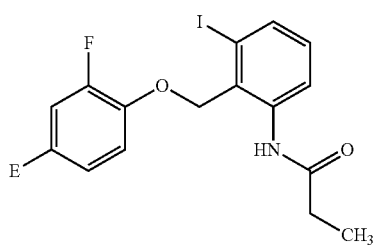
(HD1005)
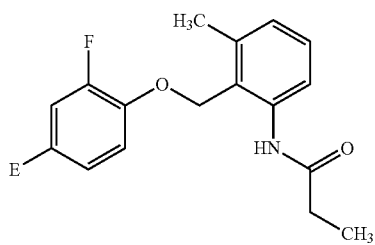
(HD1006)
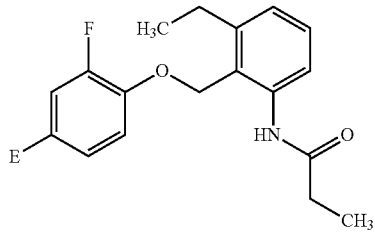
(HD1007)
-continued
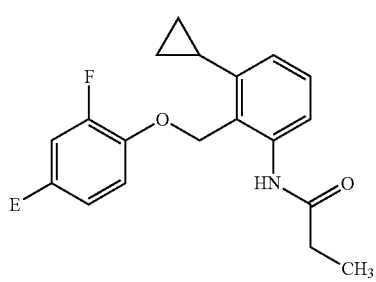
(HD1008)
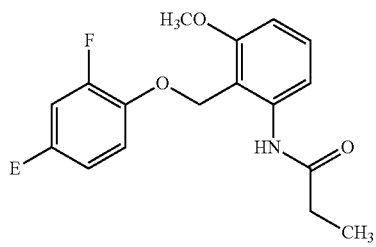
(HD1009)
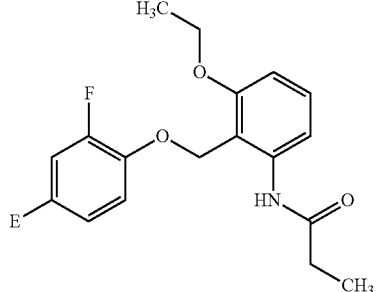
(HD1010)
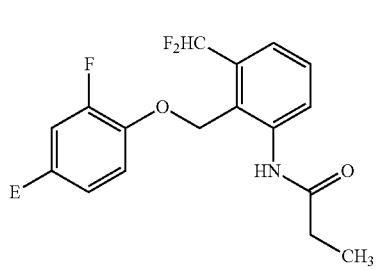
(HD1011)
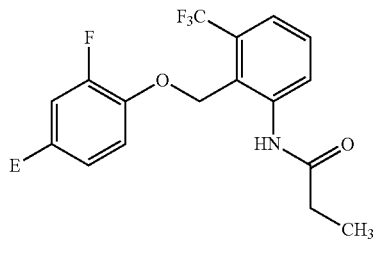
(HD1012)
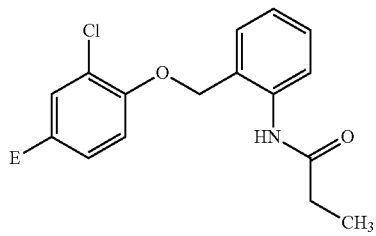
(HD1025)

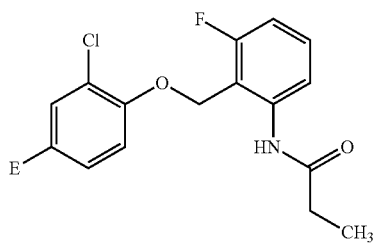
(HD1026)
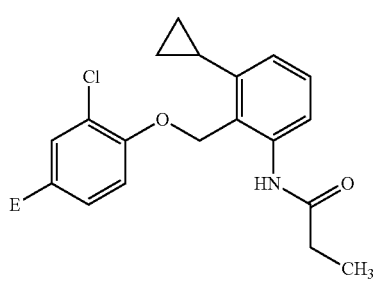
(HD1032)
(HD1027)
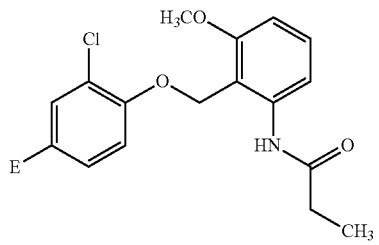
(HD1033)
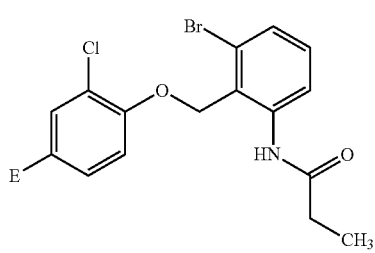
(HD1028)
(HD1034)
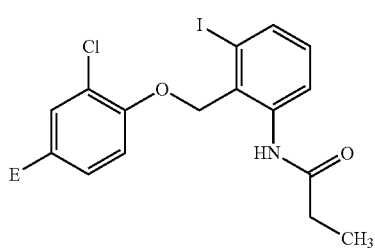
(HD1029)
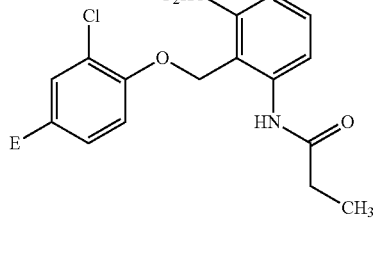
(HD1035)
(HD1030)
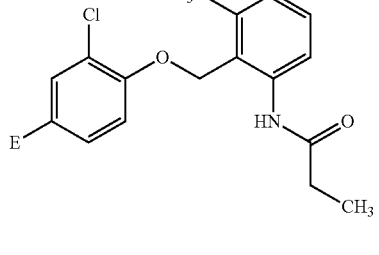
(HD1036)
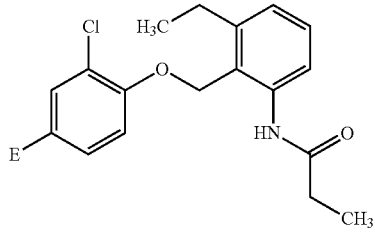
(HD1031)
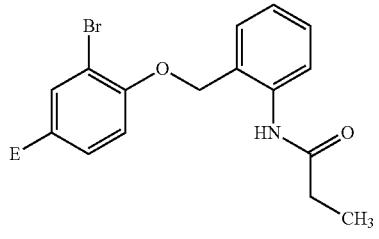
(HD1037)

(HD1038)
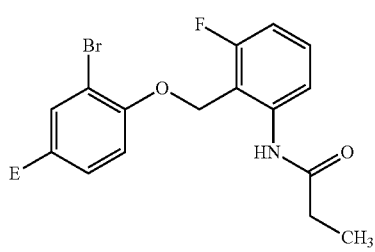
(HD1039)
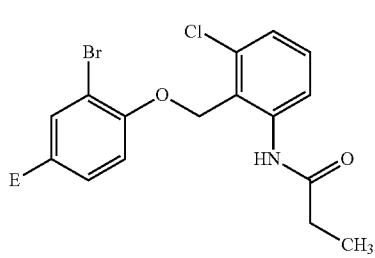
(HD1040)
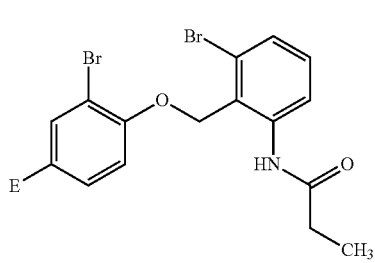
(HD1041)
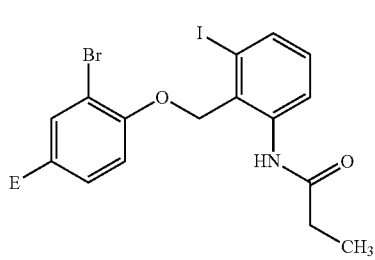
(HD1042)
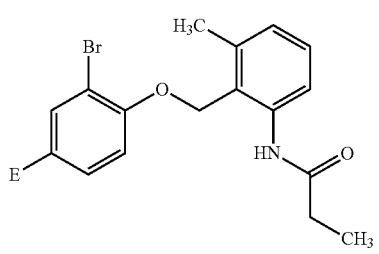
(HD1043)
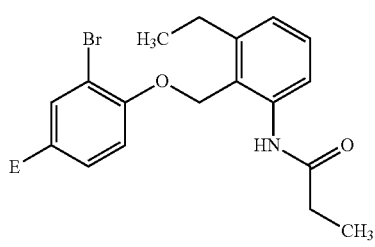
(HD1044)
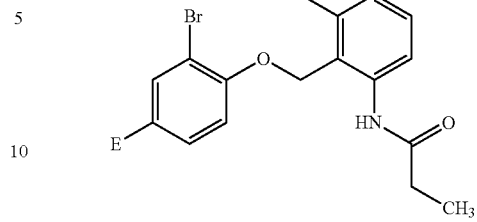
(HD1045)
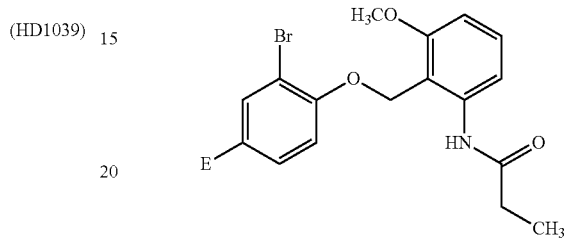
(HD1046)
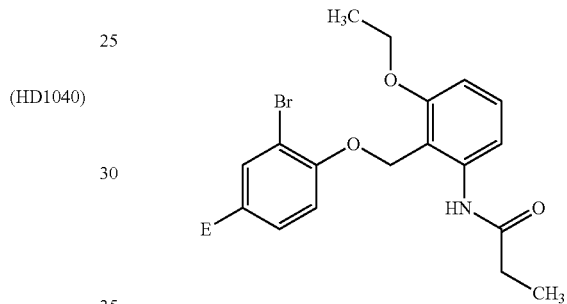
(HD1047)
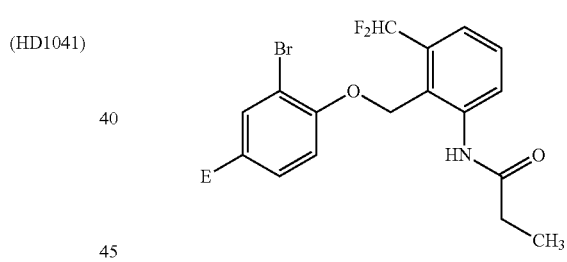
(HD1048)
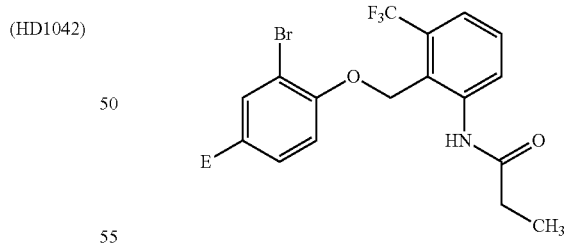
(HD1049)
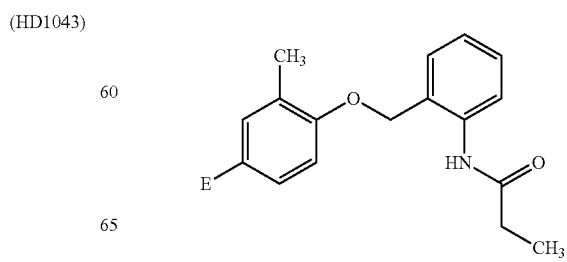

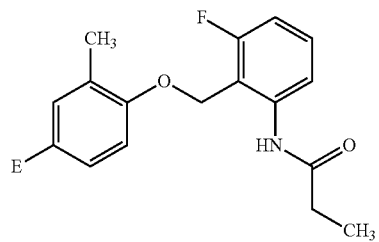
(HD1050)
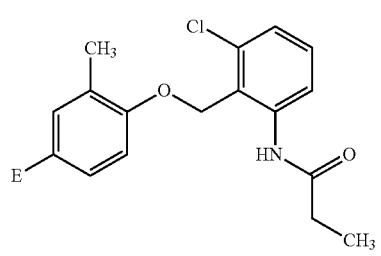
(HD1051)
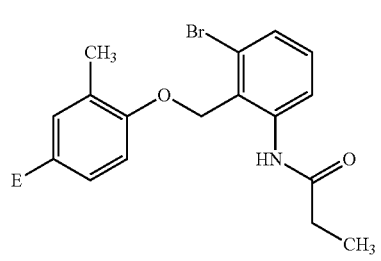
(HD1052)
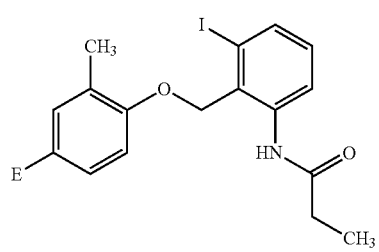
(HD1053)
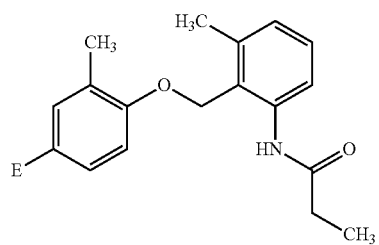
(HD1054)
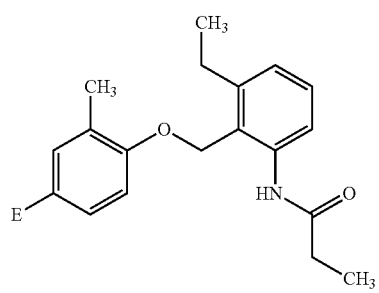
(HD1055)
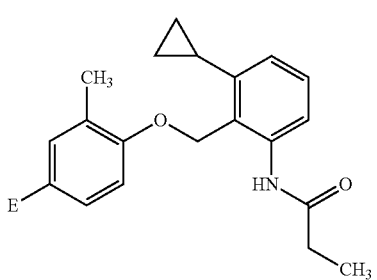
(HD1056)
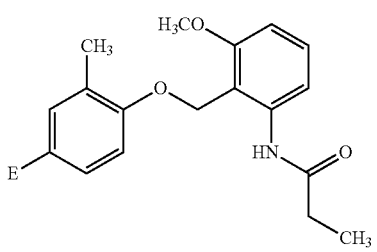
(HD1057)
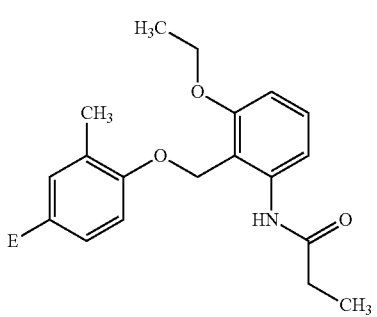
(HD1058)
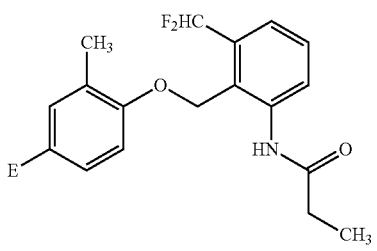
(HD1059)
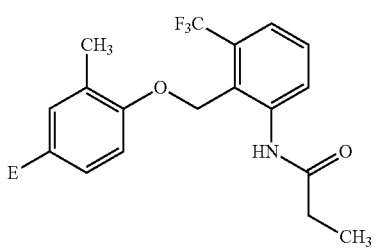
(HD1060)
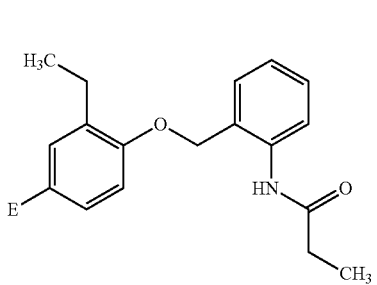
(HD1061)

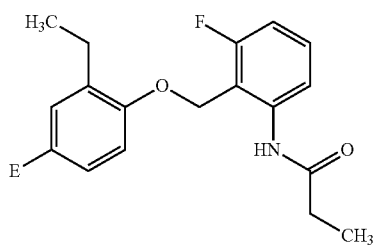 (HD1062)
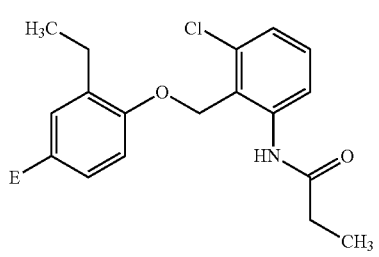 (HD1063)
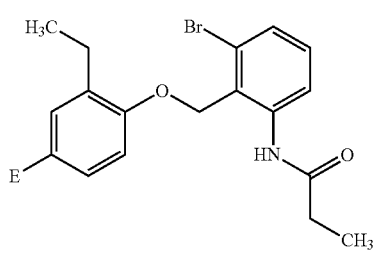 (HD1064)
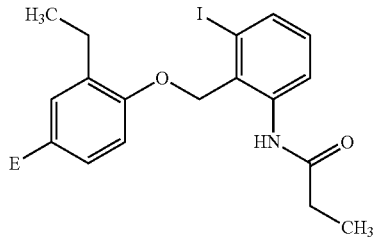 (HD1065)
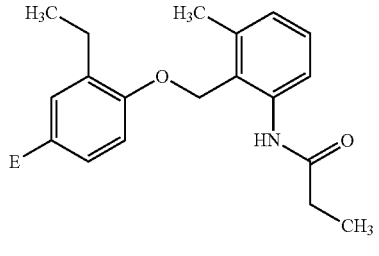 (HD1066)
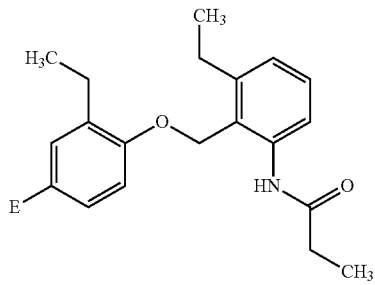 (HD1067)
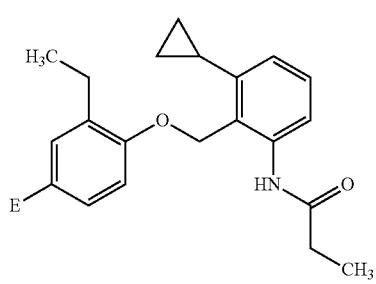 (HD1068)
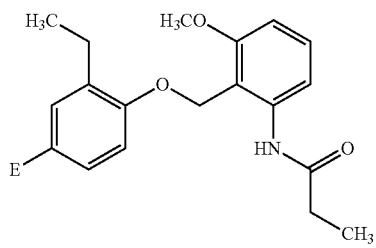 (HD1069)
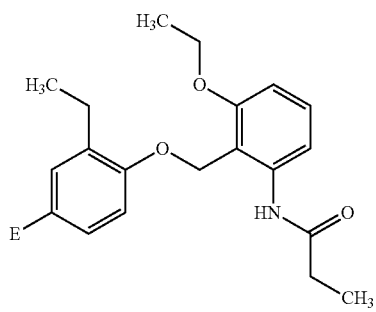 (HD1070)
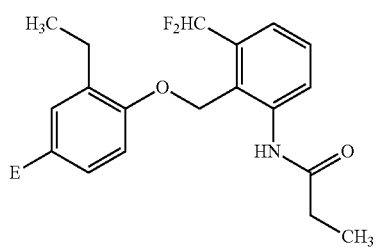 (HD1071)
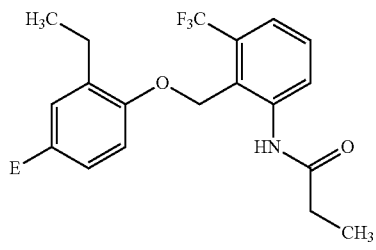 (HD1072)
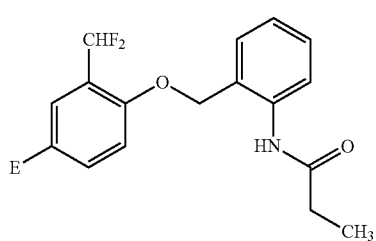 (HD1073)

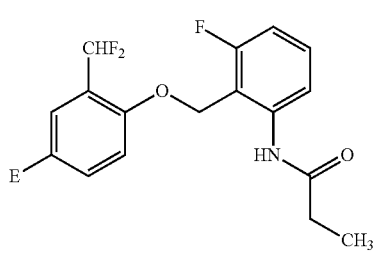
(HD1074)
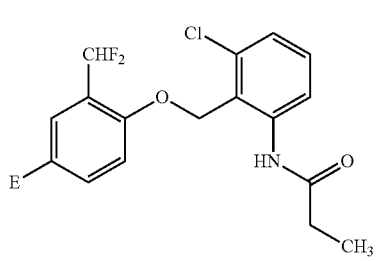
(HD1075)
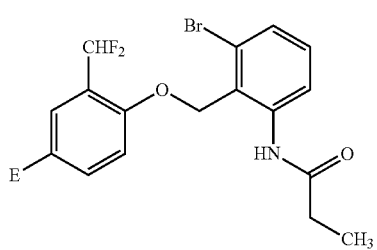
(HD1076)
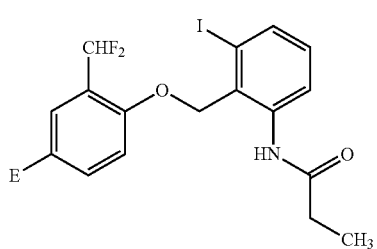
(HD1077)
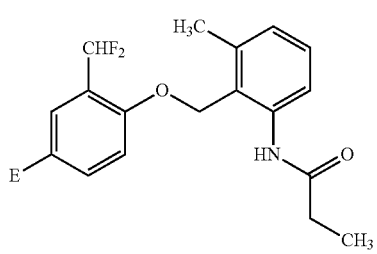
(HD1078)
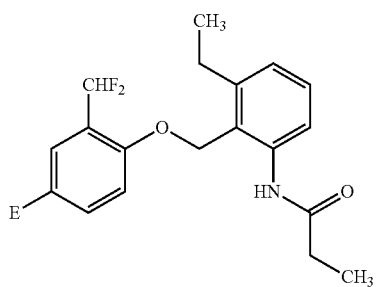
(HD1079)
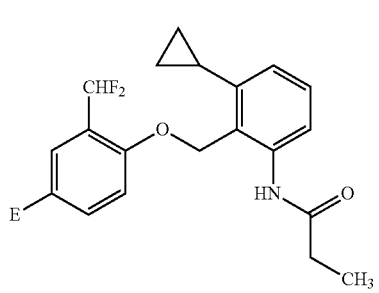
(HD1080)
(HD1081)
(HD1082)
(HD1083)
(HD1084)
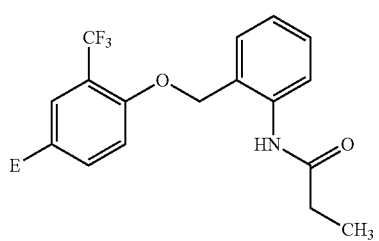
(HD1085)

(HD1086)
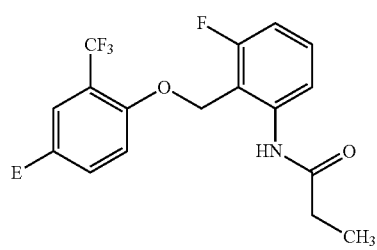
(HD1087)
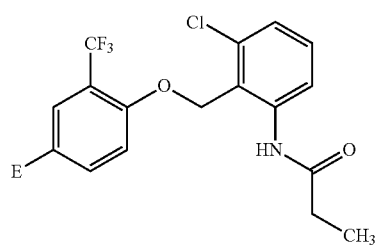
(HD1088)
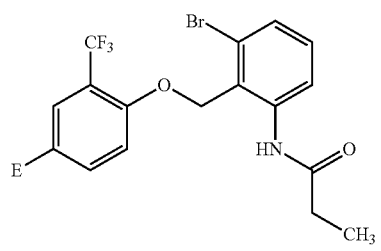
(HD1089)
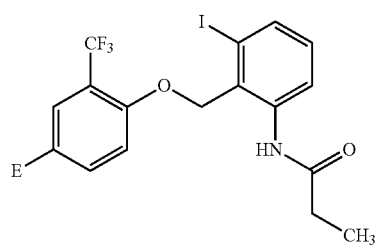
(HD1090)
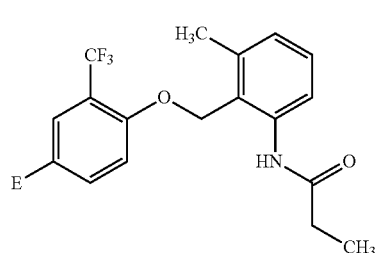
(HD1091)
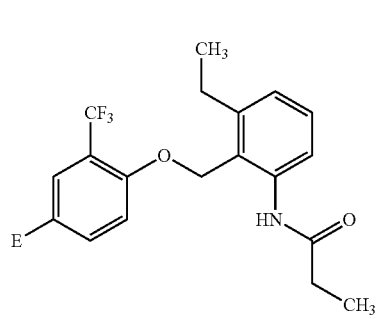
(HD1092)
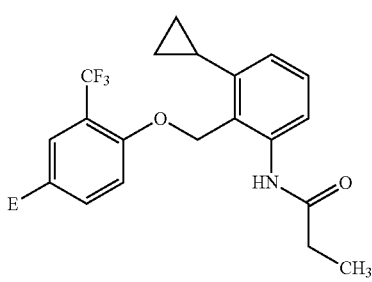
(HD1093)
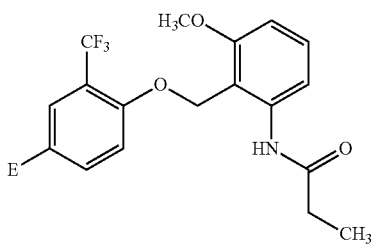
(HD1094)
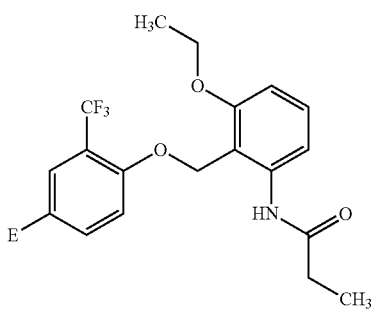
(HD1095)
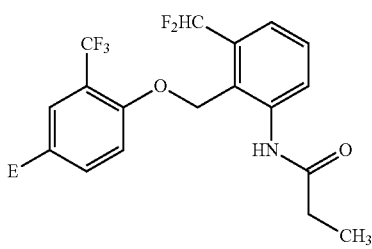
(HD1096)
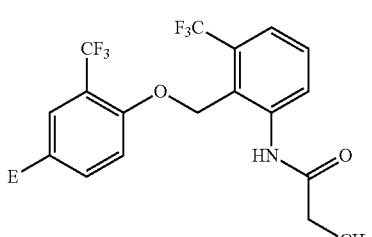
(HD4013)
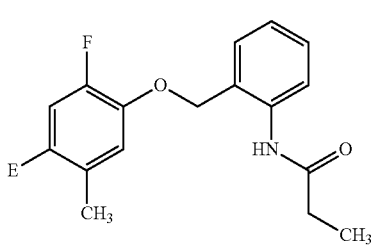

-continued
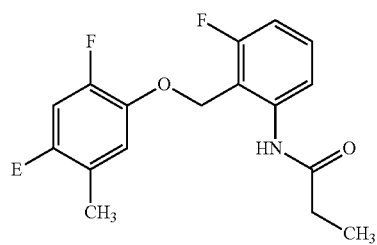
(HD4014)
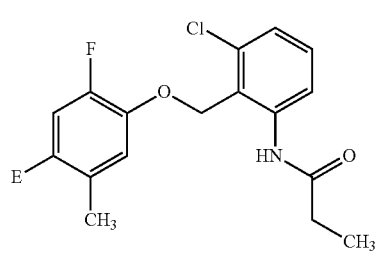
(HD4015)
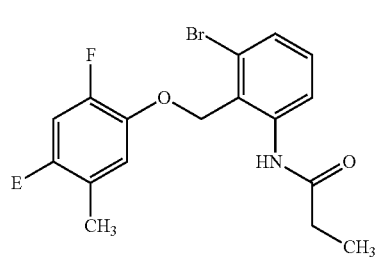
(HD4016)
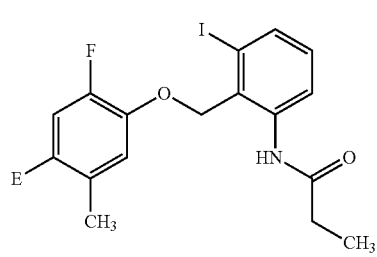
(HD4017)
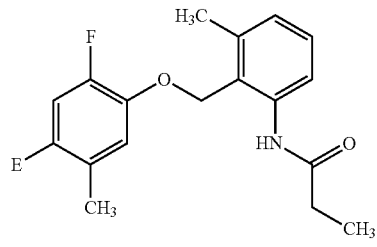
(HD4018)
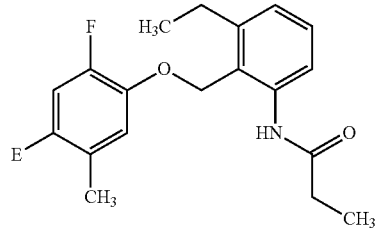
(HD4019)
-continued
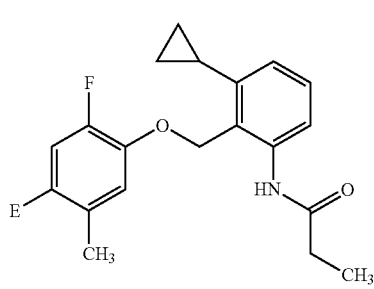
(HD4020)
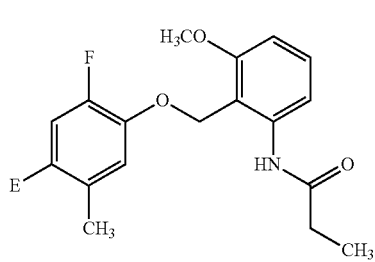
(HD4021)
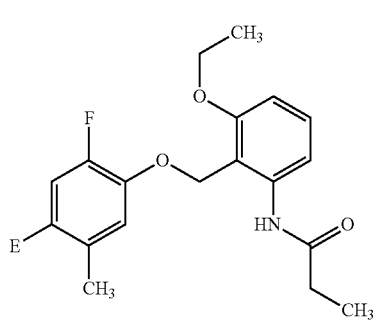
(HA4022)
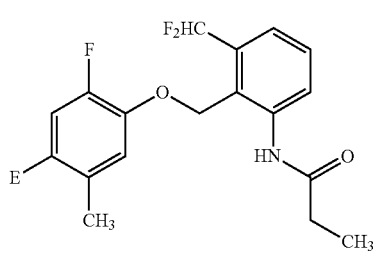
(HA4023)
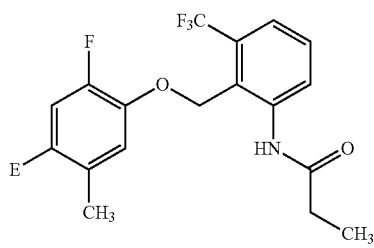
(HA4024)

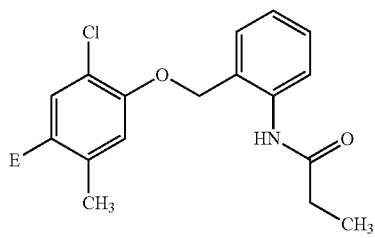
(HD4025)
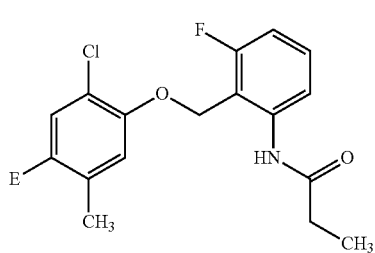
(HD4026)
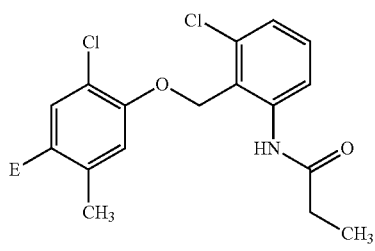
(HD4027)
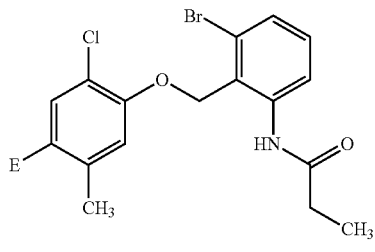
(HD4028)
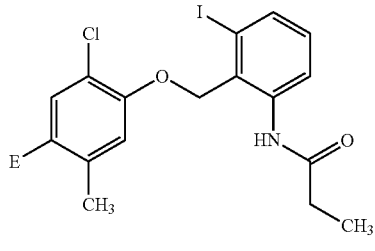
(HD4029)
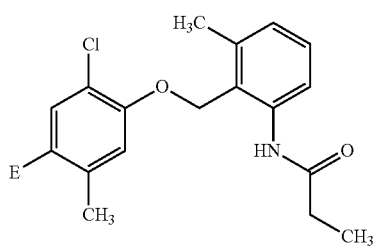
(HD4030)
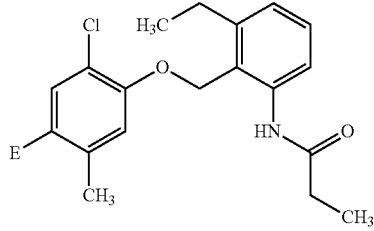
(HD4031)
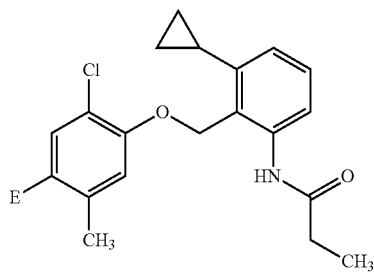
(HD4032)
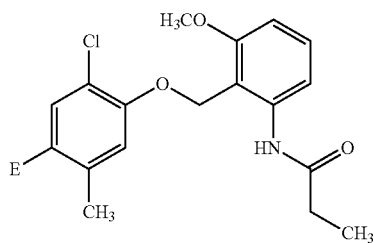
(HD4033)
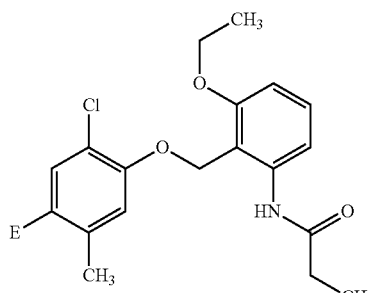
(HD4034)
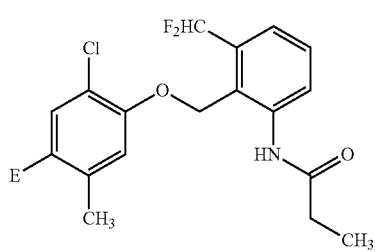
(HD4035)
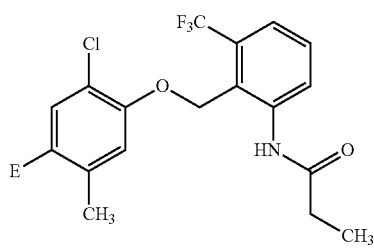
(HD4036)

-continued
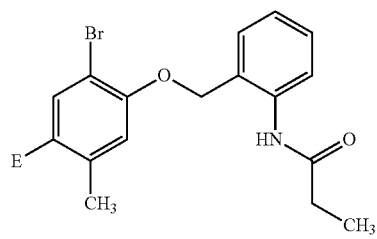
(HD4037)
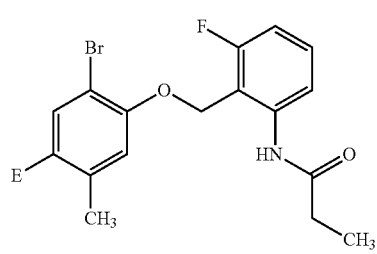
(HD4038)
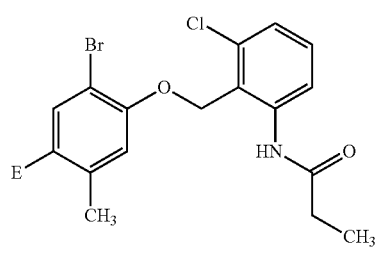
(HD4039)
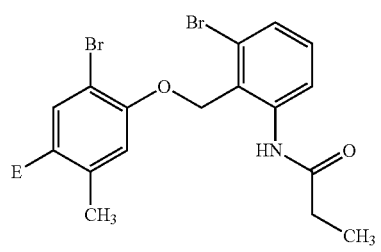
(HD4040)
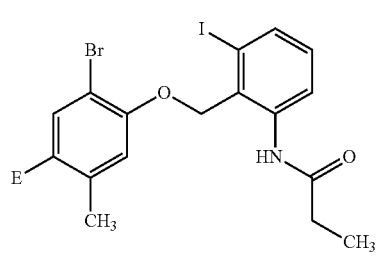
(HD4041)
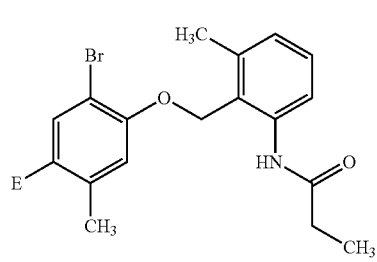
(HD4042)
-continued
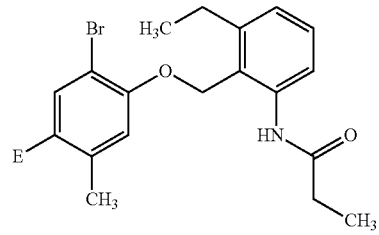
(HD4043)
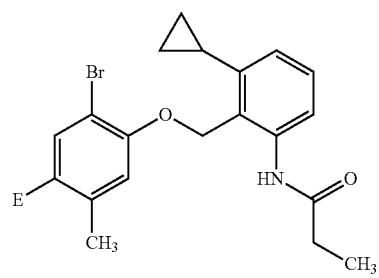
(HD4044)
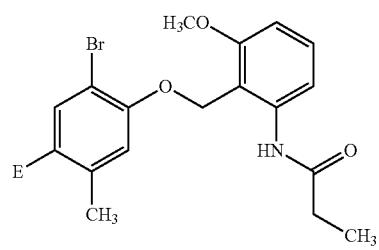
(HD4045)
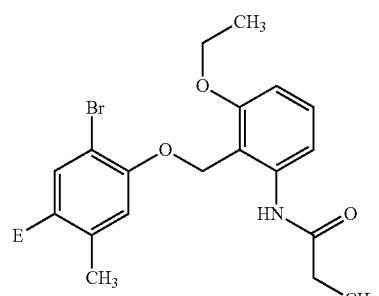
(HD4046)
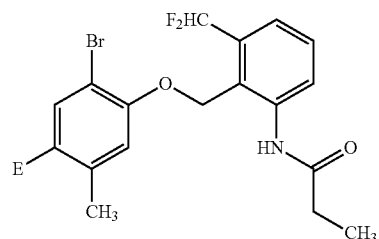
(HD4047)
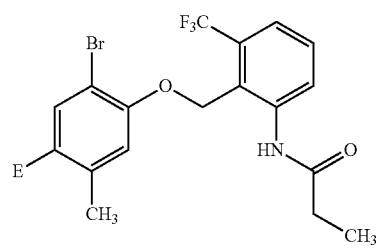
(HD4048)

(HF4049)
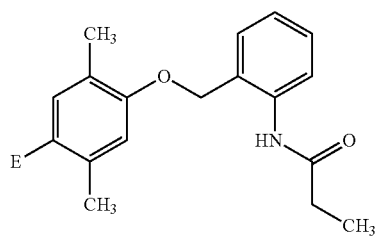
(HF4050)
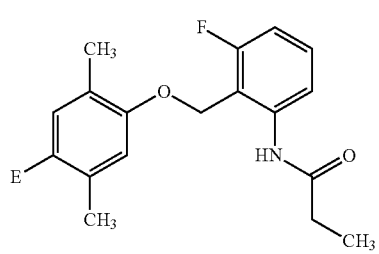
(HF4051)
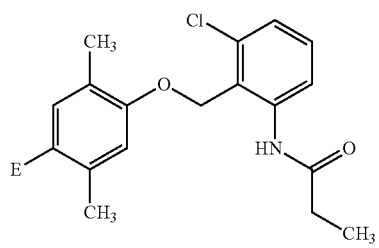
(HF4052)
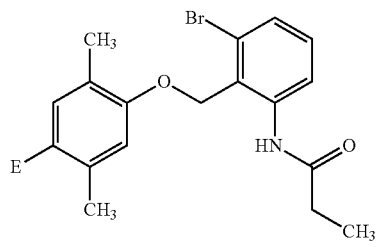
(HF4053)
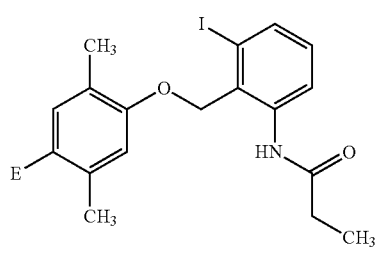
(HF4054)
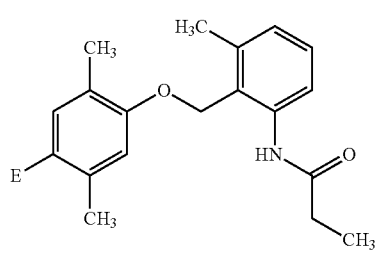
(HF4055)
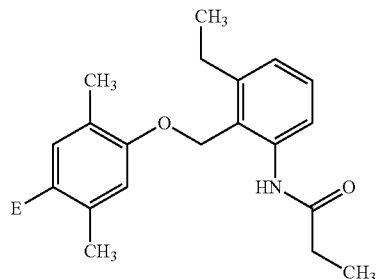
(HF4056)
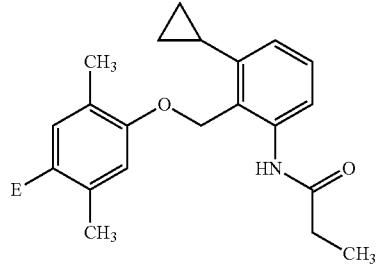
(HF4057)
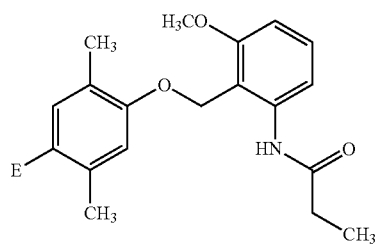
(HF4058)
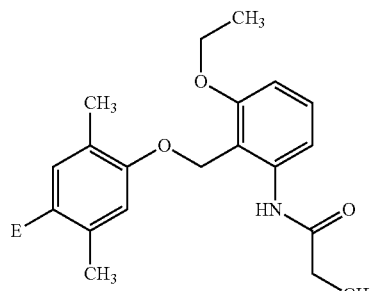
(HF4059)
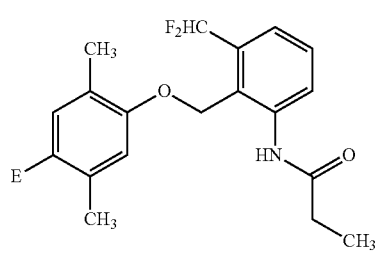
(HF4060)
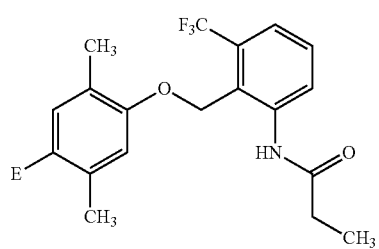

-continued
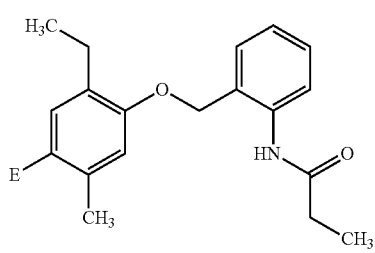 (HD4061)
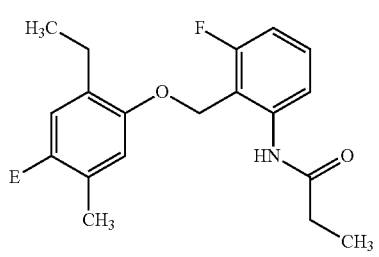 (HD4062)
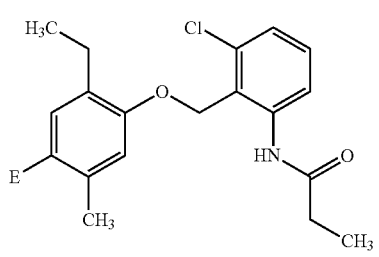 (HD4063)
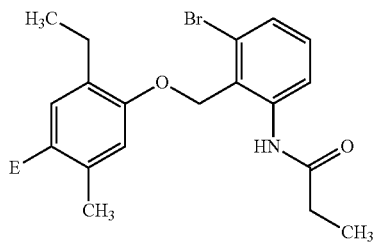 (HD4064)
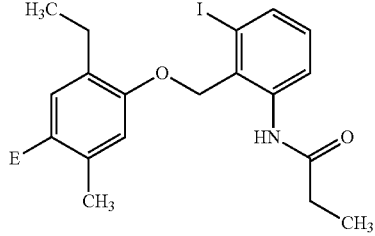 (HD4065)
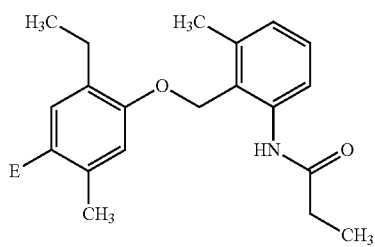 (HD4066)
-continued
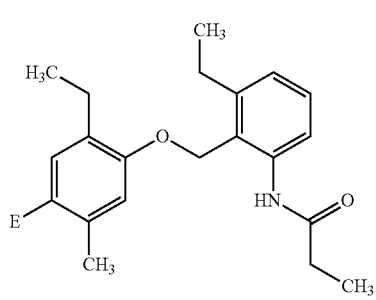 (HD4067)
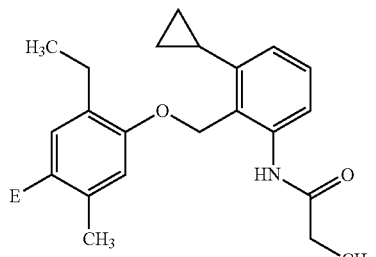 (HD4068)
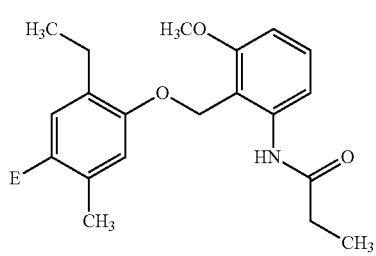 (HD4069)
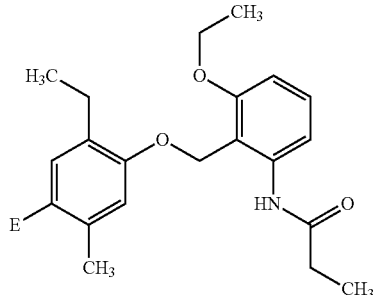 (HD4070)
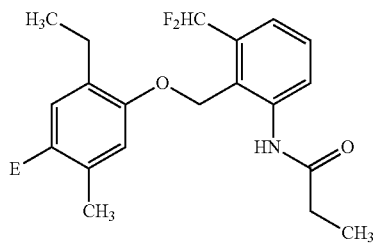 (HD4071)
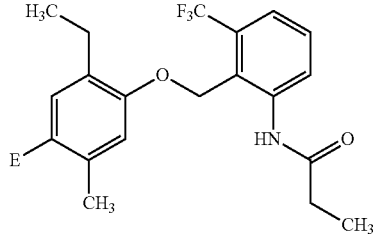 (HD4072)

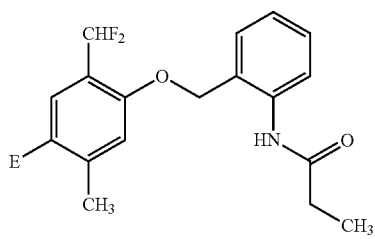 (HD4073)
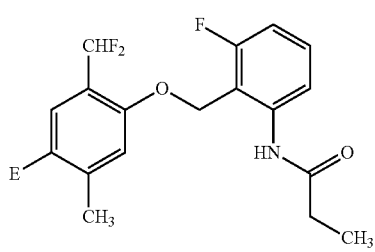 (HD4074)
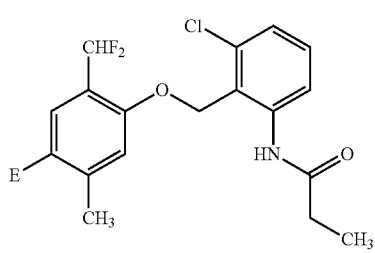 (HD4075)
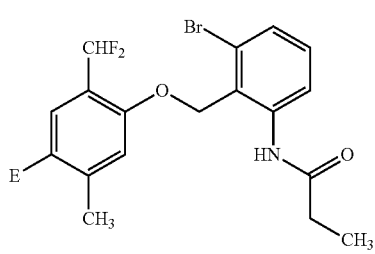 (HD4076)
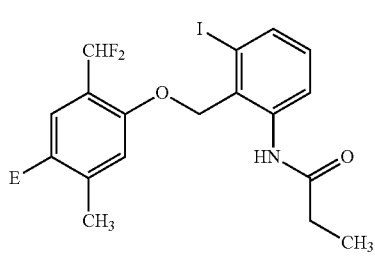 (HD4077)
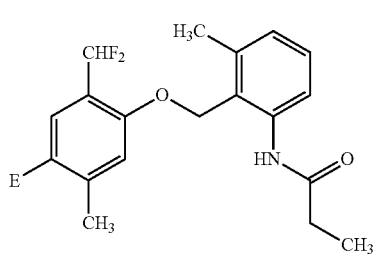 (HD4078)
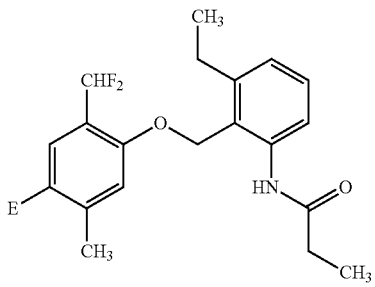 (HD4079)
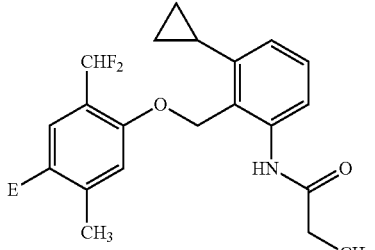 (HD4080)
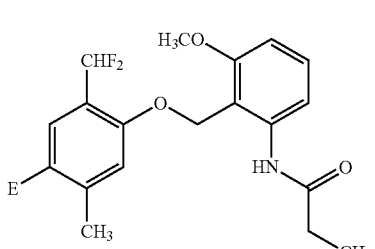 (HD4081)
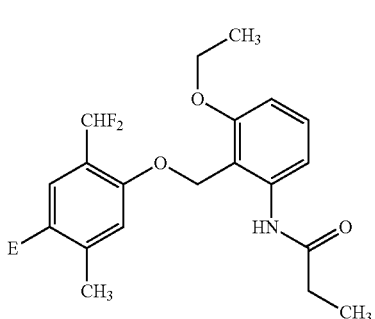 (HD4082)
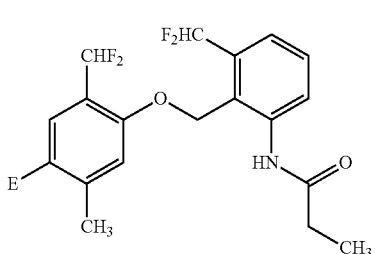 (HD4083)
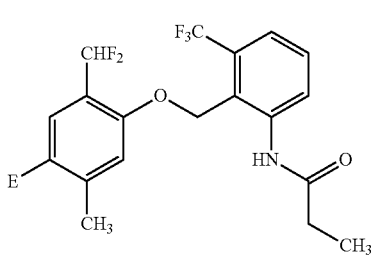 (HD4084)

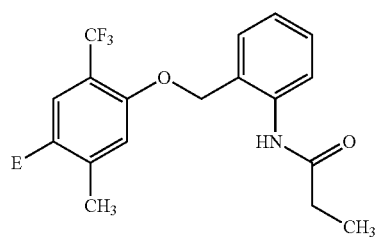 (HD4085)
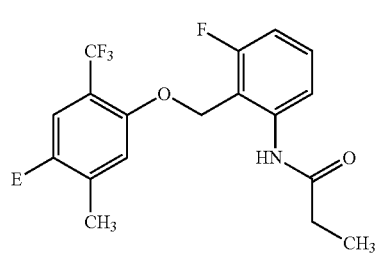 (HD4086)
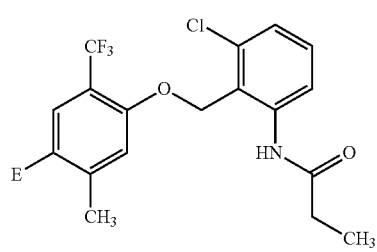 (HD4087)
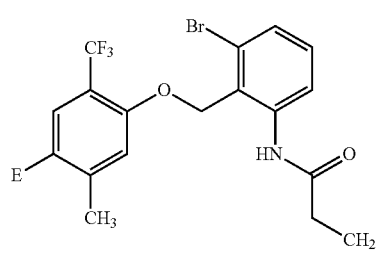 (HD4088)
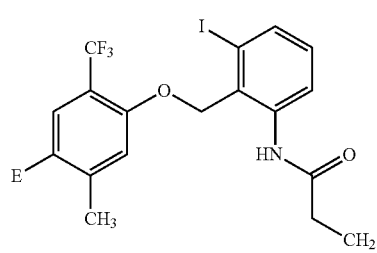 (HD4089)
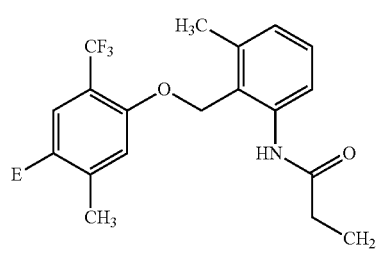 (HD4090)
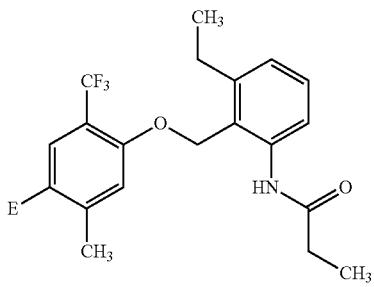 (HD4091)
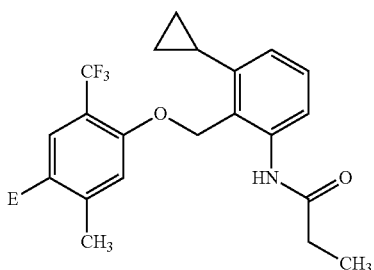 (HD4092)
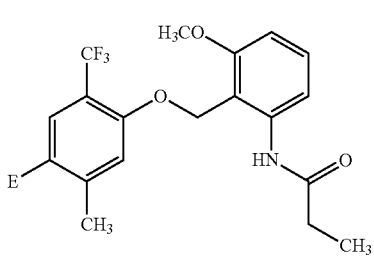 (HD4093)
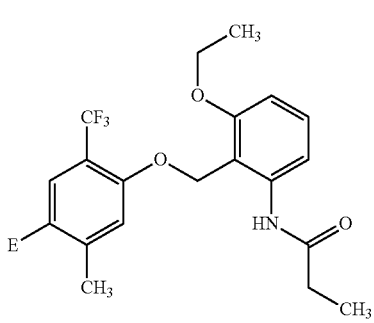 (HD4094)
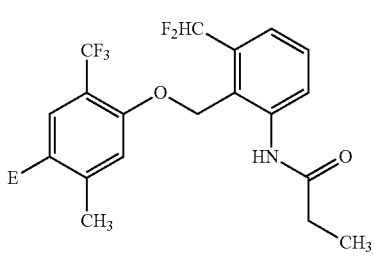 (HD4095)
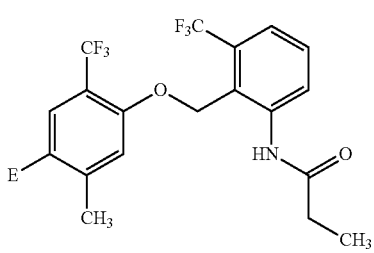 (HD4096)

(HE1013)
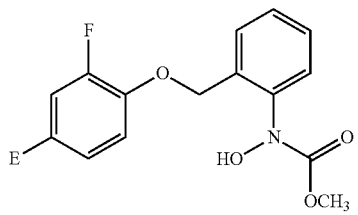
(HE1014)
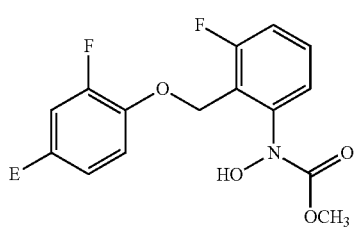
(HE1015)
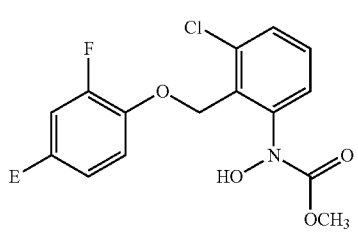
(HE1016)
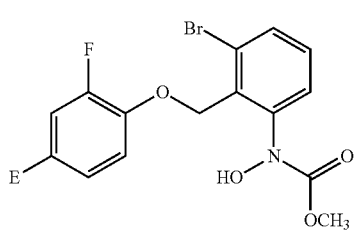
(HE1017)
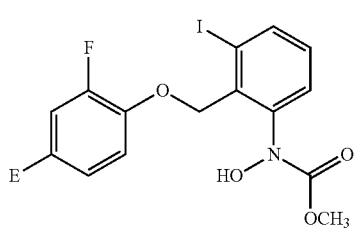
(HE1018)
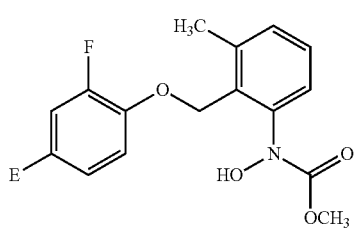
(HE1019)
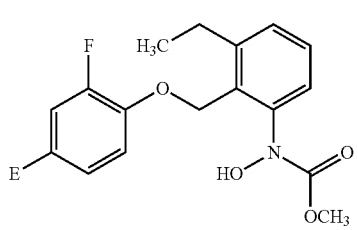
(HE1020)
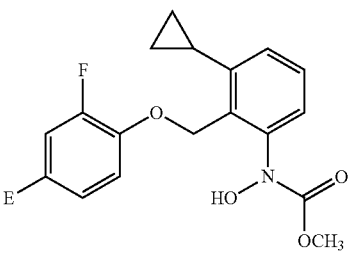
(HE1021)
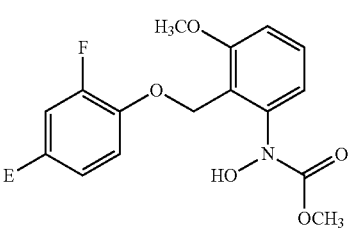
(HE1022)
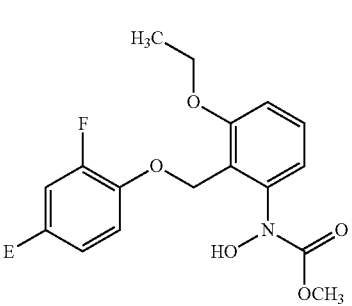
(HE1023)
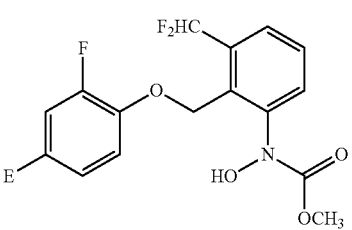
(HE1024)
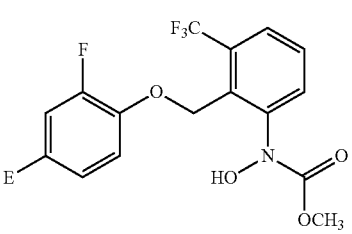
(HE1025)
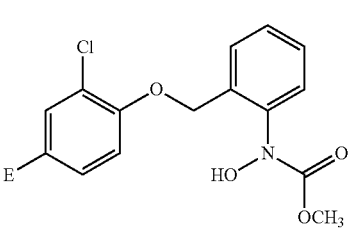

(HE1026)
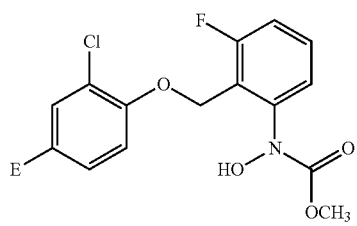
(HE1027)
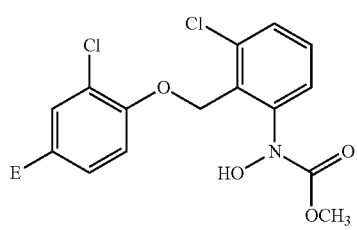
(HE1028)
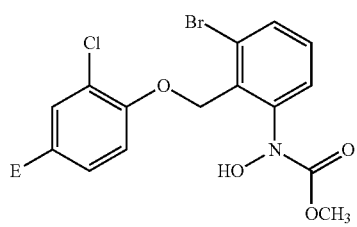
(HE1029)
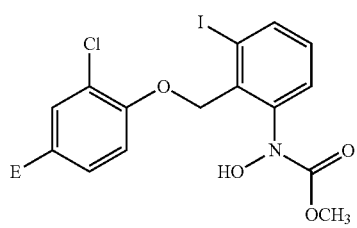
(HE1030)
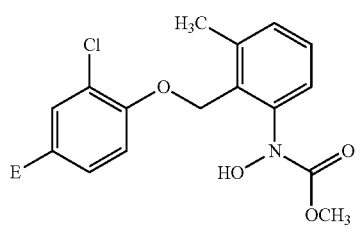
(HE1031)
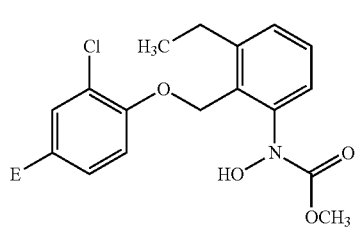
(HE1032)
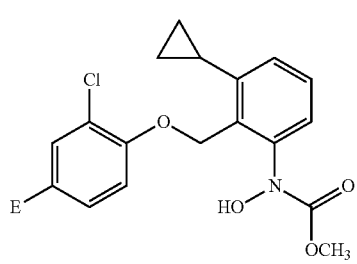
(HE1033)
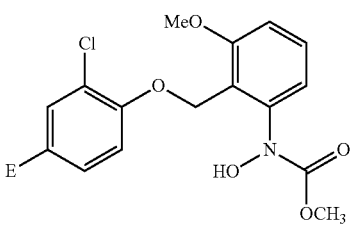
(HE1034)
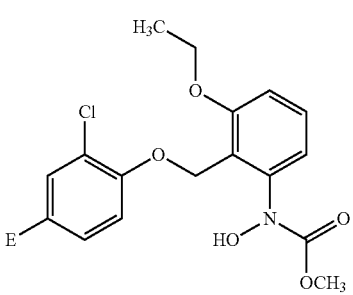
(HE1035)
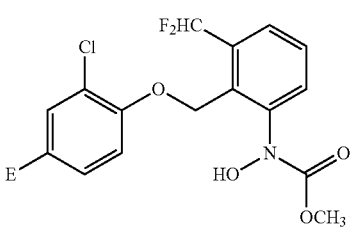
(HE1036)
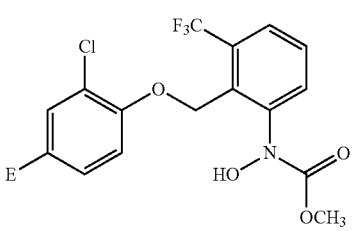
(HE1037)
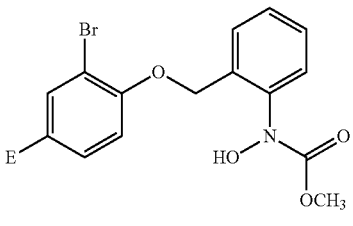
(HE1038)
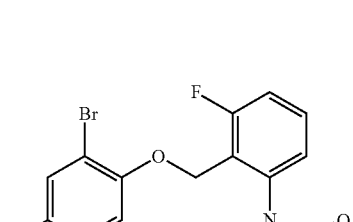

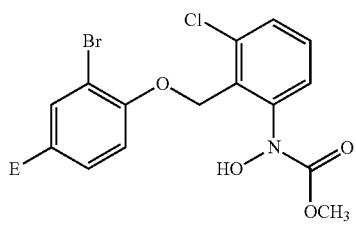
(HE1039)
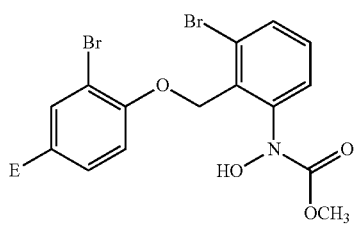
(HE1040)
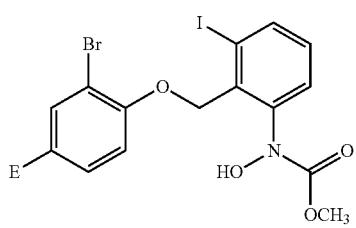
(HE1041)
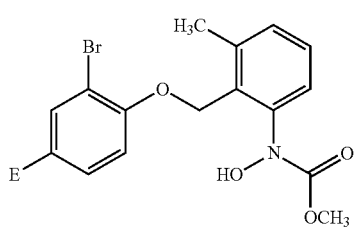
(HE1042)
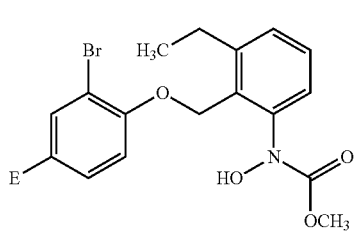
(HE1043)
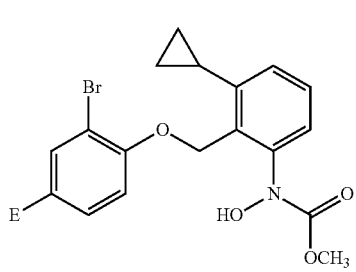
(HE1044)
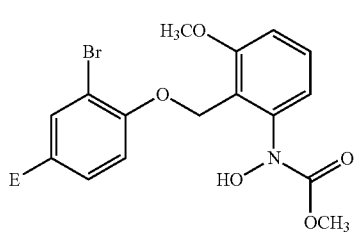
(HE1045)
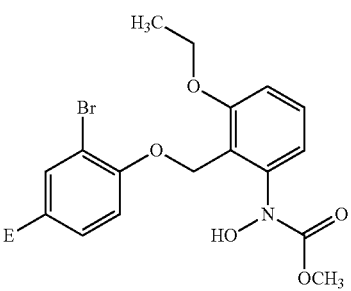
(HE1046)
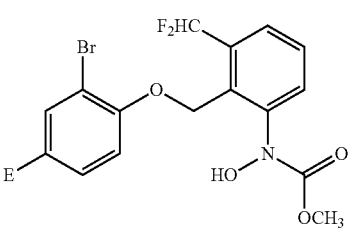
(HE1047)
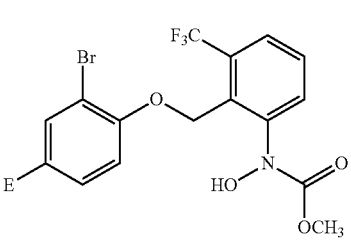
(HE1048)
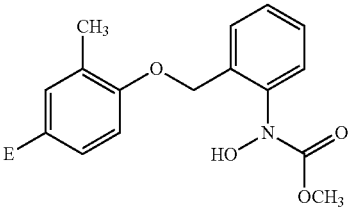
(HE1049)
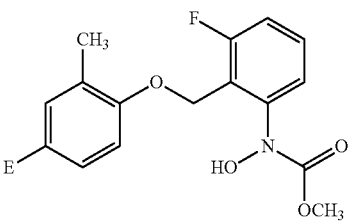
(HE1050)
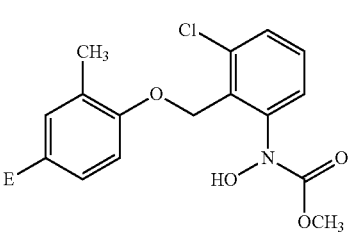
(HE1051)

(HE1052)
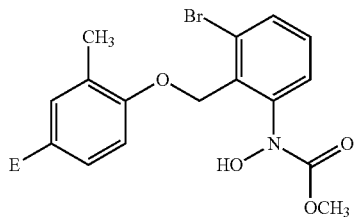
(HE1053)
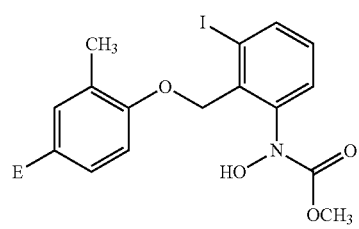
(HE1054)
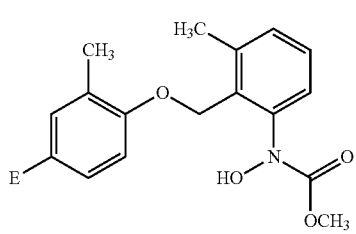
(HE1055)
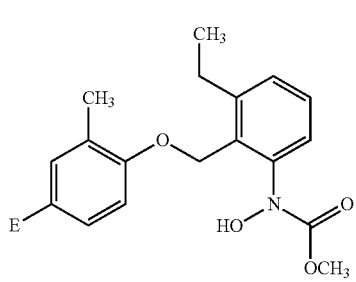
(HE1056)
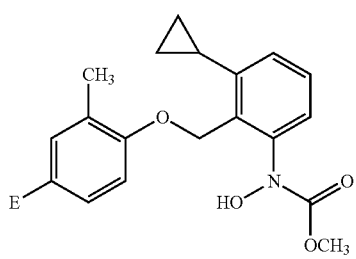
(HE1057)
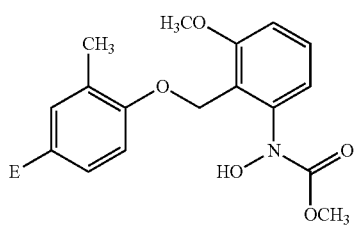
(HE1058)
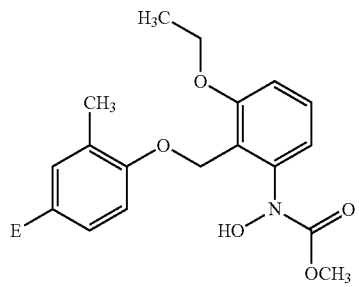
(HE1059)
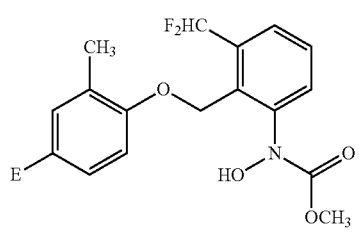
(HE1060)
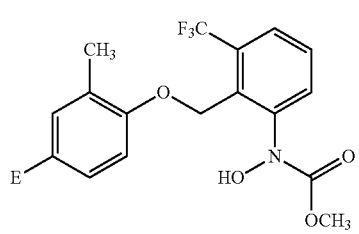
(HE1061)
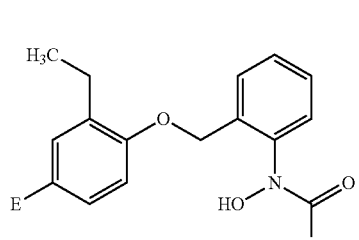
(HE1062)
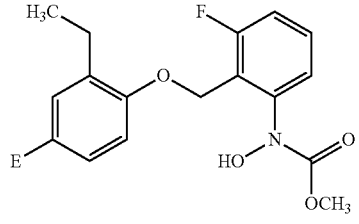
(HE1063)
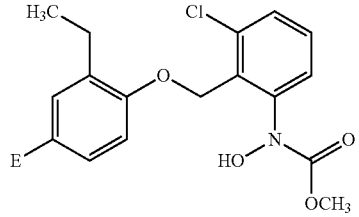

| 177 -continued | | 178 -continued | |
|---|---|---|---|
| 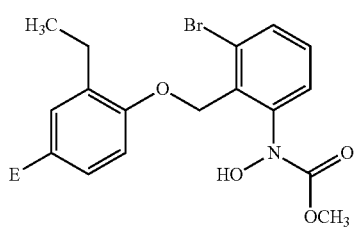 | (HE1064) | 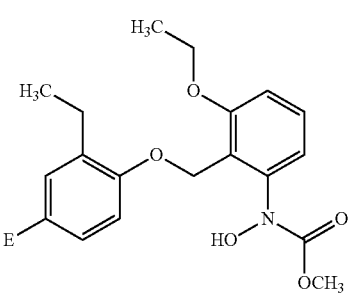 | (HE1070) |
| 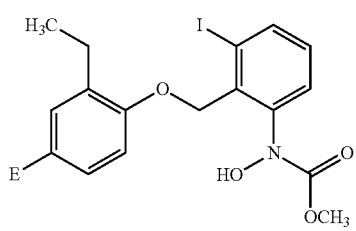 | (HE1065) | 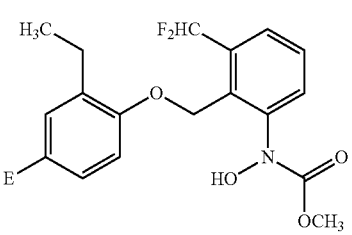 | (HE1071) |
| 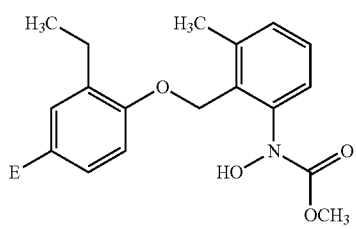 | (HE1066) | 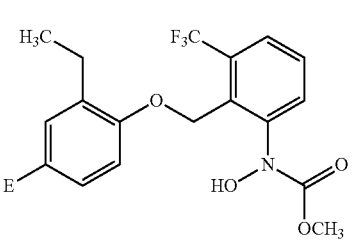 | (HE1072) |
| 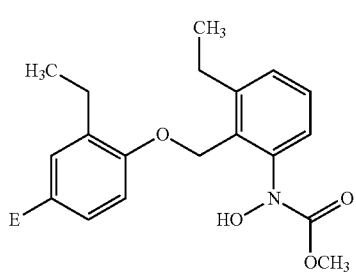 | (HE1067) | 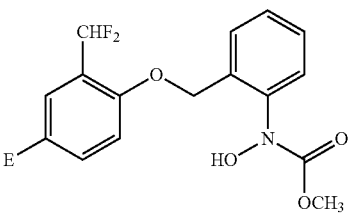 | (HE1073) |
| 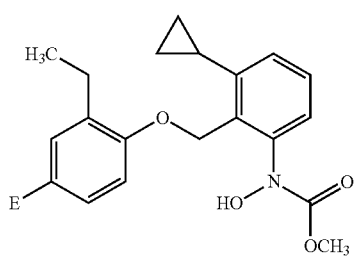 | (HE1068) | 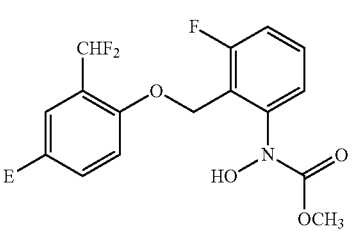 | (HE1074) |
| 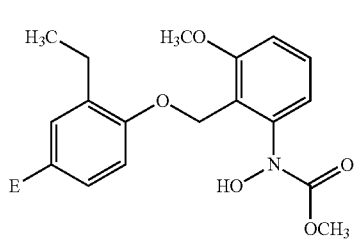 | (HE1069) | 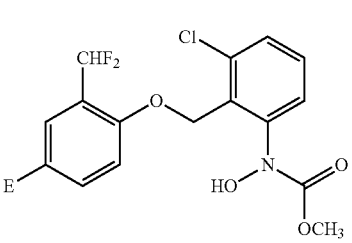 | (HE1075) |

-continued
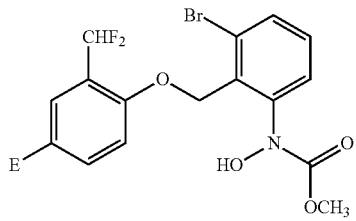
(HE1076)
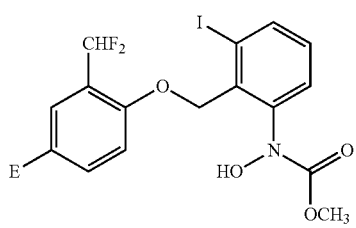
(HE1077)
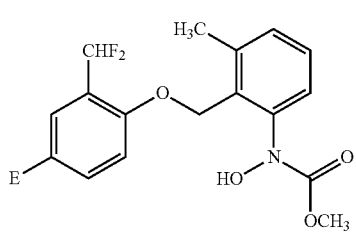
(HE1078)
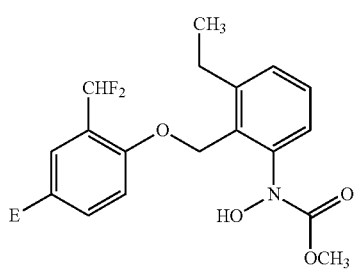
(HE1079)
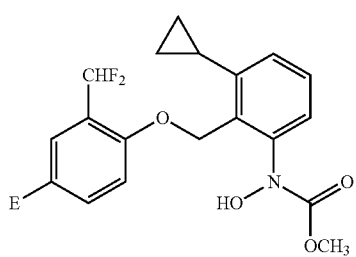
(HE1080)
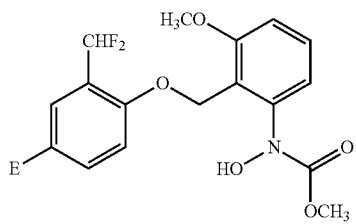
(HE1081)
-continued
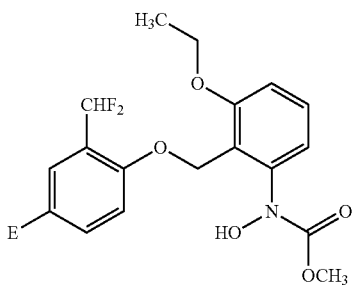
(HE1082)
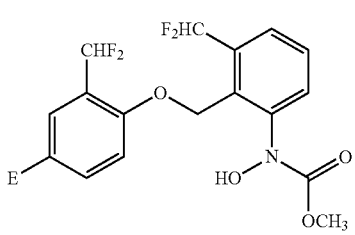
(HE1083)
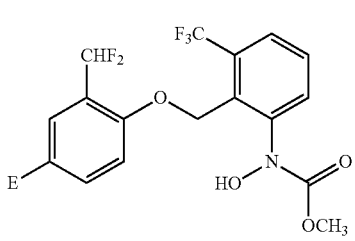
(HE1084)
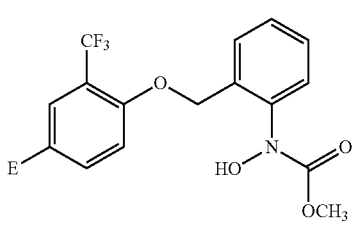
(HE1085)
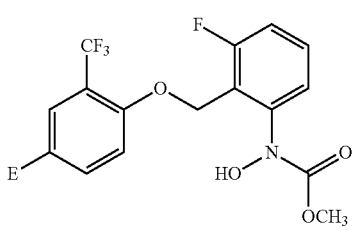
(HE1086)
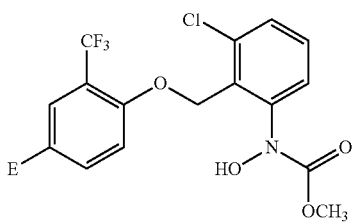
(HE1087)

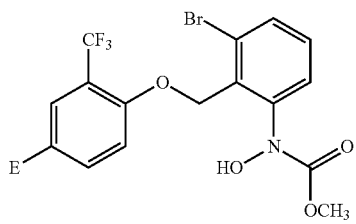
(HE1088)
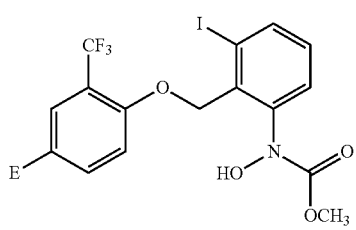
(HE1089)
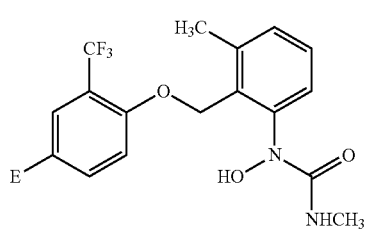
(HE1090)
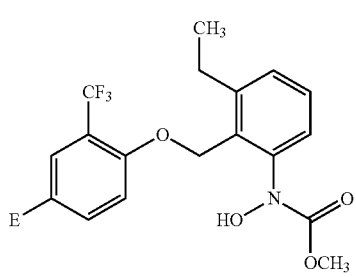
(HE1091)
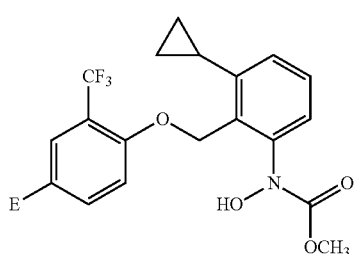
(HE1092)
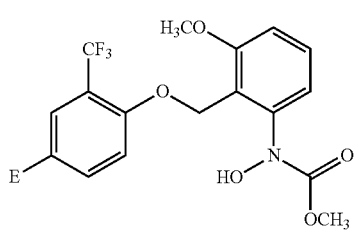
(HE1093)
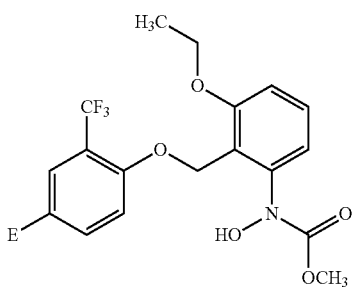
(HE1094)
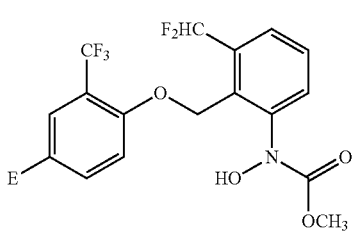
(HE1095)
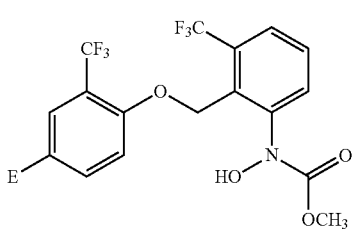
(HE1096)
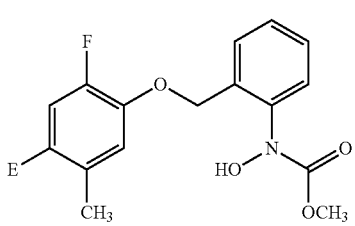
(HE4013)
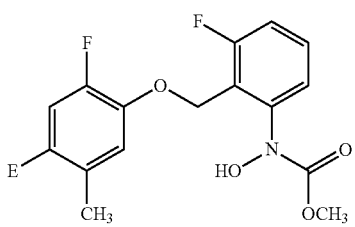
(HE4014)
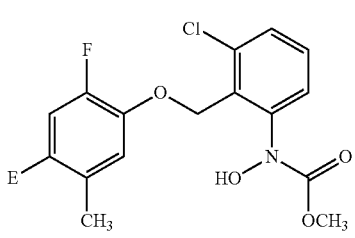
(HE4015)

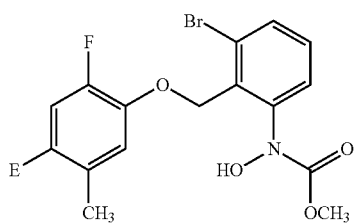
(HE4016)
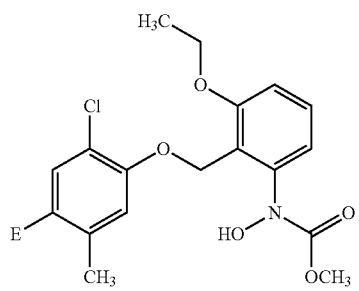
(HE4022)
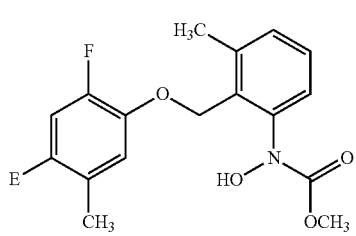
(HE4017)
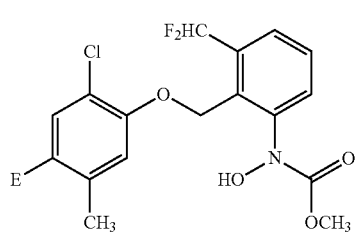
(HE4023)
(HE4018)
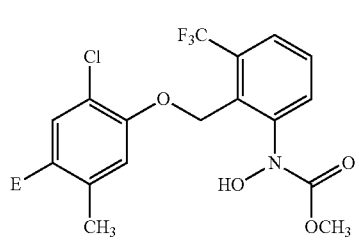
(HE4024)
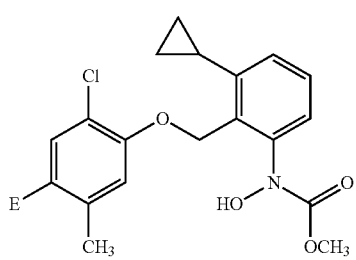
(HE4019)
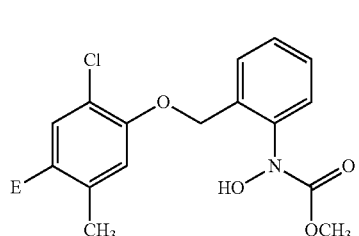
(HE4025)
(HE4020)
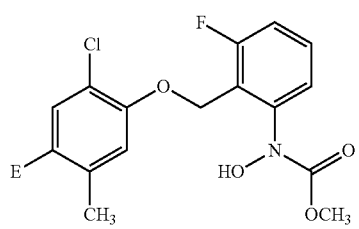
(HE4026)
(HE4021)
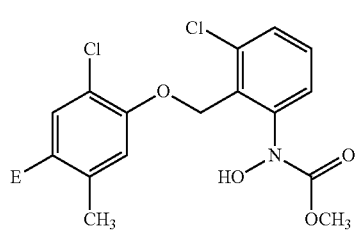
(HE4027)

-continued
(HE4028)
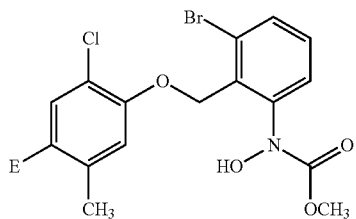
(HE4029)
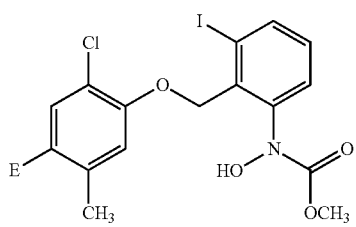
(HE4030)
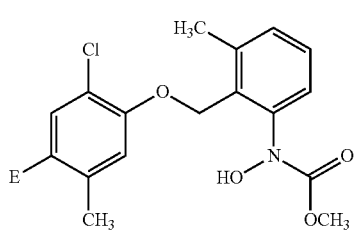
(HE4031)
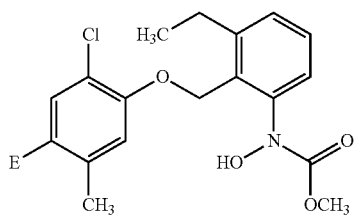
(HE4032)
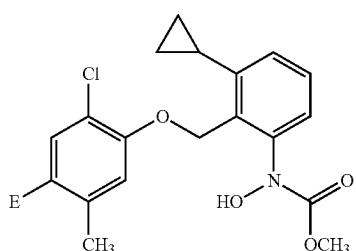
(HE4033)
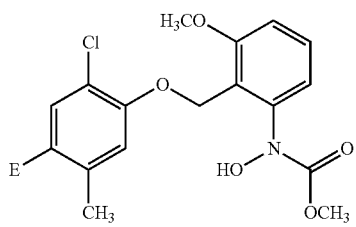
-continued
(HE4034)
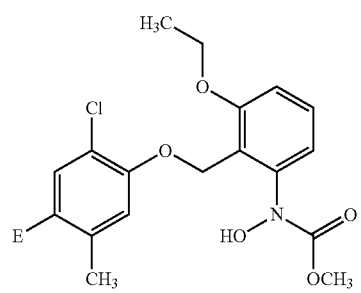
(HE4035)
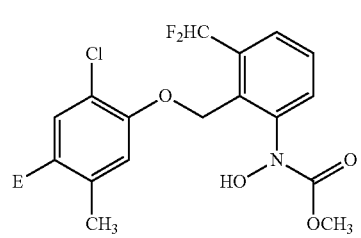
(HE4036)
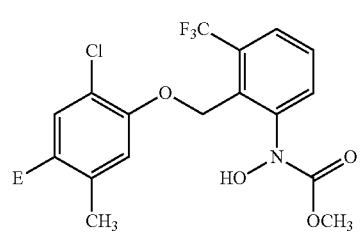
(HE4037)
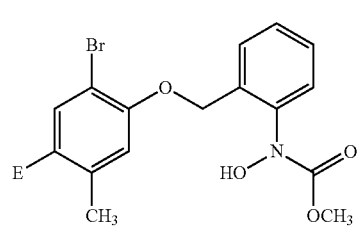
(HE4038)
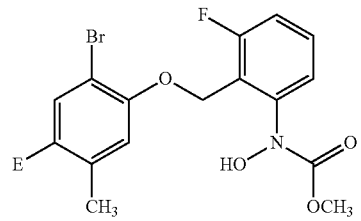
(HE4039)
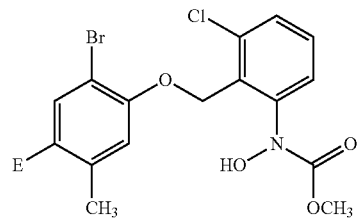

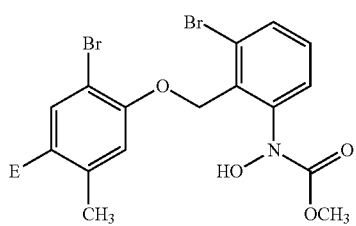
(HE4040)
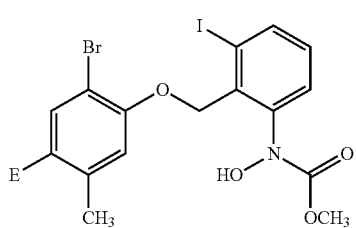
(HE4041)
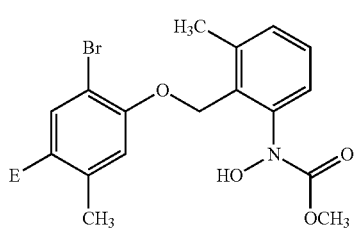
(HE4042)
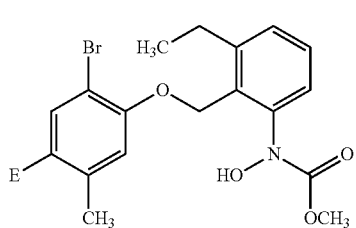
(HE4043)
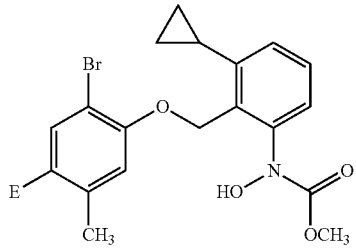
(HE4044)
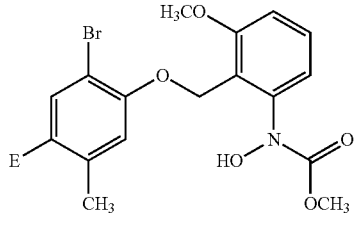
(HE4045)
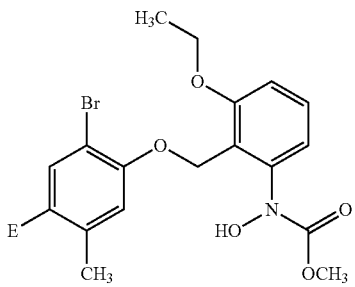
(HE4046)
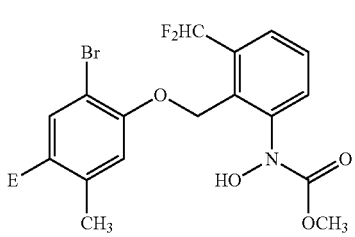
(HE4047)
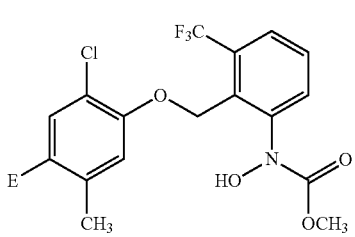
(HE4048)
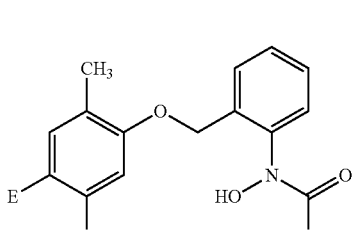
(HE4049)
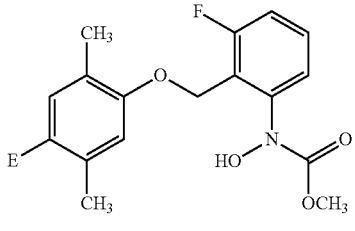
(HE4050)
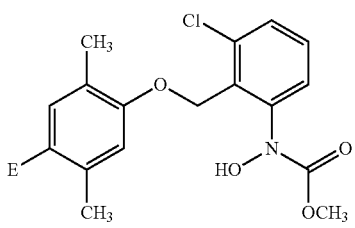
(HE4051)

-continued
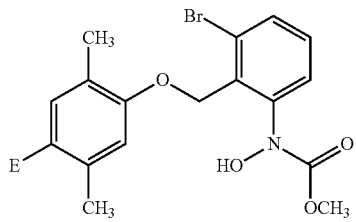 (HE4052)
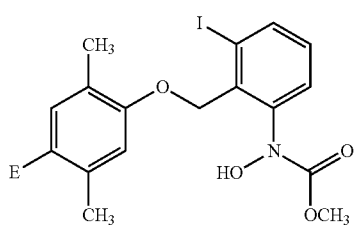 (HE4053)
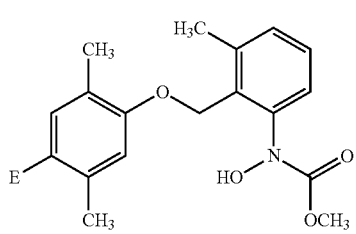 (HE4054)
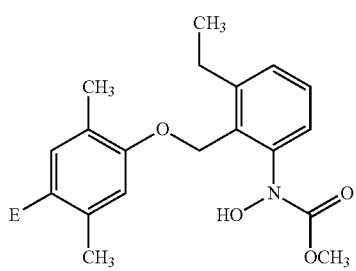 (HE4055)
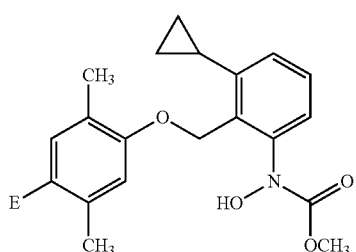 (HE4056)
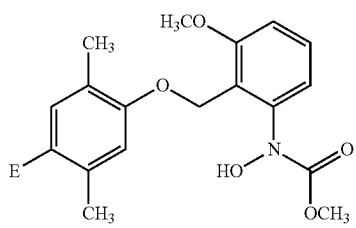 (HE4057)
-continued
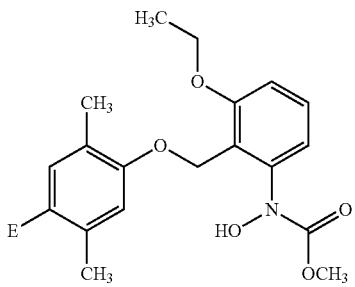 (HE4058)
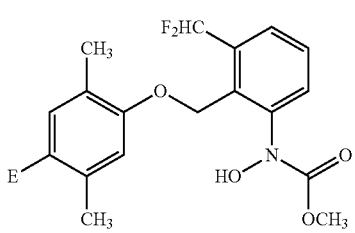 (HE4059)
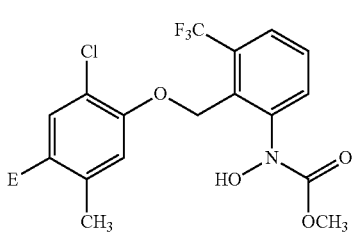 (HE4060)
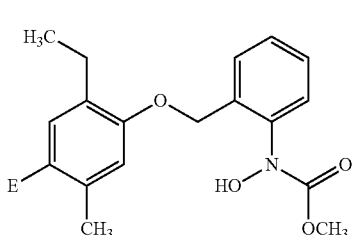 (HE4061)
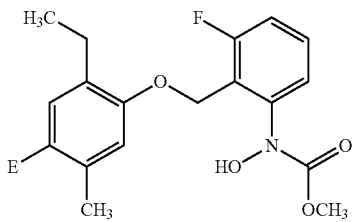 (HE4062)
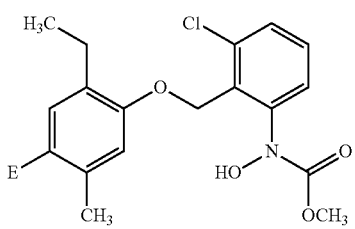 (HE4063)

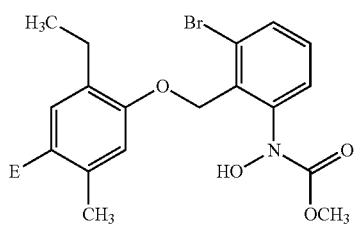 (HE4064)
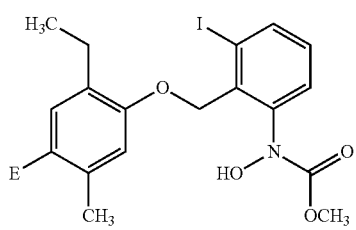 (HE4065)
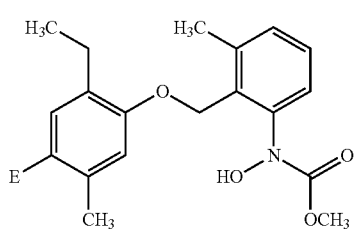 (HE4066)
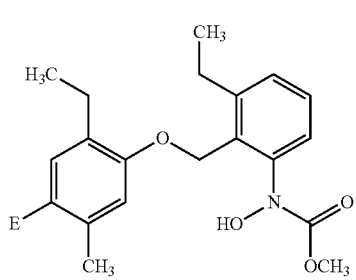 (HE4067)
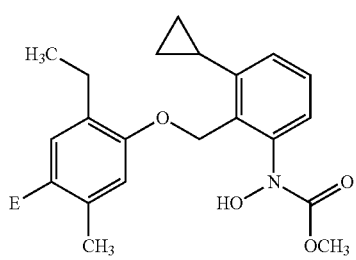 (HE4068)
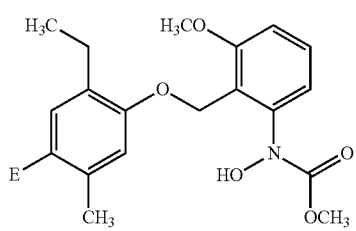 (HE4069)
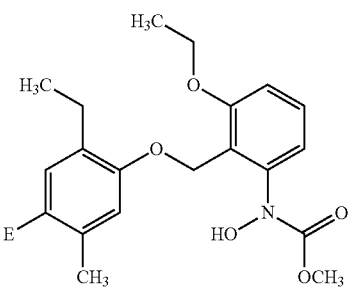 (HE4070)
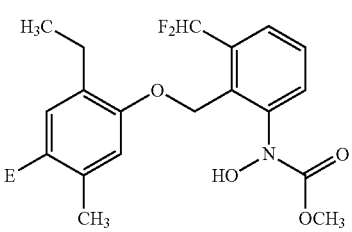 (HE4071)
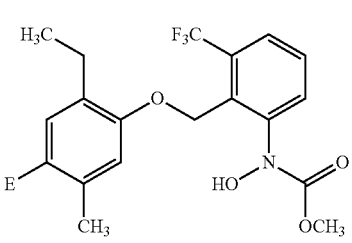 (HE4072)
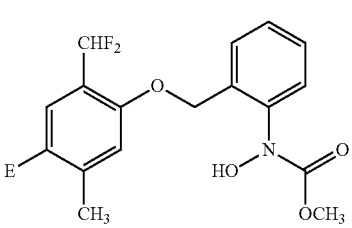 (HE4073)
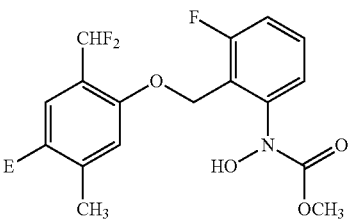 (HE4074)
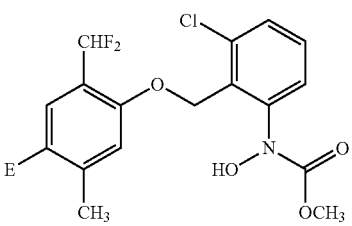 (HE4075)

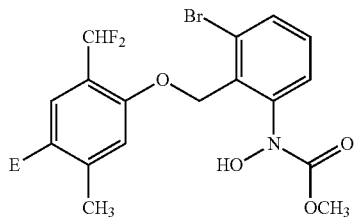
(HE4076)
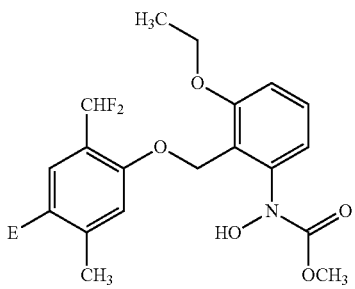
(HE4082)
(HE4077)
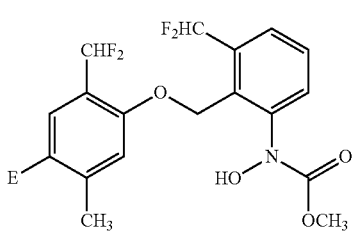
(HE4083)
(HE4078)
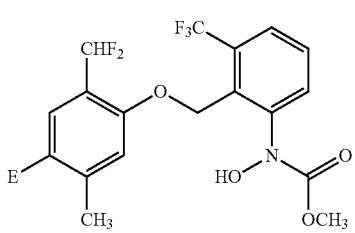
(HE4084)
(HE4079)
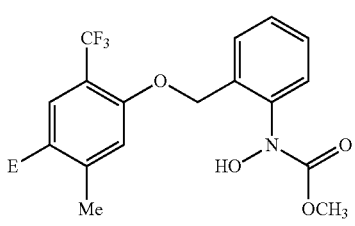
(HE4085)
(HE4080)
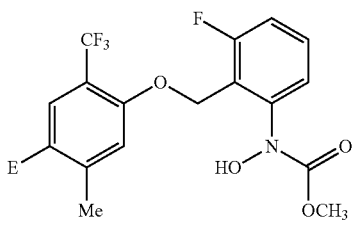
(HE4086)
(HE4081)
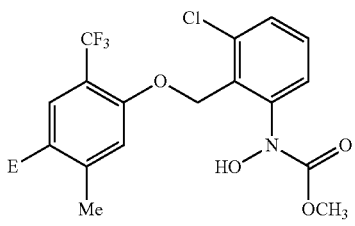
(HE4087)

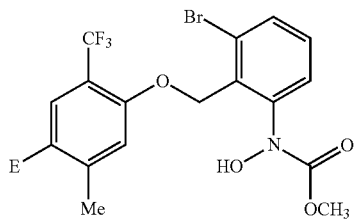
(HE4088)
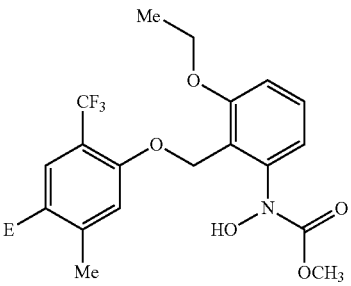
(HE4094)
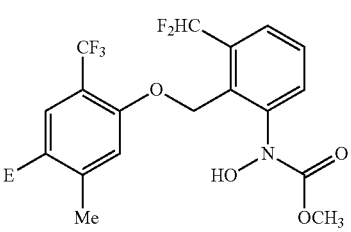
(HE4095)
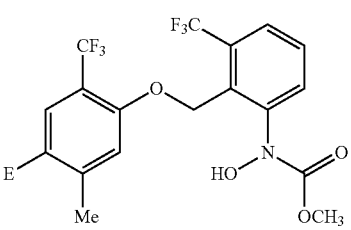
(HE4096)
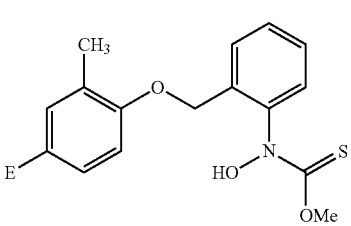
(HF1001)
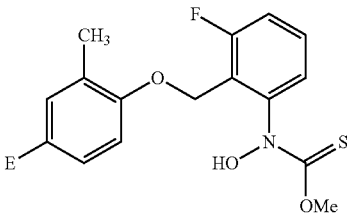
(HF1002)
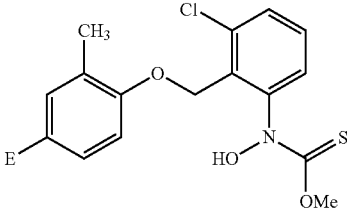
(HF1003)
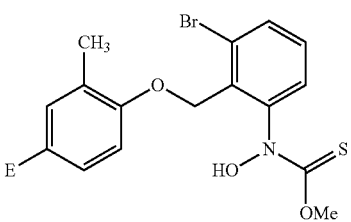
(HF1004)
(HE4089)
(HE4090)
(HE4091)
(HE4092)
(HE4093)

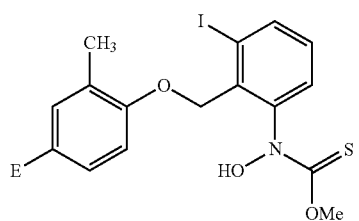
(HF1005)
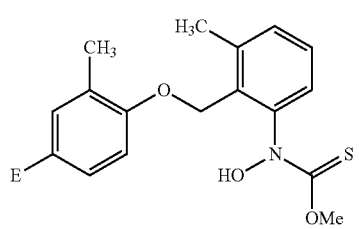
(HF1006)
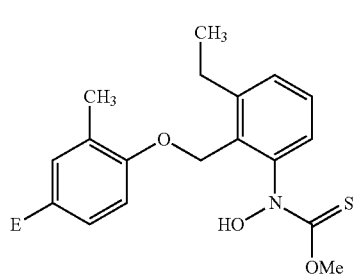
(HF1007)
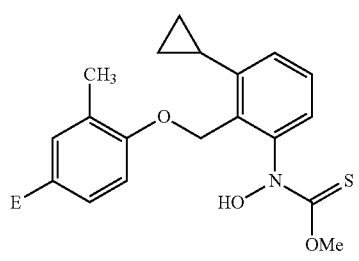
(HF1008)
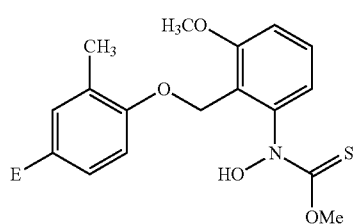
(HF1009)
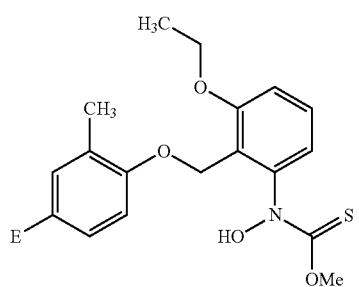
(HF1010)
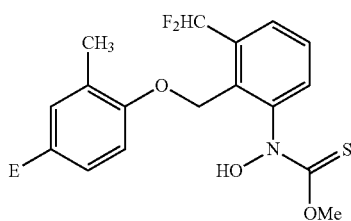
(HF1011)
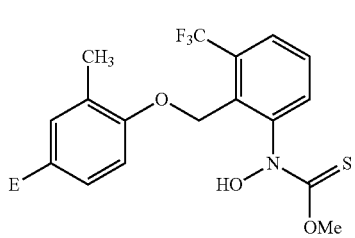
(HF1012)
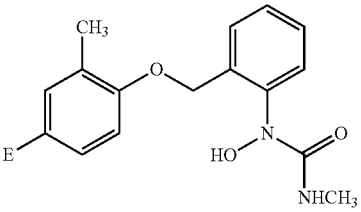
(HF1013)
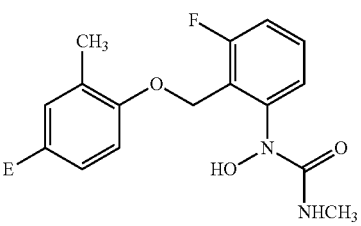
(HF1014)
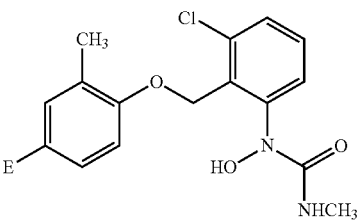
(HF1015)
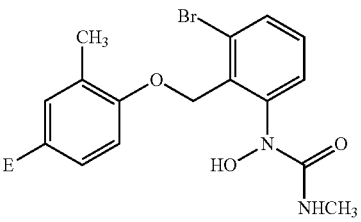
(HF1016)
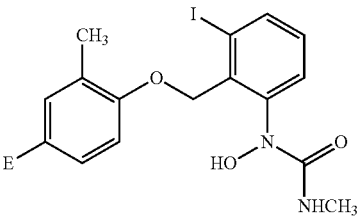
(HF1017)

-continued
(HF1018)
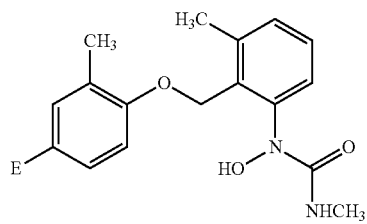
(HF1019)
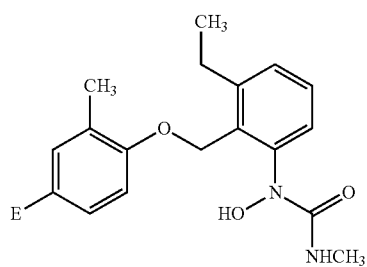
(HF1020)
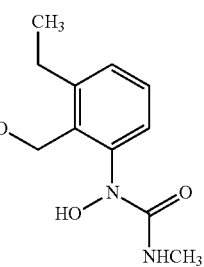
(HF1021)
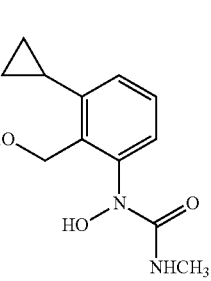
(HF1022)
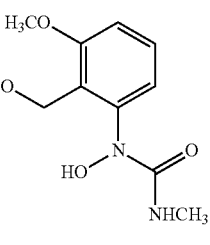
(HF1023)
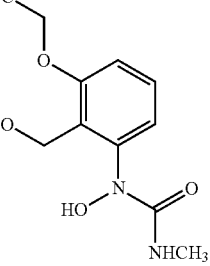
-continued
(HF1024)
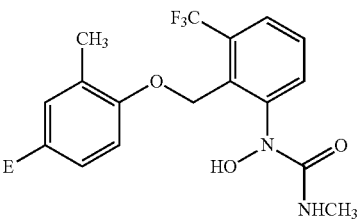
(HF1025)
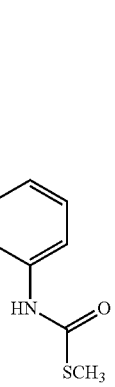
(HF1026)
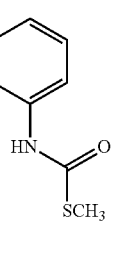
(HF1027)
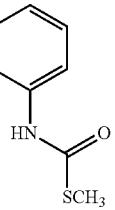
(HF1028)
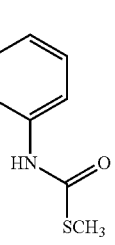
(HF1029)
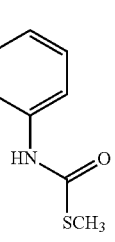

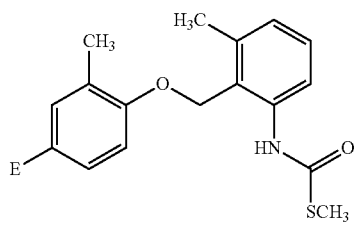 (HF1030)
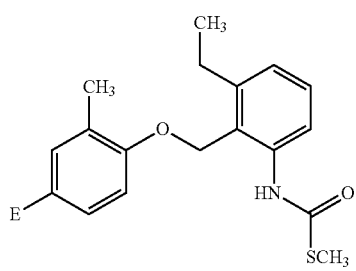 (HF1031)
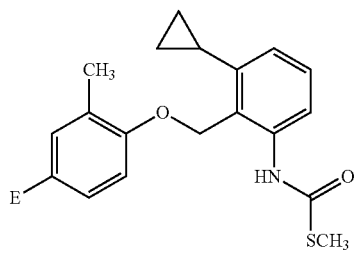 (HF1032)
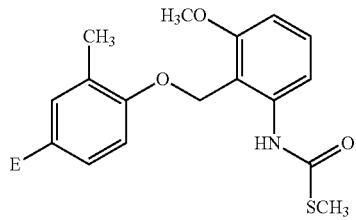 (HF1033)
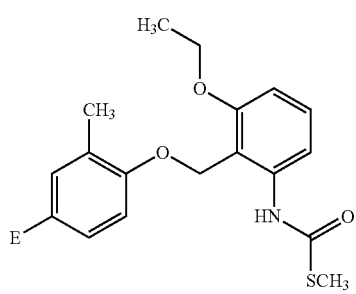 (HF1034)
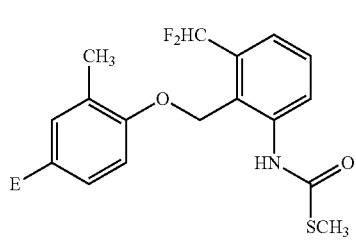 (HF1035)
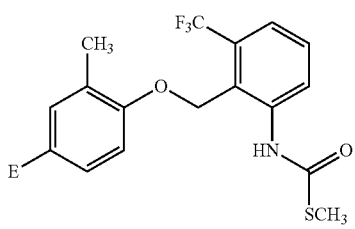 (HF1036)
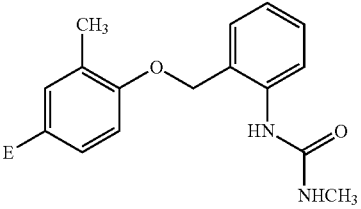 (HF1037)
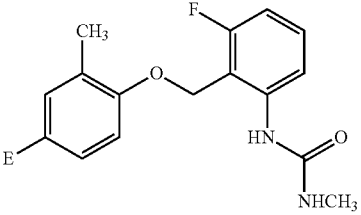 (HF1038)
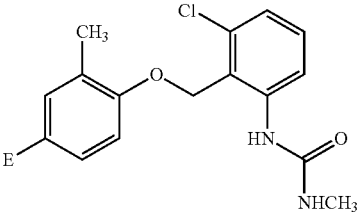 (HF1039)
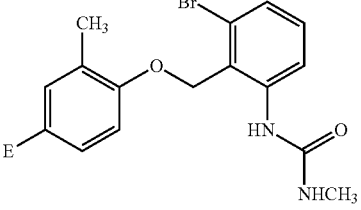 (HF1040)
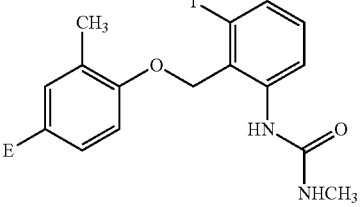 (HF1041)
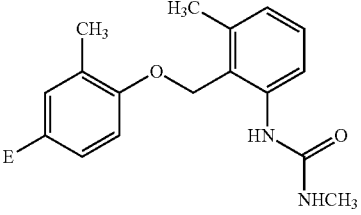 (HF1042)

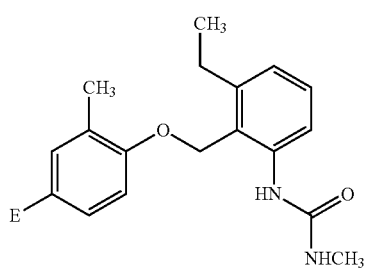
(HF1043)
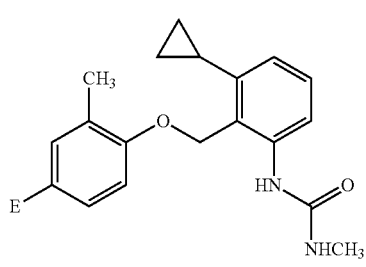
(HF1044)
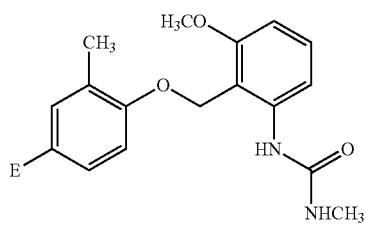
(HF1045)
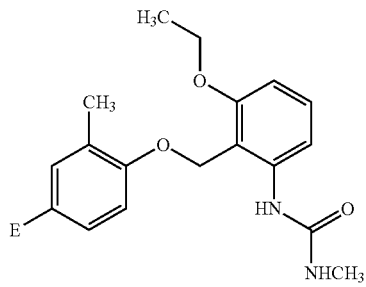
(HF1046)
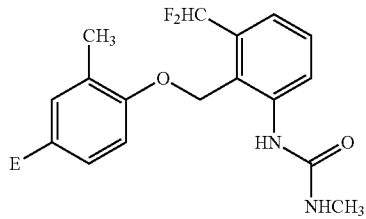
(HF1047)
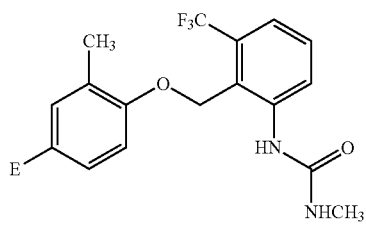
(HF1048)
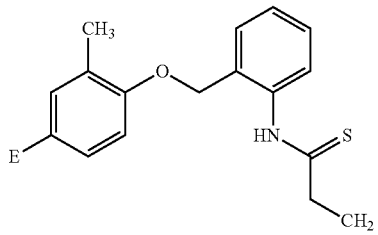
(HF1049)
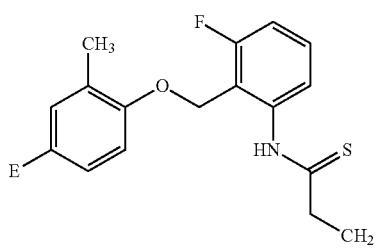
(HF1050)
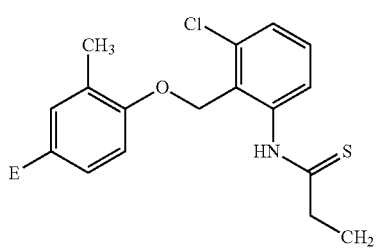
(HF1051)
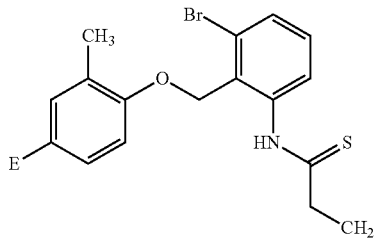
(HF1052)
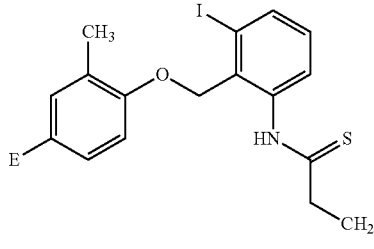
(HF1053)
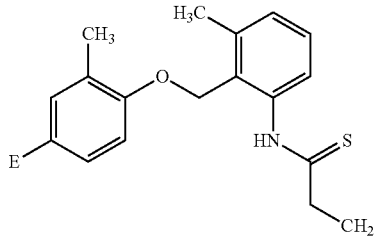
(HF1054)

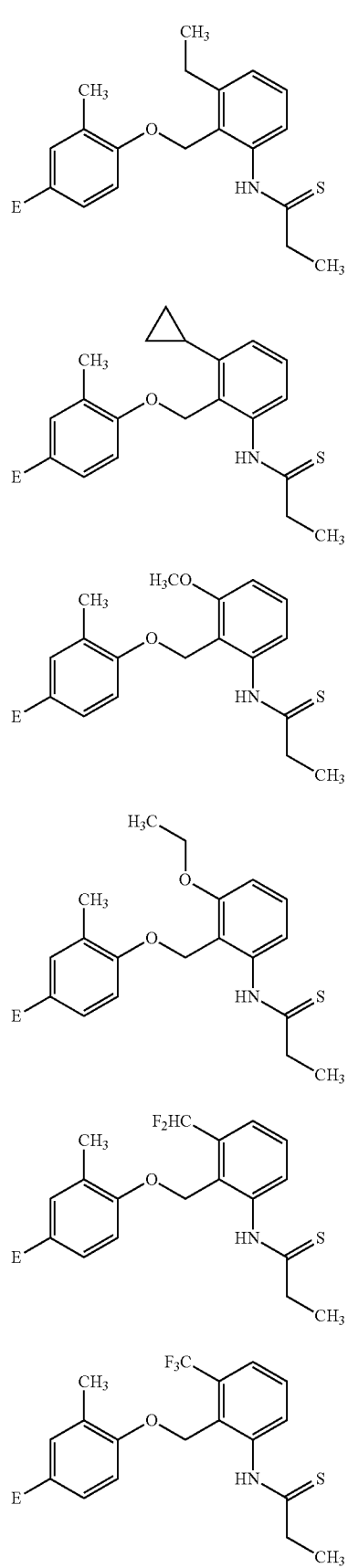
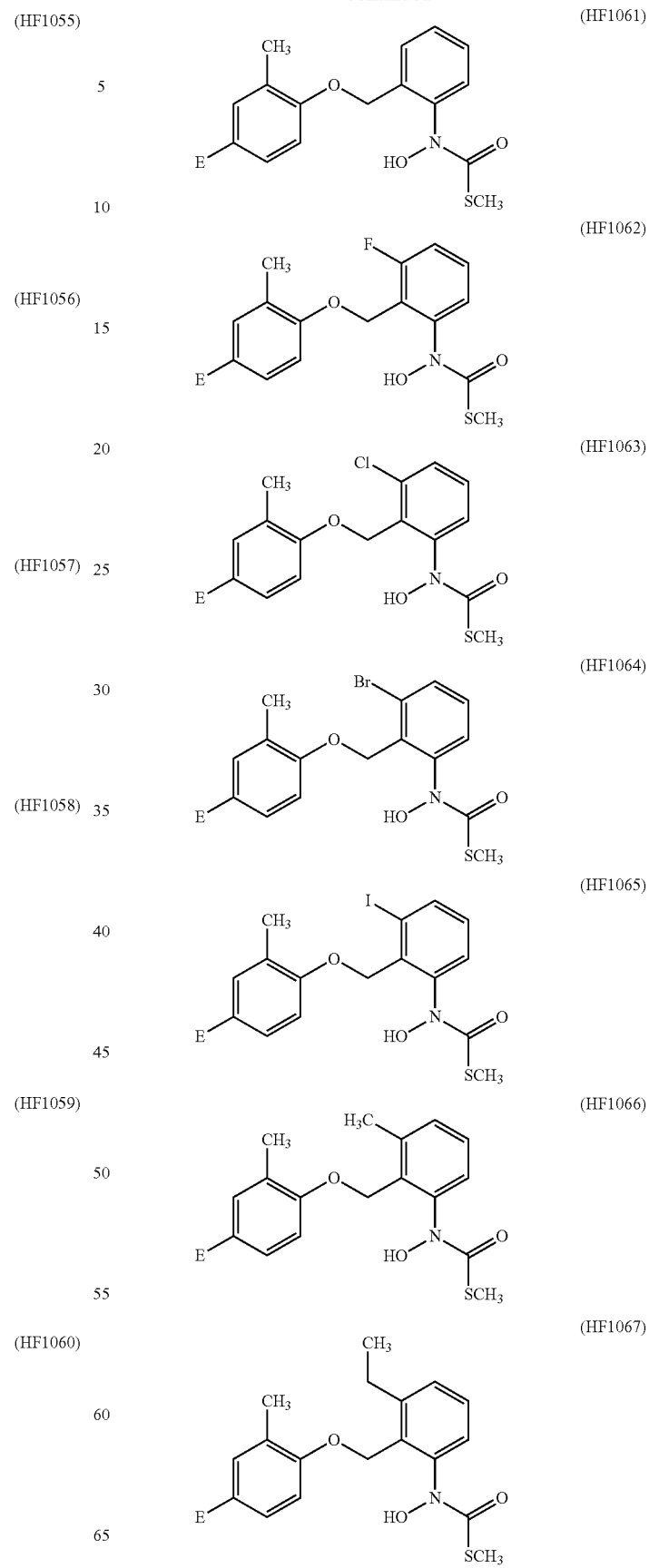

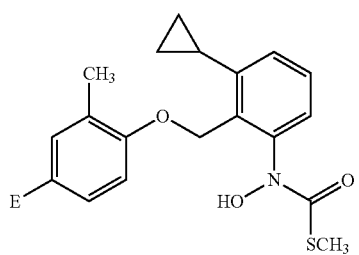
(HF1068)
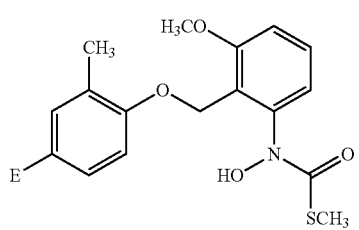
(HF1069)
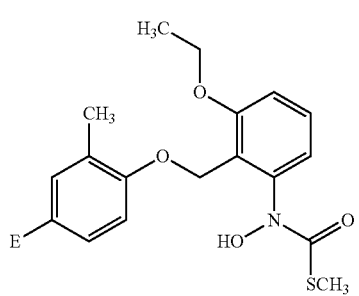
(HF1070)
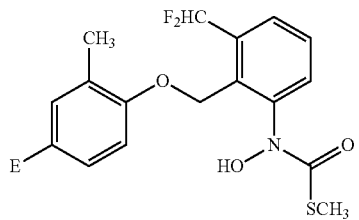
(HF1071)
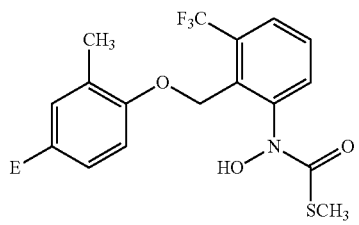
(HF1072)
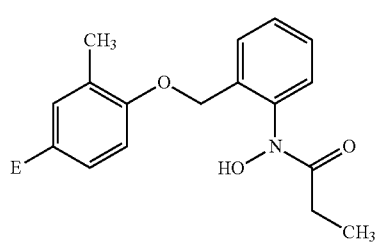
(HF1085)
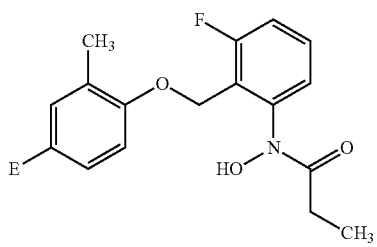
(HF1086)
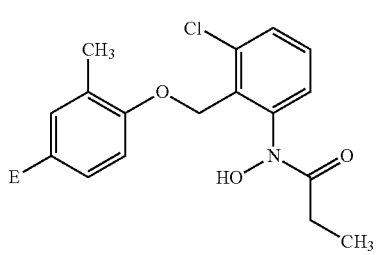
(HF1087)
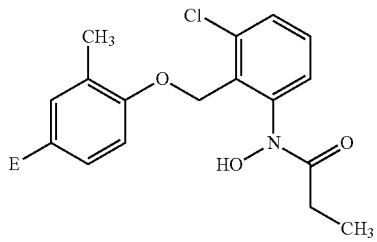
(HF1088)
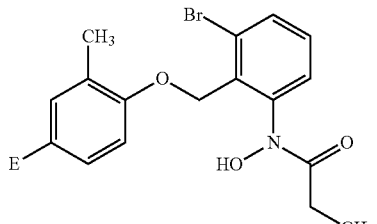
(HF1089)
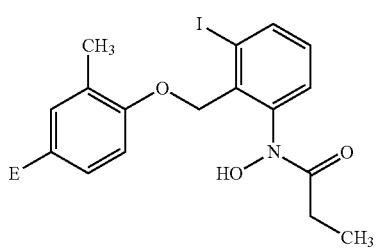
(HF1090)
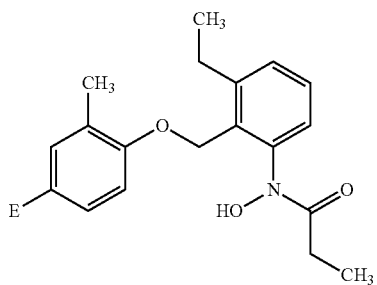
(HF1091)

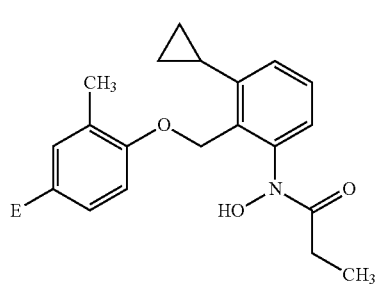
(HF1092)
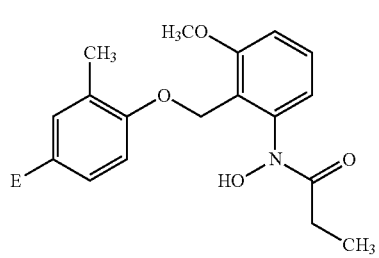
(HF1093)
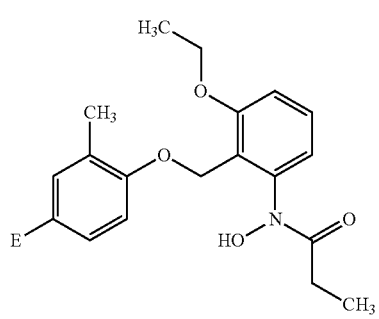
(HF1094)
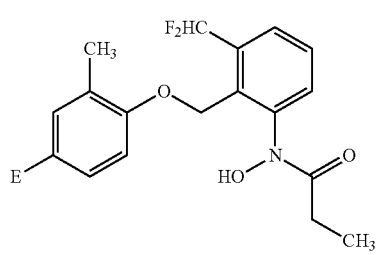
(HF1095)
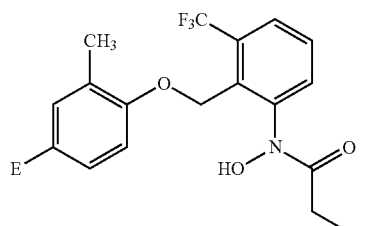
(HF1096)
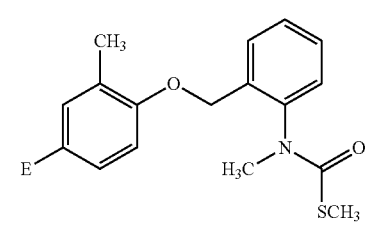
(HF1097)
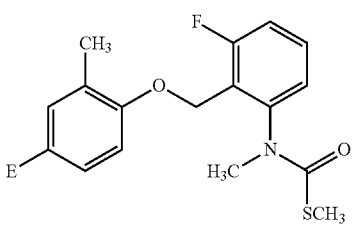
(HF1098)
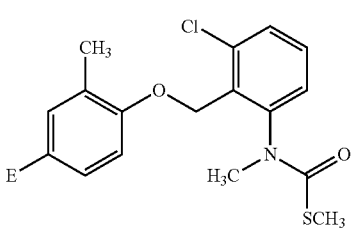
(HF1099)
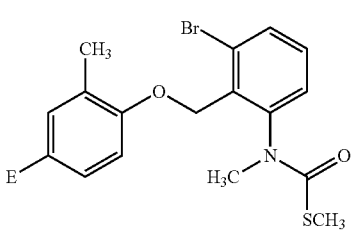
(HF1100)
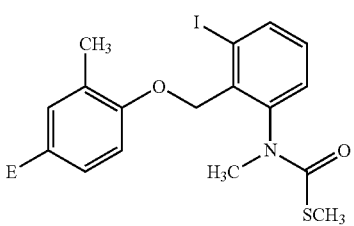
(HF1101)
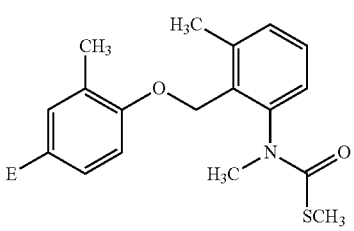
(HF1102)
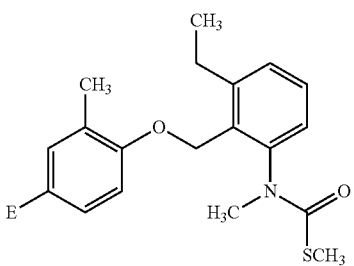
(HF1103)

(HF1104)
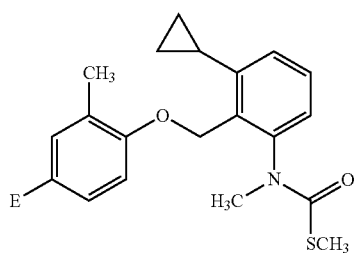
(HF1105)
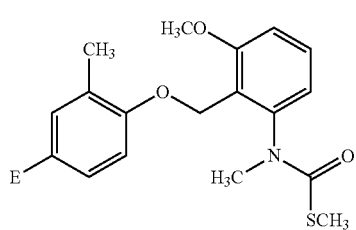
(HF1106)
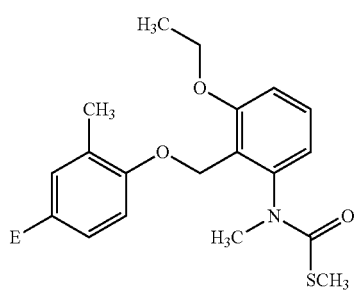
(HF1107)
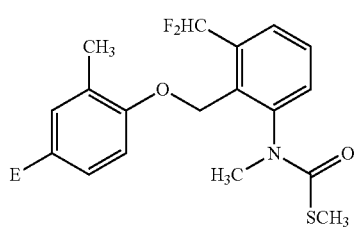
(HF1108)
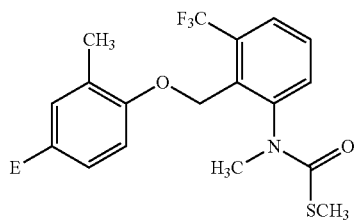
(HF1109)
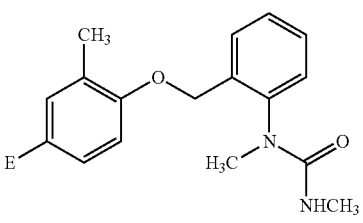
(HF1110)
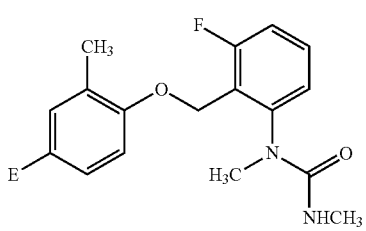
(HF1111)
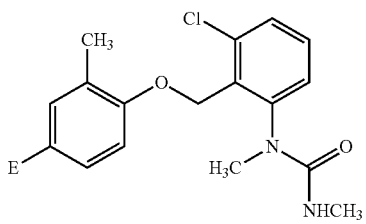
(HF1112)
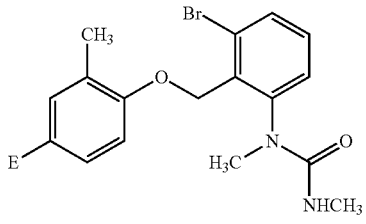
(HF1113)
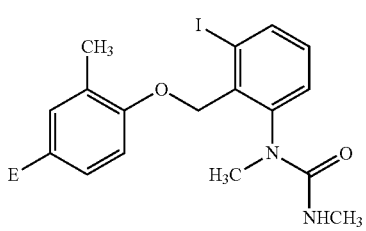
(HF1114)
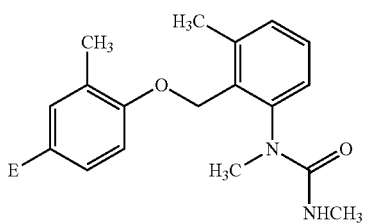
(HF1115)
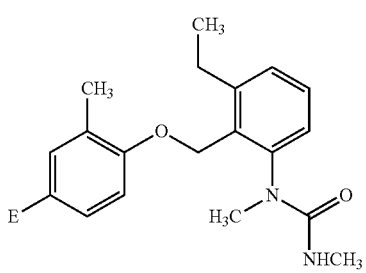

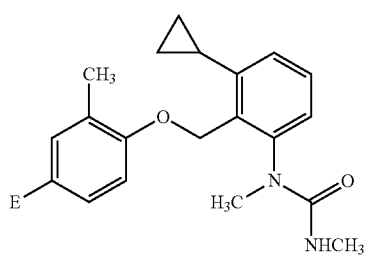
(HF1116)
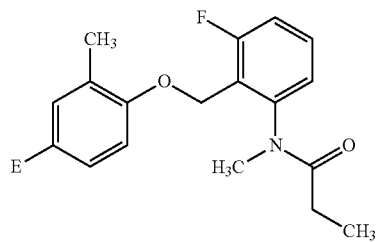
(HF1122)
(HF1117)
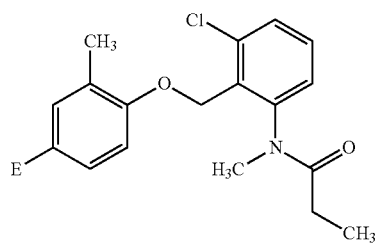
(HF1123)
(HF1118)
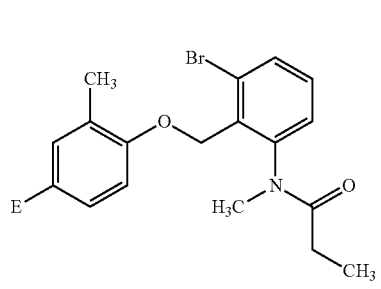
(HF1124)
(HF1119)
(HF1125)
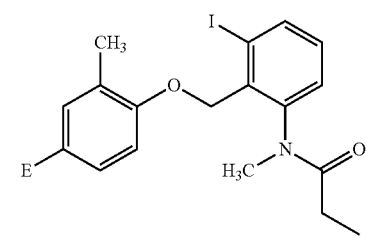
(HF1120)
(HF1126)
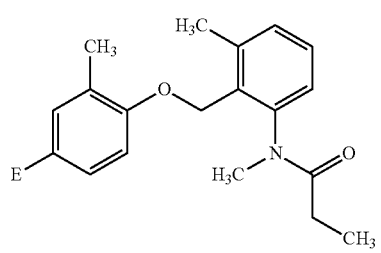
(HF1121)
(HF1127)
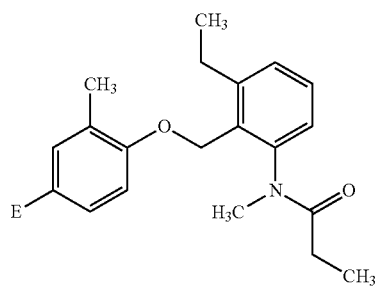

(HF1128)
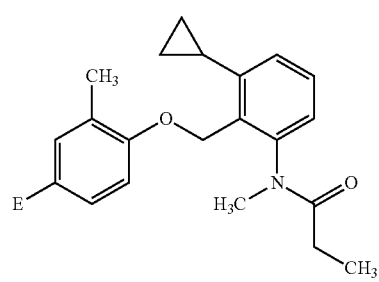
(HF1129)
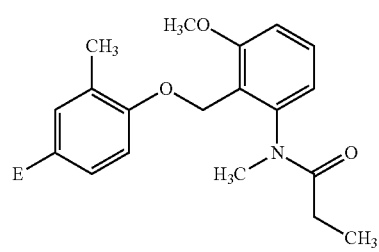
(HF1130)
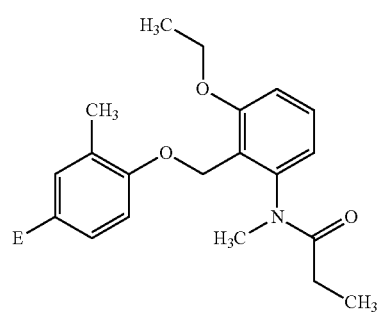
(HF1131)
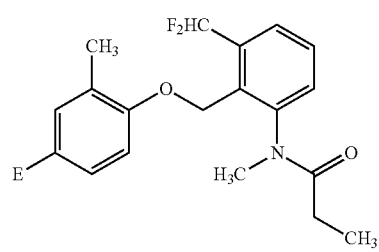
(HF1132)
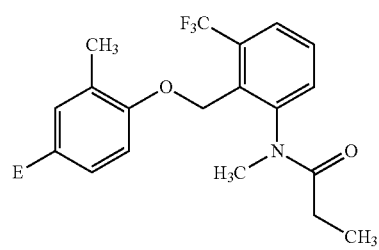
(HF1133)
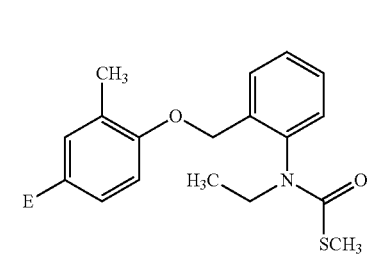
(HF1134)
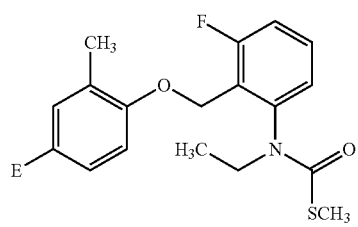
(HF1135)
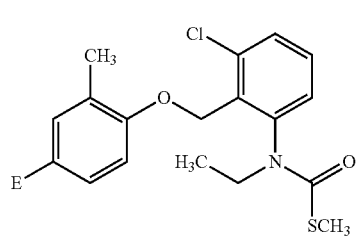
(HF1136)
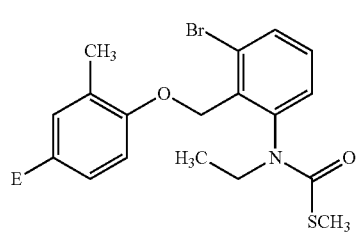
(HF1137)
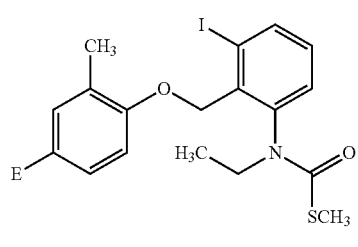
(HF1138)
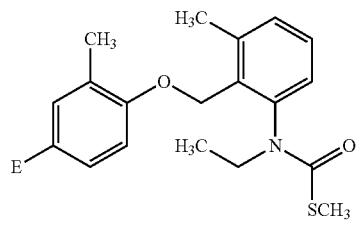
(HF1139)
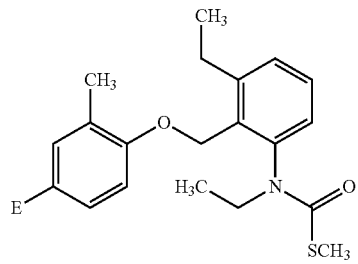

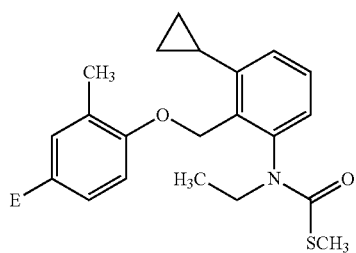 (HF1140)
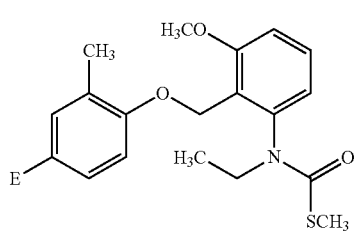 (HF1141)
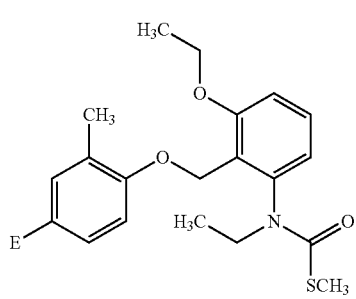 (HF1142)
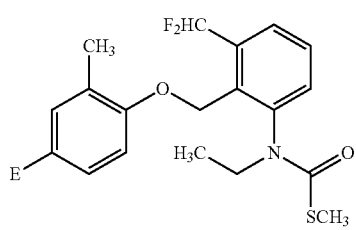 (HF1143)
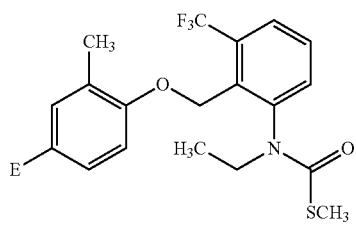 (HF1144)
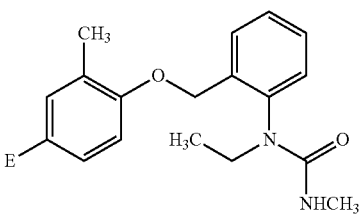 (HF1145)
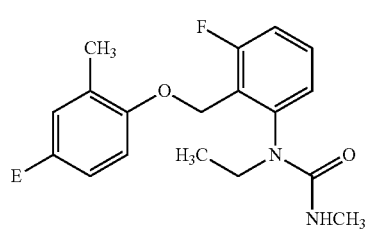 (HF1146)
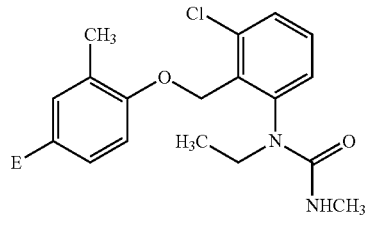 (HF1147)
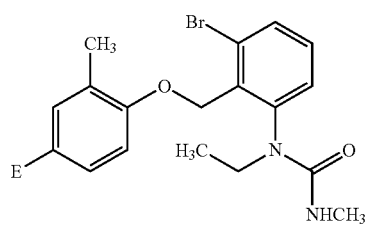 (HF1148)
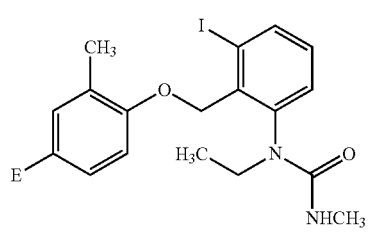 (HF1149)
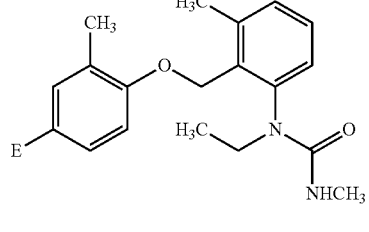 (HF1150)
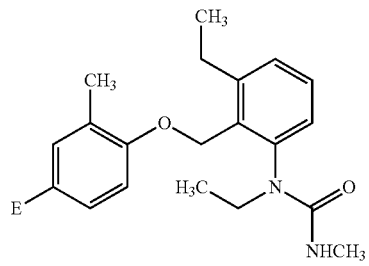 (HF1151)

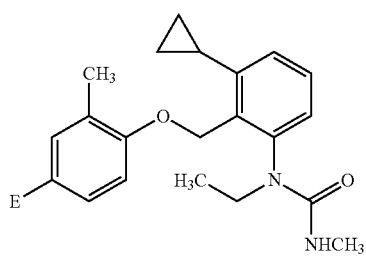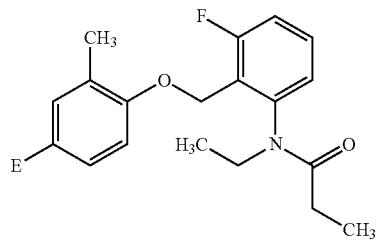

| | |
|---|---|
| (HF1164) 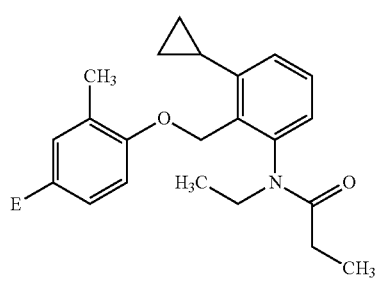 | (HF2002) 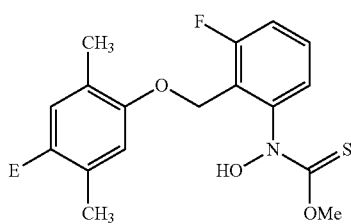 |
| (HF1165) 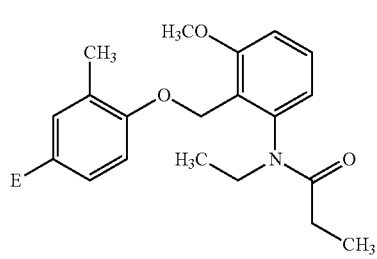 | (HF2003) 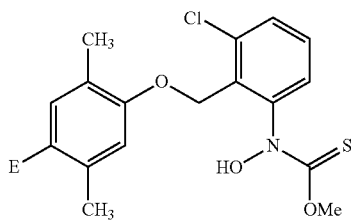 |
| (HF1166) 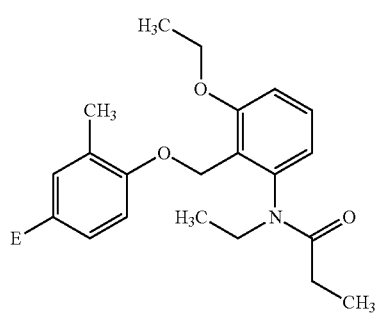 | (HF2004) 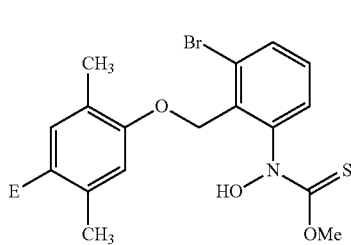 |
| (HF1167) 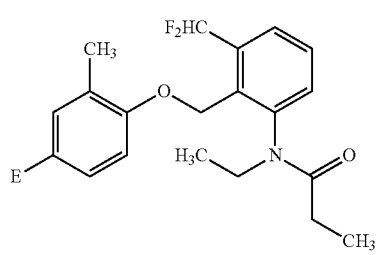 | (HF2005) 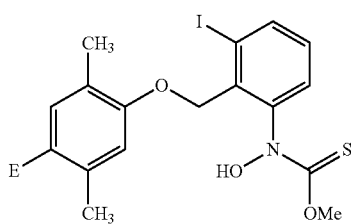 |
| (HF1168) 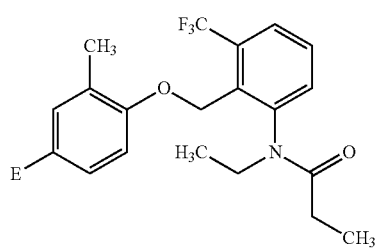 | (HF2006) 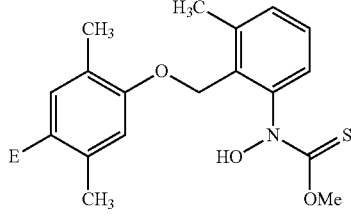 |
| (HF2001) 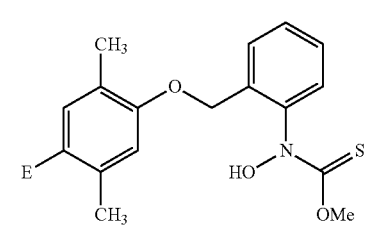 | (HF2007) 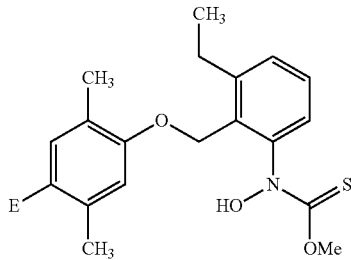 |

| 223 -continued | 224 -continued |
|---|---|
| 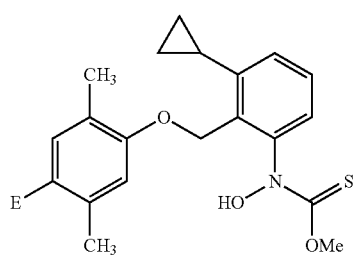 (HF2008) | 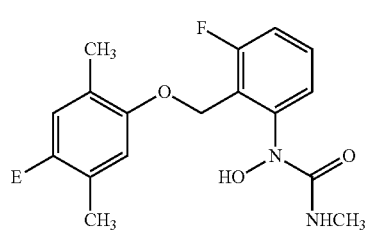 (HF2014) |
| 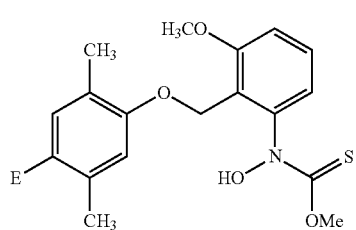 (HF2009) | 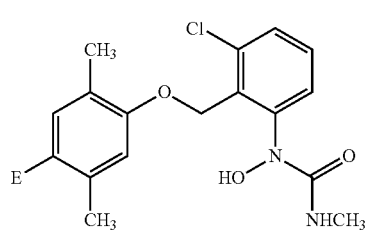 (HF2015) |
| 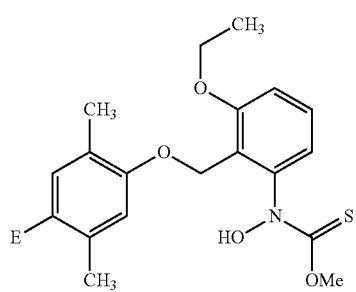 (HF2010) | 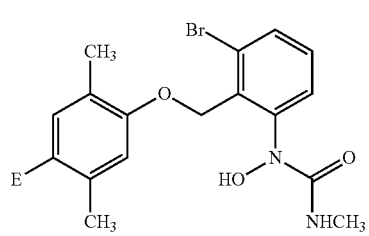 (HF2016) |
| 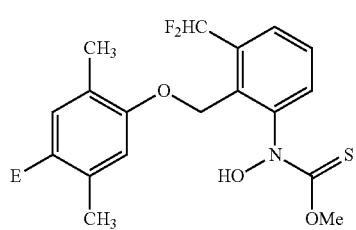 (HF2011) | 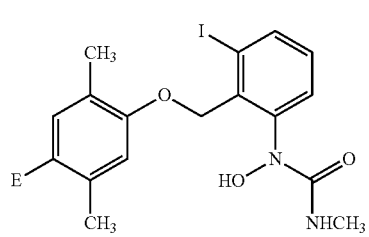 (HF2017) |
| 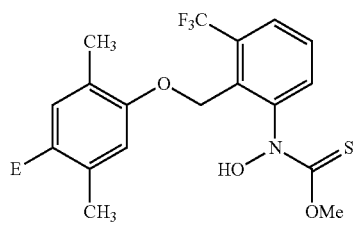 (HF2012) | 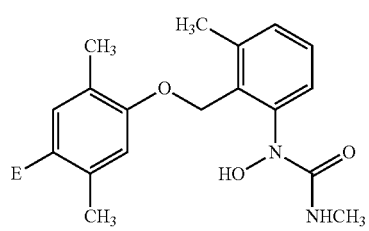 (HF2018) |
| 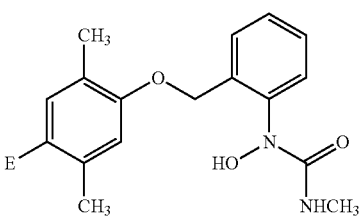 (HF2013) | 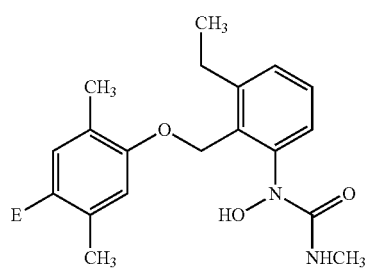 (HF2019) |

(HF2020) 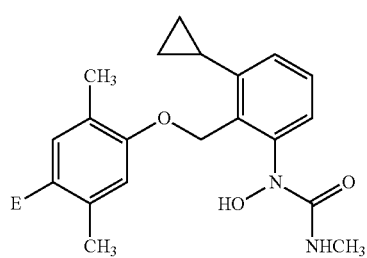
(HF2021) 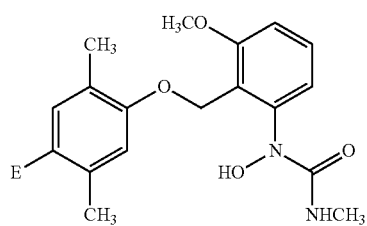
(HF2022) 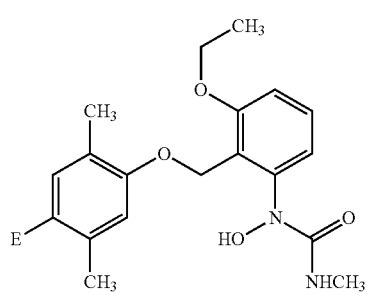
(HF2023) 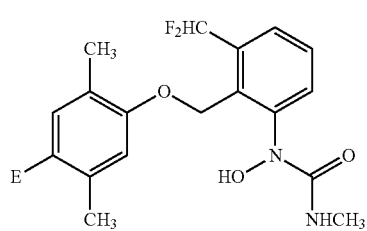
(HF2024) 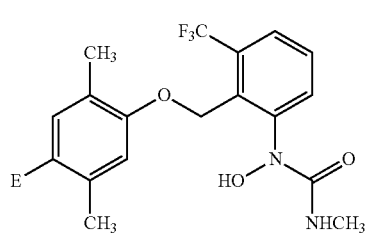
(HF2025) 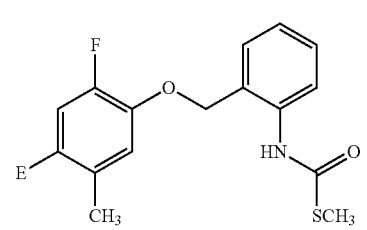
(HF2026) 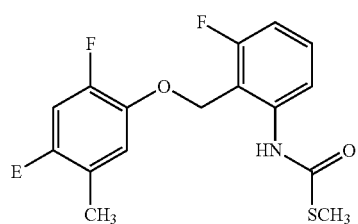
(HF2027) 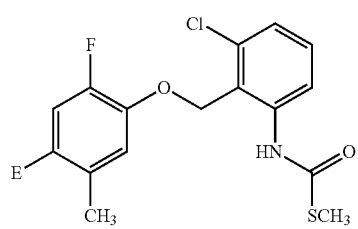
(HF2028) 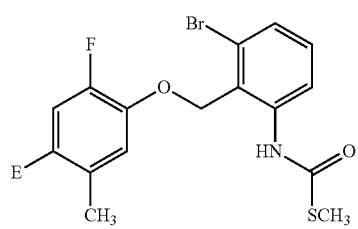
(HF2029) 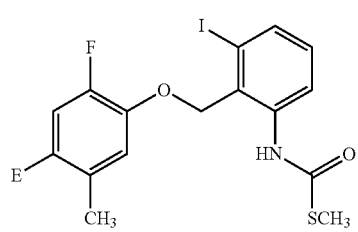
(HF2030) 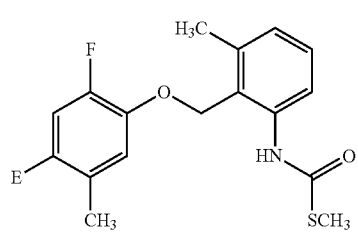
(HF2031) 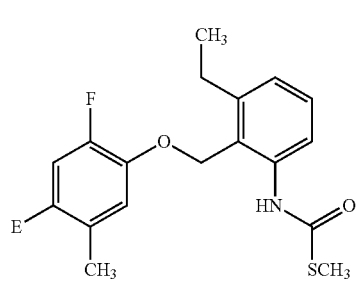

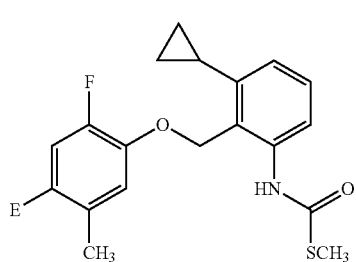
(HF2032)
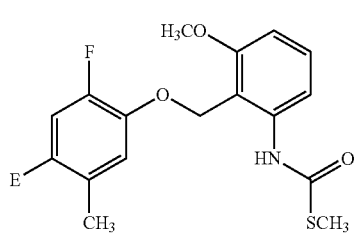
(HF2033)
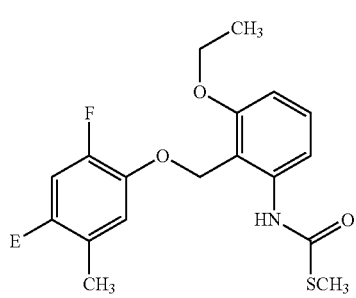
(HF2034)
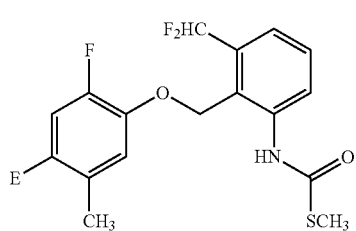
(HF2035)
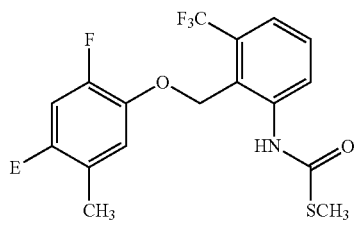
(HF2036)
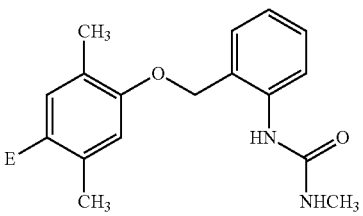
(HF2037)
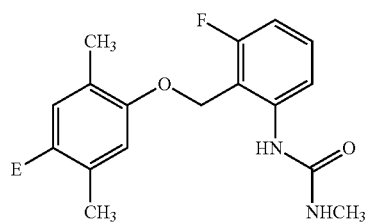
(HF2038)
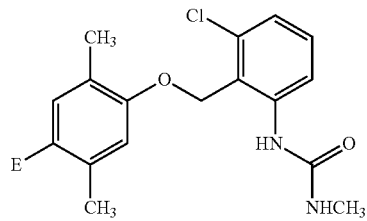
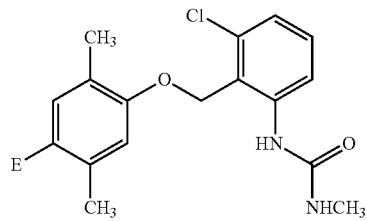
(HF2039)
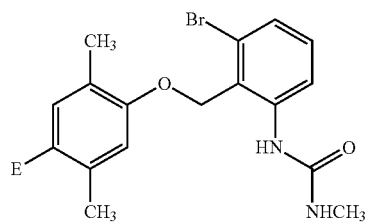
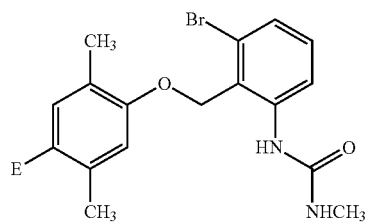
(HF2040)
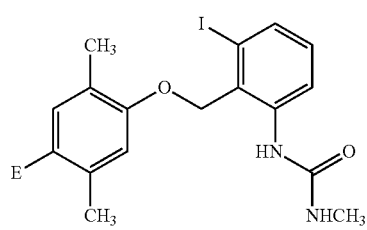
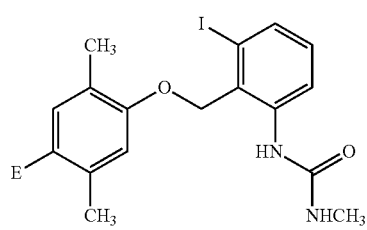
(HF2041)
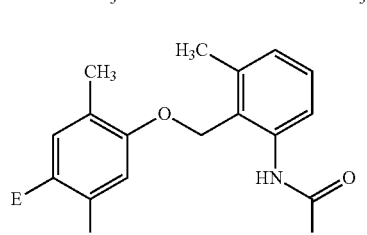
(HF2042)
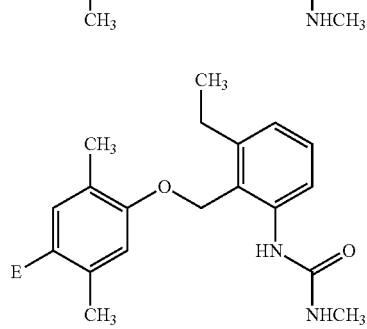
(HF2043)

-continued
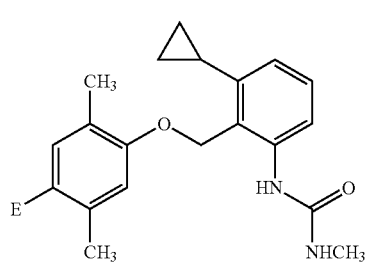 (HF2044)
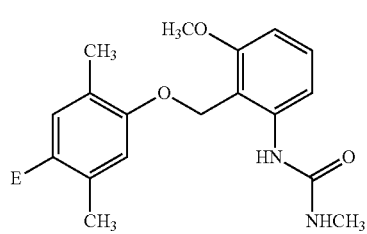 (HF2045)
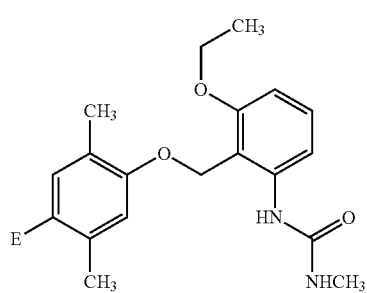 (HF2046)
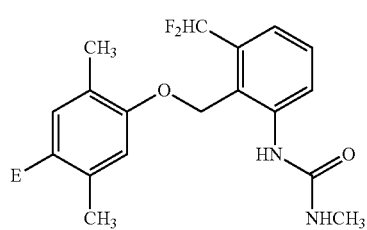 (HF2047)
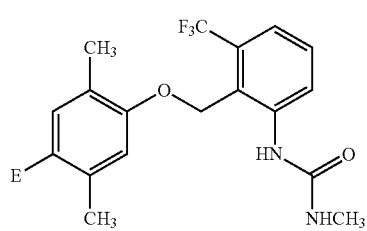 (HF2048)
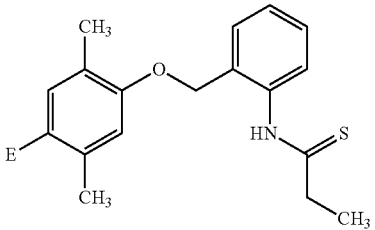 (HF2049)
-continued
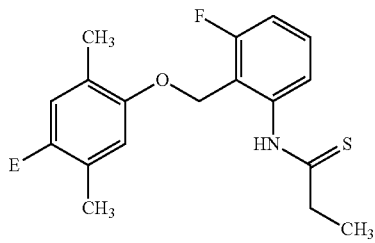 (HF2050)
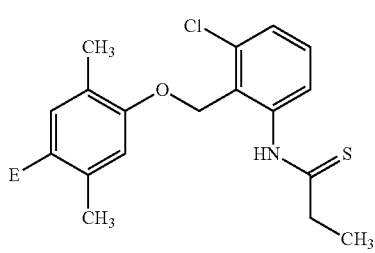 (HF2051)
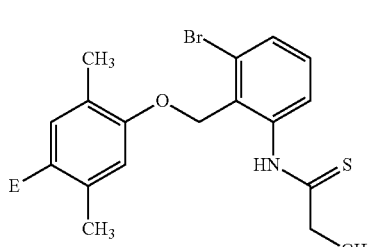 (HF2052)
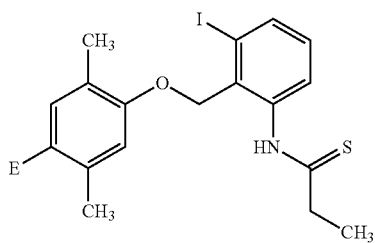 (HF2053)
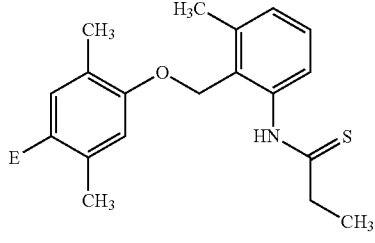 (HF2054)
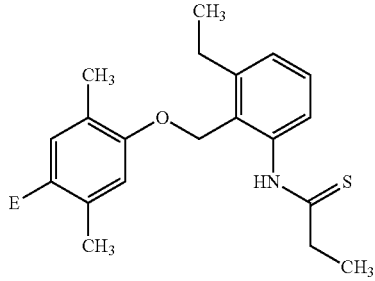 (HF2055)

(HF2056)
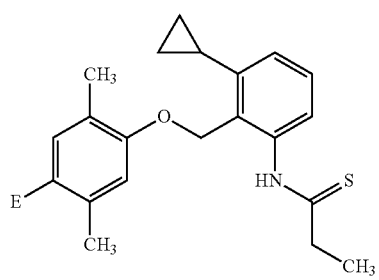
(HF2057)
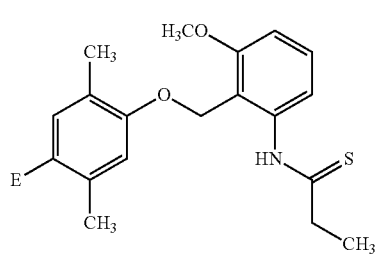
(HF2058)
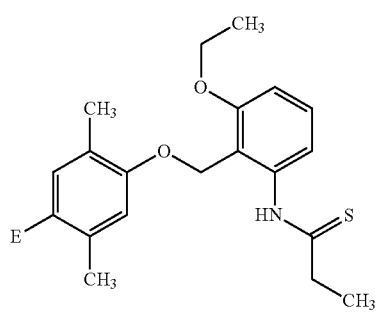
(HF2059)
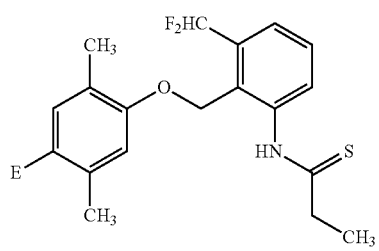
(HF2060)
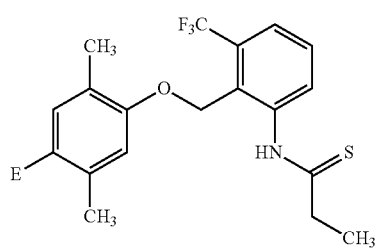
(HF2061)
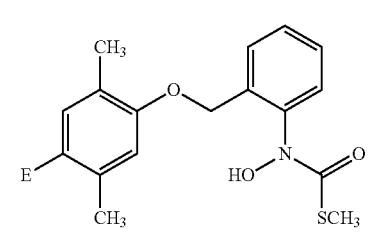
(HF2062)
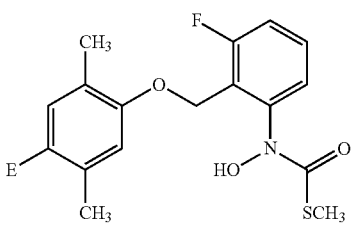
(HF2063)
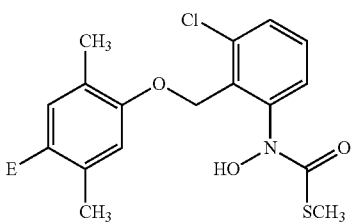
(HF2064)
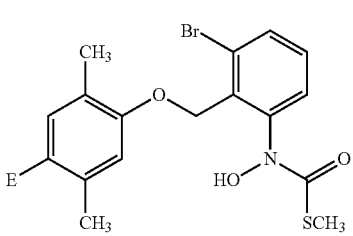
(HF2065)
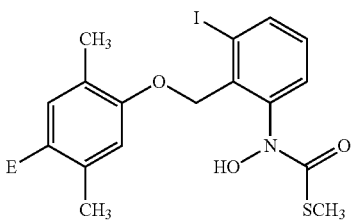
(HF2066)
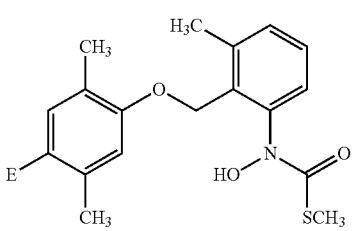
(HF2067)
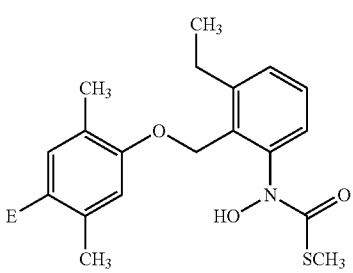

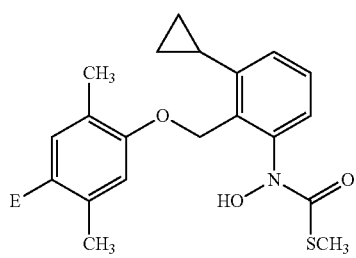
(HF2068)
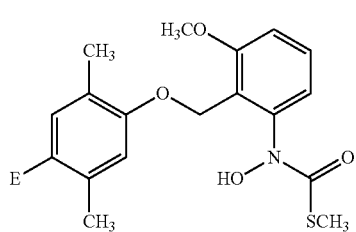
(HF2069)
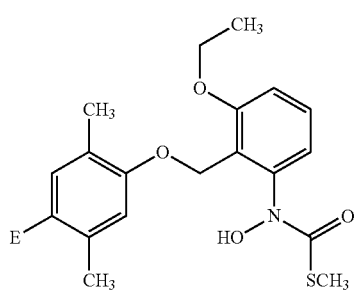
(HF2070)
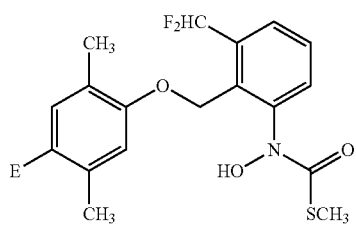
(HF2071)
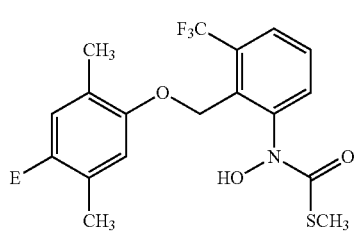
(HF2072)
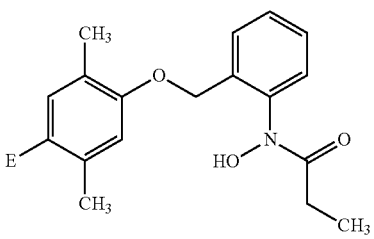
(HF2085)
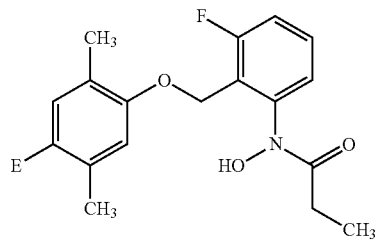
(HF2086)
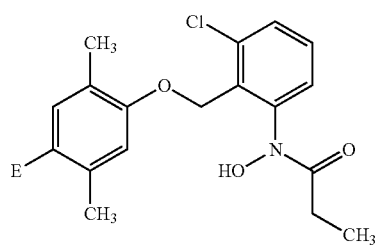
(HF2087)
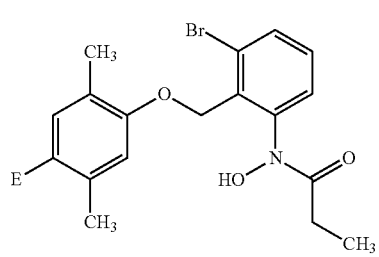
(HF2088)
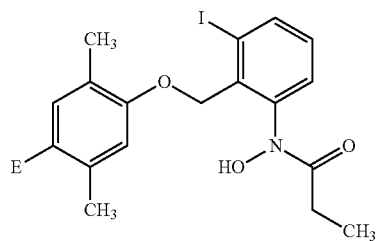
(HF2089)
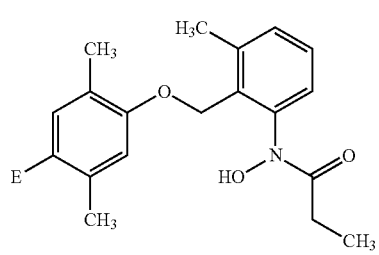
(HF2090)
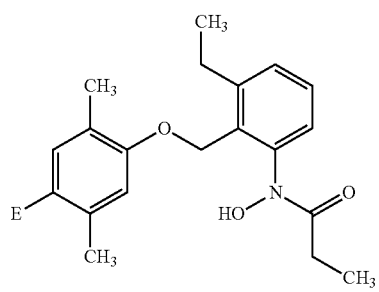
(HF2091)

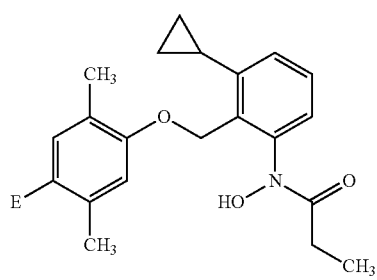
(HF2092)
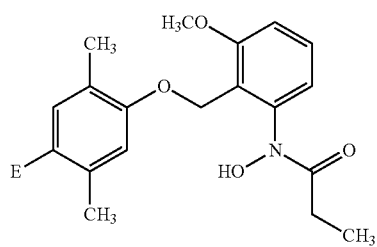
(HF2093)
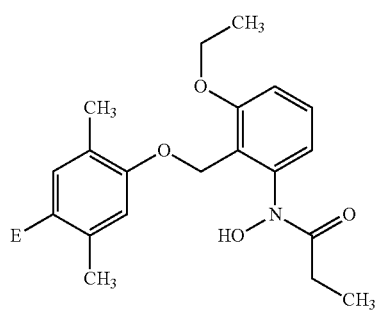
(HF2094)
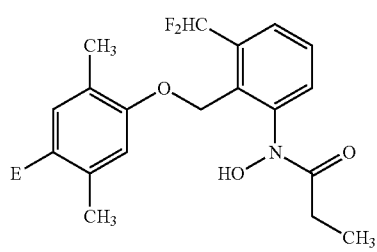
(HF2095)
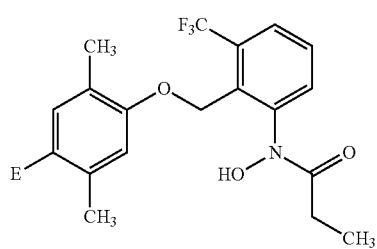
(HF2096)
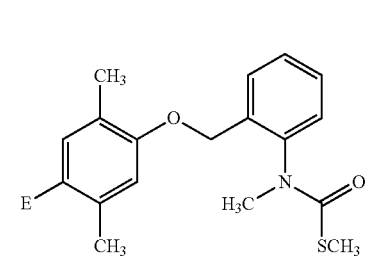
(HF2097)
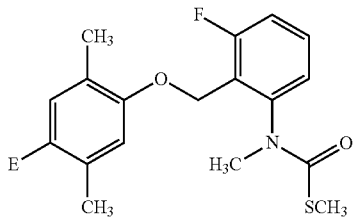
(HF2098)
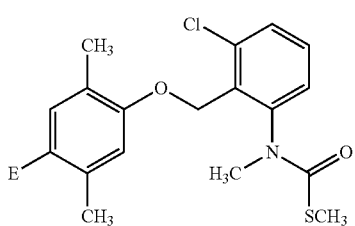
(HF2099)
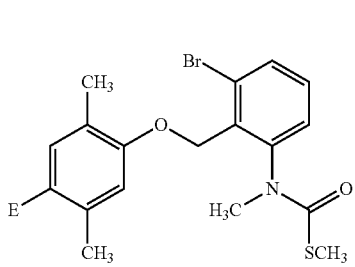
(HF2100)
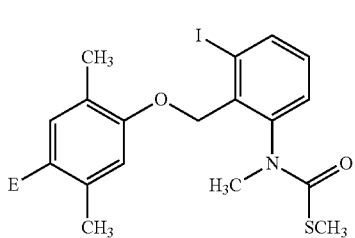
(HF2101)
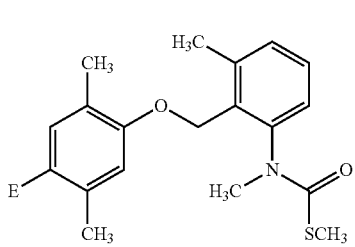
(HF2102)
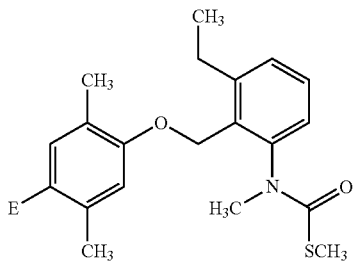
(HF2103)

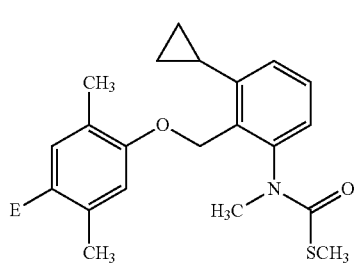 (HF2104)
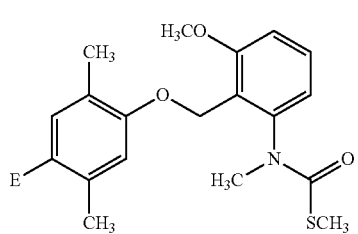 (HF2105)
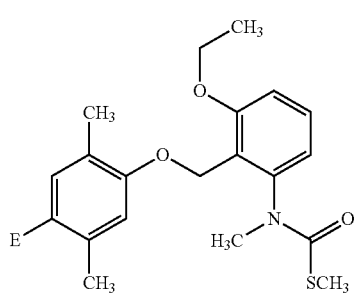 (HF2106)
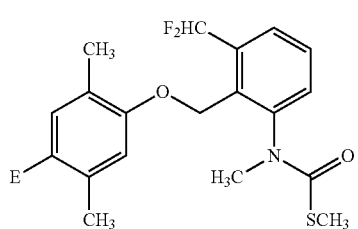 (HF2107)
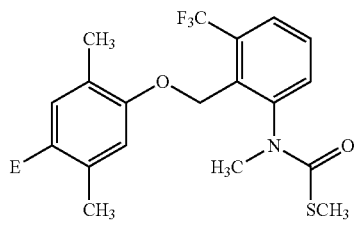 (HF2108)
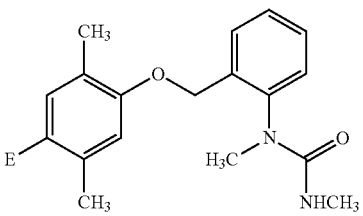 (HF2109)
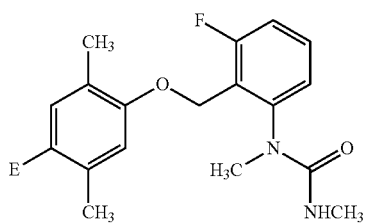 (HF2110)
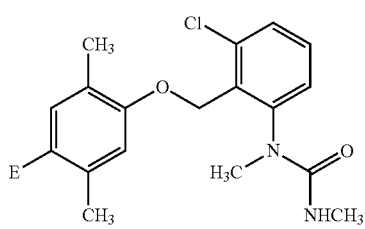 (HF2111)
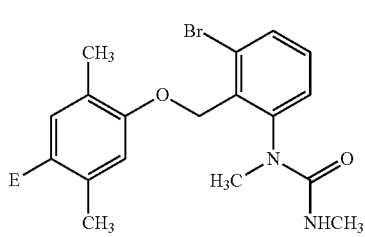 (HF2112)
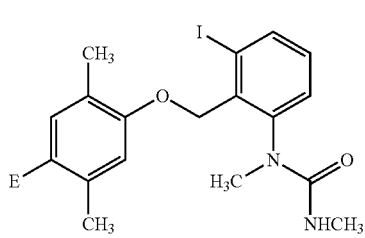 (HF2113)
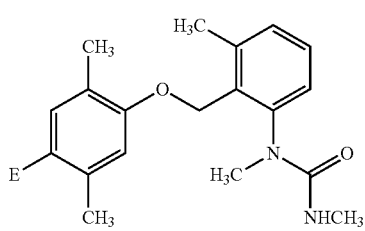 (HF2114)
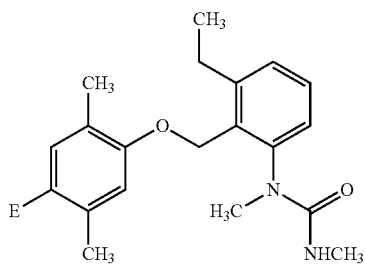 (HF2115)

| | |
|---|---|
| (HF2116) 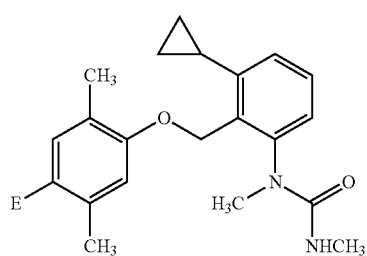 | (HF2122) 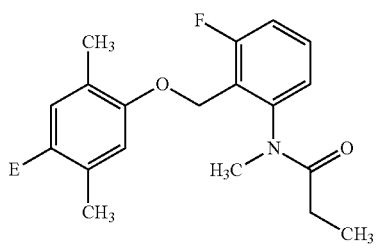 |
| (HF2117) 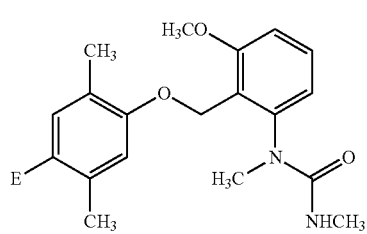 | (HF2123) 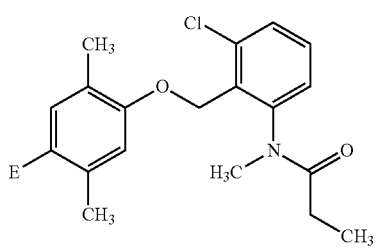 |
| (HF2118) 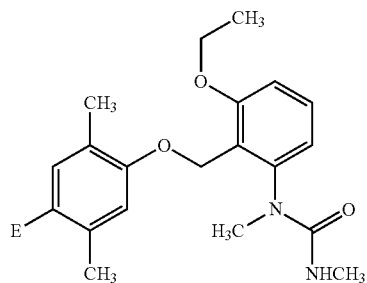 | (HF2124) 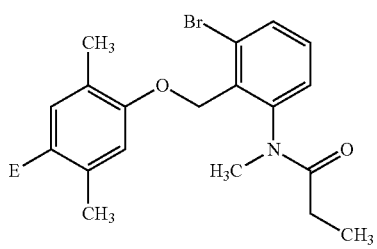 |
| (HF2119) 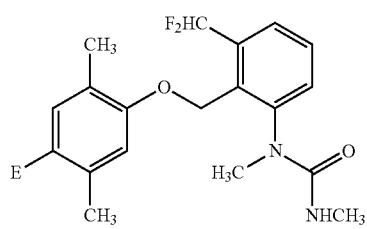 | (HF2125) 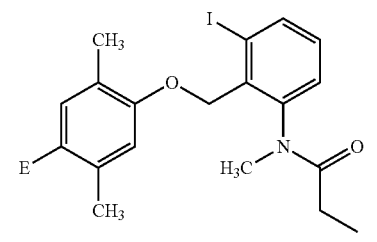 |
| (HF2120) 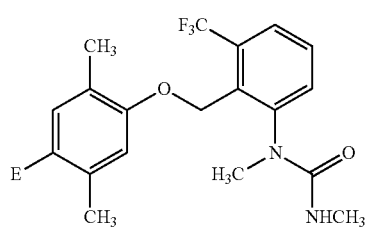 | (HF2126) 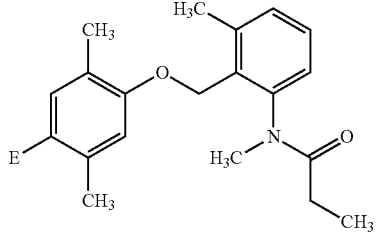 |
| (HF2121) 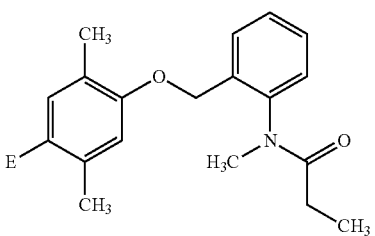 | (HF2127) 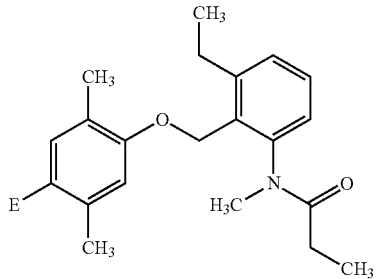 |

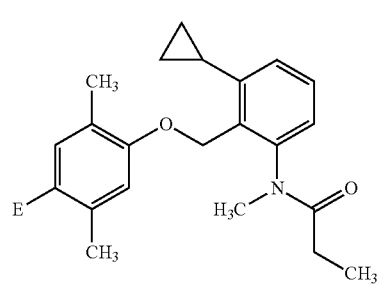 (HF2128)
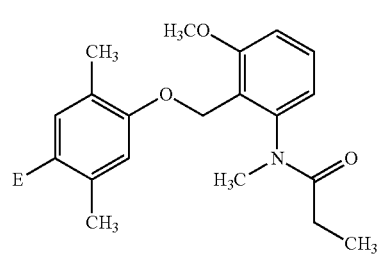 (HF2129)
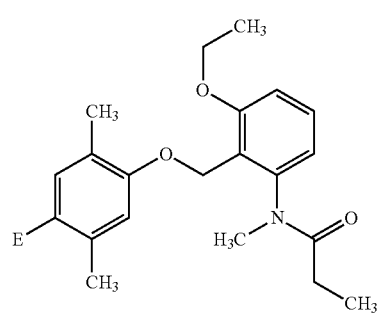 (HF2130)
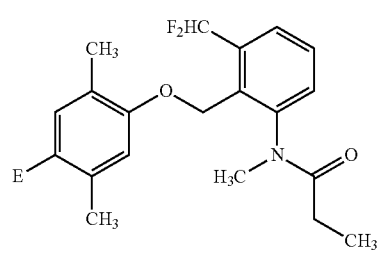 (HF2131)
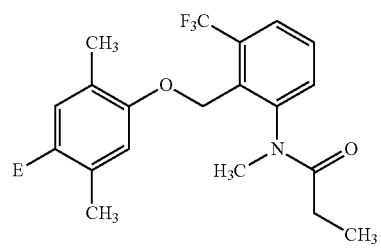 (HF2132)
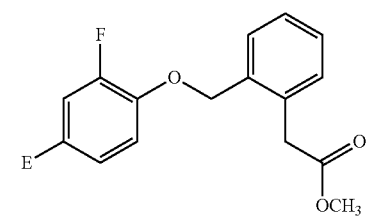 (HG1001)
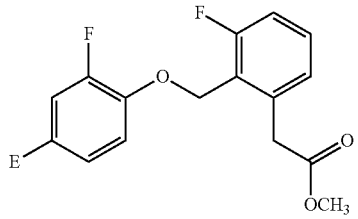 (HG1002)
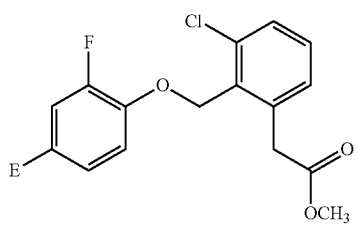 (HG1003)
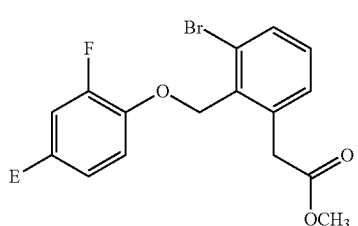 (HG1004)
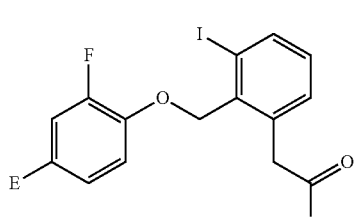 (HG1005)
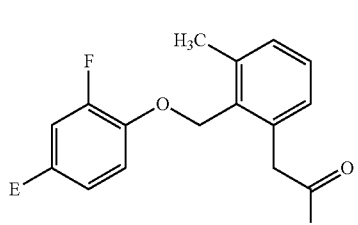 (HG1006)
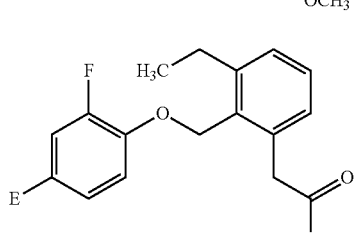 (HG1007)
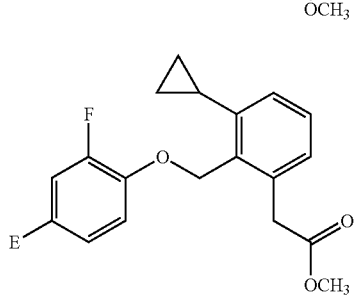 (HG1008)

-continued
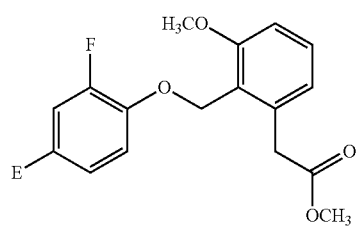 (HG1009)
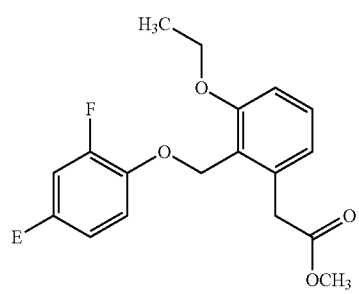 (HG1010)
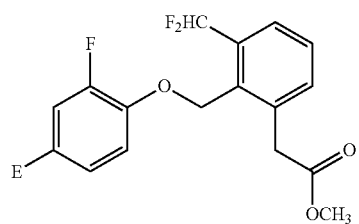 (HG1011)
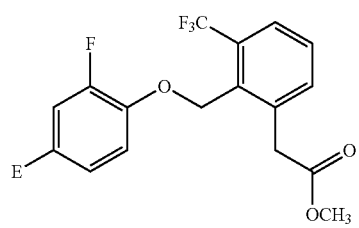 (HG1012)
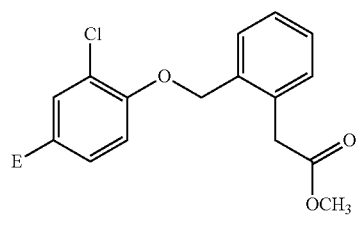 (HG1025)
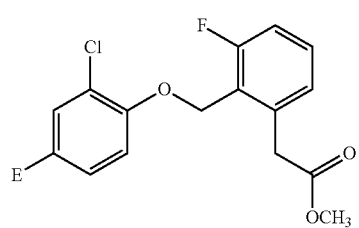 (HG1026)
-continued
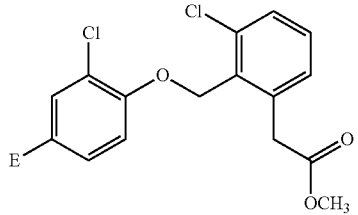 (HG1027)
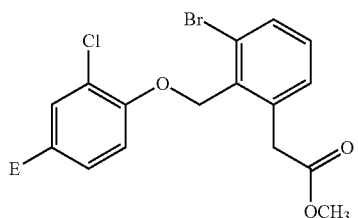 (HG1028)
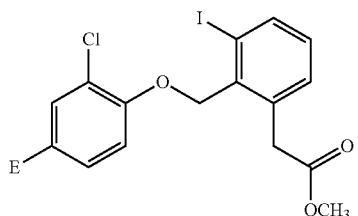 (HG1029)
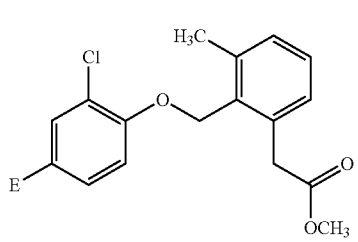 (HG1030)
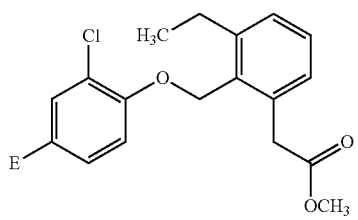 (HG1031)
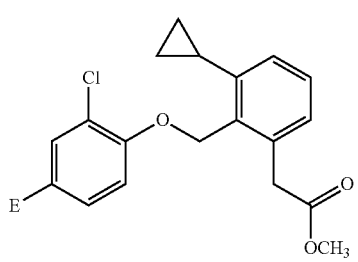 (HG1032)
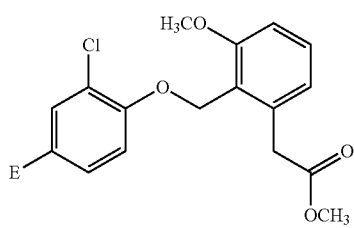 (HG1033)

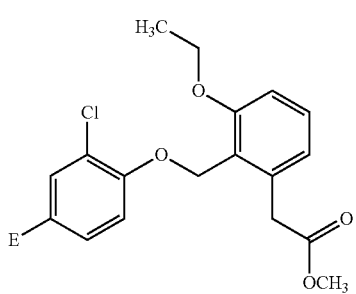
(HG1034)
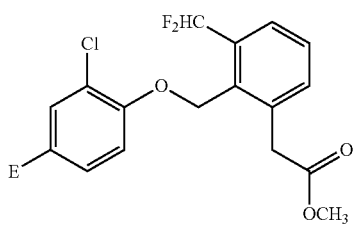
(HG1035)
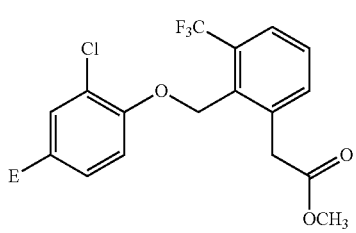
(HG1036)
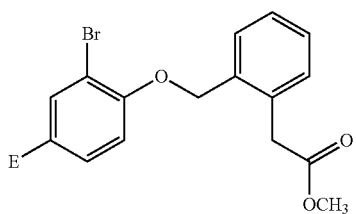
(HG1037)
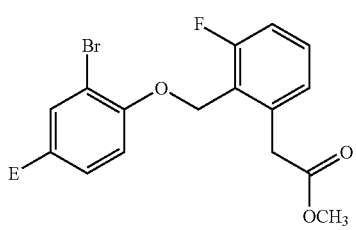
(HG1038)
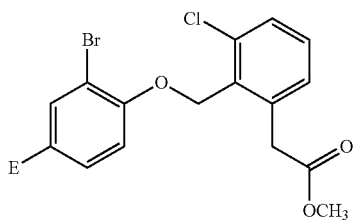
(HG1039)
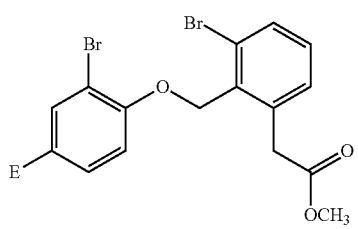
(HG1040)
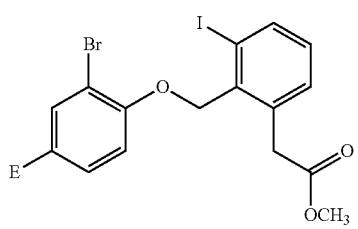
(HG1041)
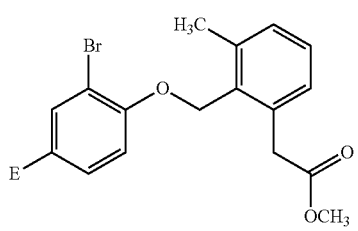
(HG1042)
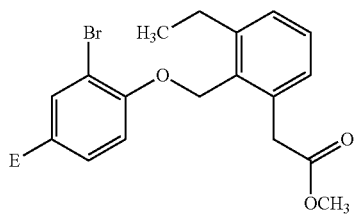
(HG1043)
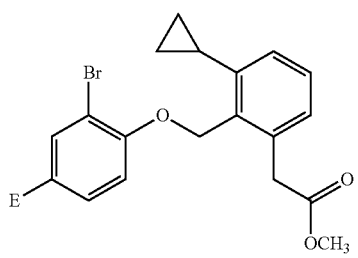
(HG1044)
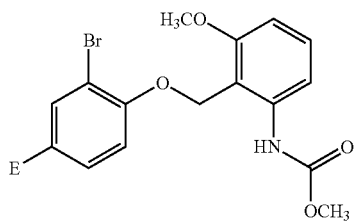
(HG1045)

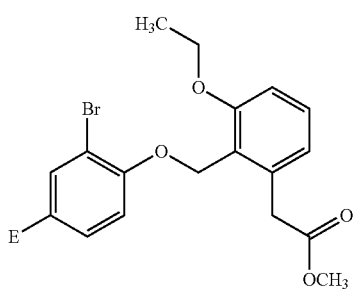
(HG1046)
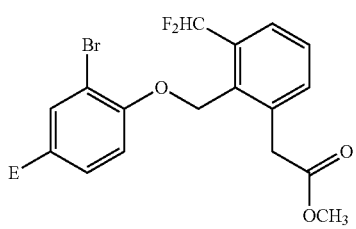
(HG1047)
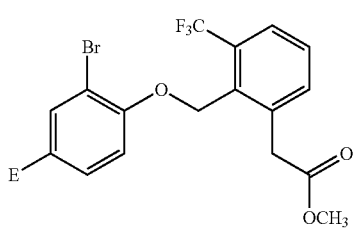
(HG1048)
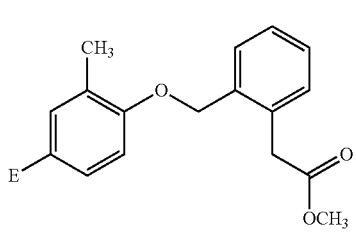
(HG1049)
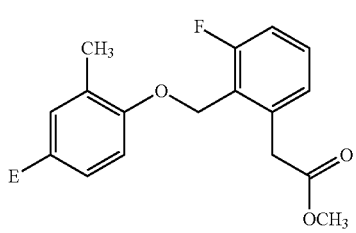
(HG1050)
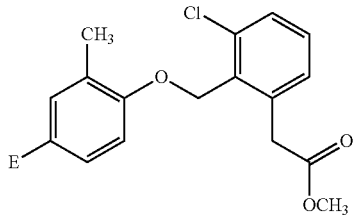
(HG1051)
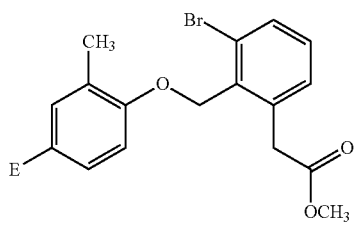
(HG1052)
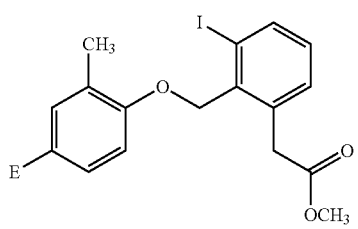
(HG1053)
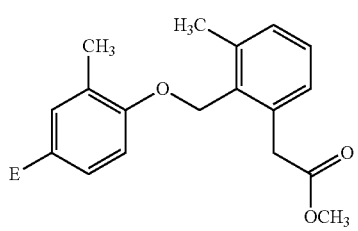
(HG1054)
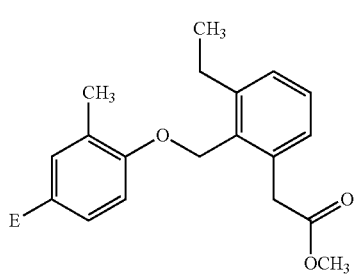
(HG1055)
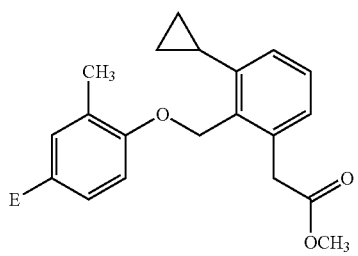
(HG1056)
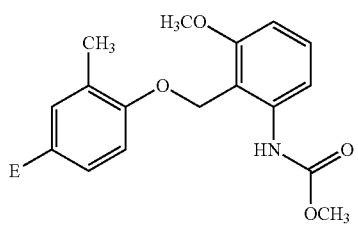
(HG1057)

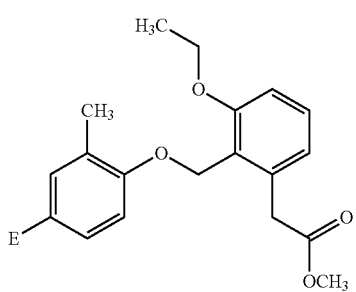
(HG1058)
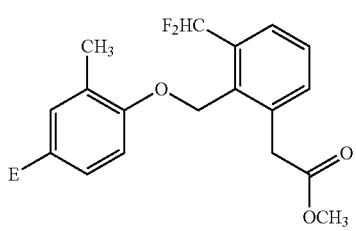
(HG1059)
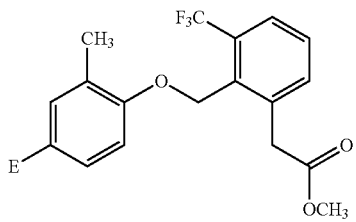
(HG1060)
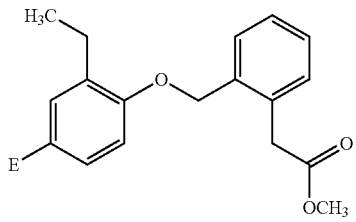
(HG1061)
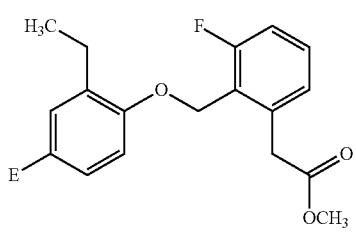
(HG1062)
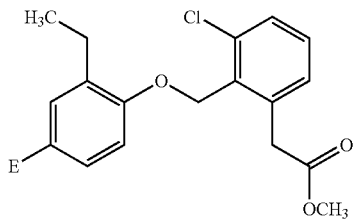
(HG1063)
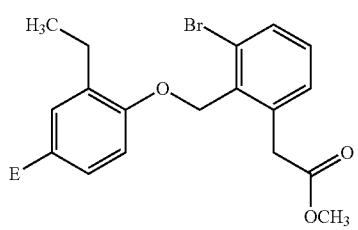
(HG1064)
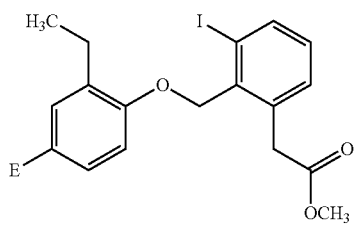
(HG1065)
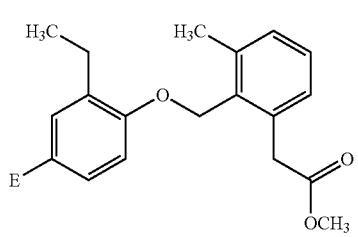
(HG1066)
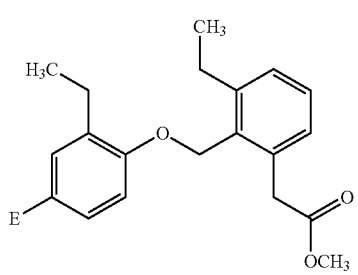
(HG1067)
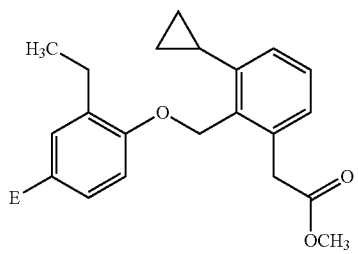
(HG1068)
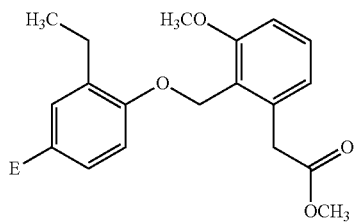
(HG1069)

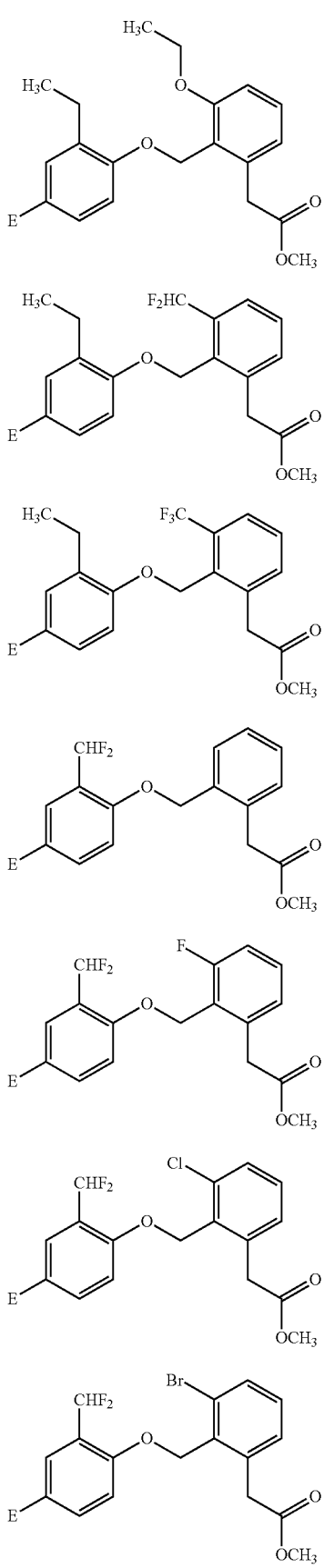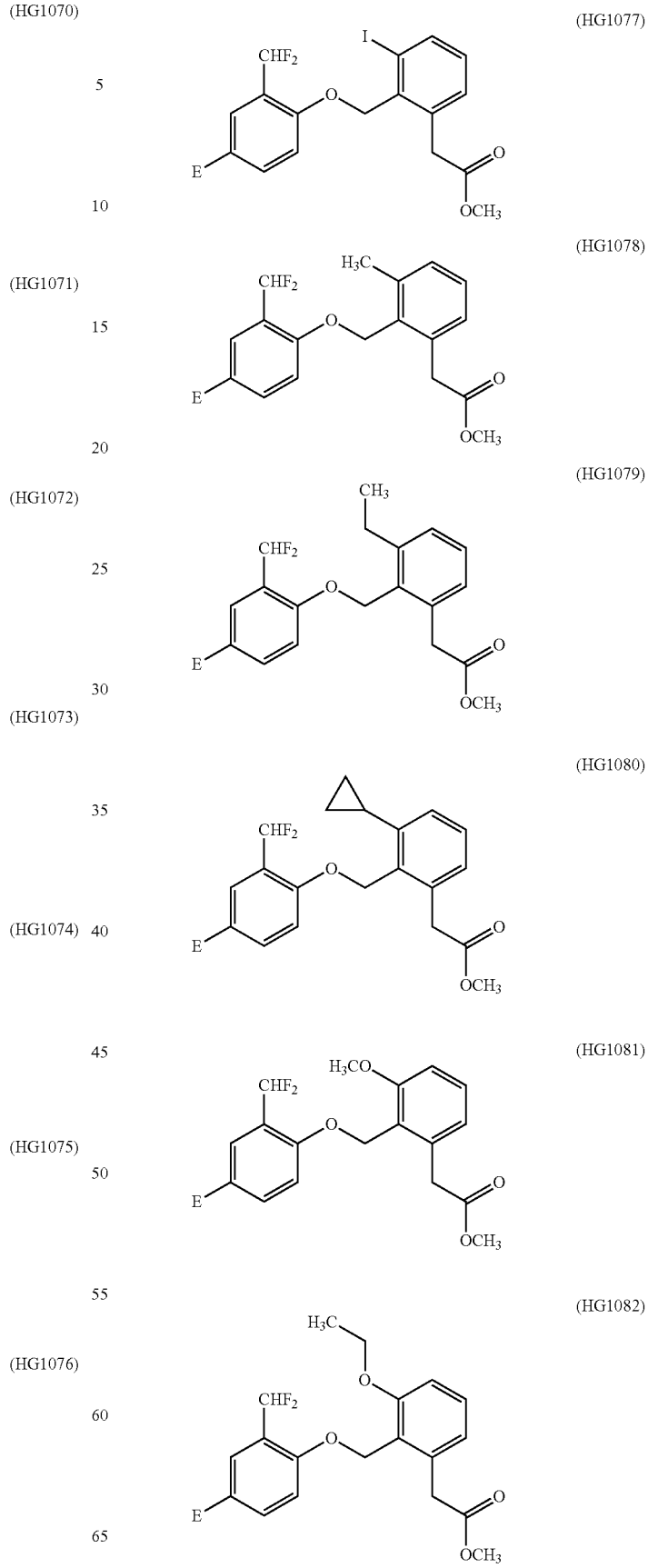

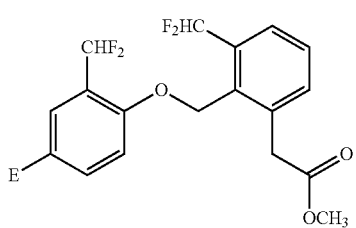
(HG1083)
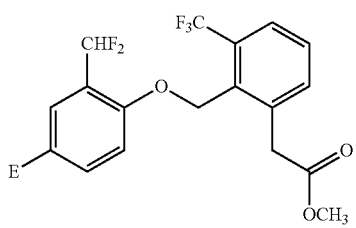
(HG1084)
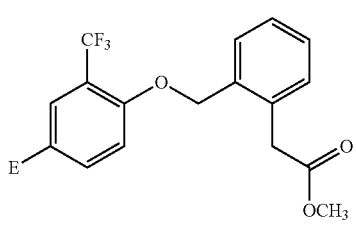
(HG1085)
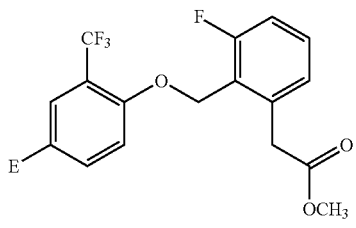
(HG1086)
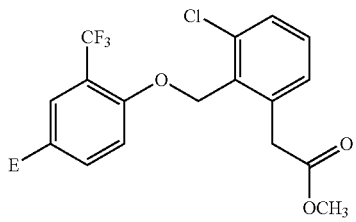
(HG1087)
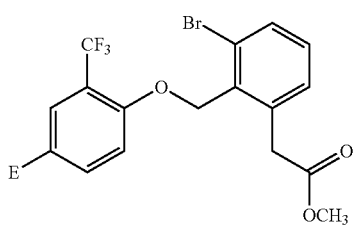
(HG1088)
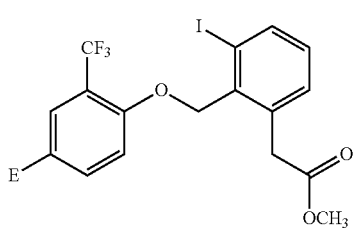
(HG1089)
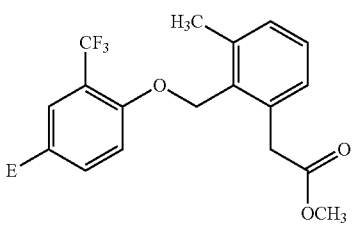
(HG1090)
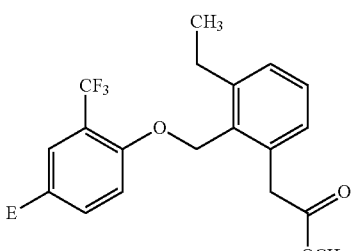
(HG1091)
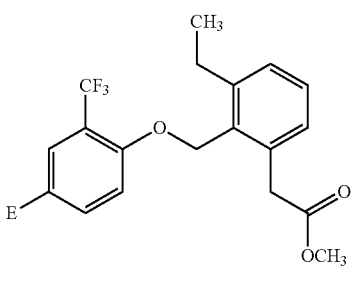
(HG1092)
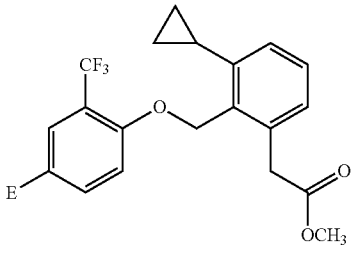
(HG1093)
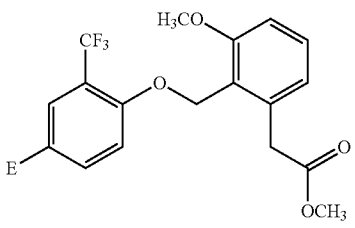
(HG1094)
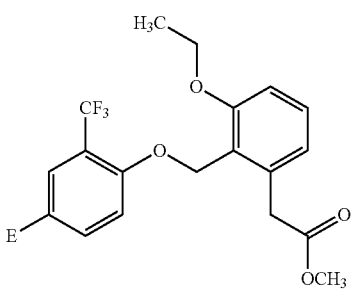
(HG1095)

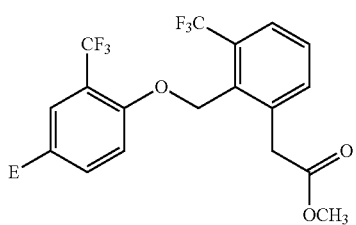 (HG1096)
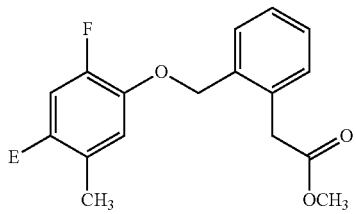 (HG4013)
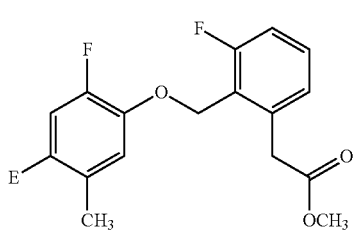 (HG4014)
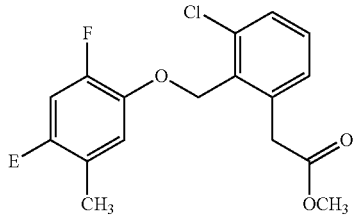 (HG4015)
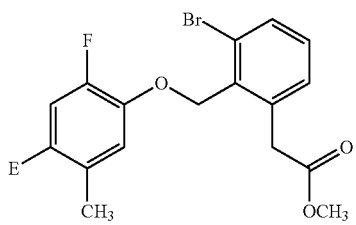 (HG4016)
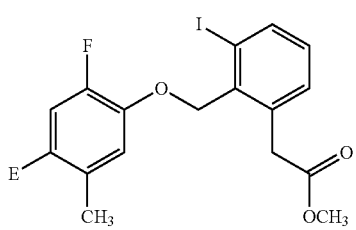 (HG4017)
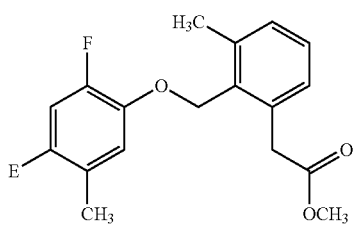 (HG4018)
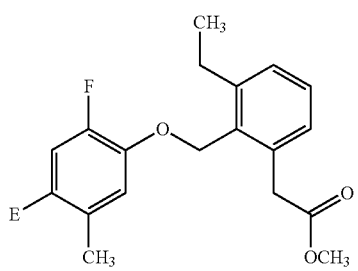 (HG4019)
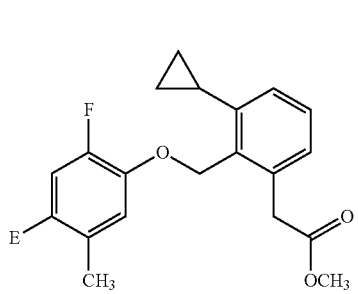 (HG4020)
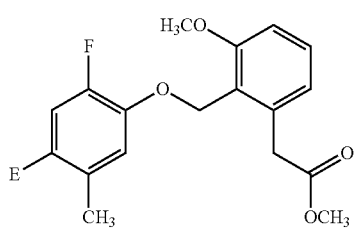 (HG4021)
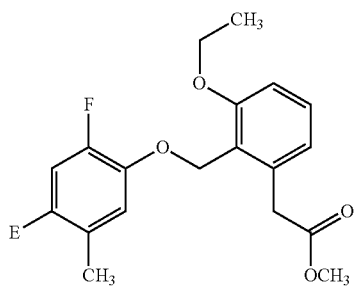 (HG4022)
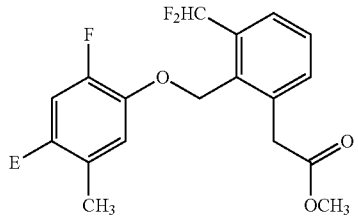 (HG4023)
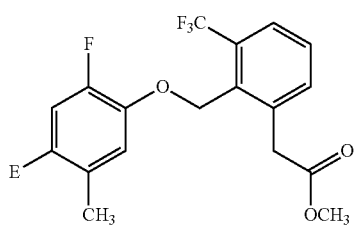 (HG4024)

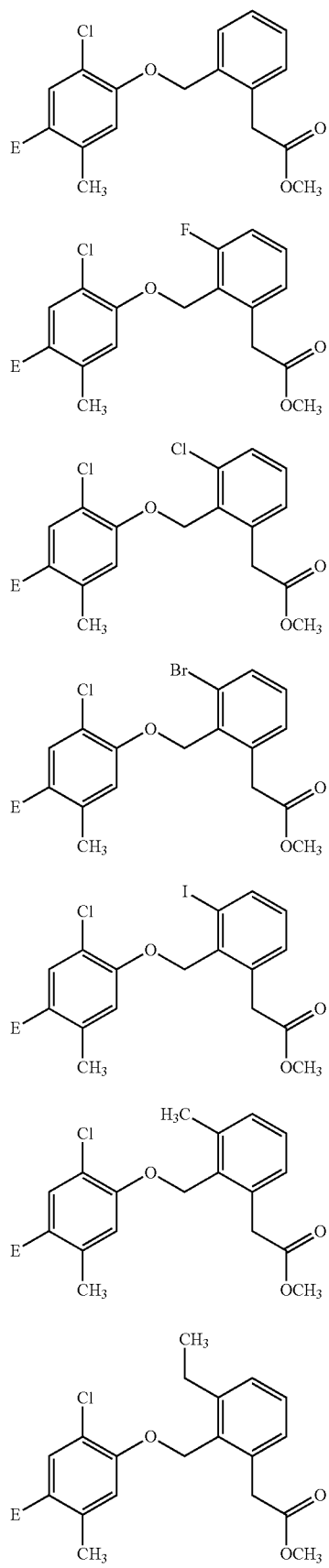
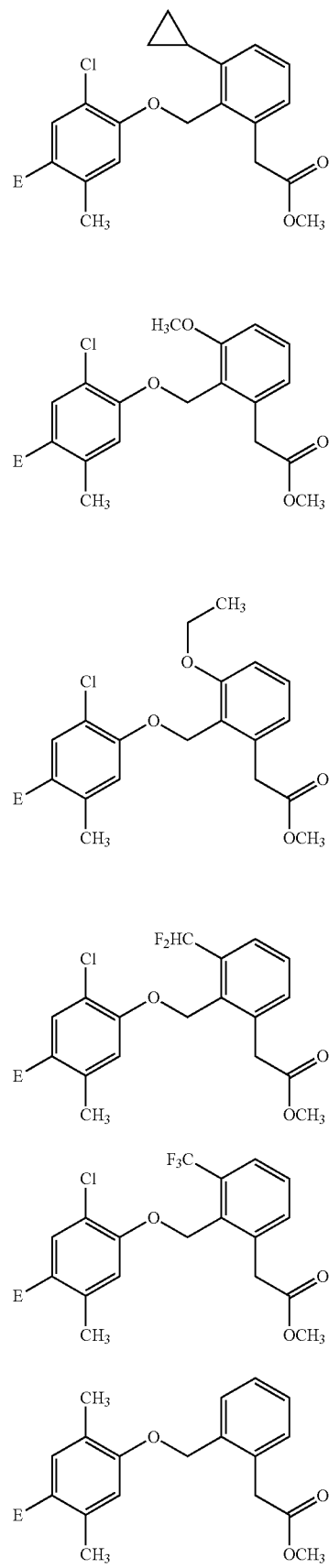

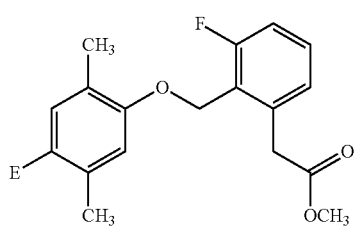 (HG4050)
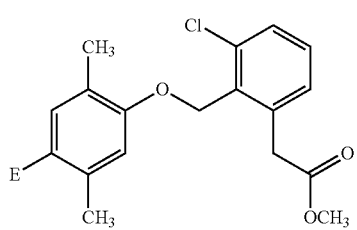 (HG4051)
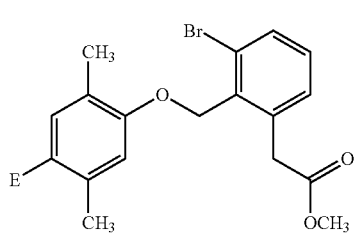 (HG4052)
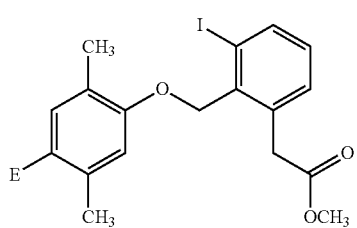 (HG4053)
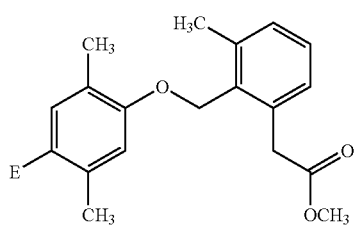 (HG4054)
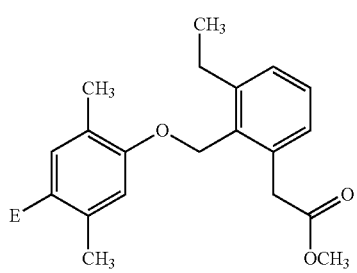 (HG4055)
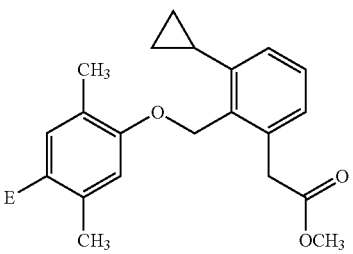 (HG4056)
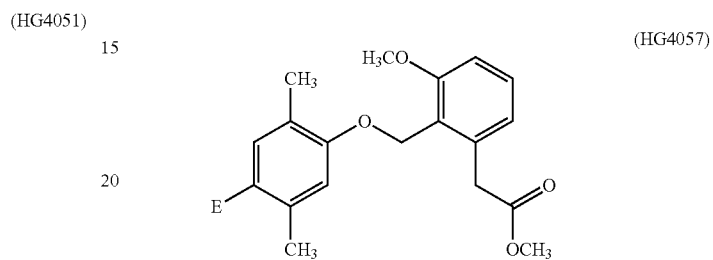 (HG4057)
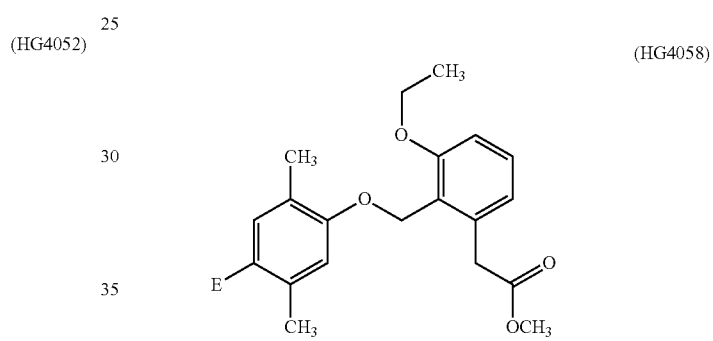 (HG4058)
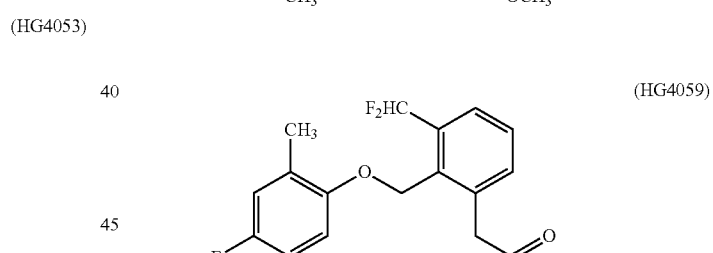 (HG4059)
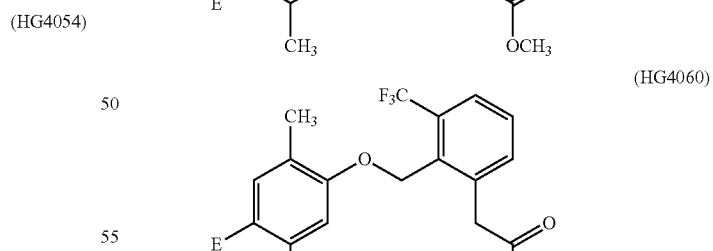 (HG4060)
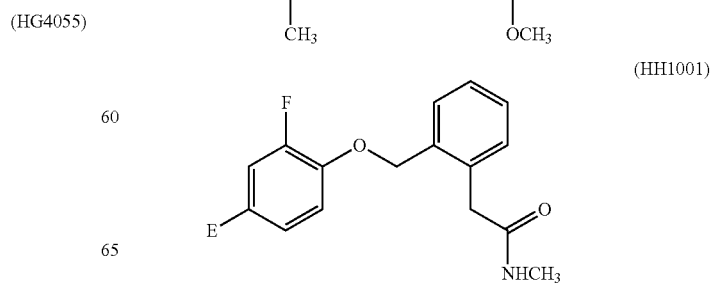 (HH1001)

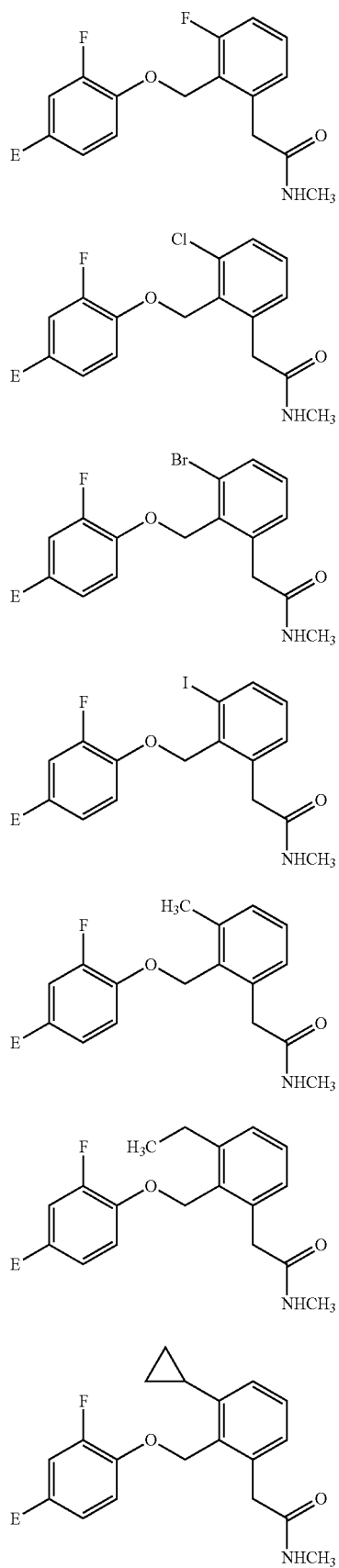
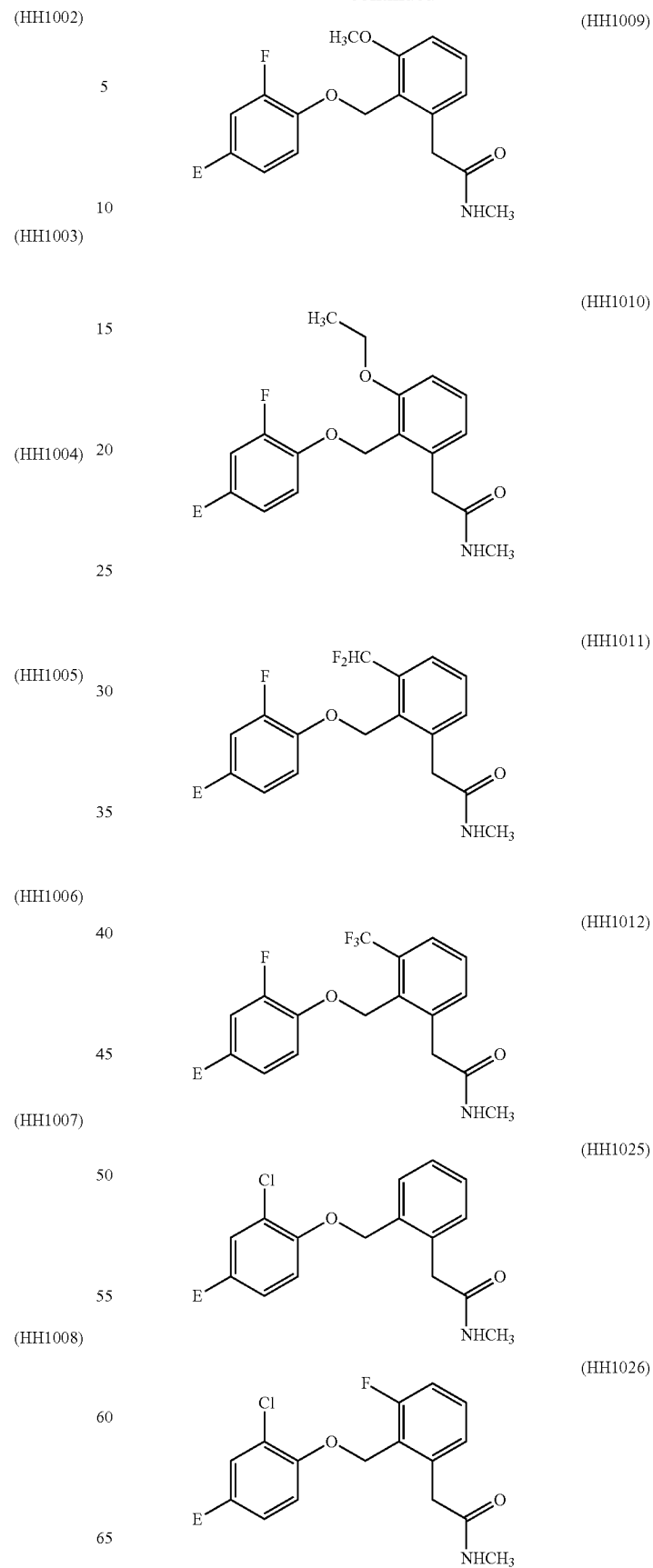

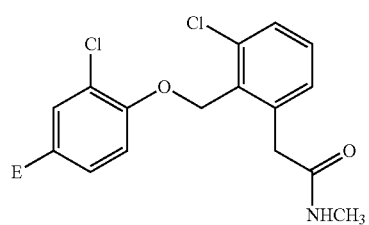
(HH1027)
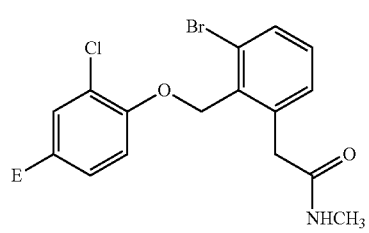
(HH1028)
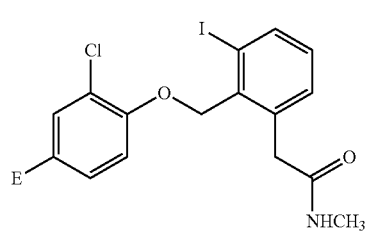
(HH1029)
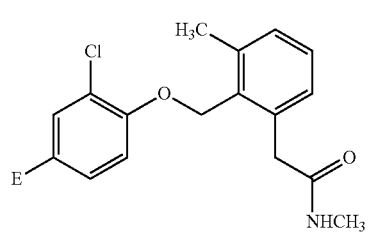
(HH1030)
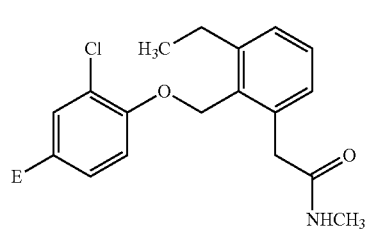
(HH1031)
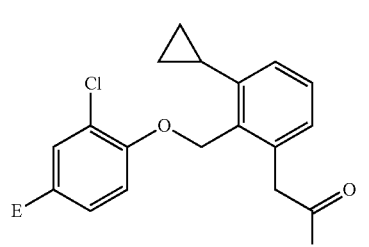
(HH1032)
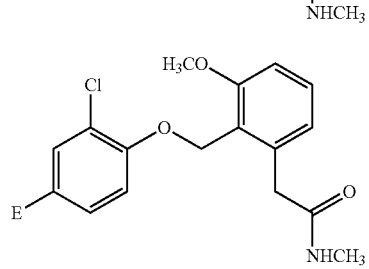
(HH1033)
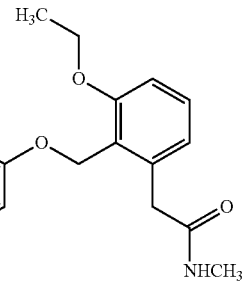
(HH1034)
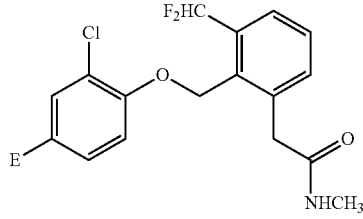
(HH1035)
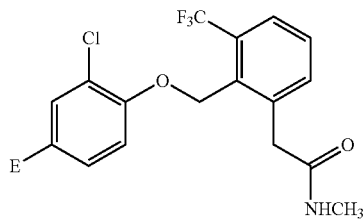
(HH1036)
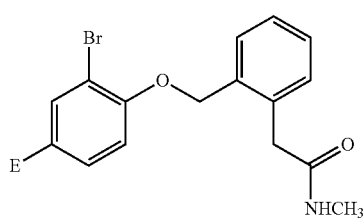
(HH1037)
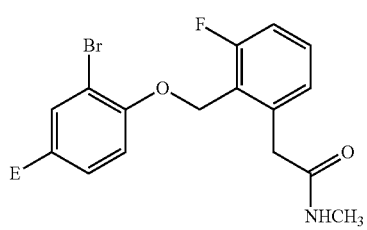
(HH1038)
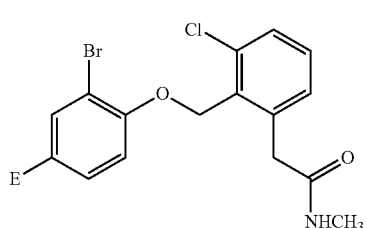
(HH1039)
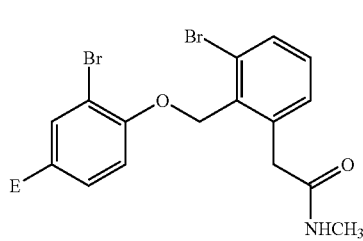
(HH1040)

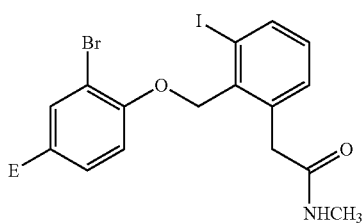 (HH1041)
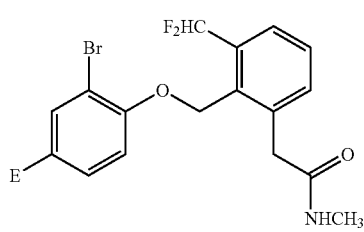 (HH1047)
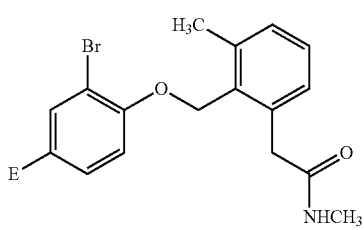 (HH1042)
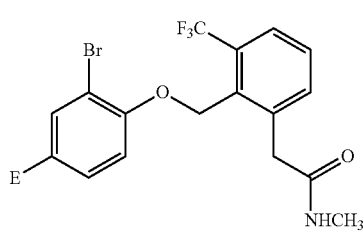 (HH1048)
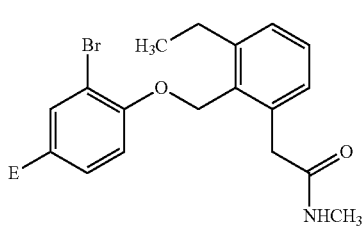 (HH1043)
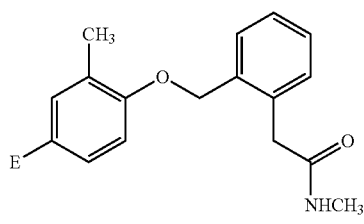 (HH1049)
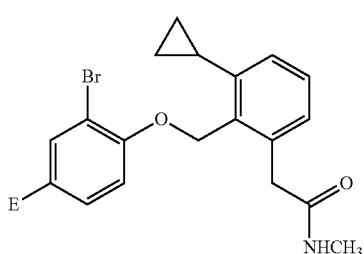 (HH1044)
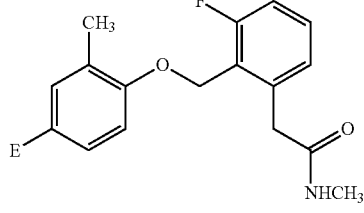 (HH1050)
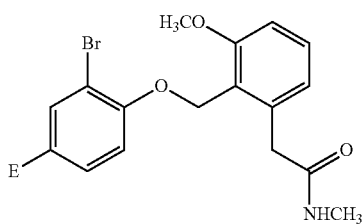 (HH1045)
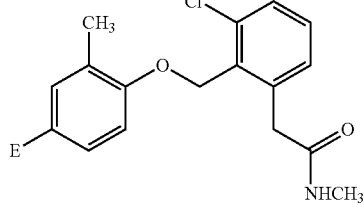 (HH1051)
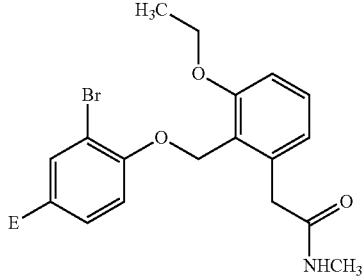 (HH1046)
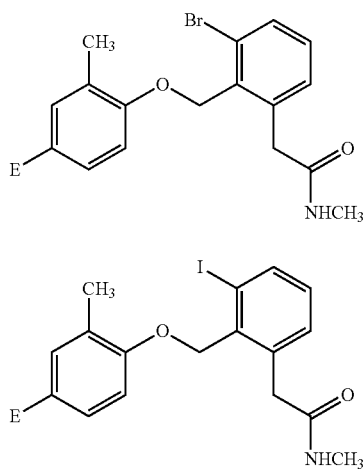 (HH1052)
(HH1053)

267
-continued
(HH1054)
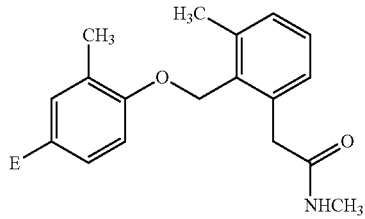
(HH1055)
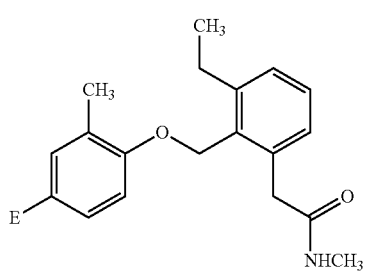
(HH1056)
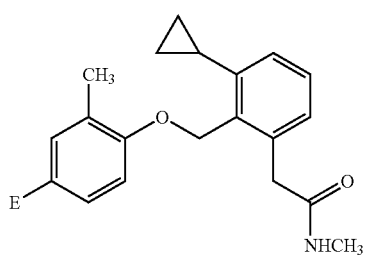
(HH1057)
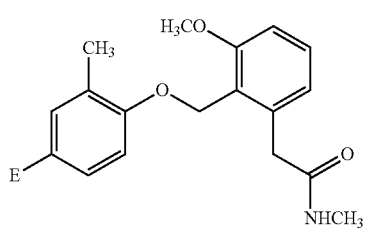
(HH1058)
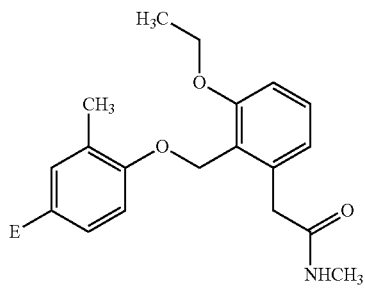
(HH1059)
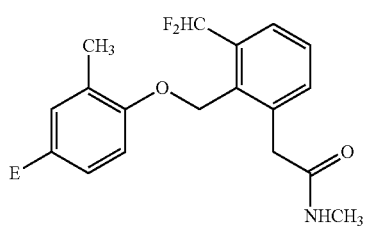
268
-continued
(HH1060)
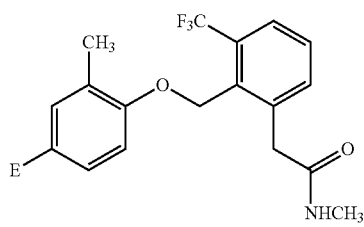
(HH1061)
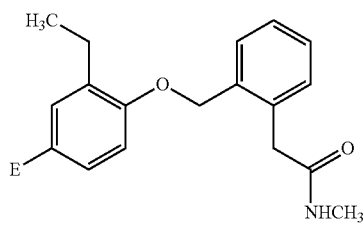
(HH1062)
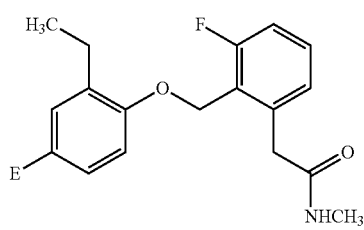
(HH1063)
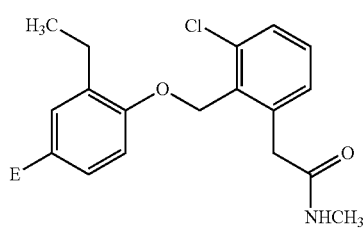
(HH1064)
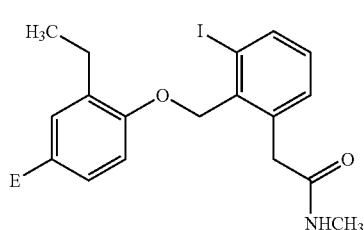
(HH1065)
(HH1066)
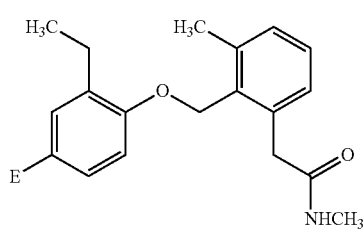

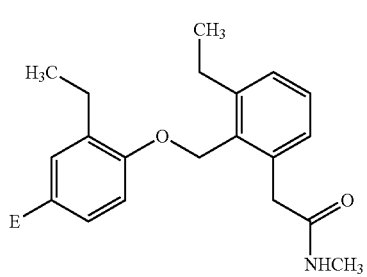
(HH1067)
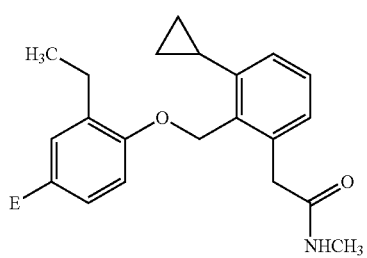
(HH1068)
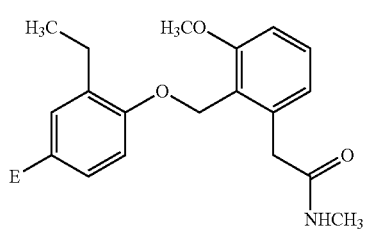
(HH1069)
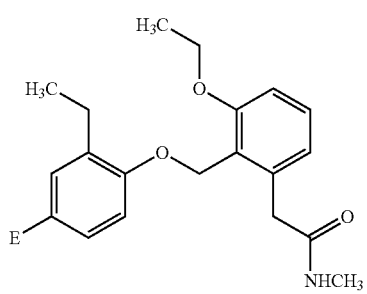
(HH1070)
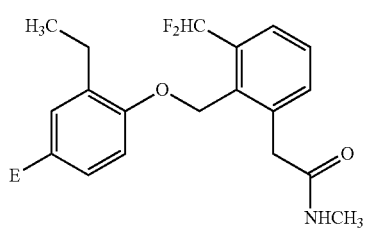
(HH1071)
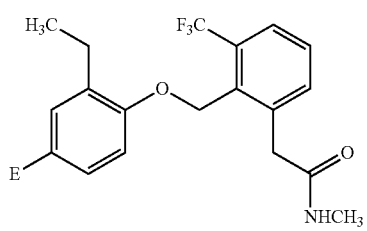
(HH1072)
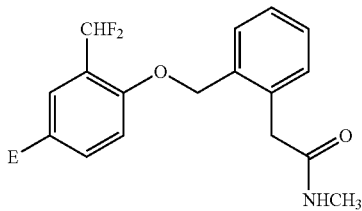
(HH1073)
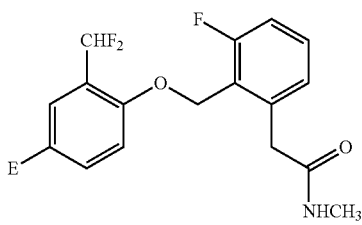
(HH1074)
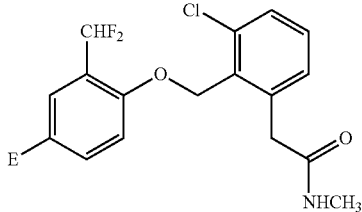
(HH1075)
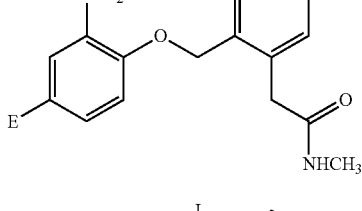
(HH1076)
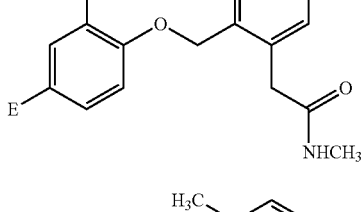
(HH1077)
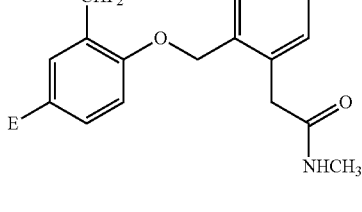
(HH1078)
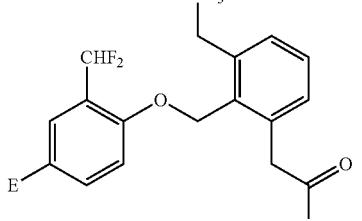
(HH1079)

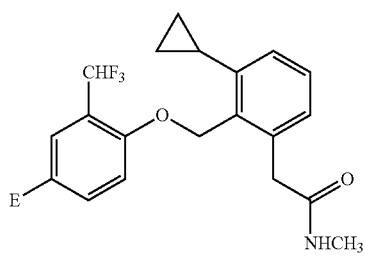
(HH1080)
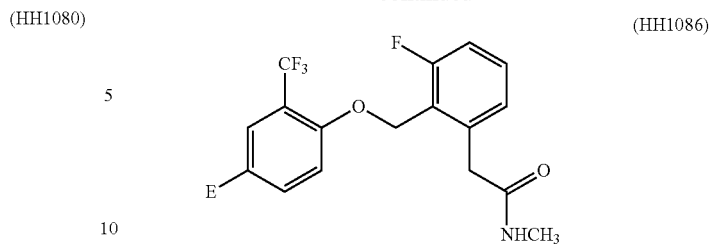
(HH1086)
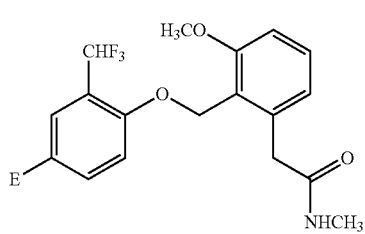
(HH1081)
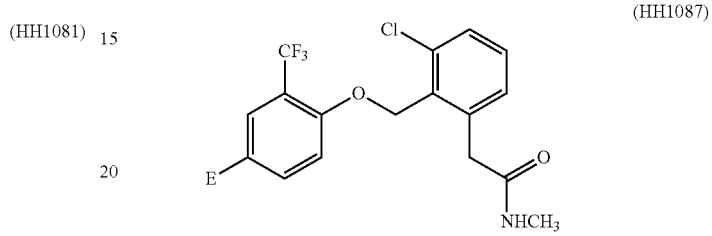
(HH1087)
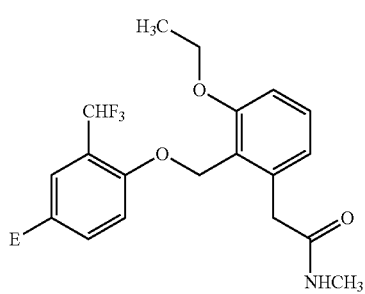
(HH1082)
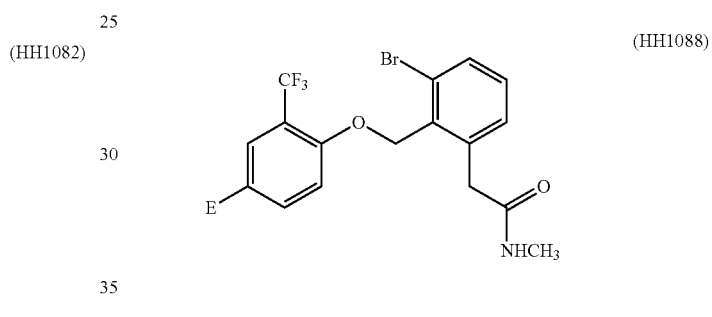
(HH1088)
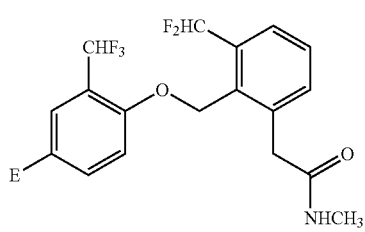
(HH1083)
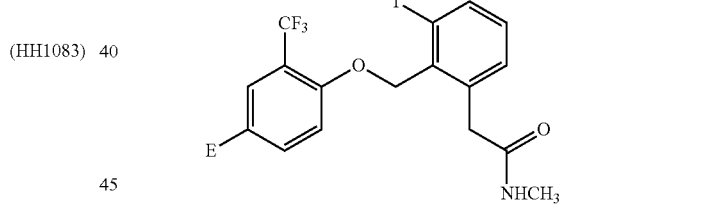
(HH1089)
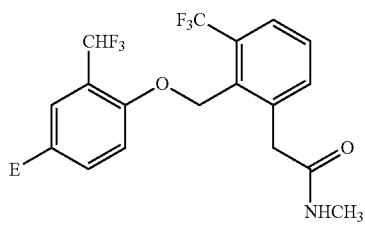
(HH1084)
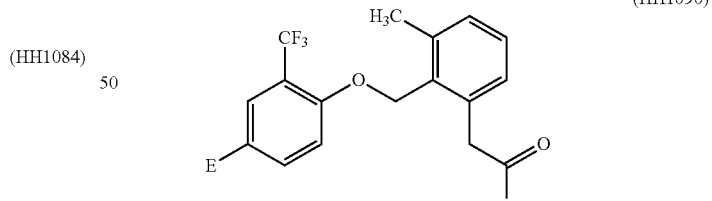
(HH1090)
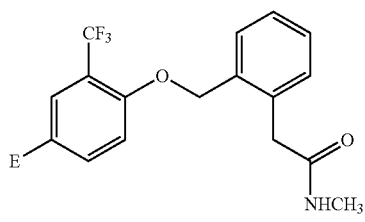
(HH1085)
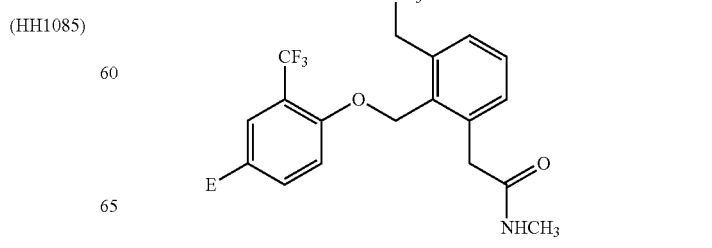
(HH1091)

273
-continued
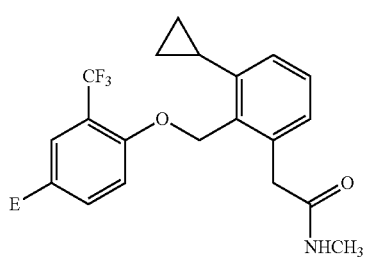
(HH1092)
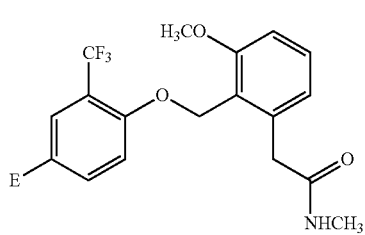
(HH1093)
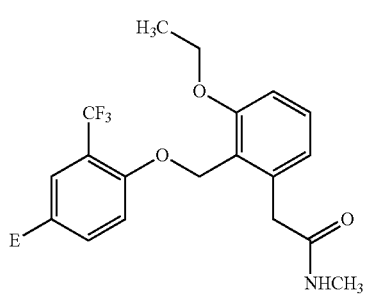
(HH1094)
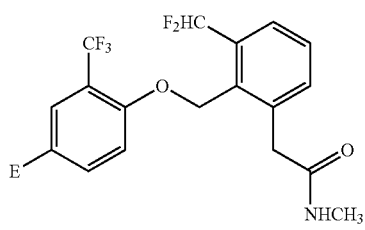
(HH1095)
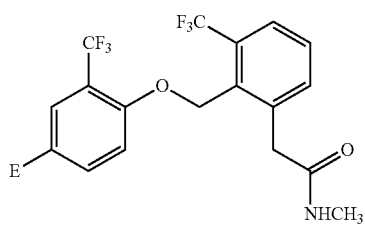
(HH1096)
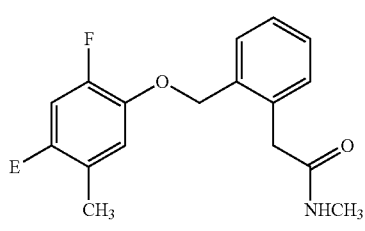
(HH4013)
274
-continued
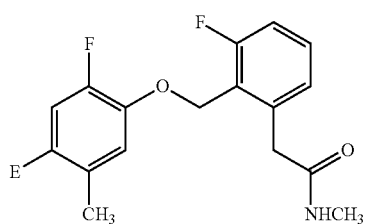
(HH4014)
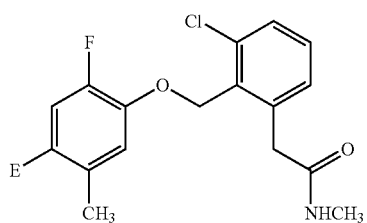
(HH4015)
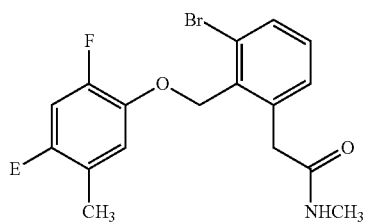
(HH4016)
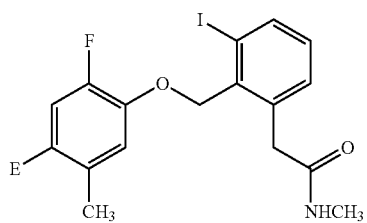
(HH4017)
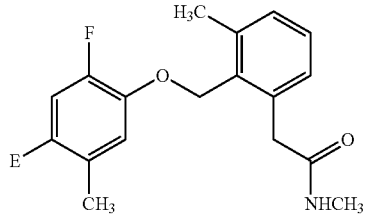
(HH4018)
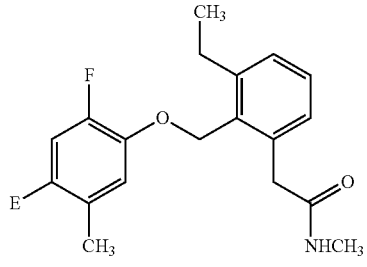
(HH4019)

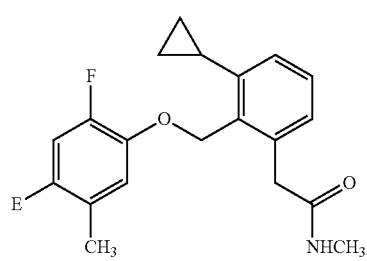
(HH4020)
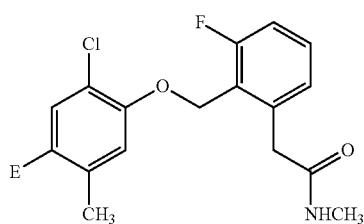
(HH4026)
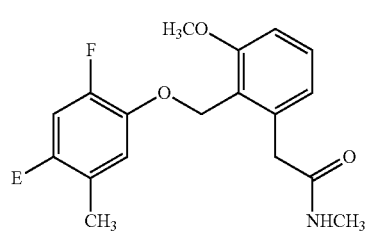
(HH4021)
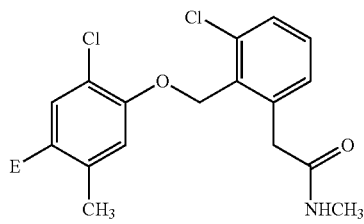
(HH4027)
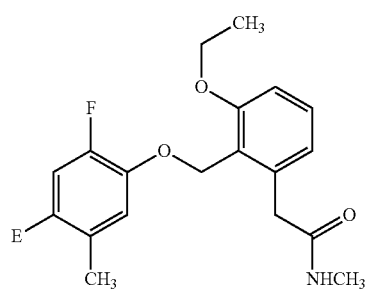
(HH4022)
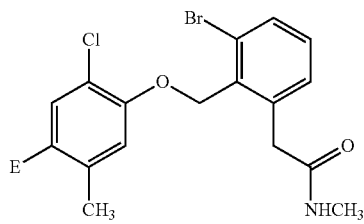
(HH4028)
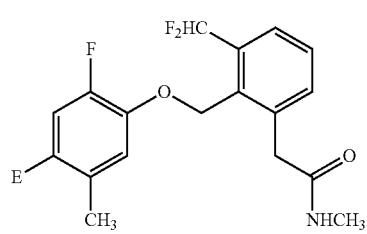
(HH4023)
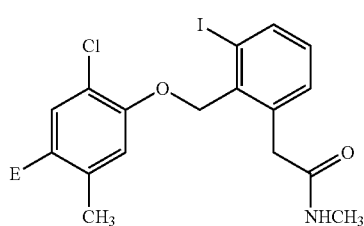
(HH4029)
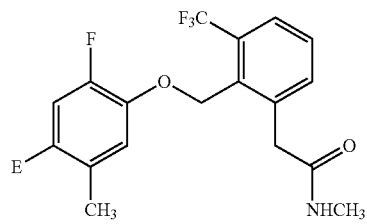
(HH4024)
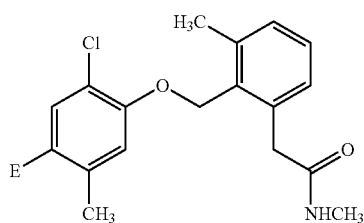
(HH4030)
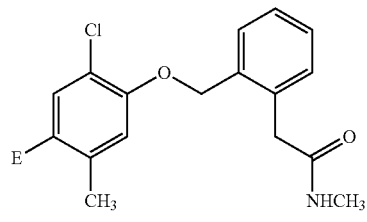
(HH4025)
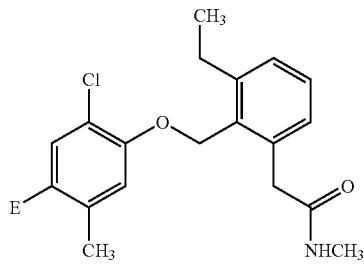
(HH4031)

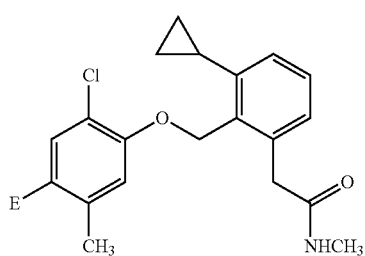 (HH4032)
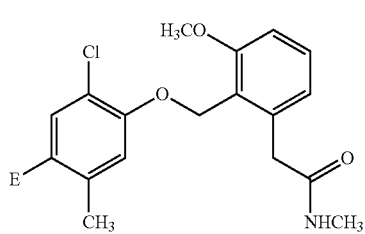 (HH4033)
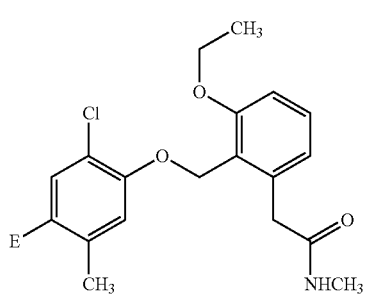 (HH4034)
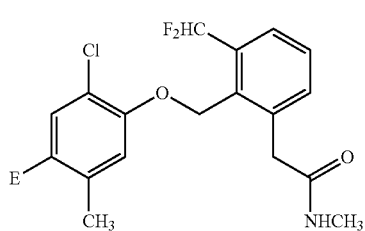 (HH4035)
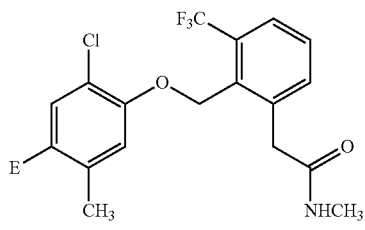 (HH4036)
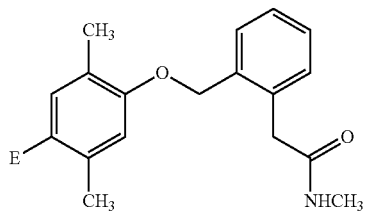 (HH4049)
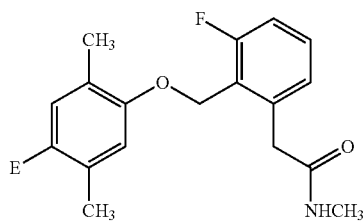 (HH4050)
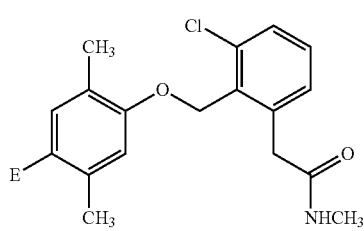 (HH4051)
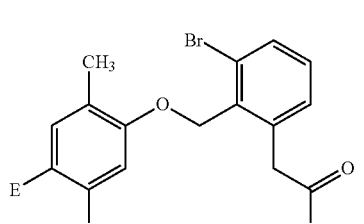 (HH4052)
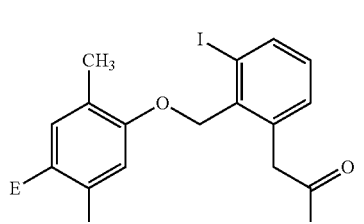 (HH4053)
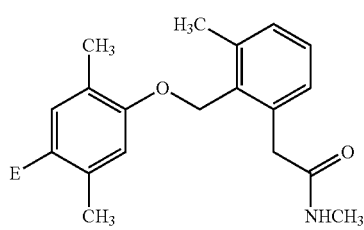 (HH4054)
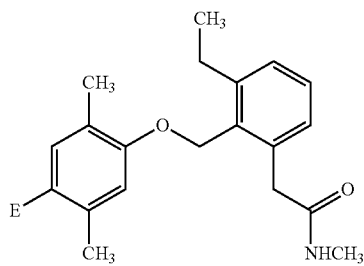 (HH4055)

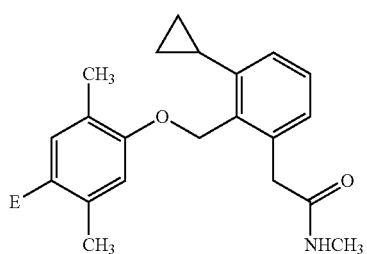 (HH4056)
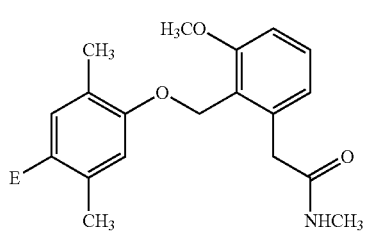 (HH4057)
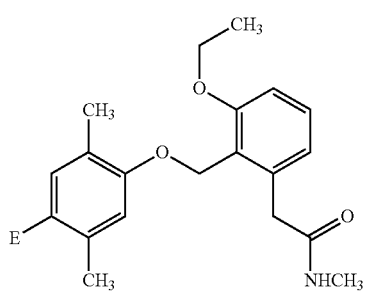 (HH4058)
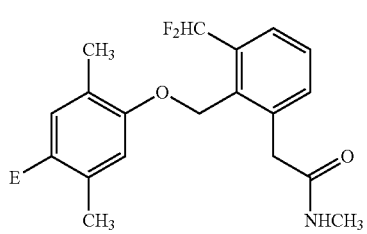 (HH4059)
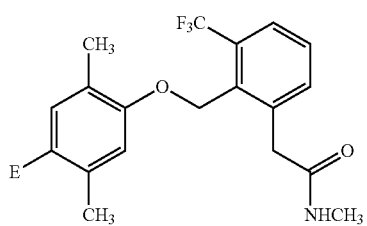 (HH4060)
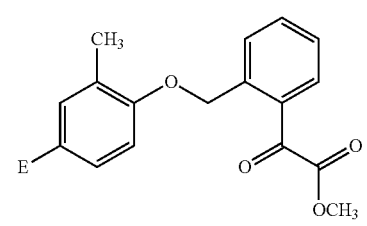 (HI1049)
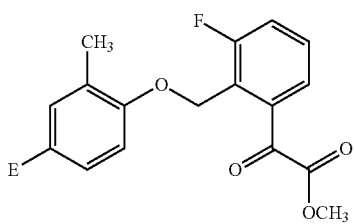 (HI1050)
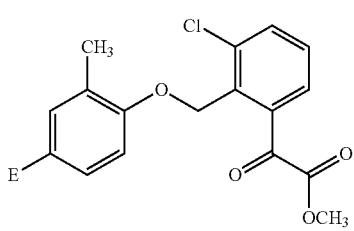 (HI1051)
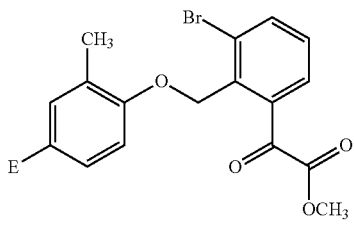 (HI1052)
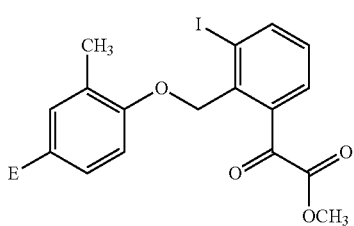 (HI1053)
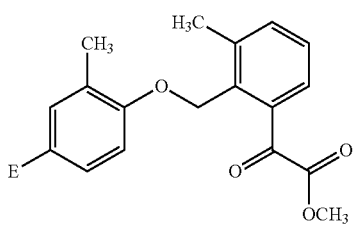 (HI1054)
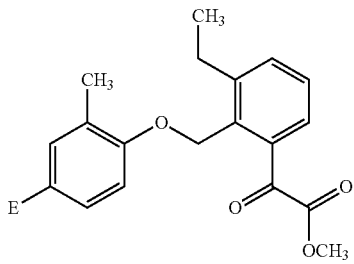 (HI1055)

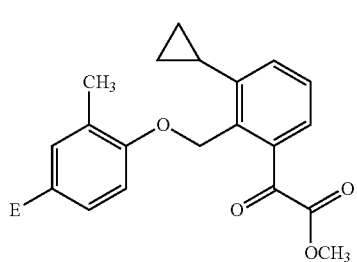
(HI1056)
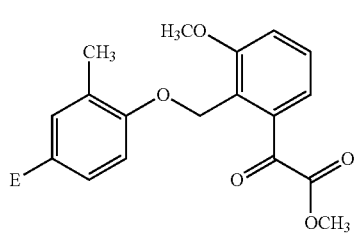
(HI1057)
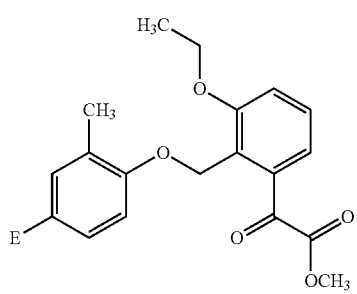
(HI1058)
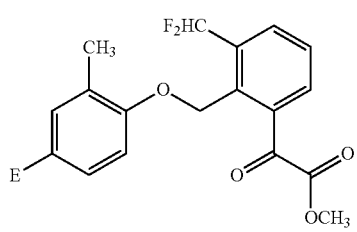
(HI1059)
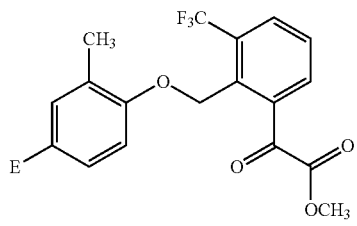
(HI1060)
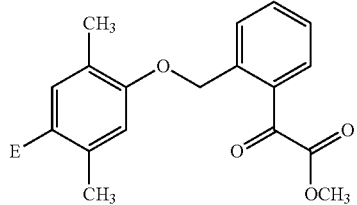
(HI4049)
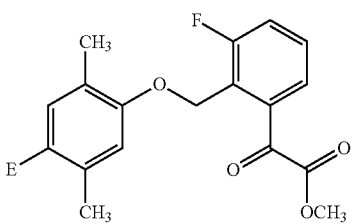
(HI4050)
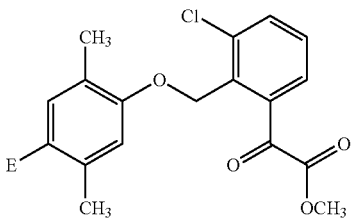
(HI4051)
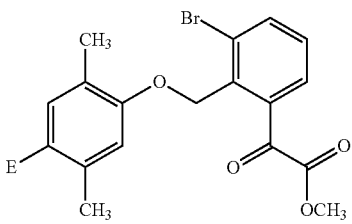
(HI4052)
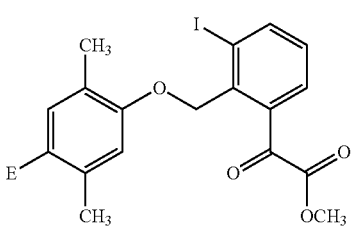
(HI4053)
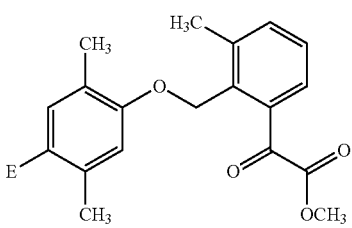
(HI4054)
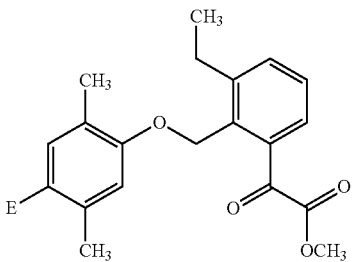
(HI4055)

| | |
|---|---|
| (HI4056) 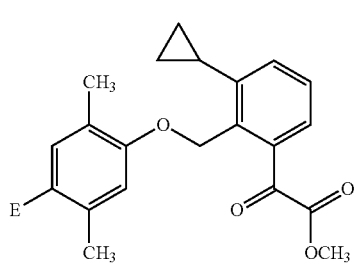 | (HJ1050) 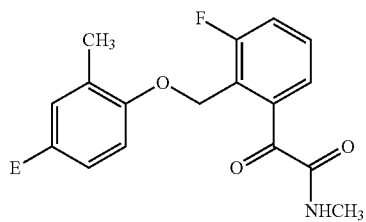 |
| (HI4057) 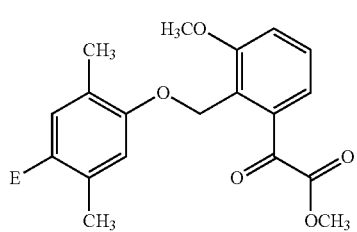 | (HJ1051) 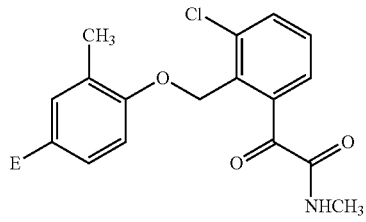 |
| (HI4058) 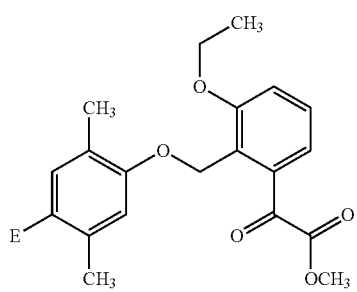 | (HJ1052) 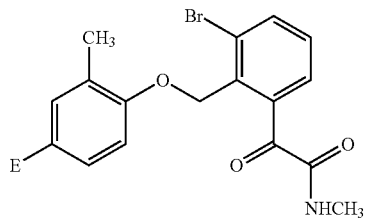 |
| (HI4059) 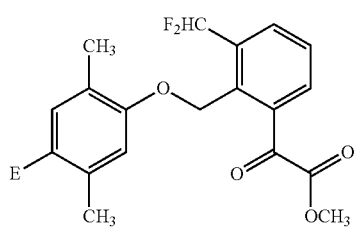 | (HJ1053) 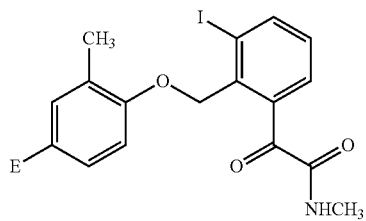 |
| (HI4060) 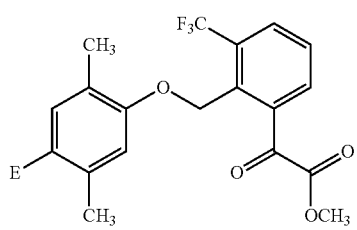 | (HJ1054) 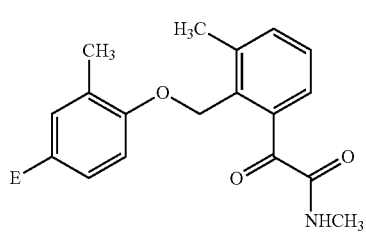 |
| (HJ1049) 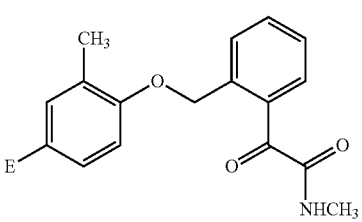 | (HJ1055) 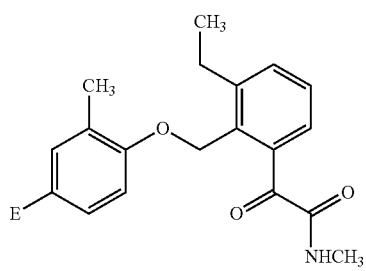 |

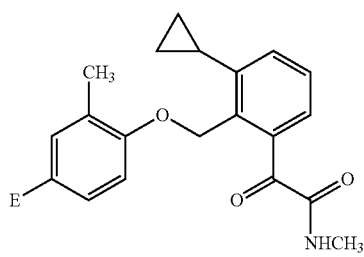
(HJ1056)
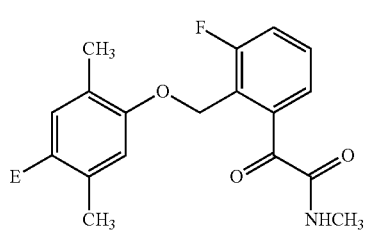
(HJ4050)
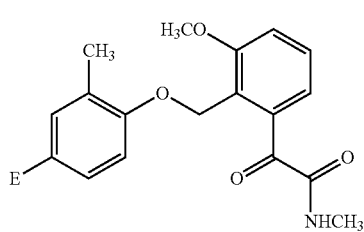
(HJ1057)
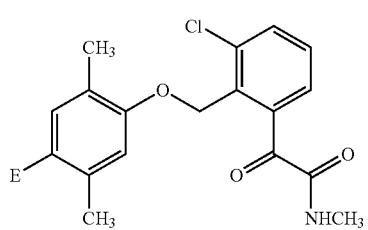
(HJ4051)
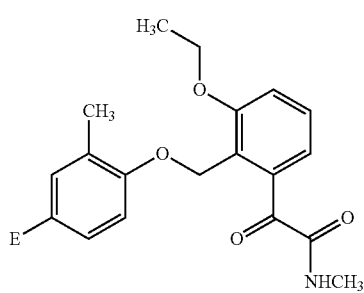
(HJ1058)
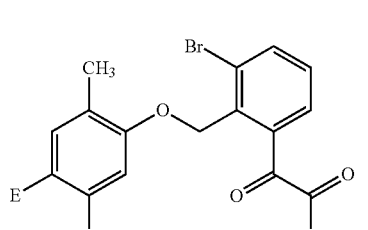
(HJ4052)
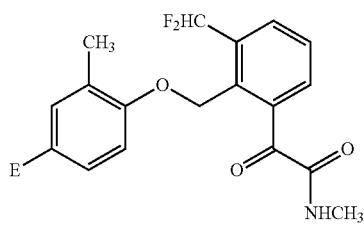
(HJ1059)
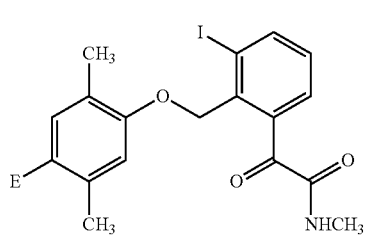
(HJ4053)
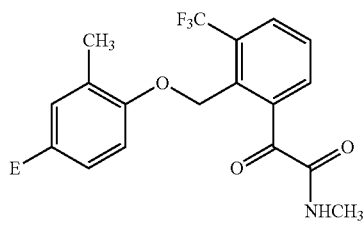
(HJ1060)
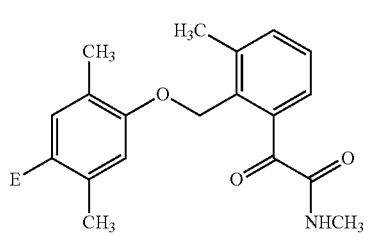
(HJ4054)
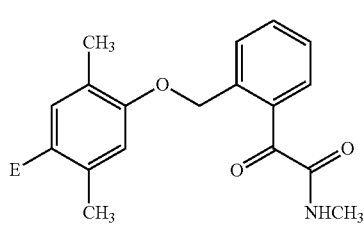
(HJ4049)
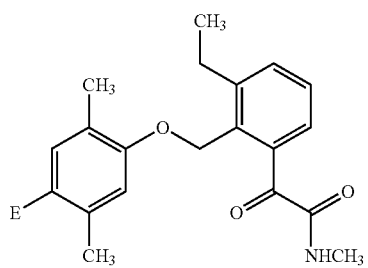
(HJ4055)

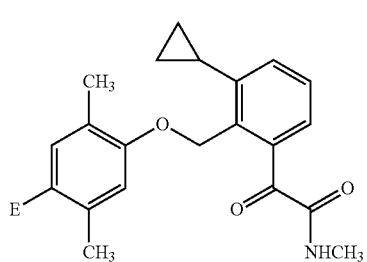
(HJ4056)
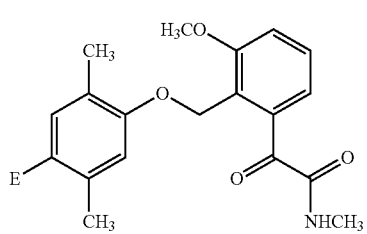
(HJ4057)
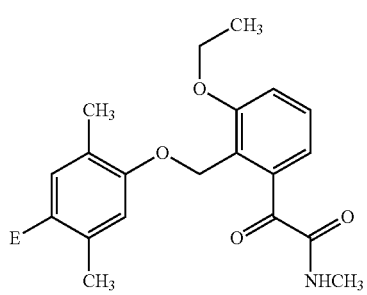
(HJ4058)
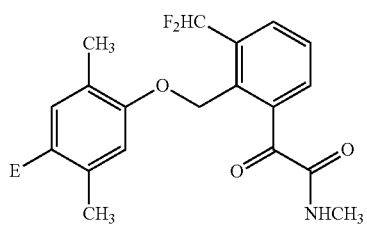
(HJ4059)
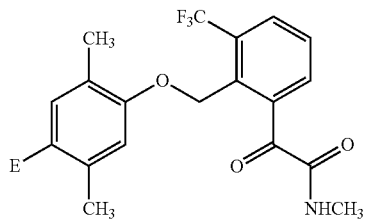
(HJ4060)
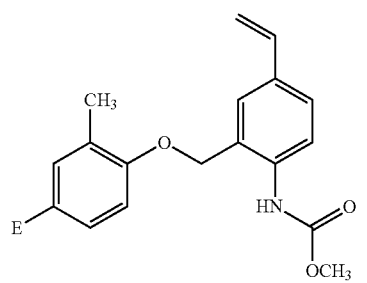
(HK1049)
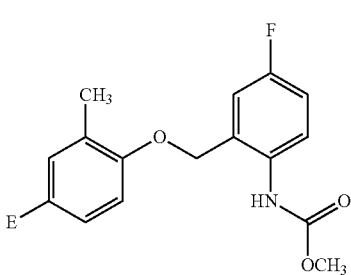
(HK1050)
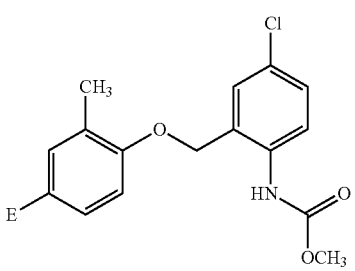
(HK1051)
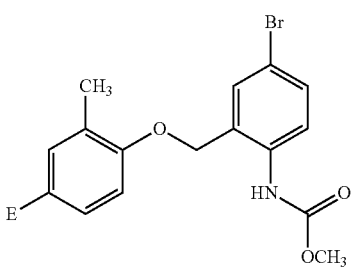
(HK1052)
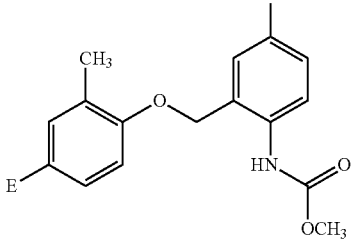
(HK1053)
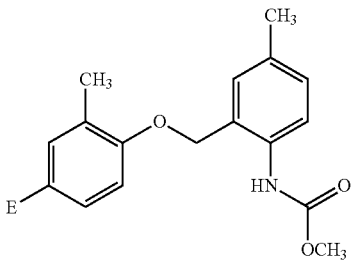
(HK1054)
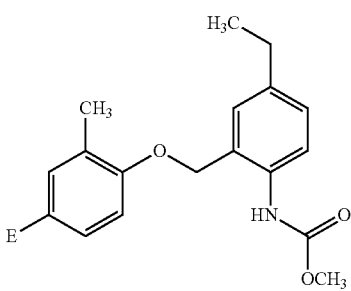
(HK1055)

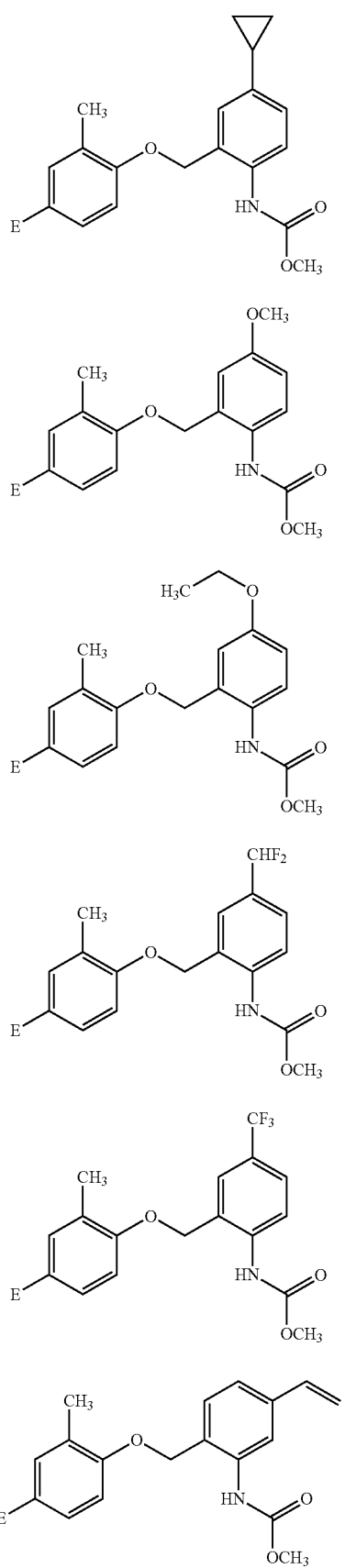
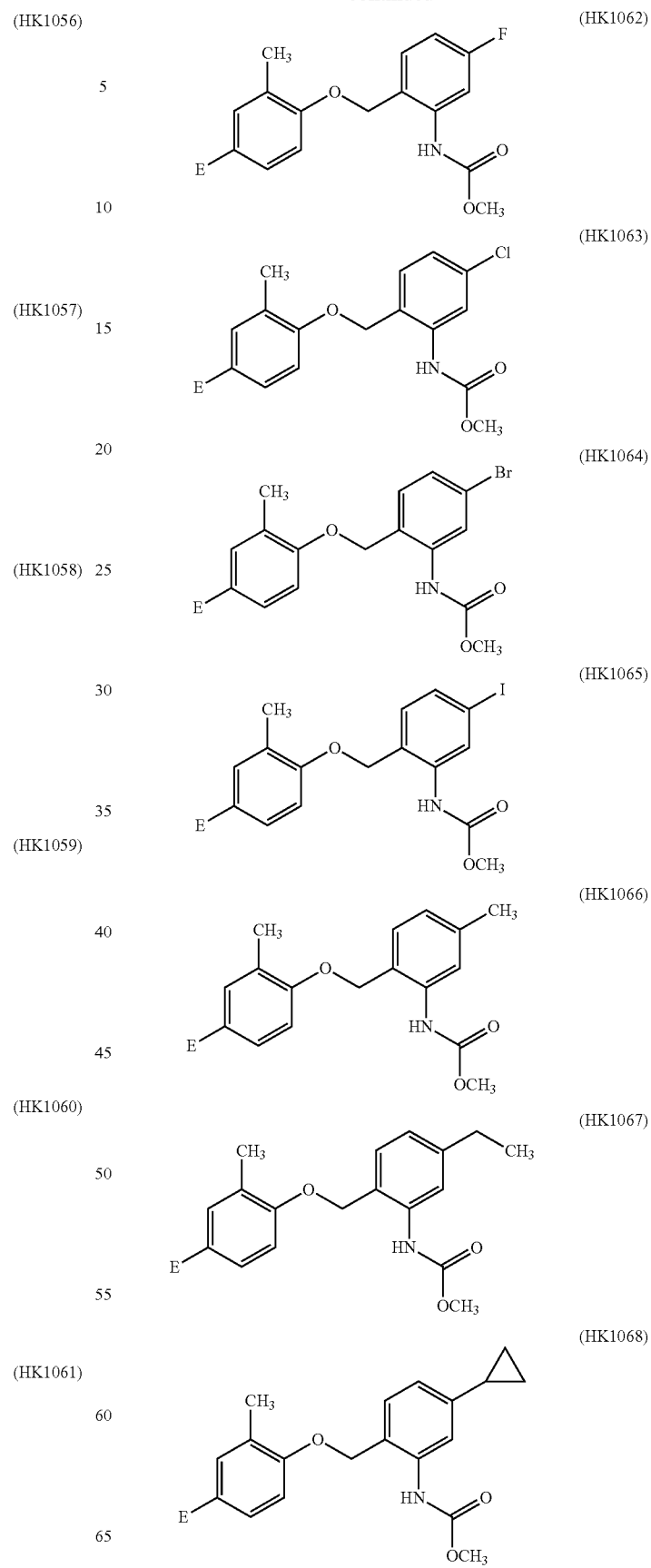

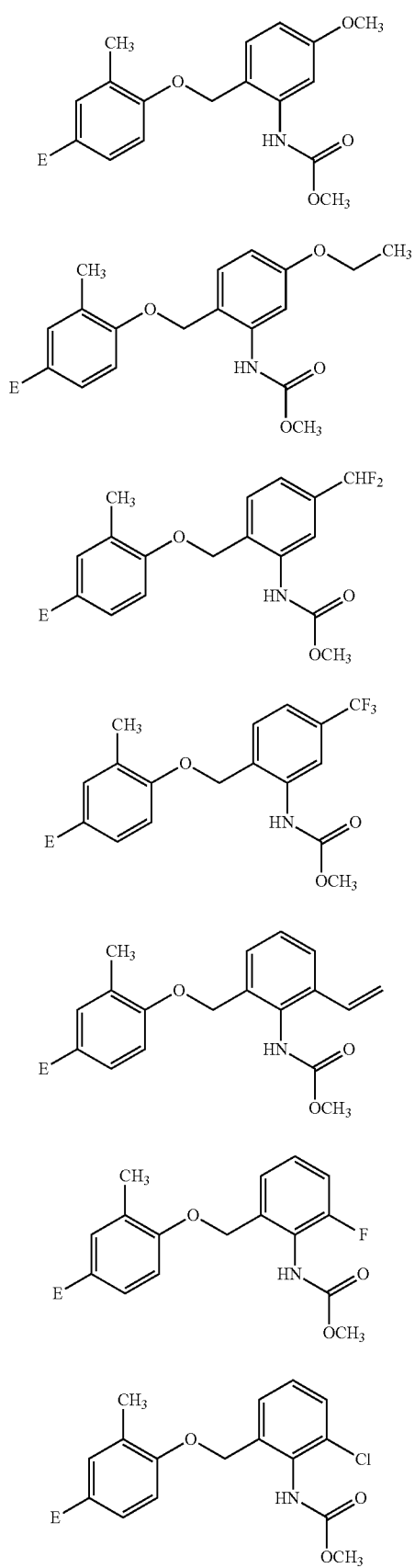
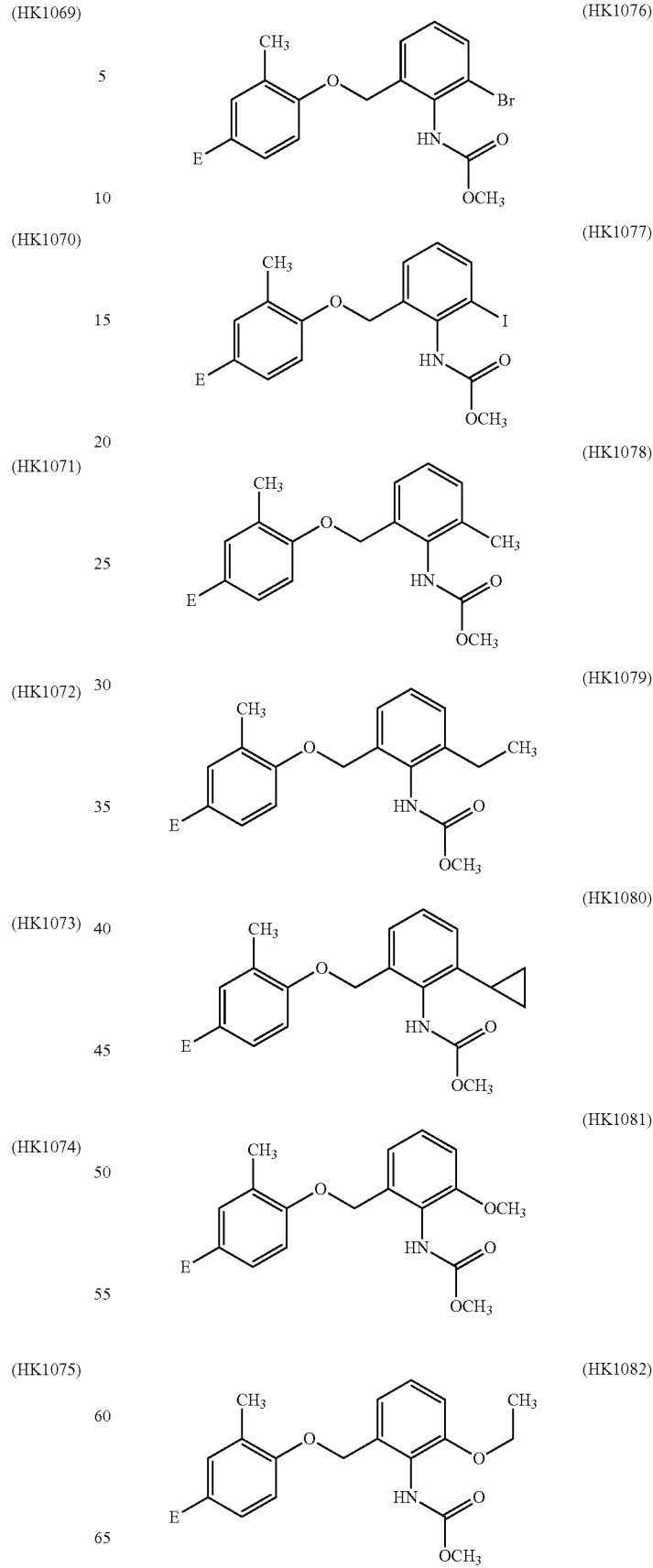

(HK1083) 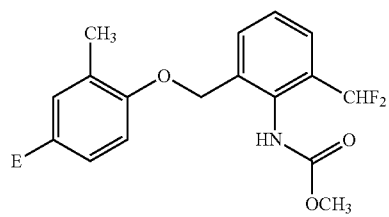
(HK1084) 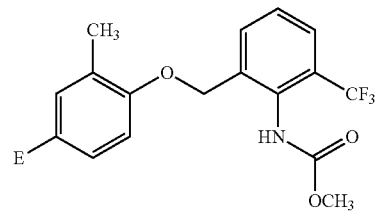
(HL1049) 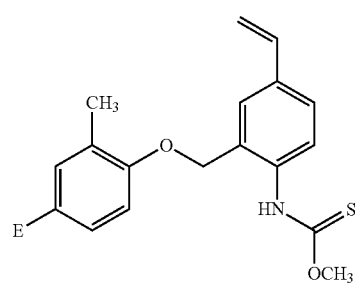
(HL1050) 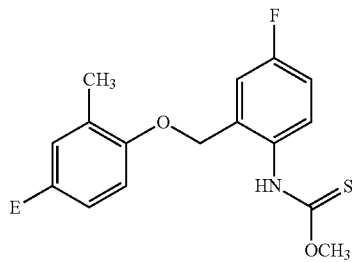
(HL1051) 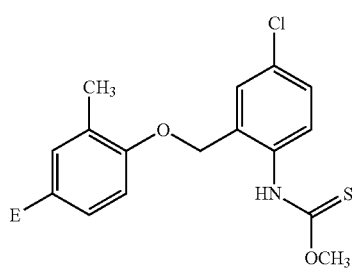
(HL1052) 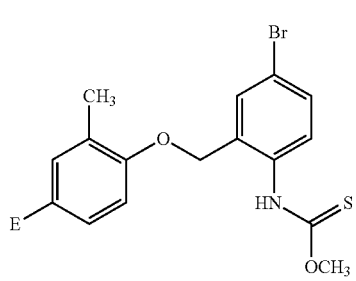
(HL1053) 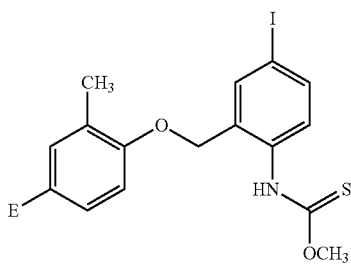
(HL1054) 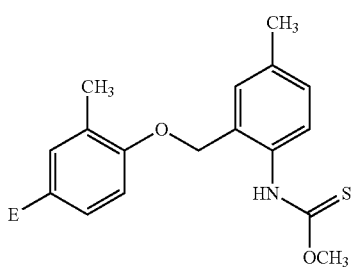
(HL1055) 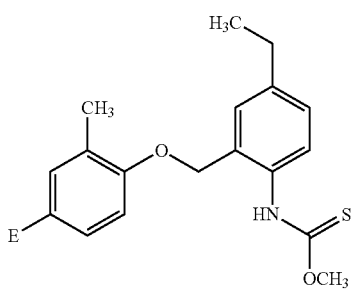
(HL1056) 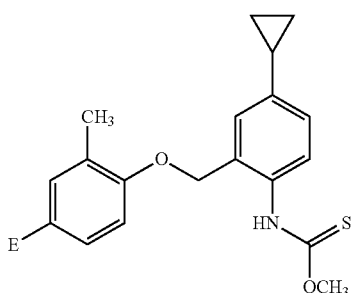
(HL1057) 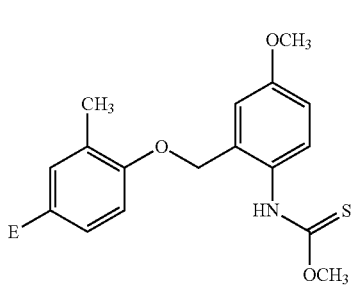

(HL1058) 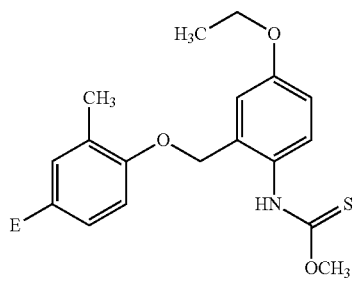
(HL1059) 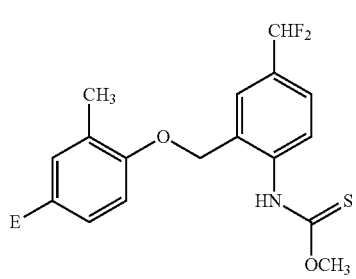
(HL1060) 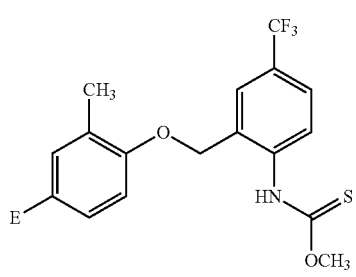
(HL1061) 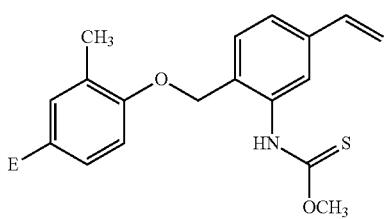
(HL1062) 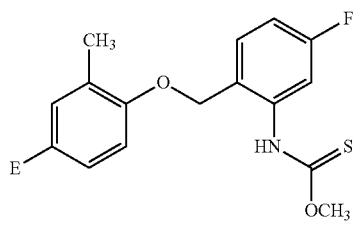
(HL1063) 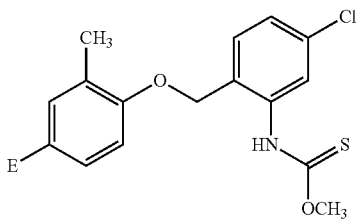
(HL1064) 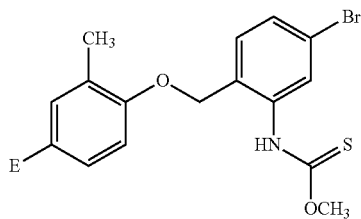
(HL1065) 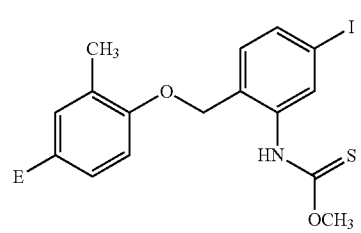
(HL1066) 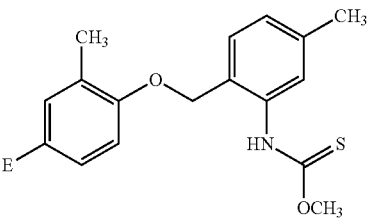
(HL1067) 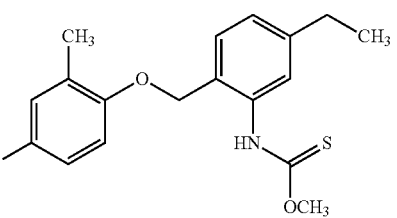
(HL1068) 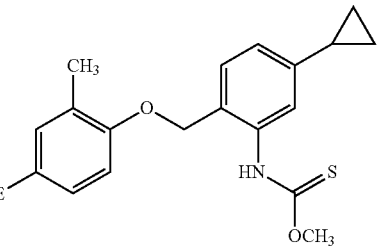
(HL1069) 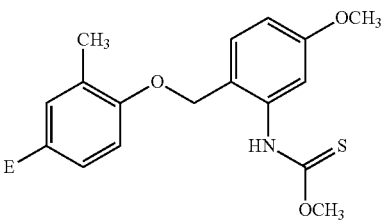
(HL1070) 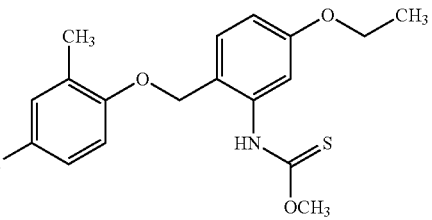

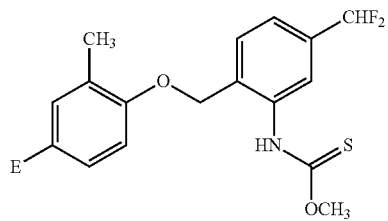 (HL1071)
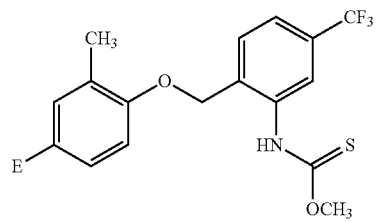 (HL1072)
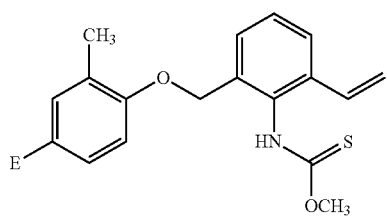 (HL1073)
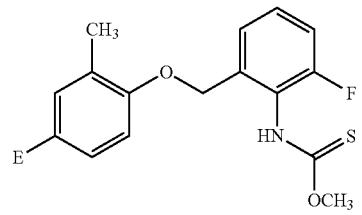 (HL1074)
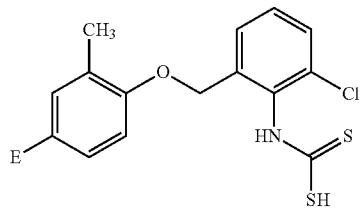 (HL1075)
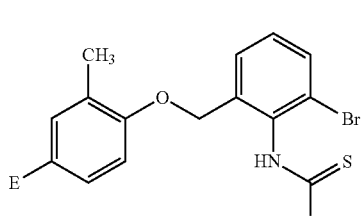 (HL1076)
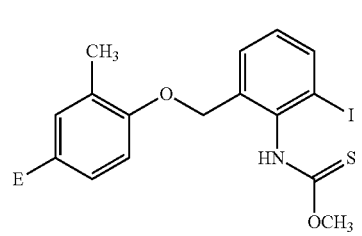 (HL1077)
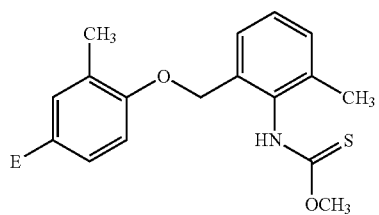 (HL1078)
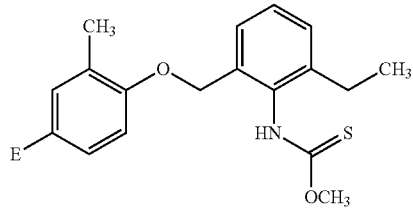 (HL1079)
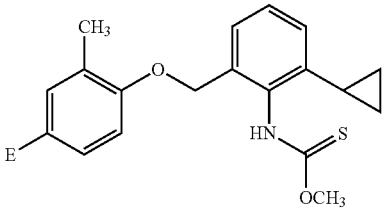 (HL1080)
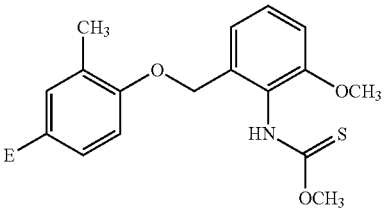 (HL1081)
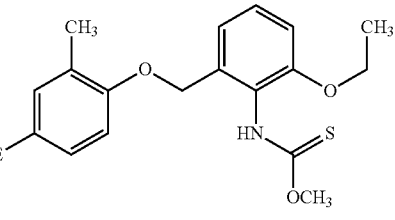 (HL1082)
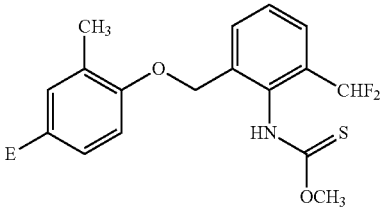 (HL1083)
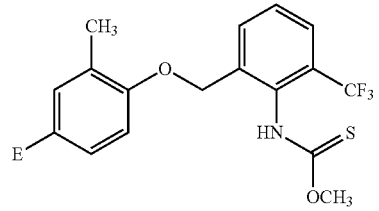 (HL1084)

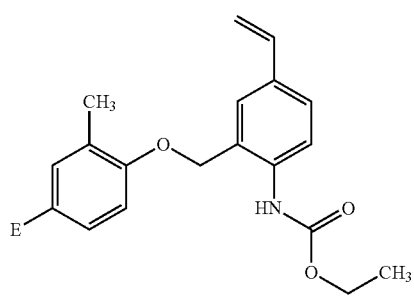 (HM1049)
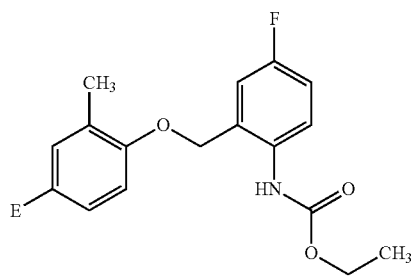 (HM1050)
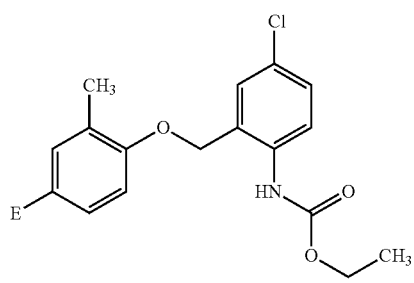 (HM1051)
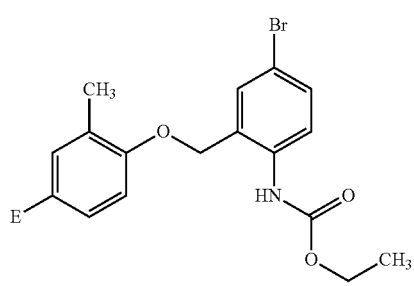 (HM1052)
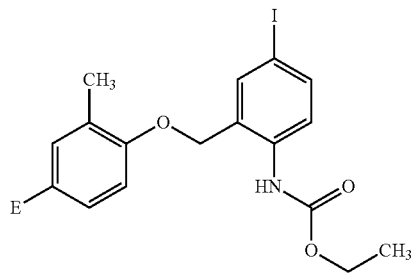 (HM1053)
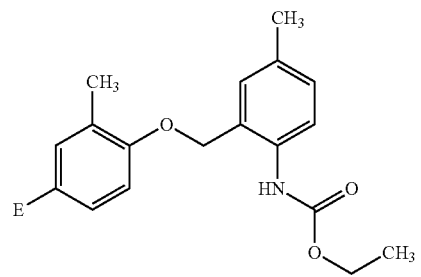 (HM1054)
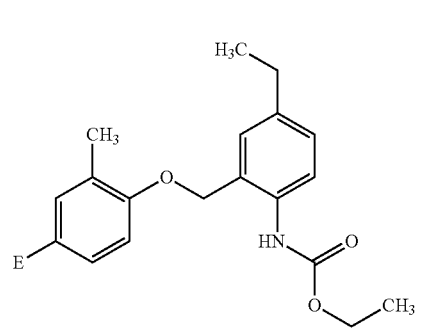 (HM1055)
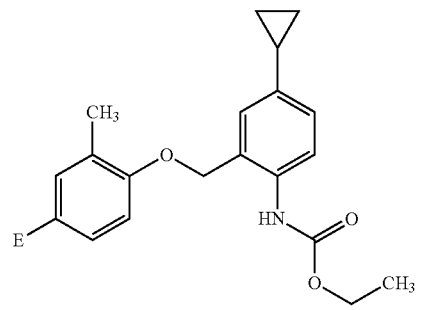 (HM1056)
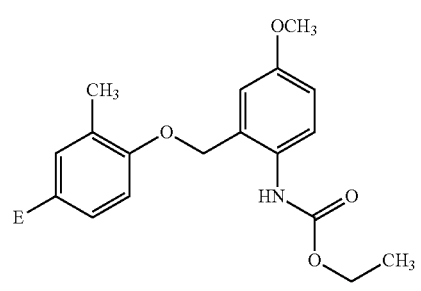 (HM1057)
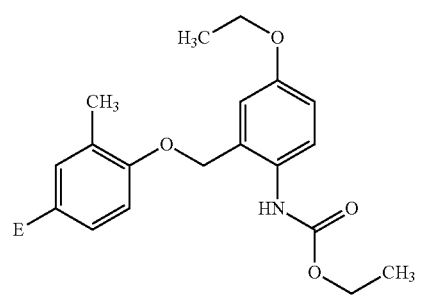 (HM1058)

(HM1059)
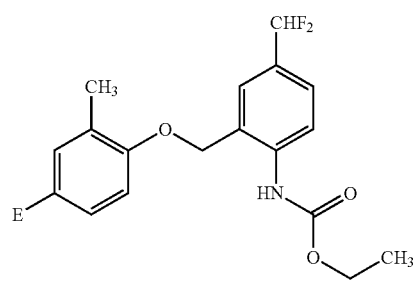
(HM1060)
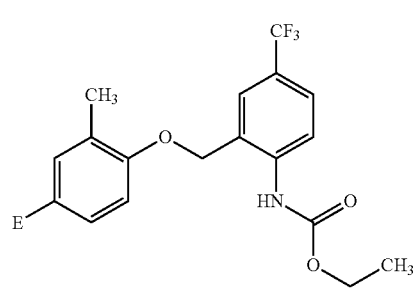
(HM1061)
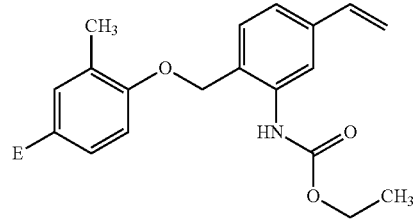
(HM1062)
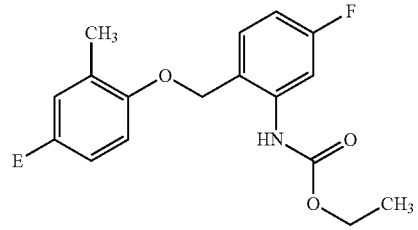
(HM1063)
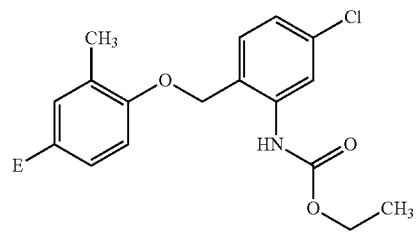
(HM1064)
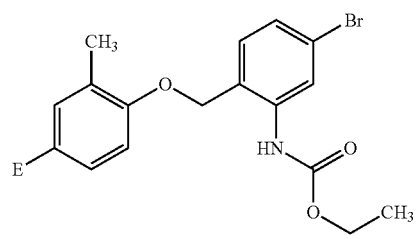
(HM1065)
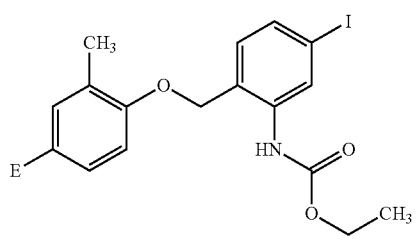
(HM1066)
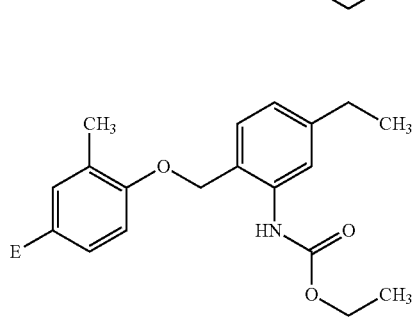
(HM1067)
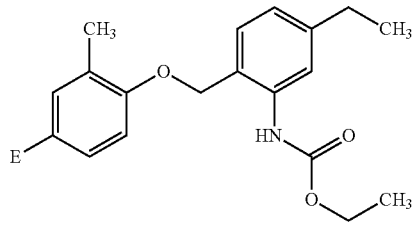
(HM1068)
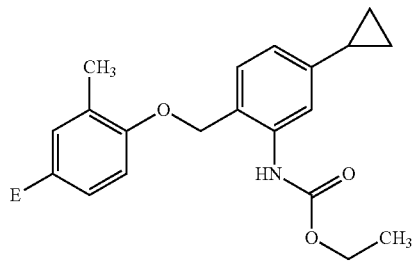
(HM1069)
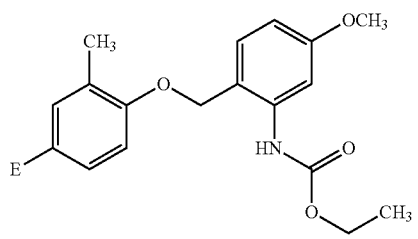
(HM1070)
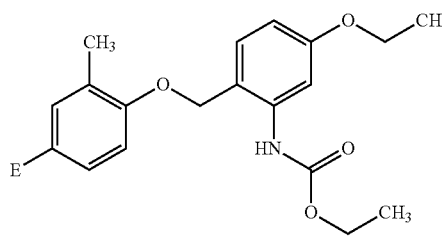

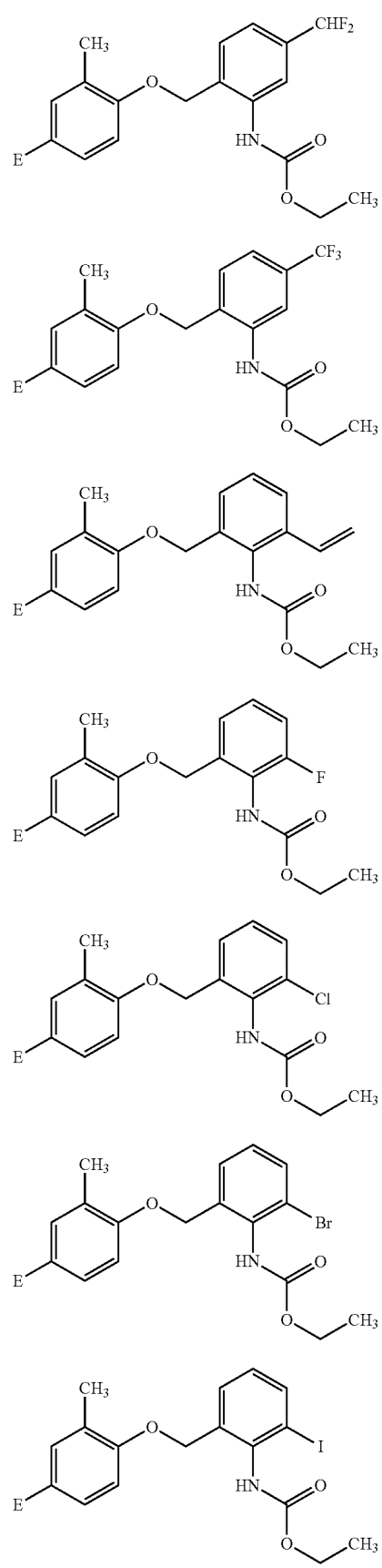
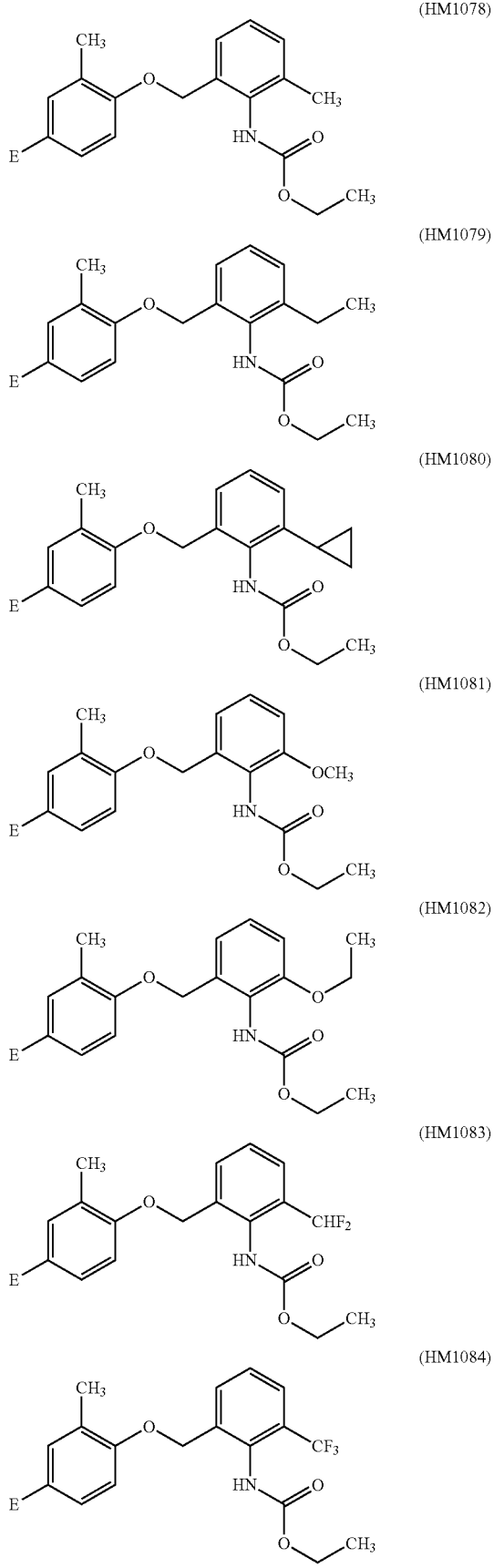

(HN1049)
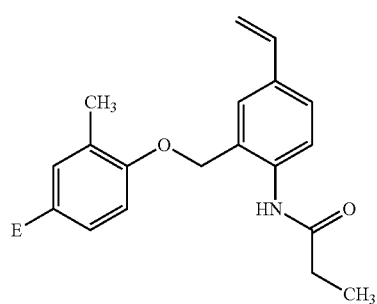
(HN1050)
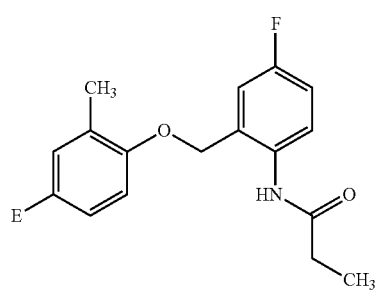
(HN1051)
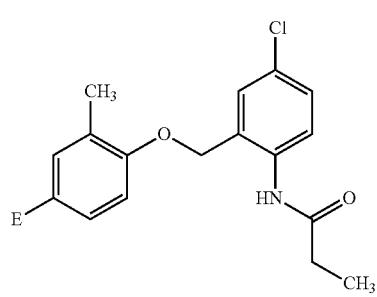
(HN1052)
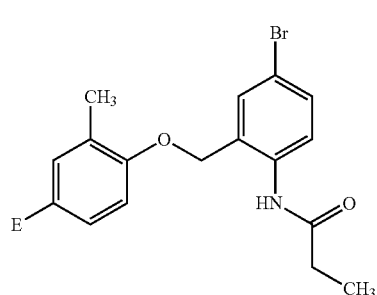
(HN1053)
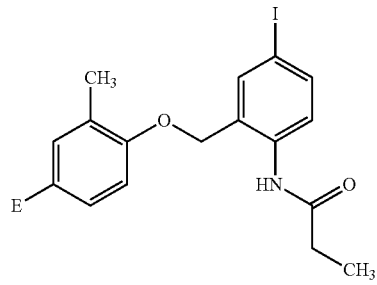
(HN1054)
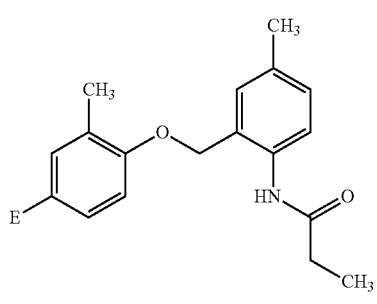
(HN1055)
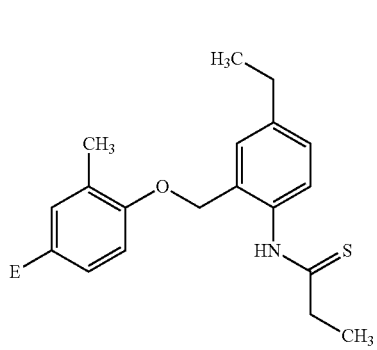
(HN1056)
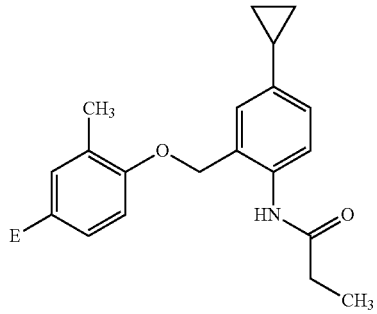
(HN1057)
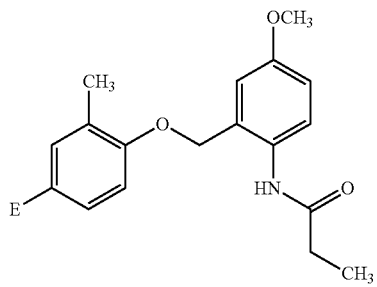
(HN1058)
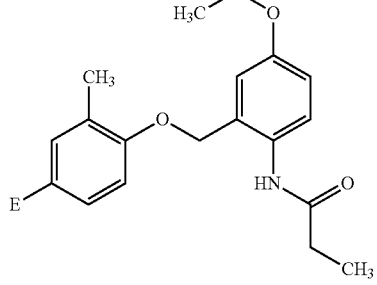

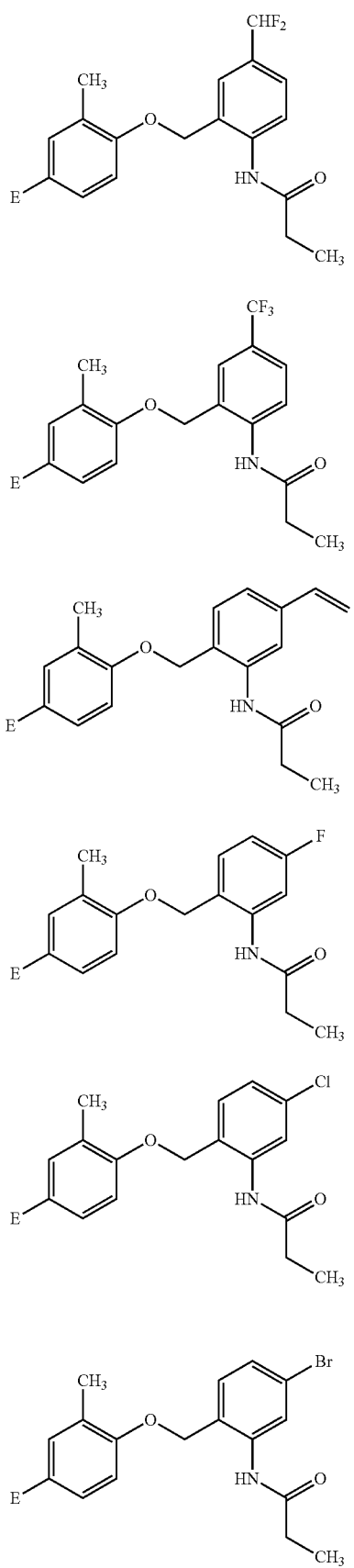
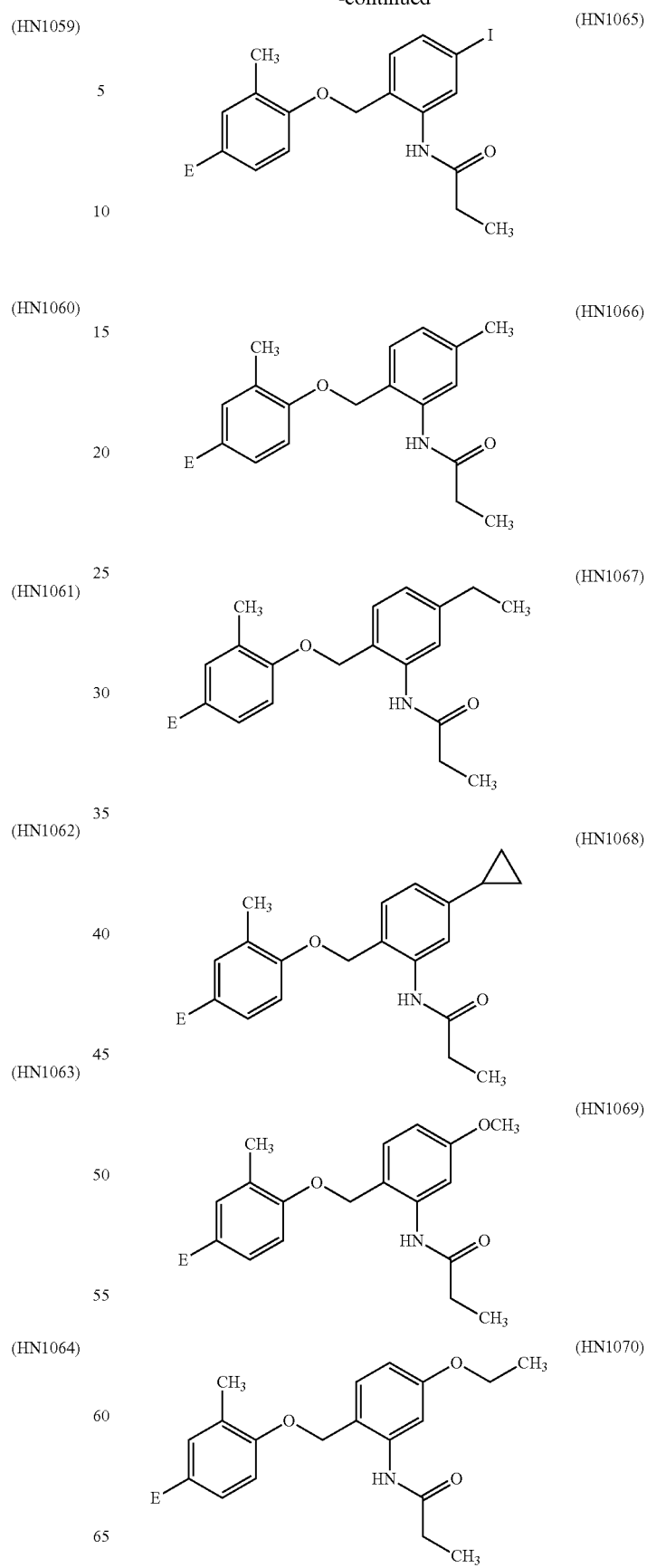

| | |
|---|---|
| (HN1071) | (HN1077) |
| (HN1072) | (HN1078) |
| (HN1073) | (HN1079) |
| (HN1074) | (HN1080) |
| (HN1075) | (HN1081) |
| (HN1076) | (HN1082) |

-continued
(HN1083)
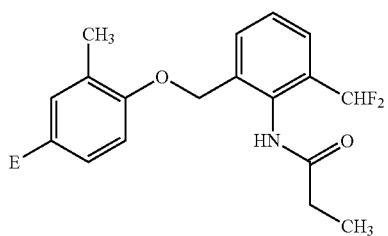
(HN1084)
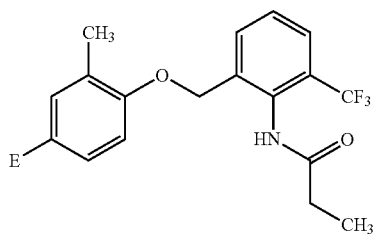
(HO1049)
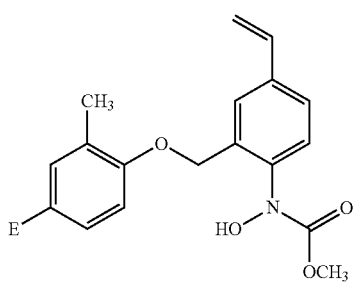
(HO1050)
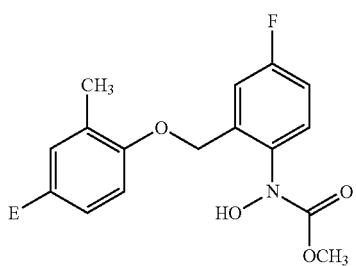
(HO1051)
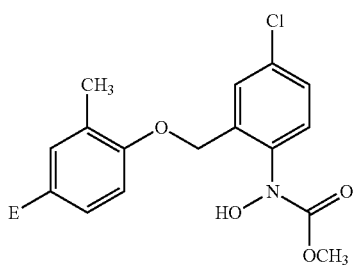
(HO1052)
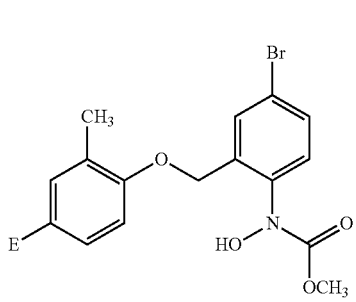
-continued
(HO1053)
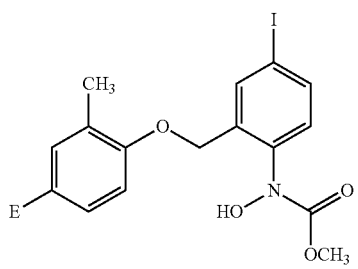
(HO1054)
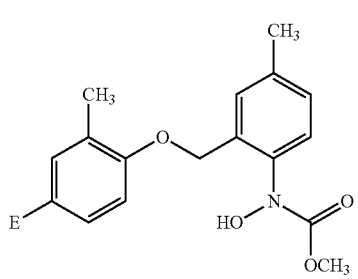
(HO1055)
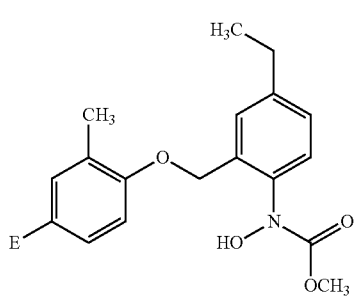
(HO1056)
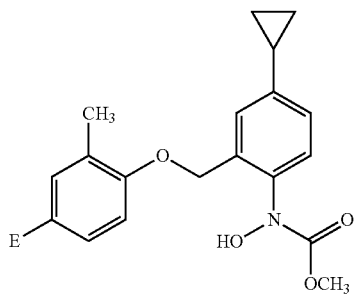
(HO1057)
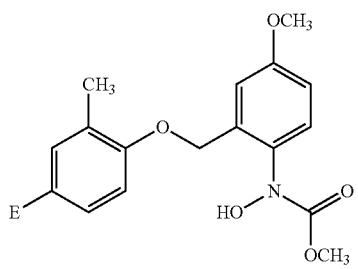

(HO1058)
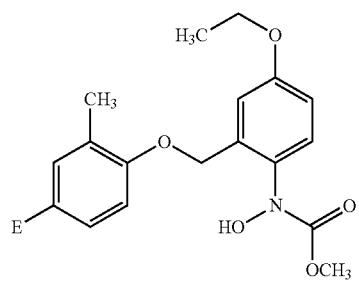
(HO1059)
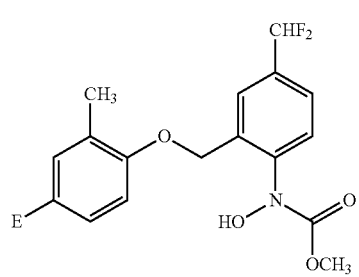
(HO1060)
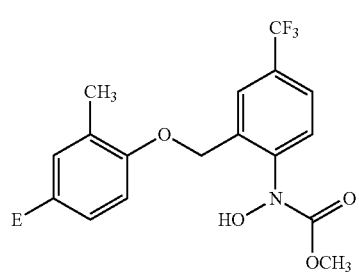
(HO1061)
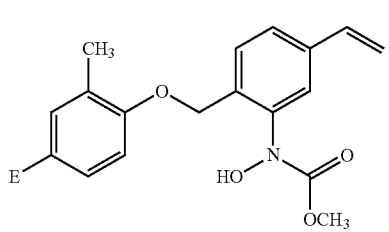
(HO1062)
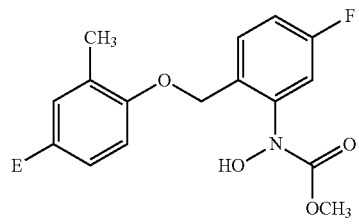
(HO1063)
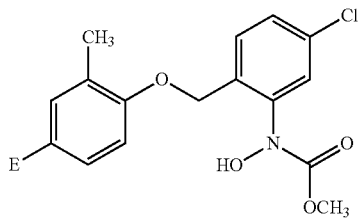
(HO1064)
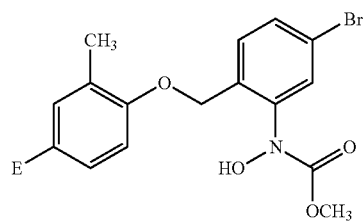
(HO1065)
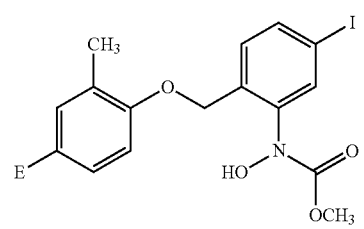
(HO1066)
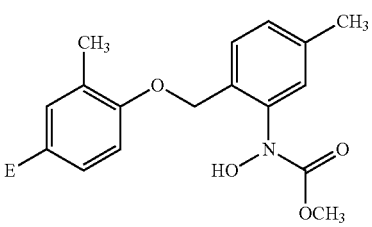
(HO1067)
(HO1068)
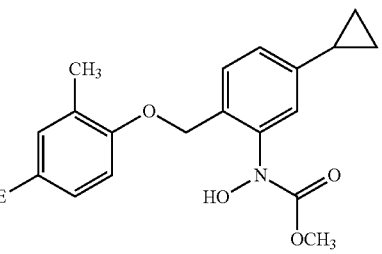
(HO1069)
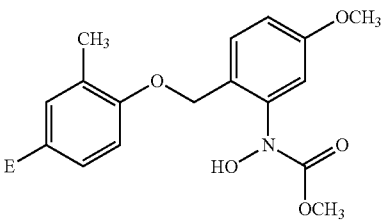
(HO1070)
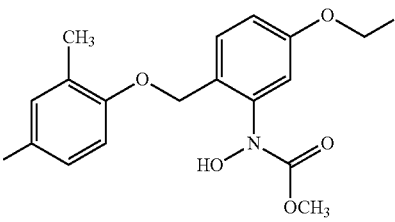

315
-continued
(HO1071)
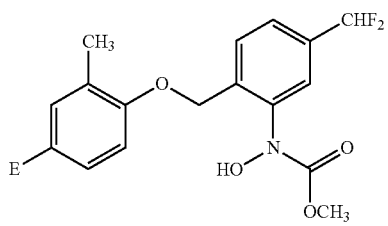
(HO1072)
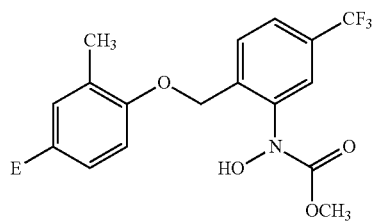
(HO1073)
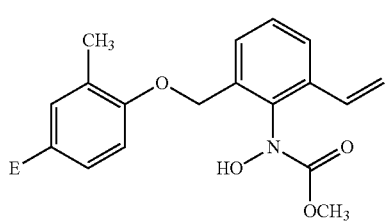
(HO1074)
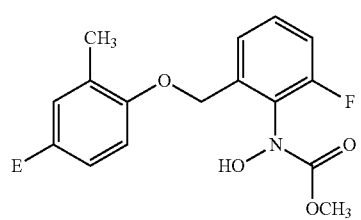
(HO1075)
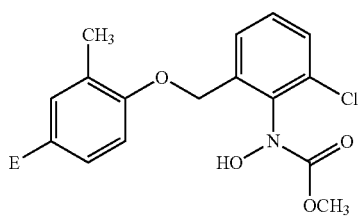
(HO1076)
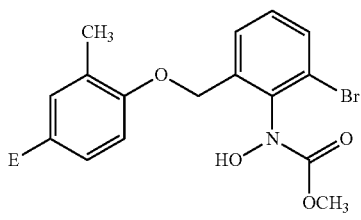
(HO1077)
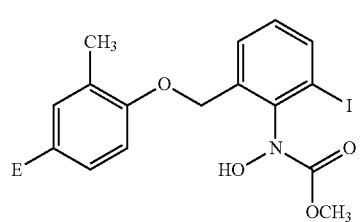
316
-continued
(HO1078)
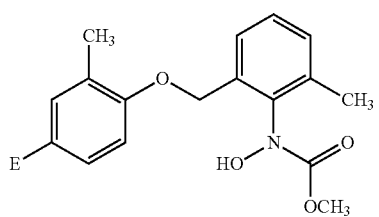
(HO1079)
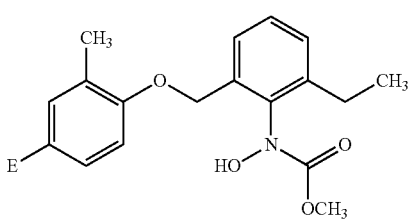
(HO1080)
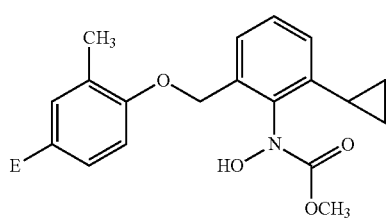
(HO1081)
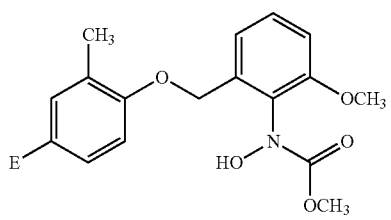
(HO1082)
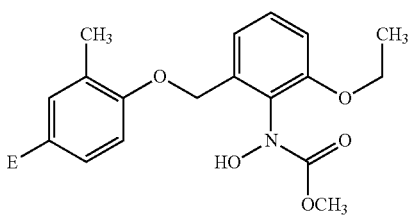
(HO1083)
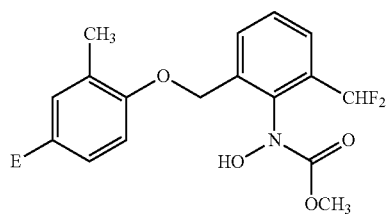
(HO1084)
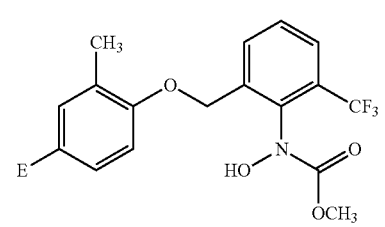

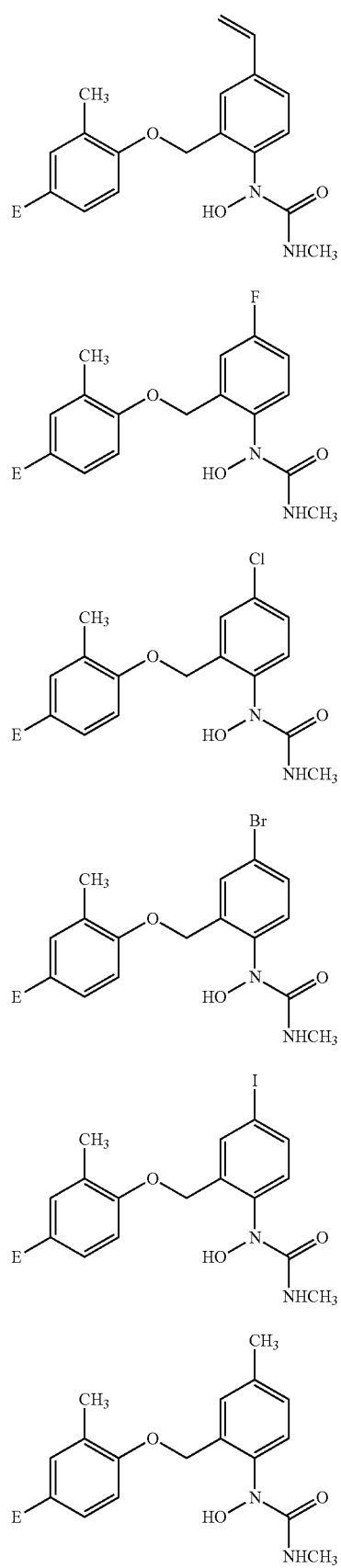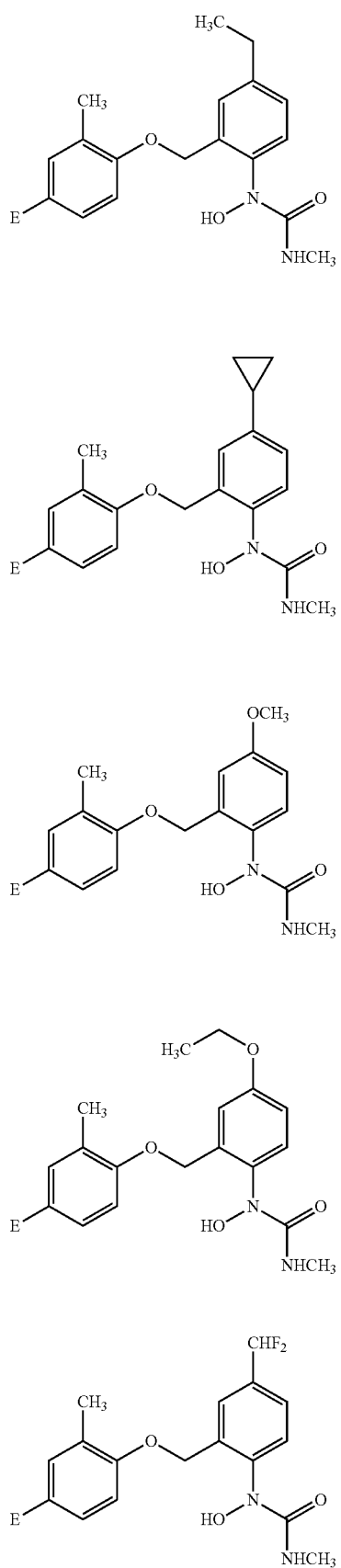

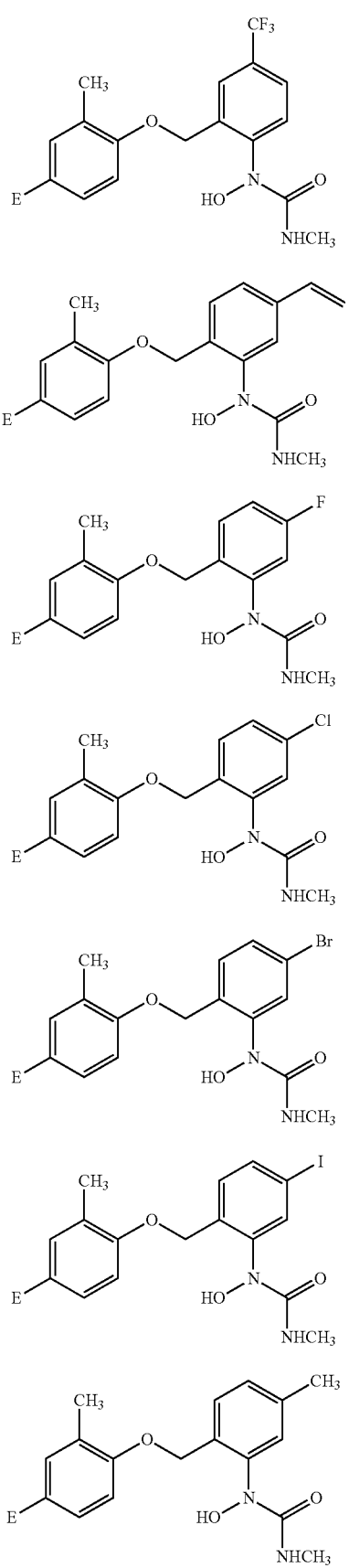
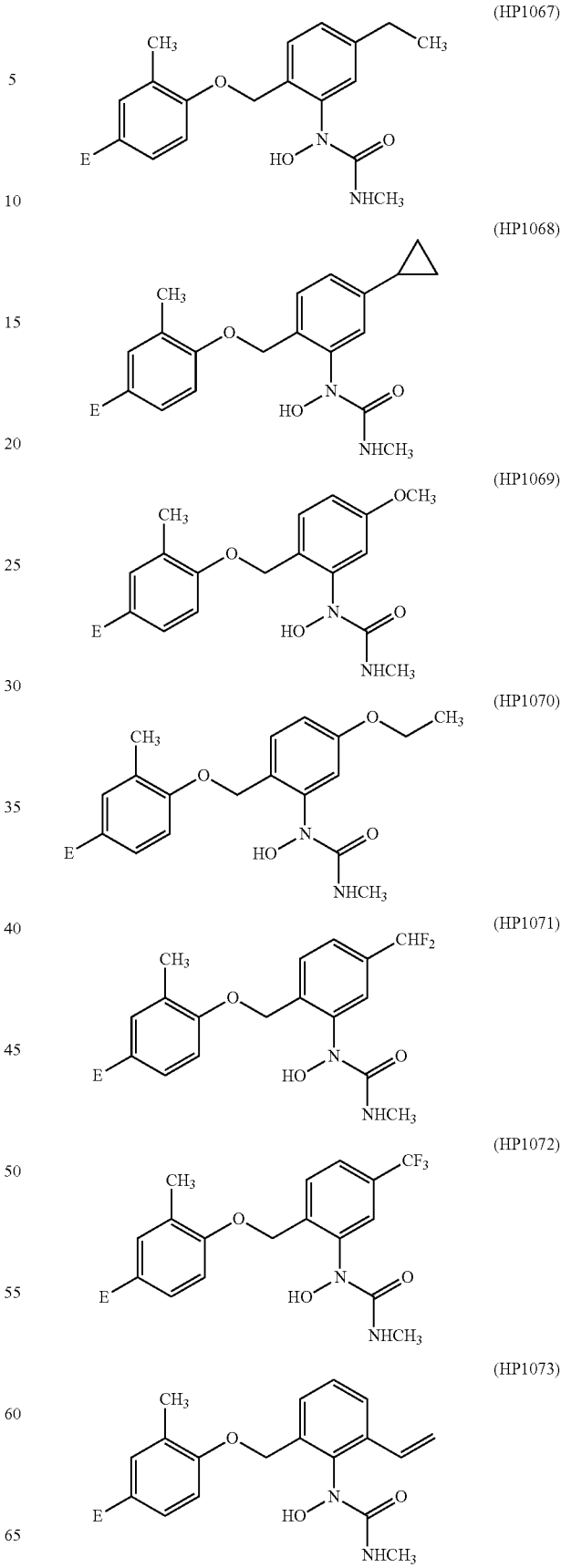

-continued
(HP1074)
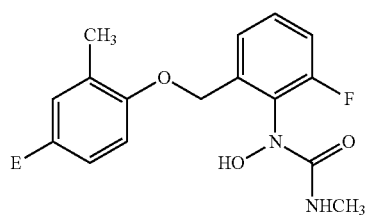
(HP1075)
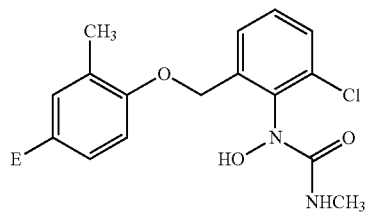
(HP1076)
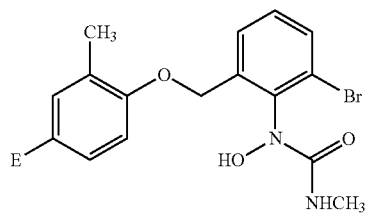
(HP1077)
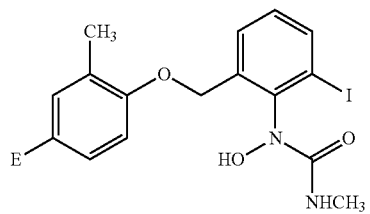
(HP1078)
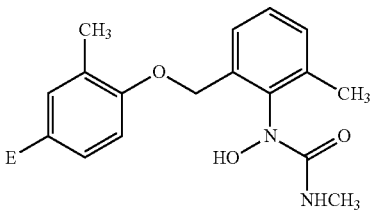
(HP1079)
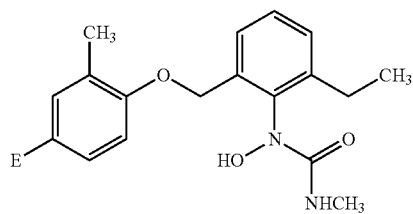
(HP1080)
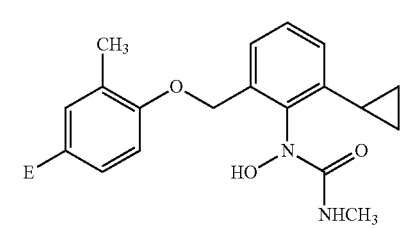
-continued
(HP1081)
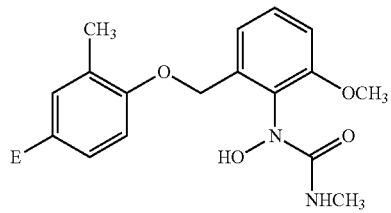
(HP1082)
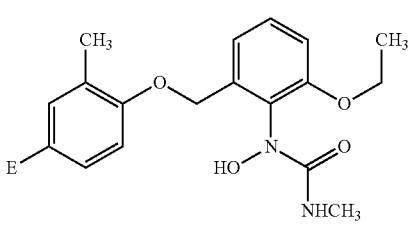
(HP1083)
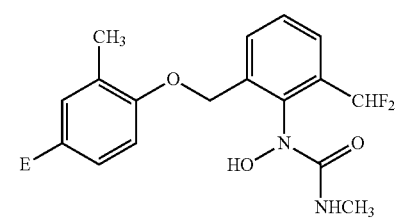
(HP1084)
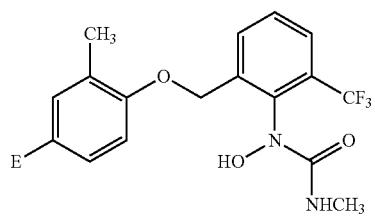
(HQ1049)
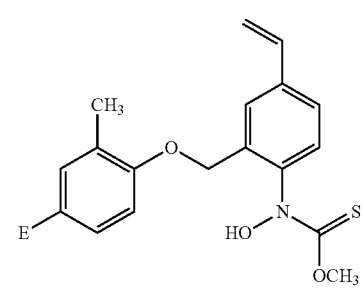
(HQ1050)
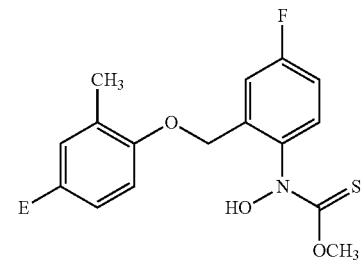

(HQ1051)
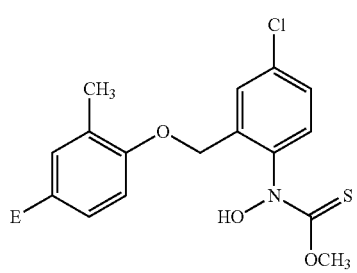
(HQ1056)
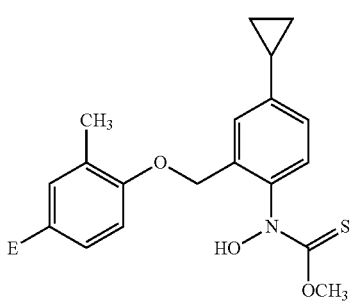
(HQ1052)
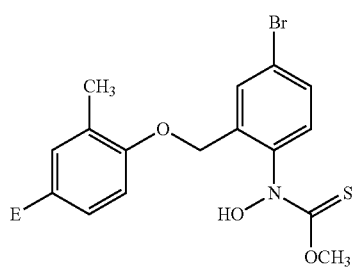
(HQ1057)
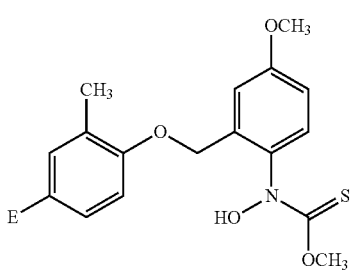
(HQ1053)
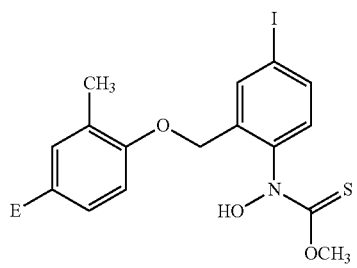
(HQ1058)
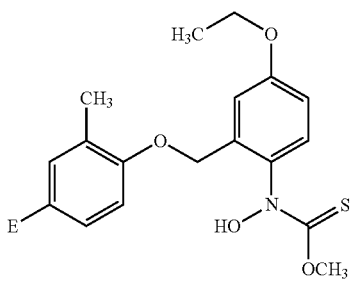
(HQ1054)
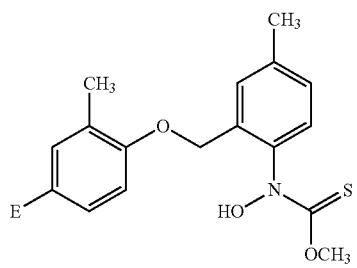
(HQ1059)
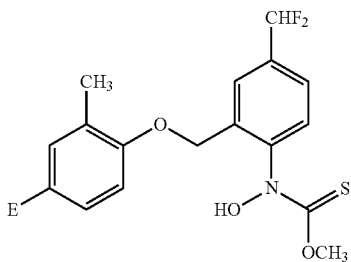
(HQ1060)
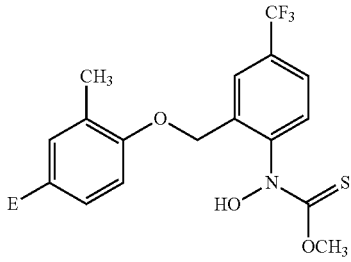
(HQ1055)
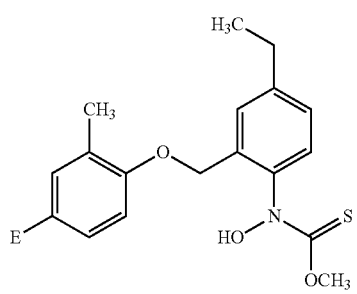
(HQ1061)
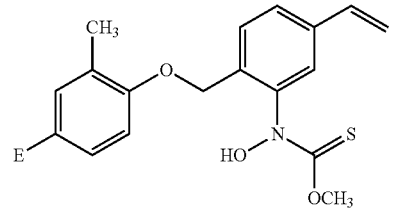

325
-continued
(HQ1062)
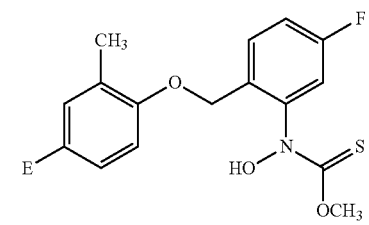
(HQ1063)
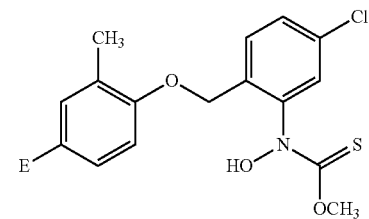
(HQ1064)
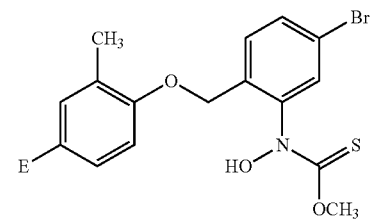
(HQ1065)
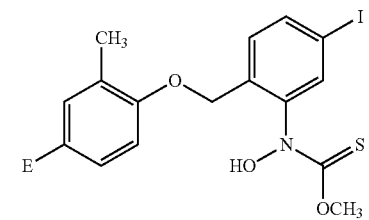
(HQ1066)
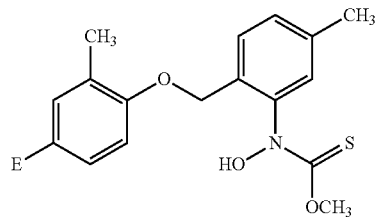
(HQ1067)
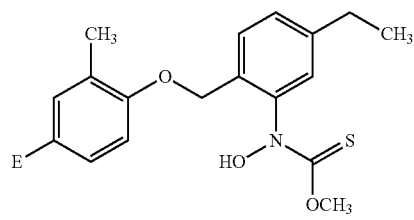
(HQ1068)
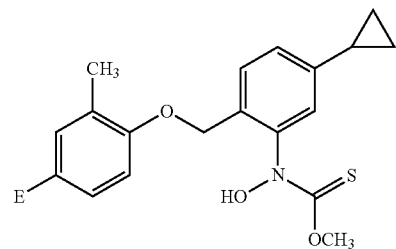
326
-continued
(HQ1069)
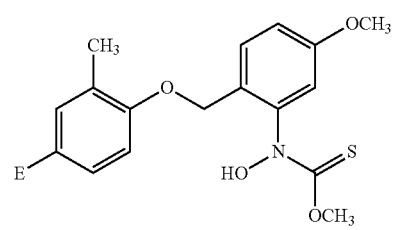
(HQ1070)
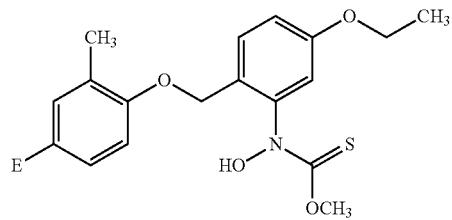
(HQ1071)
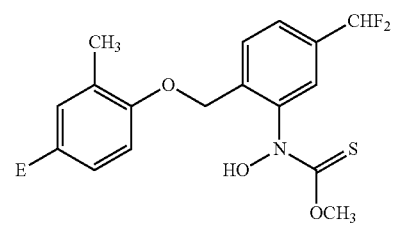
(HQ1072)
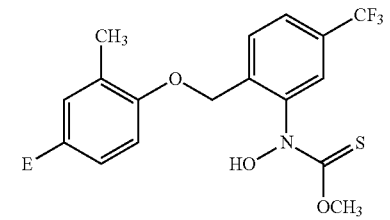
(HQ1073)
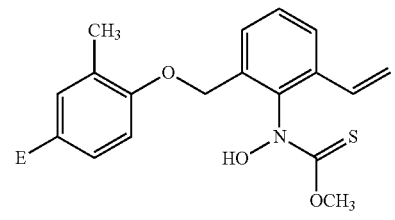
(HQ1074)
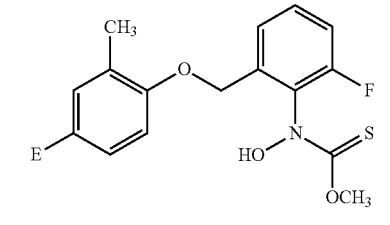
(HQ1075)

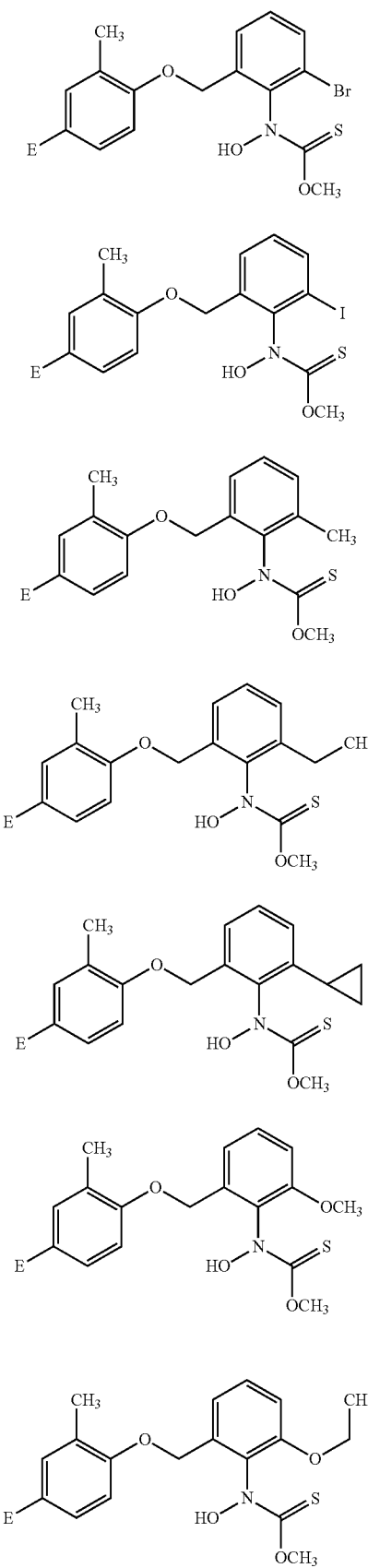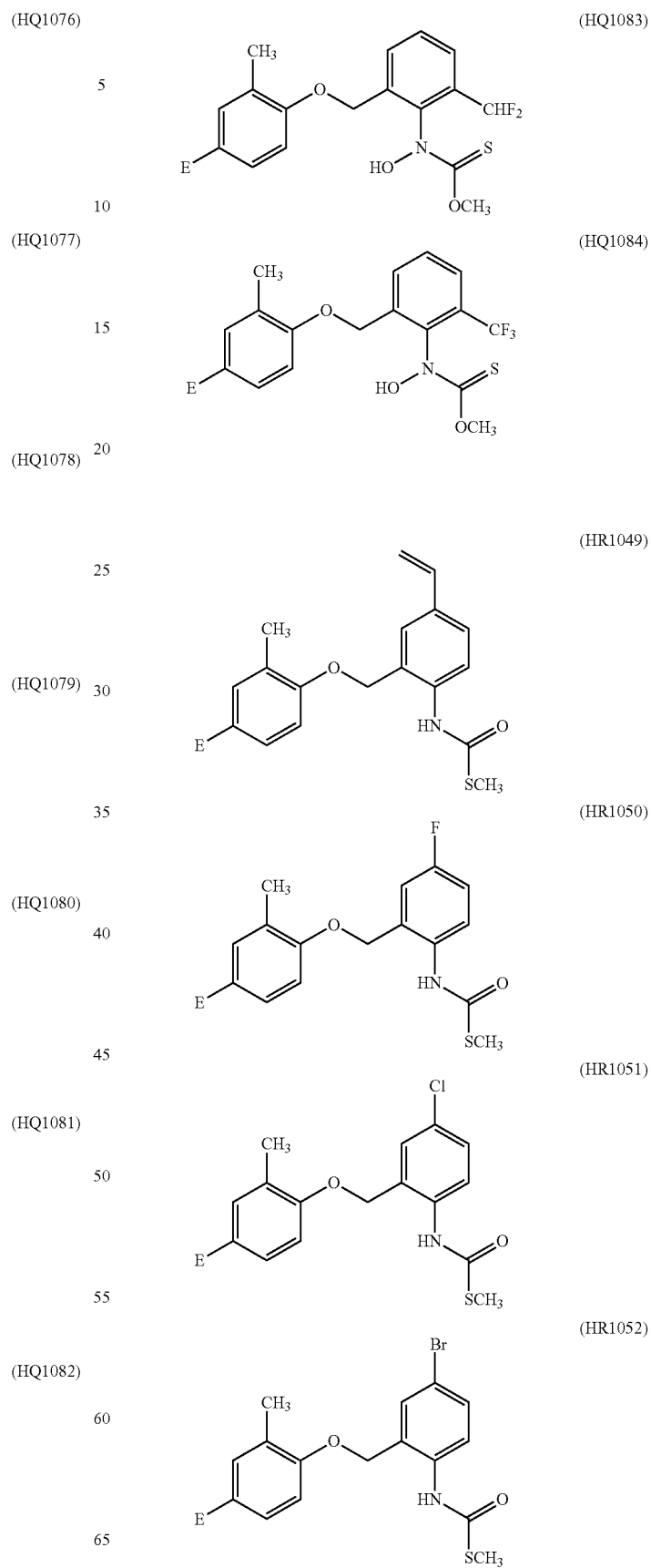

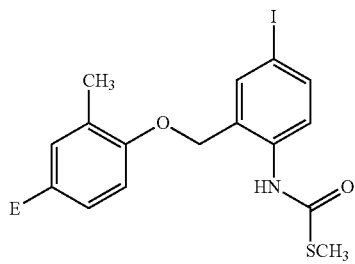 (HR1053)
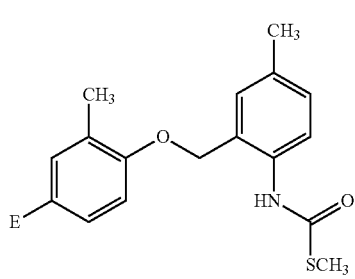 (HR1054)
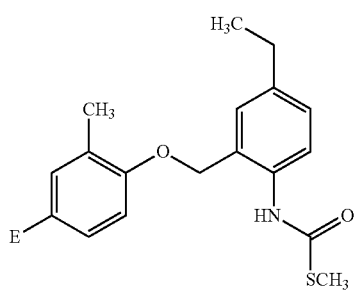 (HR1055)
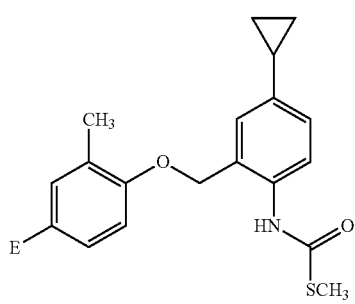 (HR1056)
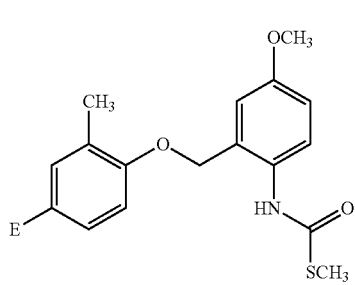 (HR1057)
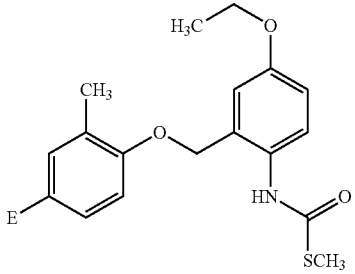 (HR1058)
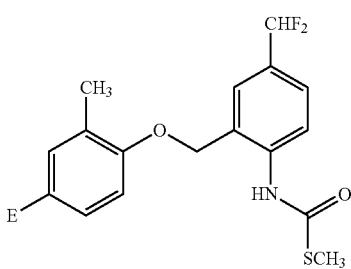 (HR1059)
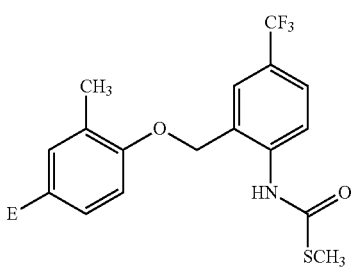 (HR1060)
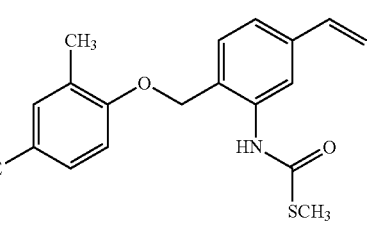 (HR1061)
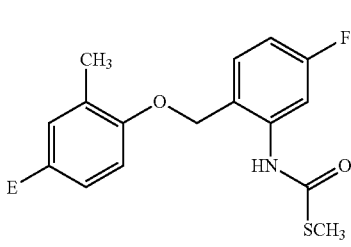 (HR1062)
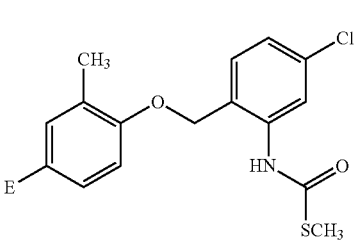 (HR1063)

-continued
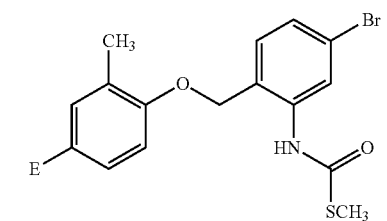
(HR1064)
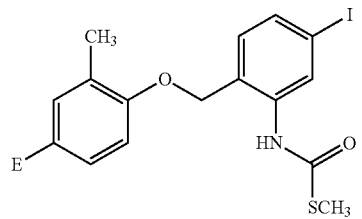
(HR1065)
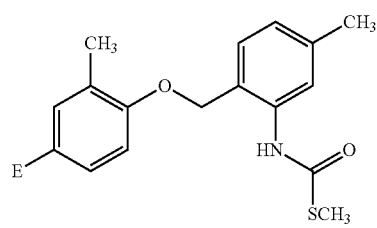
(HR1066)
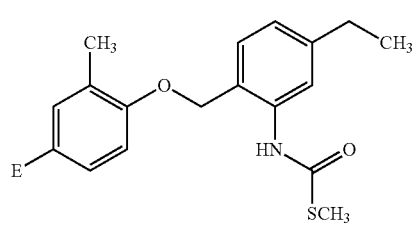
(HR1067)
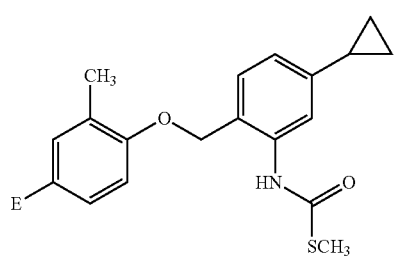
(HR1068)
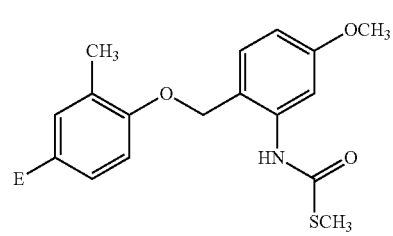
(HR1069)
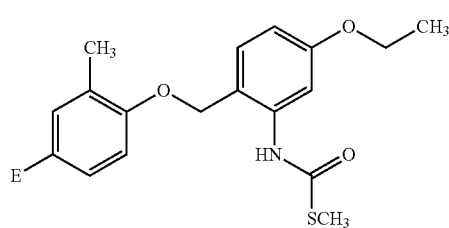
(HR1070)
-continued
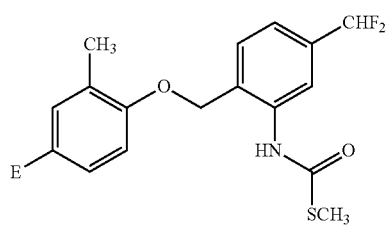
(HR1071)
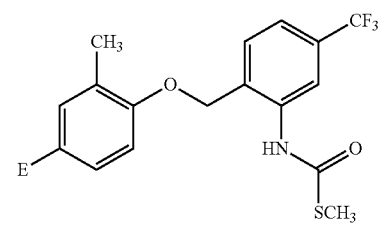
(HR1072)
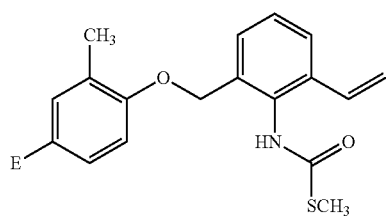
(HR1073)
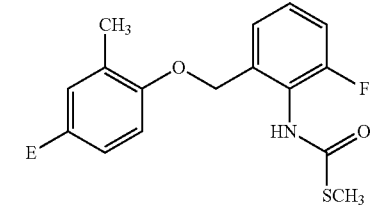
(HR1074)
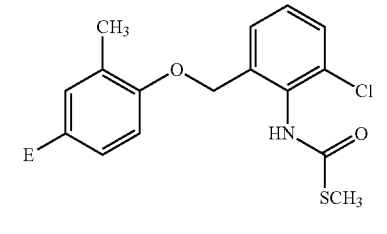
(HR1075)
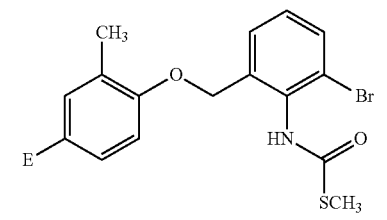
(HR1076)
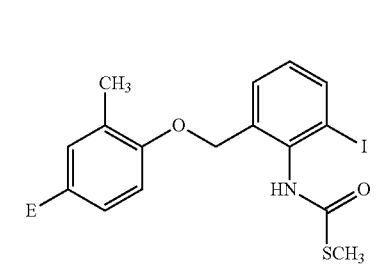
(HR1077)

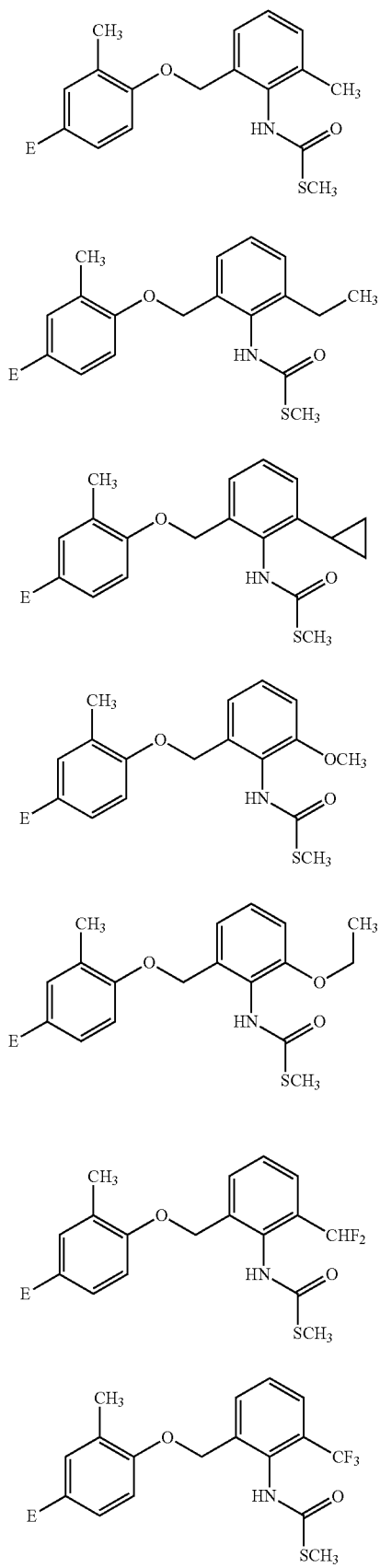
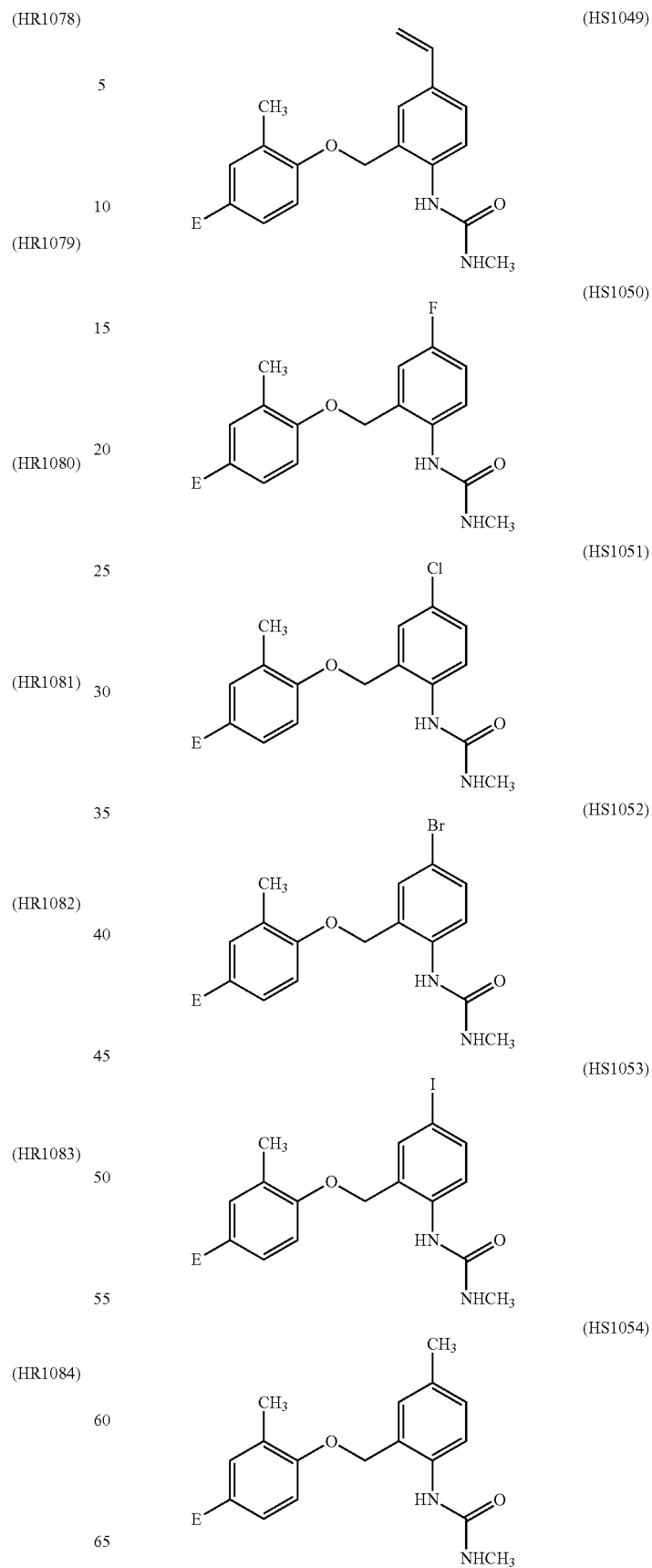

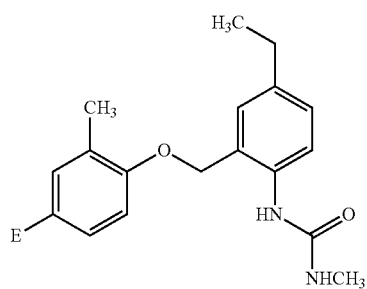
(HS1055)
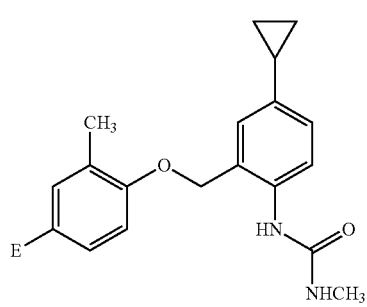
(HS1056)
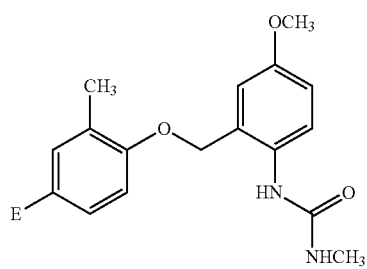
(HS1057)
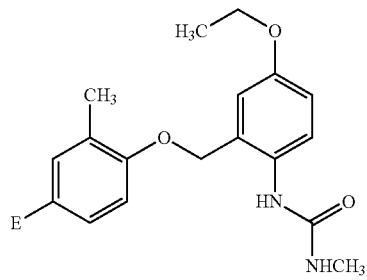
(HS1058)
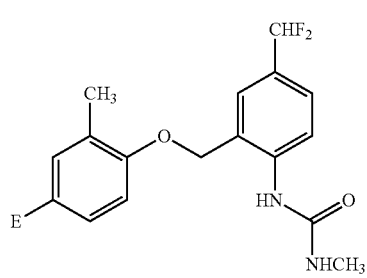
(HS1059)
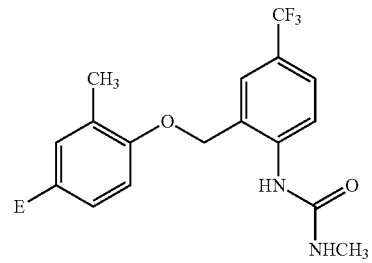
(HS1060)
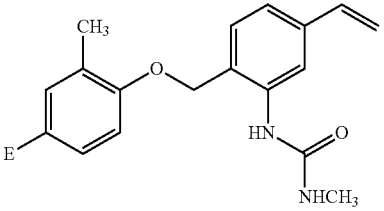
(HS1061)
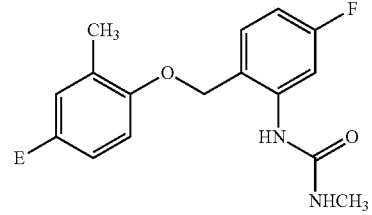
(HS1062)
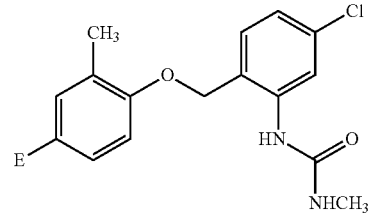
(HS1063)
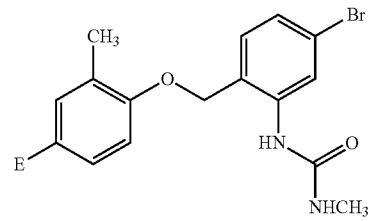
(HS1064)
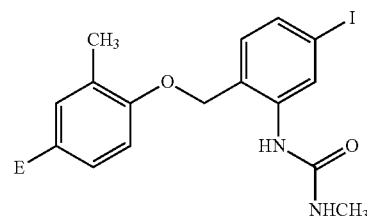
(HS1065)
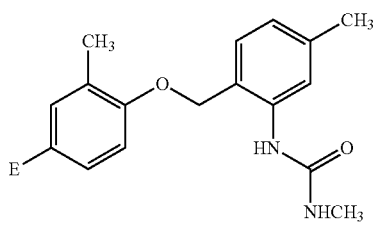
(HS1066)

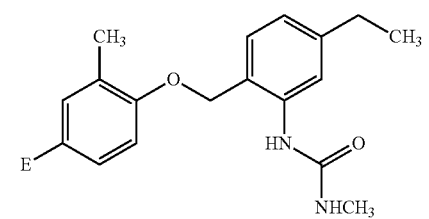 (HS1067)
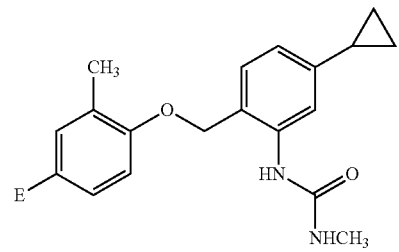 (HS1068)
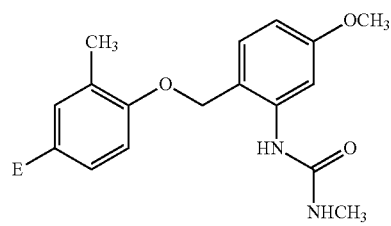 (HS1069)
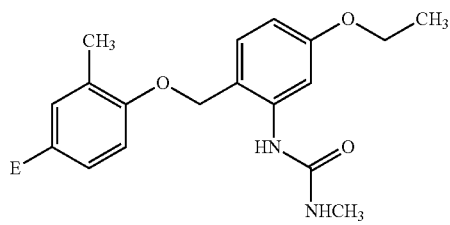 (HS1070)
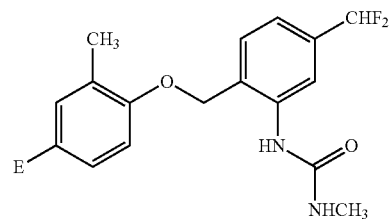 (HS1071)
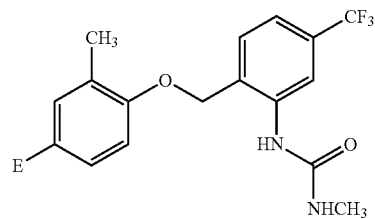 (HS1072)
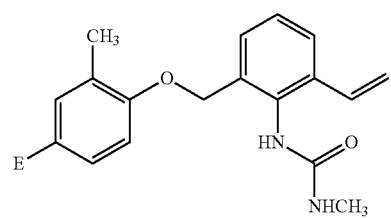 (HS1073)
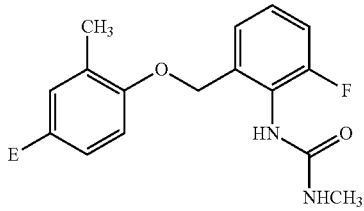 (HS1074)
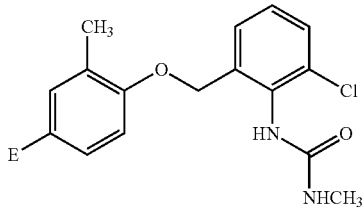 (HS1075)
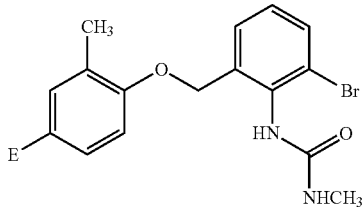 (HS1076)
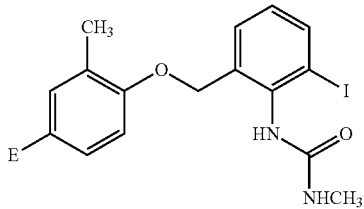 (HS1077)
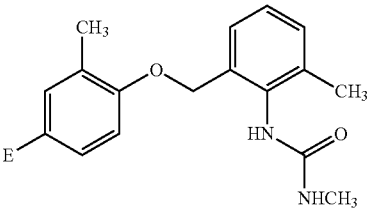 (HS1078)
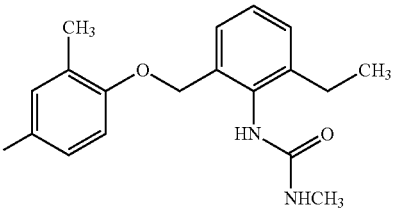 (HS1079)
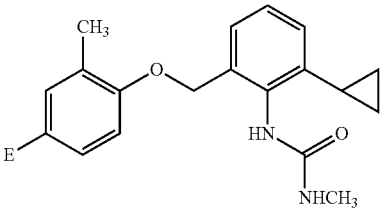 (HS1080)

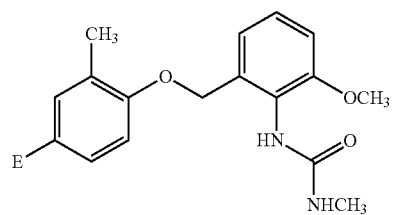
(HS1081)
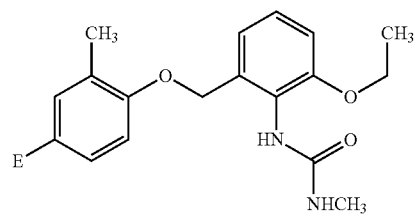
(HS1082)
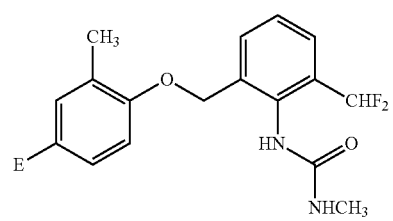
(HS1083)
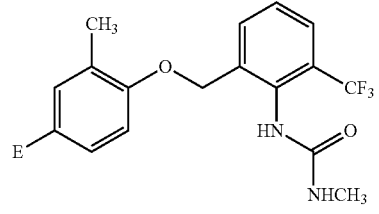
(HS1084)
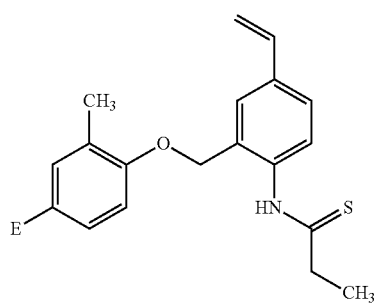
(HT1049)
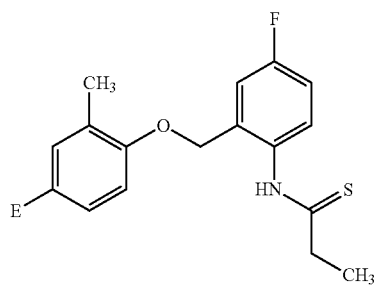
(HT1050)
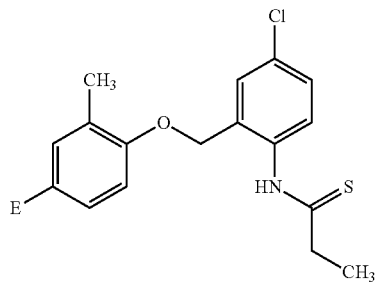
(HT1051)
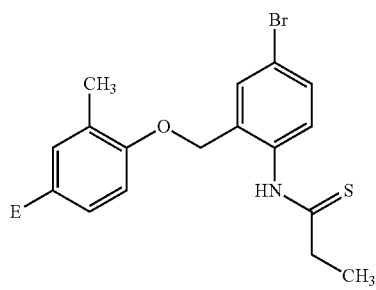
(HT1052)
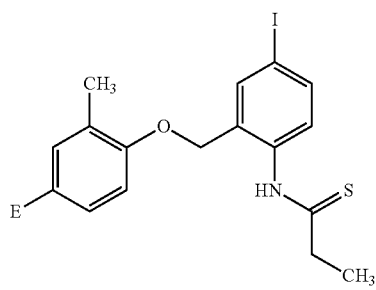
(HT1053)
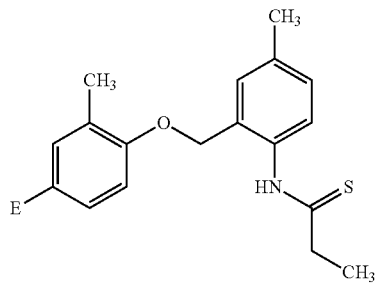
(HT1054)
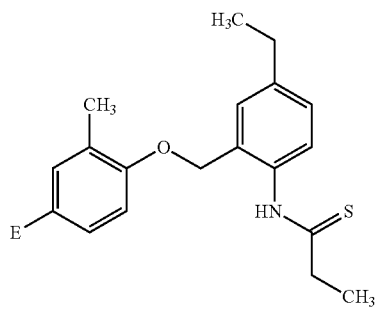
(HT1055)

(HT1056)
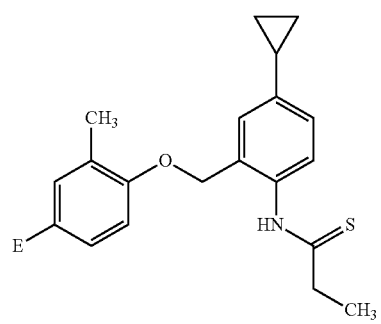
(HT1057)
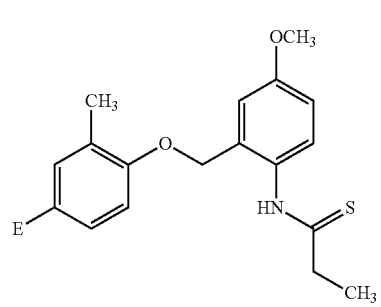
(HT1058)
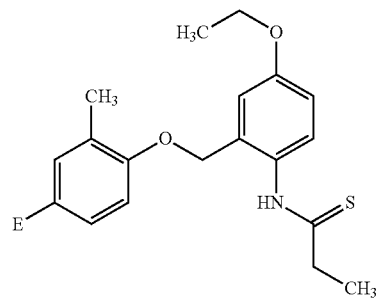
(HT1059)
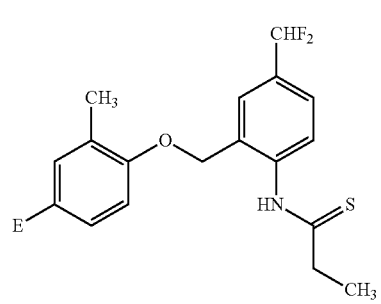
(HT1060)
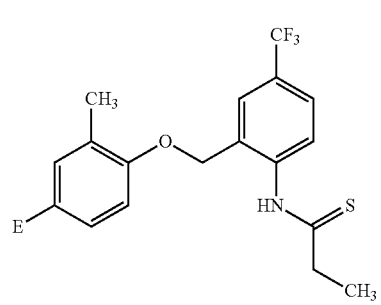
(HT1061)
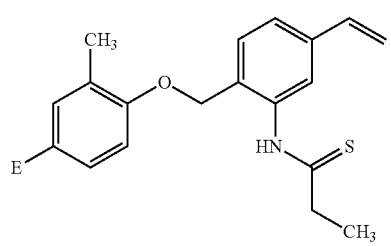
(HT1062)
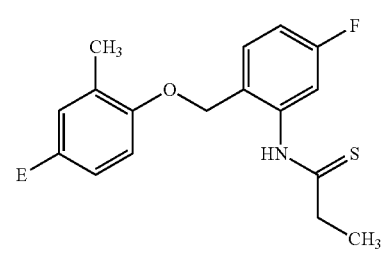
(HT1063)
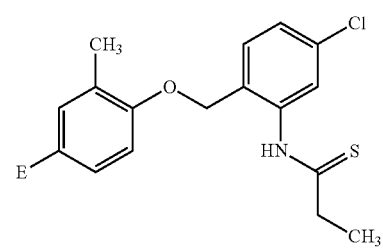
(HT1064)
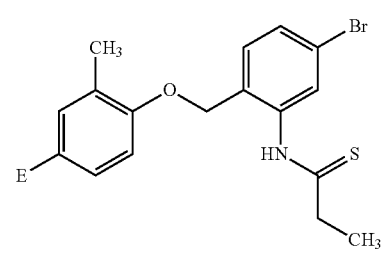
(HT1065)
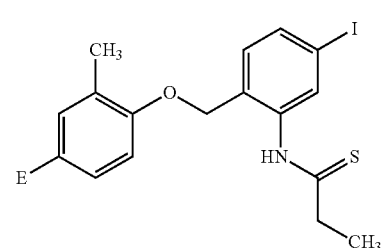
(HT1066)
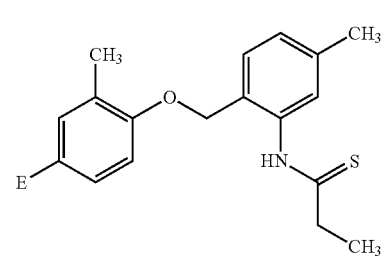

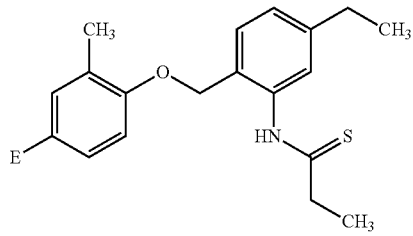
(HT1067)
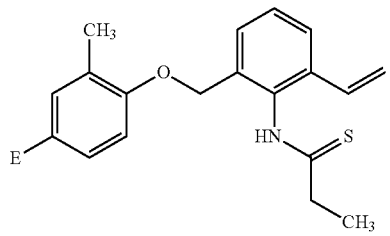
(HT1073)
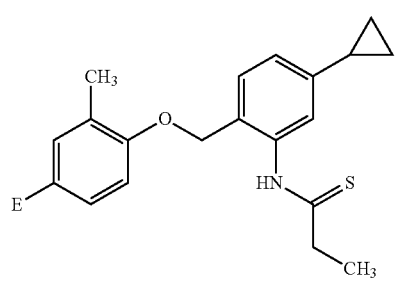
(HT1068)
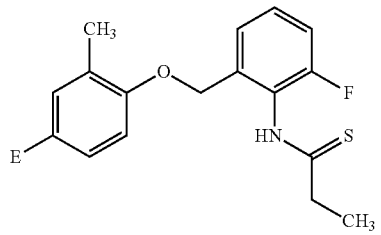
(HT1074)
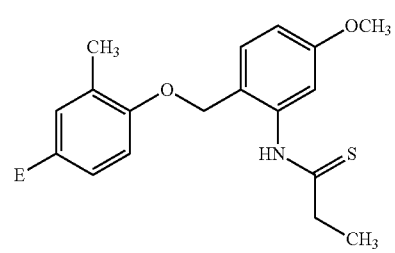
(HT1069)
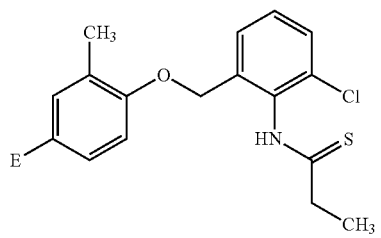
(HT1075)
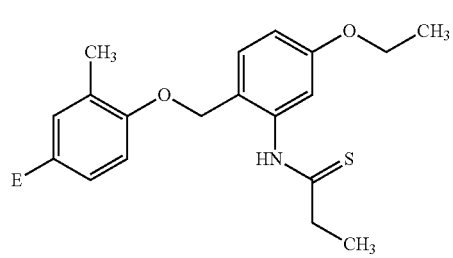
(HT1070)
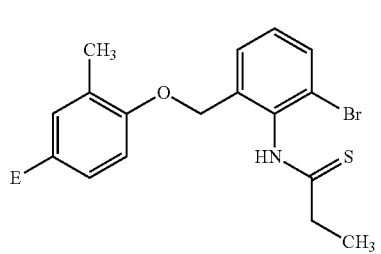
(HT1076)
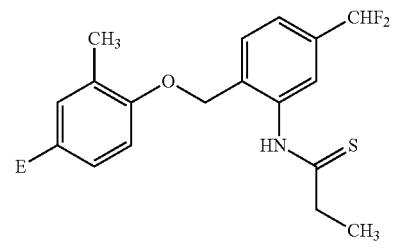
(HT1071)
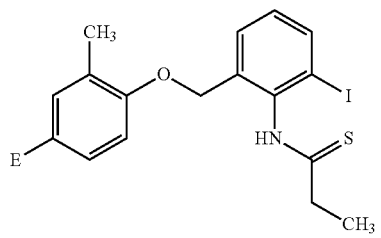
(HT1077)
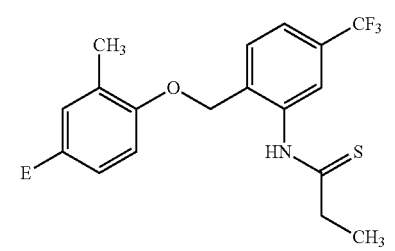
(HT1072)
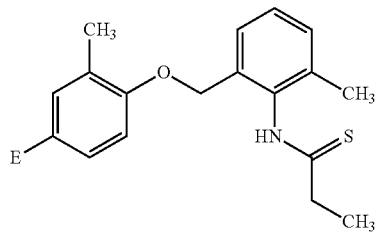
(HT1078)

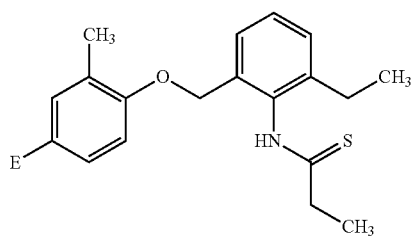 (HT1079)
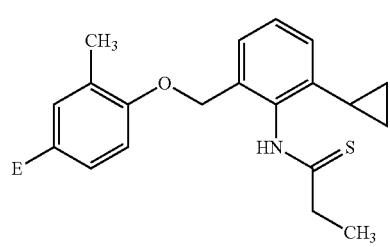 (HT1080)
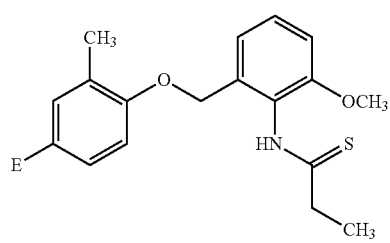 (HT1081)
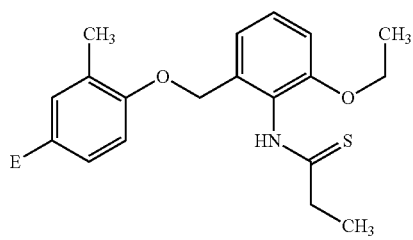 (HT1082)
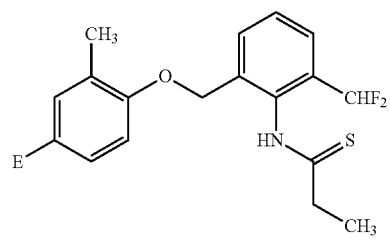 (HT1083)
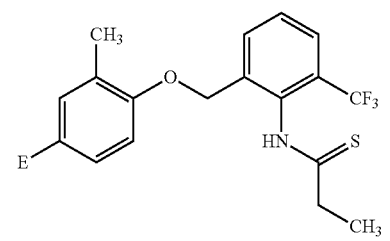 (HT1084)
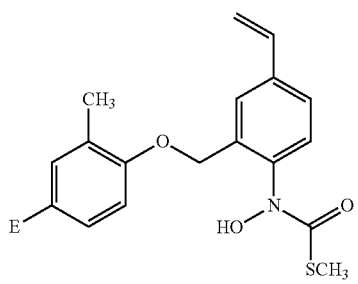 (HU1049)
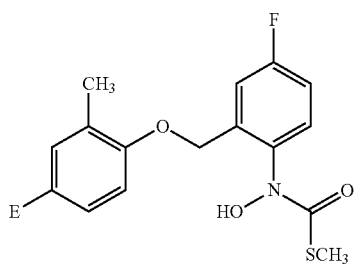 (HU1050)
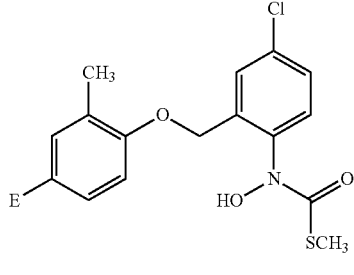 (HU1051)
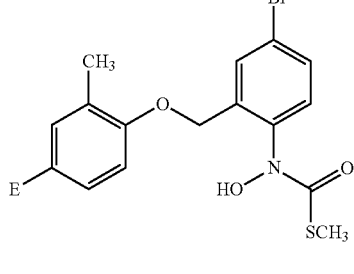 (HU1052)
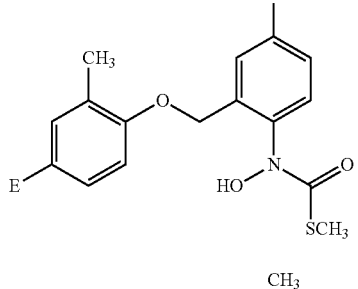 (HU1053)
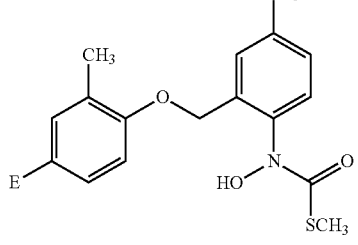 (HU1054)

| 347 -continued | 348 -continued |
|---|---|
| (HU1055) 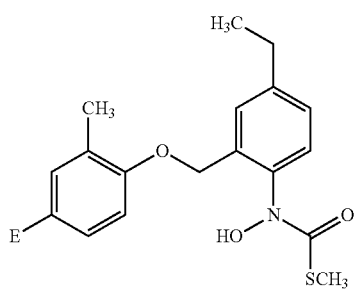 | (HU1060) 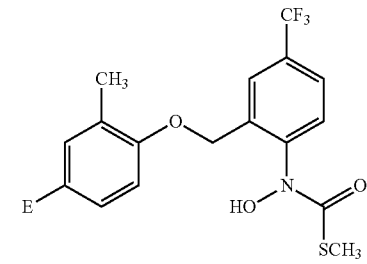 |
| (HU1056) 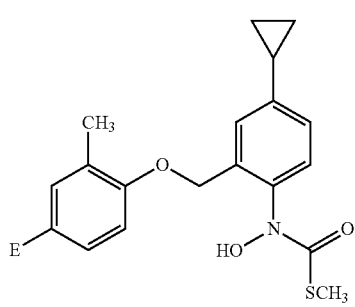 | (HU1061) 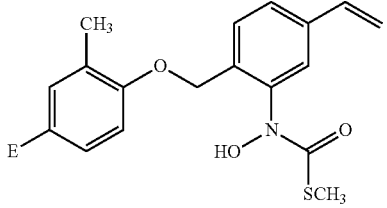 |
| | (HU1062) 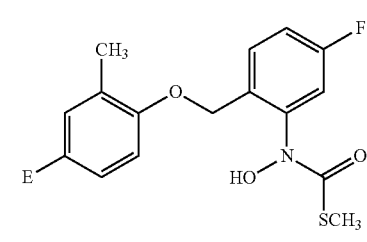 |
| (HU1057) 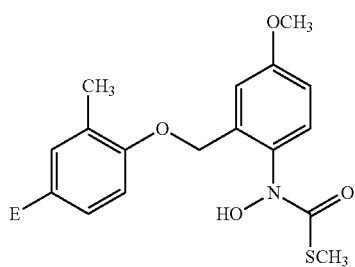 | (HU1063) 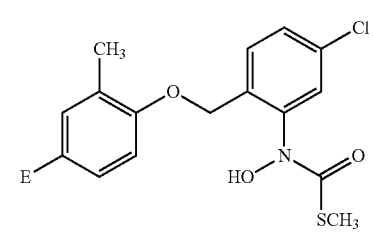 |
| (HU1058) 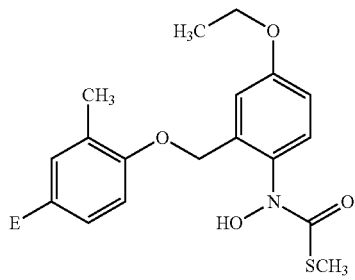 | (HU1064) 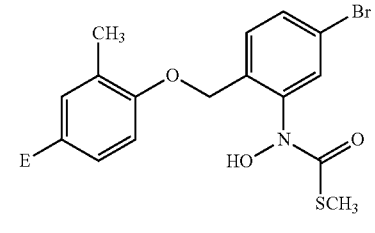 |
| | (HU1065) 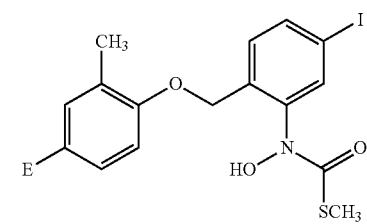 |
| (HU1059) 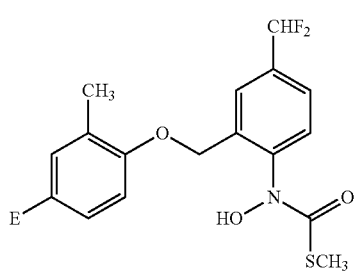 | (HU1066) 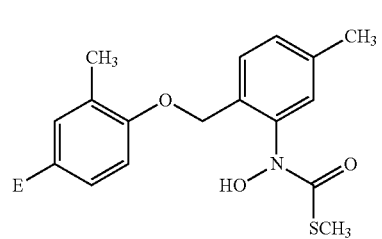 |

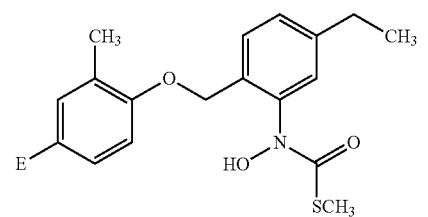 (HU1067)
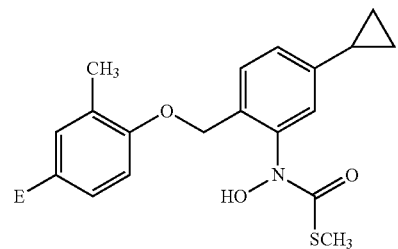 (HU1068)
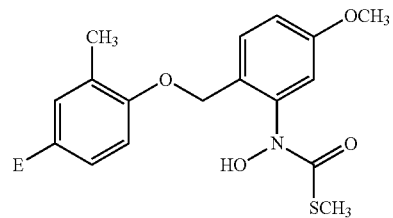 (HU1069)
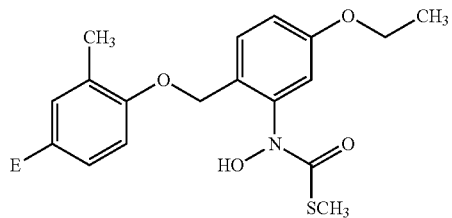 (HU1070)
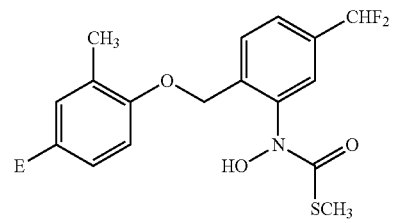 (HU1071)
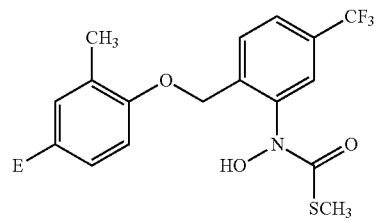 (HU1072)
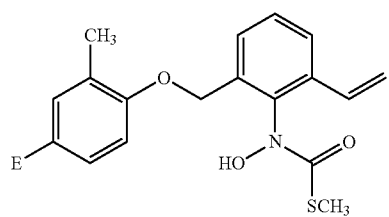 (HU1073)
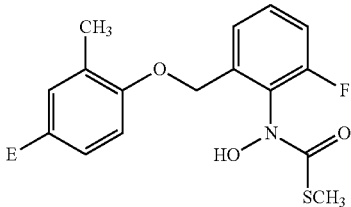 (HU1074)
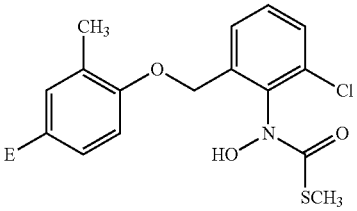 (HU1075)
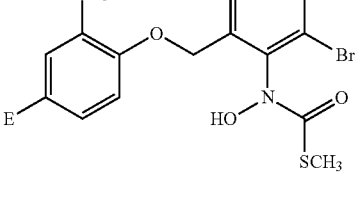 (HU1076)
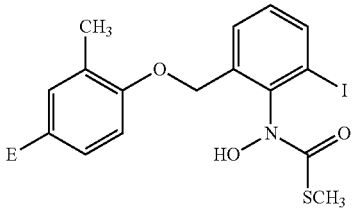 (HU1077)
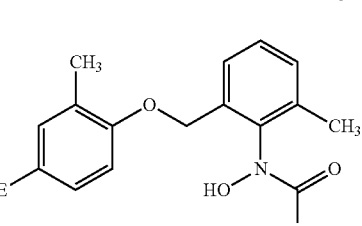 (HU1078)
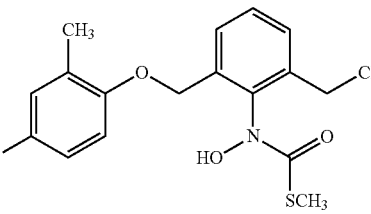 (HU1079)
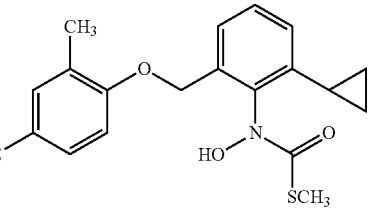 (HU1080)

351
-continued
(HU1081)
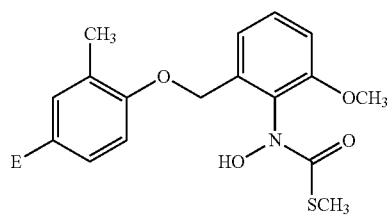
(HU1082)
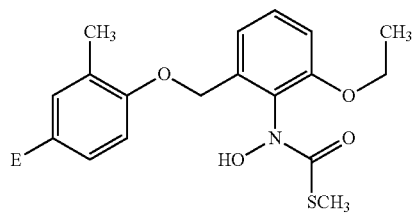
(HU1083)
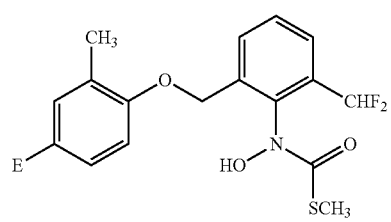
(HU1084)
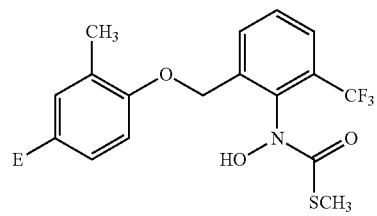
(HV1049)
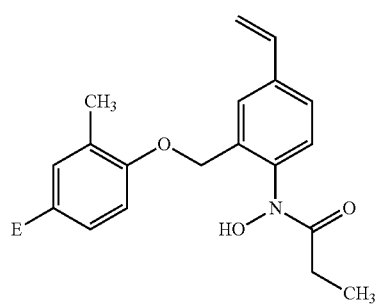
(HV1050)
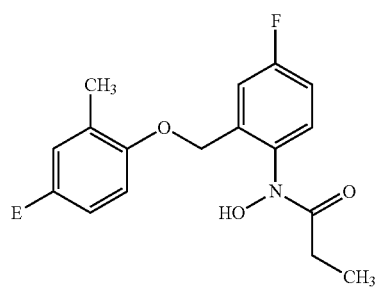
352
-continued
(HV1051)
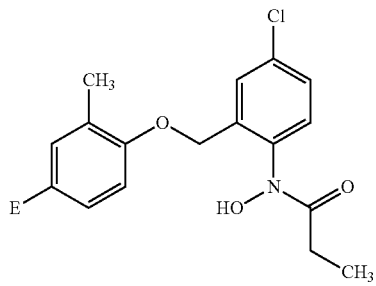
(HV1052)
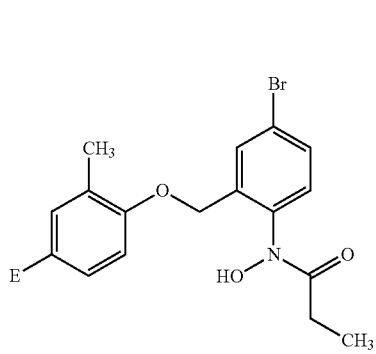
(HV1053)
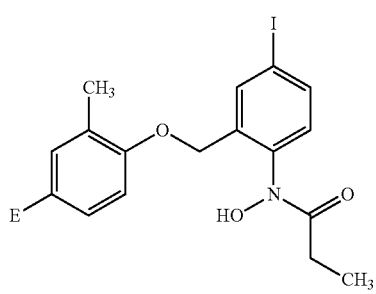
(HV1054)
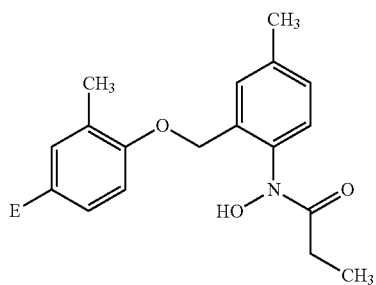
(HV1055)
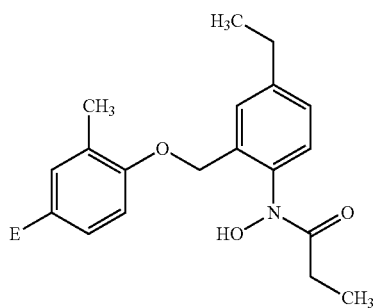

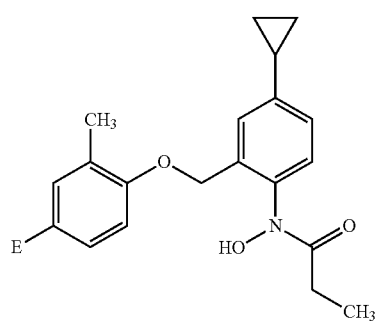
(HV1056)
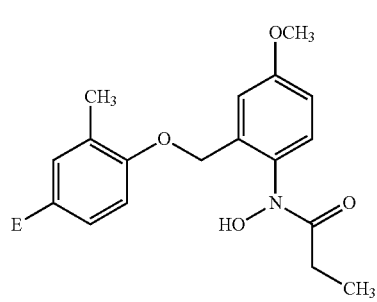
(HV1057)
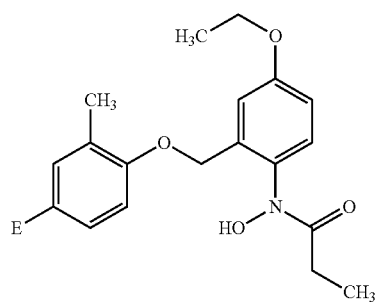
(HV1058)
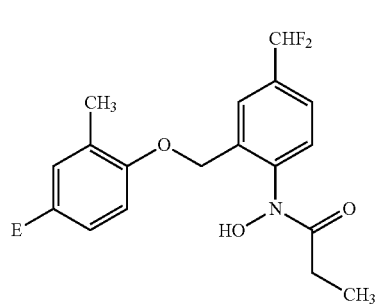
(HV1059)
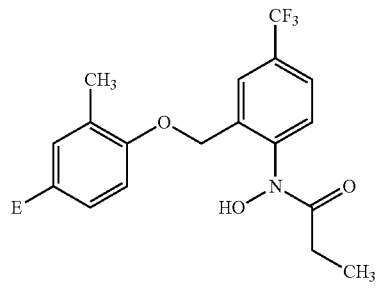
(HV1060)
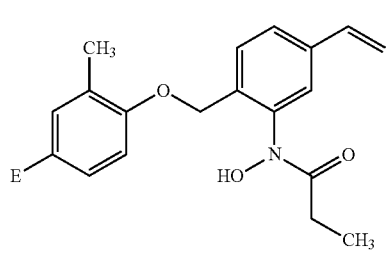
(HV1061)
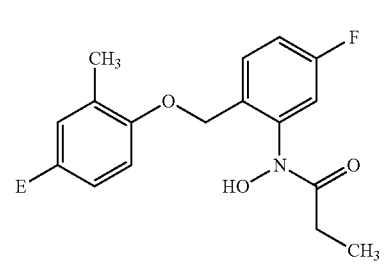
(HV1062)
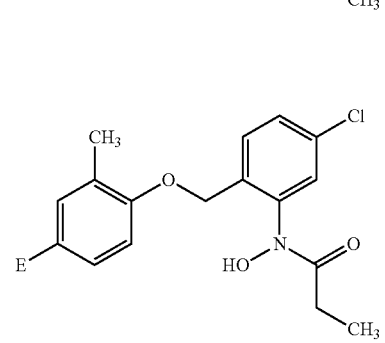
(HV1063)
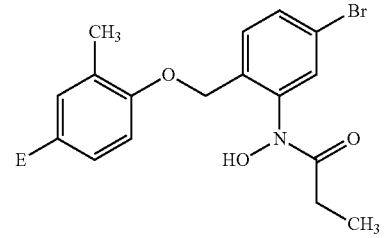
(HV1064)
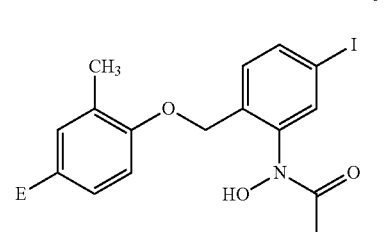
(HV1065)
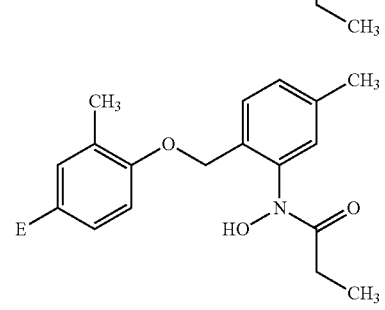
(HV1066)

-continued
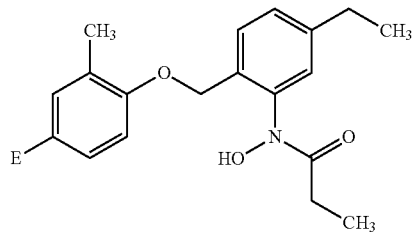 (HV1067)
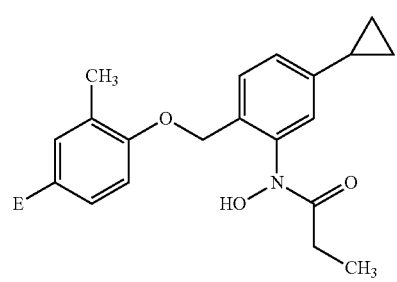 (HV1068)
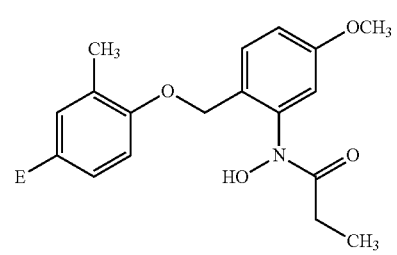 (HV1069)
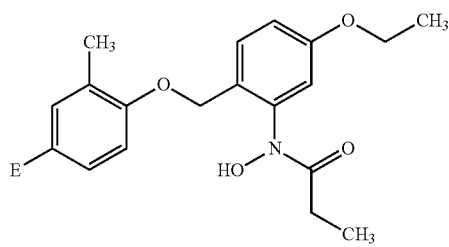 (HV1070)
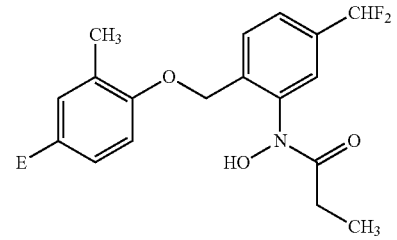 (HV1071)
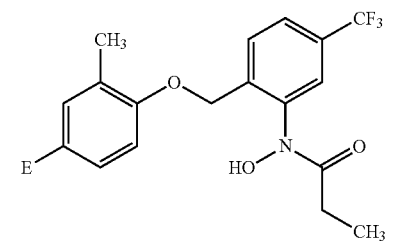 (HV1072)
-continued
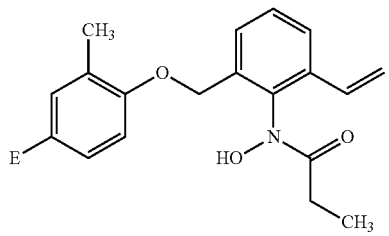 (HV1073)
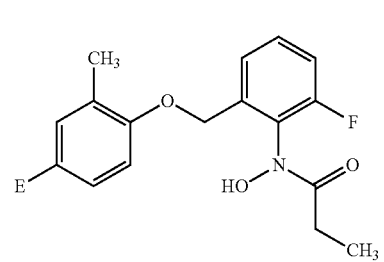 (HV1074)
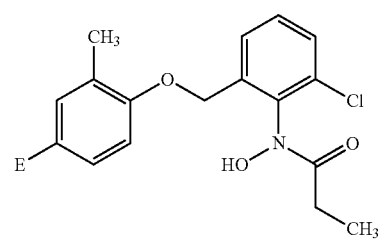 (HV1075)
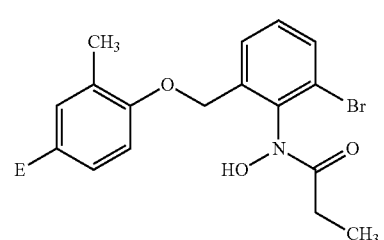 (HV1076)
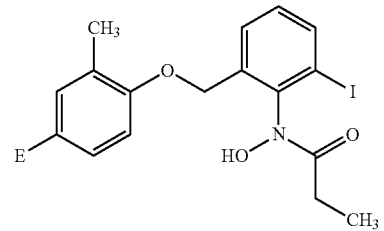 (HV1077)
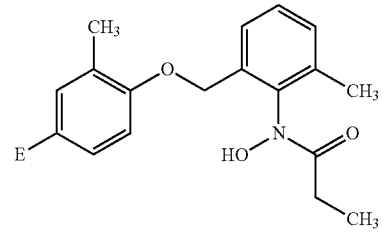 (HV1078)

| | |
|---|---|
| (HV1079) | (HW1049) |
| (HV1080) | (HW1050) |
| (HV1081) | (HW1051) |
| (HV1082) | (HW1052) |
| (HV1083) | (HW1053) |
| (HV1084) | (HW1054) |

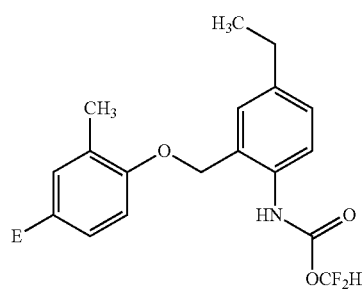
(HW1055)
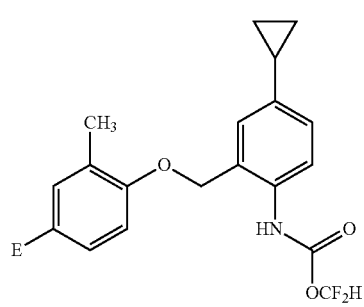
(HW1056)
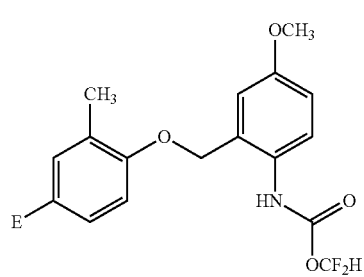
(HW1057)
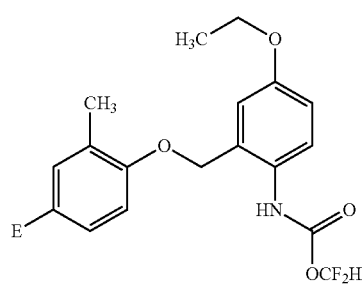
(HW1058)
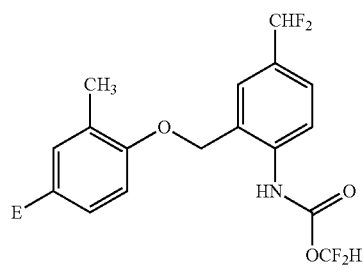
(HW1059)
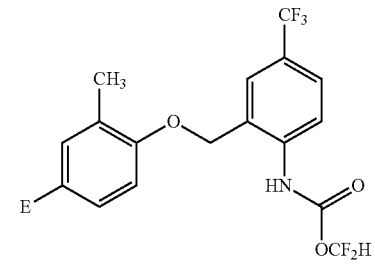
(HW1060)
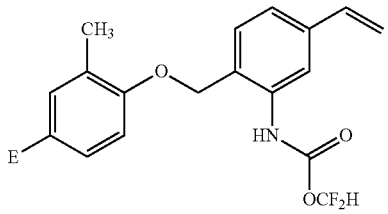
(HW1061)
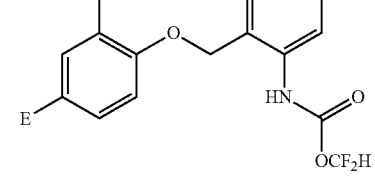
(HW1062)
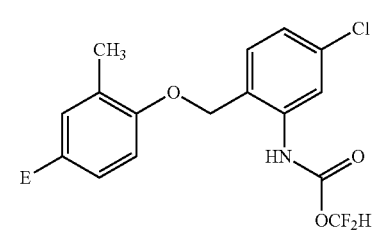
(HW1063)
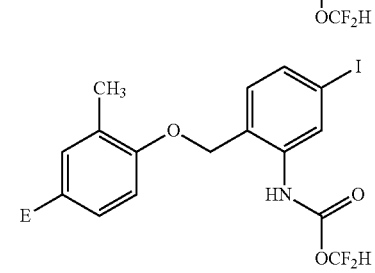
(HW1064)
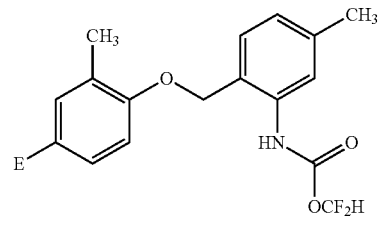
(HW1065)
(HW1066)

| | |
|---|---|
| (HW1067) 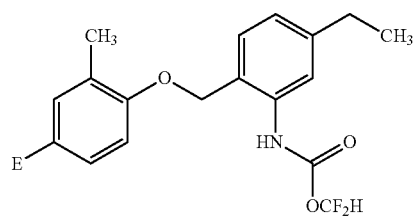 | (HW1074) 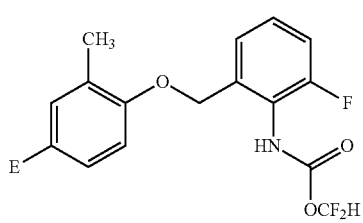 |
| (HW1068) 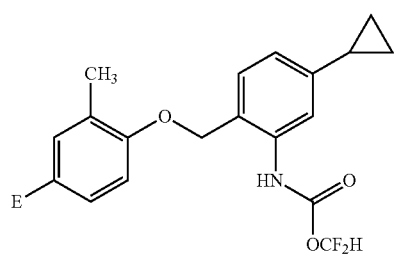 | (HW1075) 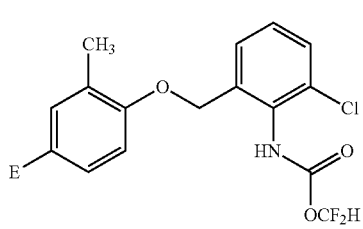 |
| (HW1069) 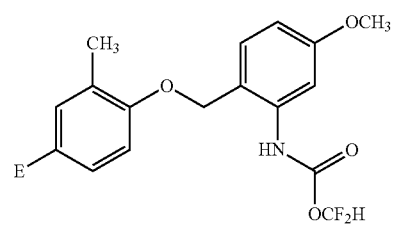 | (HW1076) 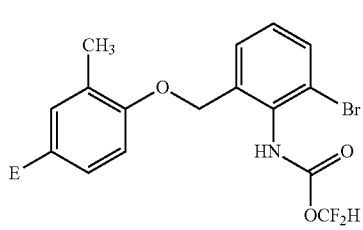 |
| (HW1070) 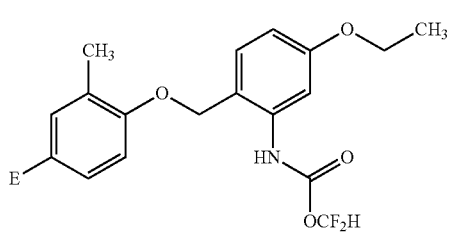 | (HW1077) 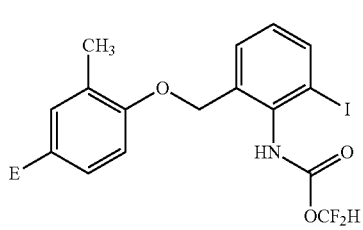 |
| (HW1071) 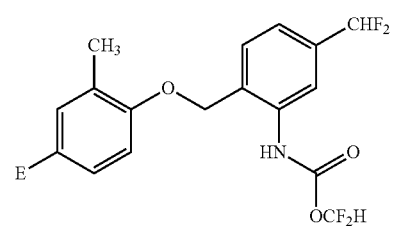 | (HW1078) 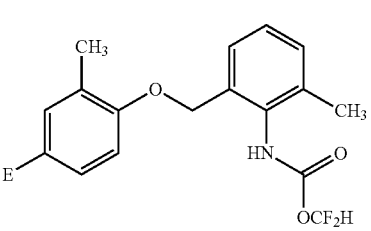 |
| (HW1072) 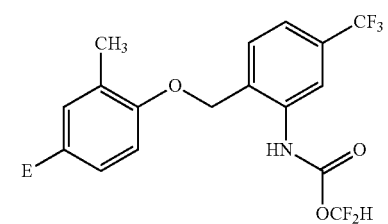 | (HW1079) 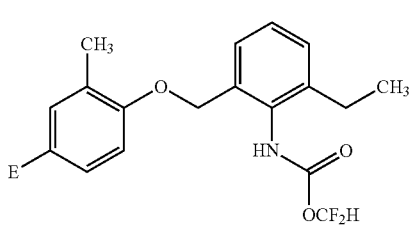 |
| (HW1073) 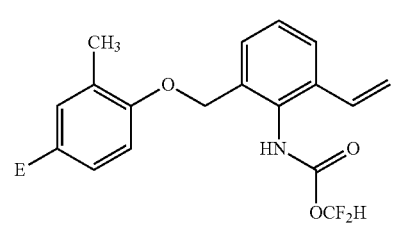 | (HW1080) 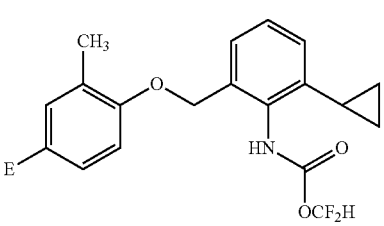 |

-continued

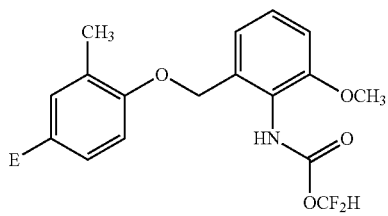
(HW1081)

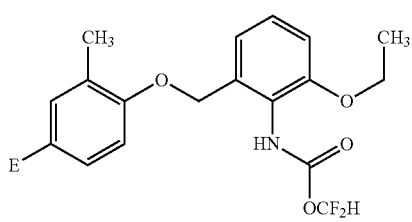
(HW1082)

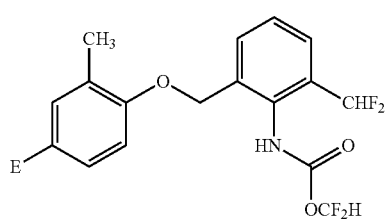
(HW1083)

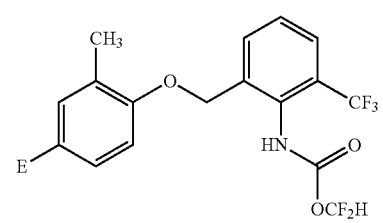
(HW1084)

[substituent number; E] [0001; 1-Me-4-F-5-F-PYR3], [0002; 1-Me-4-Cl-5-F-PYR3], [0003; 1-Me-4-Br-5-F-PYR3], [0004; 1-Me-4-Me-5-F-PYR3], [0005; 1-Me-4-Et-5-F-PYR3], [0006; 1-Me-4-F-5-Cl-PYR3], [0007; 1-Me-4-Cl-5-Cl-PYR3], [0008; 1-Me-4-Br-5-Cl-PYR3], [0009; 1-Me-4-Me-5-Cl-PYR3], [0010; 1-Me-4-Et-5-Cl-PYR3], [0011; 1-Me-4-F-5-Br-PYR3], [0012; 1-Me-4-Cl-5-Br-PYR3], [0013; 1-Me-4-Br-5-Br-PYR3], [0014; 1-Me-4-Me-5-Br-PYR3], [0015; 1-Me-4-Et-5-Br-PYR3], [0016; 1-Me-4-F-5-Me-PYR3], [0017; 1-Me-4-Cl-5-Me-PYR3], [0018; 1-Me-4-Br-5-Me-PYR3], [0019; 1-Me-4-Me-5-Me-PYR3], [0020; 1-Me-4-Et-5-Me-PYR3], [0021; 1-Me-4-F-5-Et-PYR3], [0022; 1-Me-4-Cl-5-Et-PYR3], [0023; 1-Me-4-Br-5-Et-PYR3], [0024; 1-Me-4-Me-5-Et-PYR3], [0025; 1-Me-4-Et-5-Et-PYR3], [0026; 1-Me-4-F-5-OMe-PYR3], [0027; 1-Me-4-Cl-5-OMe-PYR3], [0028; 1-Me-4-Br-5-OMe-PYR3], [0029; 1-Me-4-Me-5-OMe-PYR3], [0030; 1-Me-4-Et-5-OMe-PYR3], [0031; 1-Me-4-F-5-OEt-PYR3], [0032; 1-Me-4-Cl-5-OEt-PYR3], [0033; 1-Me-4-Br-5-OEt-PYR3], [0034; 1-Me-4-Me-5-OEt-PYR3], [0035; 1-Me-4-Et-5-OEt-PYR3], [0036; 1-Me-4-F-5-F-PYR3], [0037; 1-Me-4-Cl-5-F-PYR3], [0038; 1-Me-4-Br-5-F-PYR3], [0039; 1-Me-4-Me-5-F-PYR3], [0040; 1-Me-4-Et-5-F-PYR3], [0041; 1-Me-4-F-5-Cl-PYR3], [0042; 1-Me-4-Cl-5-Cl-PYR3], [0043; 1-Me-4-Br-5-Cl-PYR3], [0044; 1-Me-4-Me-5-Cl-PYR3], [0045; 1-Me-4-Et-5-Cl-PYR3], [0046; 1-Me-4-F-5-Br-PYR3], [0047; 1-Me-4-Cl-5-Br-PYR3], [0048; 1-Me-4-Br-5-Br-PYR3], [0049; 1-Me-4-Me-5-Br-PYR3], [0050; 1-Me-4-Et-5-Br-PYR3], [0051; 1-Me-4-F-5-Me-PYR3], [0052; 1-Me-4-Cl-5-Me-PYR3], [0053; 1-Me-4-Br-5-Me-PYR3], [0054; 1-Me-4-Me-5-Me-PYR3], [0055; 1-Me-4-Et-5-Me-PYR3], [0056; 1-Me-4-F-5-Et-PYR3], [0057; 1-Me-4-Cl-5-Et-PYR3], [0058; 1-Me-4-Br-5-Et-PYR3], [0059; 1-Me-4-Me-5-Et-PYR3], [0060; 1-Me-4-Et-5-Et-PYR3], [0061; 1-Me-4-F-5-OMe-PYR3], [0062; 1-Me-4-Cl-5-OMe-PYR3], [0063; 1-Me-4-Br-5-OMe-PYR3], [0064; 1-Me-4-Me-5-OMe-PYR3], [0065; 1-Me-4-Et-5-OMe-PYR3], [0066; 1-Me-4-F-5-OEt-PYR3], [0067; 1-Me-4-Cl-5-OEt-PYR3], [0068; 1-Me-4-Br-5-OEt-PYR3], [0069; 1-Me-4-Me-5-OEt-PYR3], [0070; 1-Me-4-Et-5-OEt-PYR3], [0071; 1-Me-4-CF2H-5-F-PYR3], [0072; 1-Me-4-CF2H-5-Cl-PYR3], [0073; 1-Me-4-CF2H-5-Br-PYR3], [0074; 1-Me-4-CF2H-5-OMe-PYR3], [0075; 1-Me-4-CF2H-5-OEt-PYR3], [0076; 1-Me-4-CF2H-5-Me-PYR3], [0077; 1-Me-4-CF2H-5-Et-PYR3], [0078; 1-Me-4-CF3-5-F-PYR3], [0079; 1-Me-4-CF3-5-Cl-PYR3], [0080; 1-Me-4-CF3-5-Br-PYR3], [0081; 1-Me-4-CF3-5-OMe-PYR3], [0082; 1-Me-4-CF3-5-OEt-PYR3], [0083; 1-Me-4-CF3-5-Me-PYR3], [0084; 1-Me-4-CF3-5-Et-PYR3], [0085; 1-Me-4-Me-5-Me-PYR3], [0086; 1-Me-4-Et-5-Me-PYR3], [0087; 1-Me-4-F-5-Me-PYR3], [0088; 1-Me-4-Cl-5-Me-PYR3], [0089; 1-Me-4-Br-5-Me-PYR3], [0090; 1-Me-4-Me-5-Et-PYR3], [0091; 1-Me-4-Et-5-Et-PYR3], [0092; 1-Me-4-F-5-Et-PYR3], [0093; 1-Me-4-Cl-5-Et-PYR3], [0094; 1-Me-4-Br-5-Et-PYR3]

For example, HA1001-0046 is a compound in which a substituent number is 46 in a compound represented by formula (HA1001), and is a compound having the following structure.

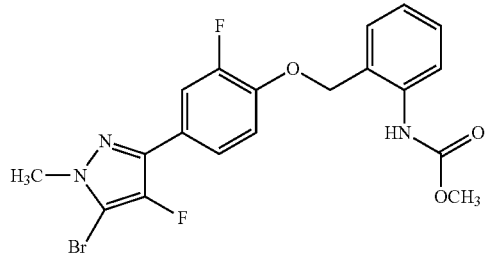
(HA1001-0046)

Examples of the present control agent will be shown below.

Formulation Example 1

Fifty parts (50 parts) of any one of the present compounds A, 3 parts of calcium ligninsulfonate, 2 parts of laurylmagnesium sulfate, and 45 parts of synthetic hydrated silicon oxide are thoroughly ground and mixed to obtain each formulation.

Formulation Example 2

Twenty parts (20 parts) of any one of the present compounds A and 1.5 parts of sorbitan trioleate are mixed with 28.5 parts of an aqueous solution containing 2 parts of polyvinyl alcohol, and the mixture was finely ground by a wet grinding method. Then, 40 parts of an aqueous solution containing 0.05 part of xanthan gum and 0.1 part of aluminum magnesium silicate is added thereto and 10 parts of propylene glycol is further added, followed by stirring and mixing to obtain each formulation.

Formulation Example 3

Two parts (2 parts) of any one of the present compounds A, 88 parts of kaolin clay, and 10 parts of talc are thoroughly ground and mixed to obtain each formulation.

Formulation Example 4

Five parts (5 parts) of any one of the present compounds A, 14 parts of polyoxyethylene styryl phenyl ether, 6 parts of calcium dodecylbenzenesulfonate, and 75 parts of xylene are thoroughly ground and mixed to obtain each formulation.

Formulation Example 5

Two parts (2 parts) of any one of the present compounds A, 1 part of synthetic hydrated silicon oxide, 2 parts of calcium ligninsulfonate, 30 parts of bentonite, and 65 parts of kaolin clay are thoroughly ground and mixed. After the addition of water, the mixture is thoroughly kneaded and further granulated and dried to obtain each formulation.

Formulation Example 6

Ten parts (10 parts) of any one of the present compounds A, 35 parts of a mixture of a polyoxyethylene alkyl ether sulfate ammonium salt and white carbon (weight ratio of 1:1), and 55 parts of water are finely ground by a wet grinding method to obtain each formulation.

Next, Test Examples will be shown.

The control effect was evaluated by visually observing the area of lesion on each of test plants at the time of investigation, and comparing the area of lesion on a plant treated with the present compound with that on an untreated plant.

Test Example 1

Each of plastic pots was filled with soil and rice (cultivar: NIHONBARE) was sowed and grown in a greenhouse for 20 days. Then, each water dilution prepared by adjusting so as to contain a predetermined concentration (500 ppm) of any one compound of the present compounds 2, 3, 4, 9, 13, 19, 20, 21, 22, 24, 26, 27, 29, 31, 32, 33, 34, 35, 36, 37, and 38 was sprayed over stems and leaves so that it sufficiently adhered to the surface of the leaves of the rice. After spraying, the plant was air-dried and placed for 6 days at 24° C. in the daytime and 20° C. at night under high humidity condition, while being in contact with the rice seedling (cultivar: NIHONBARE) infected by the rice blast fungus (*Magnaporthe grisea*), and then the area of lesion was investigated. As a result, the lesion areas on the plant treated with the present compound were 30% or less with respect to the lesion area on the non-treated plant.

Test Example 2

Each of plastic pots was filled with soil and wheat (cultivar: SHIROGANE) was sowed and grown in a greenhouse for 9 days. Then, each water dilution prepared by adjusting so as to contain a predetermined concentration (500 ppm) of any one compound of the present compounds 2, 3, 4, 9, 13, 15, 16, 17, 18, 19, 20, 21, 22, 24, 26, 27, 29, 30, 31, 32, 33, 34, 35, 36, 37, 38, 42, and 44 was sprayed over stems and leaves of the wheat so that it sufficiently adhered to the surface of the leaves of the wheat. After spraying, the plant was air-dried and cultivated at 20° C. for 5 days under illumination, and then inoculated by sprinkling with spores of wheat rust fungus (*Puccinia recondita*). After the inoculation, the plant was placed at 23° C. for one day under dark and high humidity condition, and cultivated under illumination at 20° C. for 8 days, and then the area of lesion was investigated. As a result, it has been found that the area of lesion on the plant treated with the present compound was 30% or less of that on an untreated plant.

Test Example 3

Each of plastic pots was filled with soil and barley (cultivar: NISHINOHOSHI) was sowed and grown in a greenhouse for 7 days. Then, each water dilution prepared by adjusting so as to contain a predetermined concentration (500 ppm) of any one compound of the present compounds 2, 3, 4, 6, 8, 9, 10, 13, 15, 16, 17, 18, 19, 20, 21, 22, 23, 24, 26, 27, 28, 29, 30, 31, 32, 33, 34, 35, 36, 37, 38, 42, and 44 was sprayed over stems and leaves of the barley so that it sufficiently adhered to the surface of the leaves of the barley. After spraying, the plant was air-dried. After 2 days, an aqueous suspension containing spores of barley net blotch fungus (*Pyrenophora teres*) was sprayed to inoculate the spores. After completion of the inoculation, the plant was placed for 3 days in a greenhouse at 23° C. in the daytime and 20° C. at night under high humidity condition and cultivated in a greenhouse for 7 days, and then the area of lesion was investigated. As a result, the area of lesion on the plant treated with the present compound was 30% or less of that on an untreated plant.

Test Example 4

Each of plastic pots was filled with soil and kidney bean (cultivar: NAGAUZURA SAITOU) was sowed and grown in a greenhouse for 8 days. Then, each water dilution prepared by adjusting so as to contain a predetermined concentration (500 ppm) of any one compound of the present compounds 2, 3, 4, 6, 9, 10, 13, 15, 16, 19, 21, 22, 23, 24, 26, 27, 28, 29, 30, 31, 32, 33, 34, 35, 36, 37, 38, and 44 was sprayed over stems and leaves of the kidney bean so that it sufficiently adhered to the surface of the leaves of the kidney bean. After spraying, the plant was air-dried and a potato dextrose agar (PDA) medium containing hyphae of the kidney bean stem rot fungus (*Sclerotinia sclerotiorum*) was placed on the leaves of the kidney bean. After the inoculation, all kidney beans were placed under high humidity condition only at night. Four days after the inoculation, the area of lesion was investigated. As a result, the area of lesion on the plant treated with the present compound was 30% or less of that on an untreated plant.

Test Example 5

Each of plastic pots was filled with soil and wheat (cultivar: APOGEE) was sowed and grown in a greenhouse for 10 days. Then, each water dilution prepared by adjusting so as to contain a predetermined concentration (200 ppm) of any one compound of the present compounds 2, 3, 4, 19, 20, 21, 22, 24, 27, 28, 29, 31, 32, 33, 34, 35, 36, 37, 38, and 42 was sprayed over stems and leaves of the wheat so that it sufficiently adhered to the surface of the leaves of the wheat. After spraying, the plant was air-dried. After 4 days, an aqueous suspension containing spores of wheat leaf blotch fungus (*Septoria tritici*) was sprayed to inoculate the spores. After completion of the inoculation, the plant was placed at 18° C. under high humidity condition for 3 days and placed under illumination for 14 to 18 days, and then the area of lesion was investigated. As a result, the area of lesion on the plant treated with the present compound was 30% or less of that on an untreated plant.

Test Example 6

Each of plastic pots was filled with soil and cucumber (cultivar: SAGAMI HANJIRO) was sowed and grown in a greenhouse for 12 days. Then, each water dilution prepared by adjusting so as to contain a predetermined concentration (500 ppm) of any one compound of the present compounds 2, 3, 4, 8, 16, 17, 18, 19, 20, 21, 22, 24, 27, 29, 31, 32, 33, 34, 35, 36, and 37 was sprayed over stems and leaves of the cucumber so that it sufficiently adhered to the surface of the leaves of the cucumber. After spraying, the plant was air-dried and then inoculated by sprinkling with spores of cucumber powdery mildew fungus (Sphaerotheca *fuliginea*, a QoI-resistant strain in which, among the genes encoding cytochrome b, the amino acid residue at position 143 of cytochrome b is mutated from glycine to alanine). After the inoculation, the plant was cultivated in a greenhouse at 24° C. in the daytime and 20° C. at night for 8 days, and then the area of lesion was investigated. As a result, the area of lesion on the plant treated with the present compound was 30% or less of that on an untreated plant.

Test Example 7

Each of plastic pots was filled with soil and soybean (cultivar: KUROSENGOKU) was sowed and grown in a greenhouse for 13 days. Then, each water dilution prepared by adjusting so as to contain a predetermined concentration (200 ppm) of any one compound of the present compounds 1, 2, 3, 4, 5, 6, 9, 12, 13, 15, 16, 17, 18, 19, 20, 21, 22, 24, 25, 26, 27, 28, 29, 30, 31, 32, 33, 34, 35, 36, 37, 38, 39, 40, and 44 was sprayed over stems and leaves of the soybean so that it sufficiently adhered to the surface of the leaves of the soybean. After spraying, the plant was air-dried. After 2 days, an aqueous suspension containing spores of soybean rust fungus (*Phakopsora pachyrhizi*) was sprayed to inoculate the spores. After completion of the inoculation, the plant was placed for 3 days in a greenhouse at 23° C. in the daytime and 20° C. at night under high humidity condition and cultivated in a greenhouse for 14 days, and then the area of lesion was investigated. As a result, the area of lesion on the plant treated with the present compound was 30% or less of that on an untreated plant.

Test Example 8

Each of plastic pots was filled with soil and barley (cultivar: NISHINOHOSHI) was sowed and grown in a greenhouse for 7 days. Then, each water dilution prepared by adjusting so as to contain a predetermined concentration (200 ppm) of any one compound of the present compounds 1, 2, 3, 4, 5, 6, 8, 9, 12, 13, 15, 16, 17, 18, 19, 20, 21, 22, 23, 24, 25, 26, 27, 28, 29, 30, 31, 32, 33, 34, 35, 36, 37, 38, 39, 40, 42, and 44 was sprayed over stems and leaves of the barley so that it sufficiently adhered to the surface of the leaves of the barley. After spraying, the plant was air-dried. After 2 days, an aqueous suspension containing spores of barley scald fungus (Rhynchosporiumsecalis) was sprayed to inoculate the spores. After completion of the inoculation, the plant was placed for 3 days in a greenhouse at 23° C. in the daytime and 20° C. at night under high humidity condition and cultivated in a greenhouse for 7 days, and then the area of lesion was investigated. As a result, the area of lesion on the plant treated with of the present compound was 30% or less of that on an untreated plant.

Test Example 9

Each of plastic pots was filled with soil and cucumber (cultivar: SAGAMI HANJIRO) was sowed and grown in a greenhouse for 19 days. Then, each water dilution prepared by adjusting so as to contain a predetermined concentration (200 ppm) of any one compound of the present compounds 1, 11, 31, and 34 was sprayed over stems and leaves of the cucumber so that it sufficiently adhered to the surface of the leaves of the cucumber. After spraying, the plant was air-dried. After one day, an aqueous suspension containing spores of cucumber target leaf spot fungus (*Corynespora cassiicola*) was sprayed to inoculate the spores. After the inoculation, the plant was cultivated in a greenhouse at 24° C. in the daytime and 20° C. at night for 7 days, followed by investigation of the area of lesion. As a result, the area of lesion on the plant treated with the present compound was 30% or less of that on an untreated plant.

Test Example 10

Each of plastic pots was filled with soil and cucumber (cultivar: SAGAMI HANJIRO) was sowed and grown in a greenhouse for 19 days. Then, each water dilution prepared by adjusting so as to contain a predetermined concentration (200 ppm) of the present compounds 1, 2, 5, 6, 9, 11, 12, 13, 15, 16, 17, 18, 19, 20, 21, 22, 24, 25, 26, 27, 28, 29, 30, 31, 32, 33, 34, 35, 36, 37, 38, 39, 40, 42, and 44 was sprayed over stems and leaves of the cucumber so that it sufficiently adhered to the surface of the leaves of the cucumber. After spraying, the plant was air-dried. After one day, an aqueous suspension containing spores of cucumber anthracnose fungus (*Colletotrichum lagenarium*) was sprayed to inoculate the spores. After the inoculation, the plant was placed at 23° C. for one day under high humidity condition, and then cultivated in a greenhouse at 24° C. in the daytime and 20° C. at night for 6 days, and then the area of lesion was investigated. As a result, the area of lesion on the plant treated with the present compound was 30% or less of that on an untreated plant.

Test Example 11

In accordance with Formulation Example 2, a formulation was obtained from each of the present compounds 2, 4, 9, 19, 21, 27, 28, 29, 31, 32, 35, and 38, and then diluted with water so as to contain 500 ppm of an active ingredient to obtain a dilution.

Thirty (30) heads of cotton aphid (*Aphis gossypii*) (including adults and larvae) were released on the leaves of cucumber grown in a polyethylene cup until the first true leaf was developed. Next day, 20 mL of the dilution was sprayed. After 6 days, the number of the surviving insects was counted and the control value was calculated by the following equation.

Control value (%)=$\{1-(Cb \times Tai)/(Cai \times Tb)\} \times 100$ wherein symbols in the equation represent the followings:
Cb: Number of tested insects in untreated area;
Cai: Number of surviving insects in untreated area;
Tb: Number of tested insects in treated area; and
Tai: Number of surviving insects in treated area.

As a result, the present compound showed 90% or more of the control value.

The present control agent has control activity against pests and is useful as an active ingredient of a pest control agent.

The invention claimed is:

1. An aromatic compound represented by formula (1):

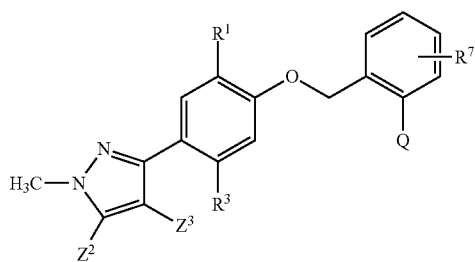

(1)

wherein $R^1$ represents a halogen atom or a C1-C4 alkyl group optionally having one or more halogen atoms;
$R^3$ represents a hydrogen atom or a C1-C4 alkyl group optionally having one or more halogen atoms;
$R^7$ represents a C1-C3 alkyl group optionally having one or more halogen atoms, a hydrogen atom, a halogen atom, a C1-C3 alkoxy group optionally having one or more halogen atoms, a C3-C4 cycloalkyl group optionally having one or more halogen atoms, or a C2-C4 alkenyl group optionally having one or more halogen atoms;
$Z^2$ represents a halogen atom, a C1-C3 alkoxy group, or a C1-C3 alkyl group;
$Z^3$ represents a C1-C3 alkyl group optionally having one or more halogen atoms, or a halogen atom;
Q represents the following group Q1, Q2, or Q3;

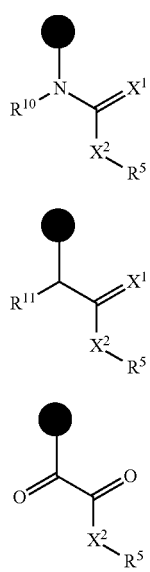

$R^5$ represents a C1-C3 alkyl group optionally having one or more halogen atoms;
$R^{10}$ represents a hydrogen atom, a hydroxyl group, or a methyl group;
$R^{11}$ represents a hydrogen atom, a hydroxyl group, a methyl group, or a methoxy group;
$X^1$ represents an oxygen atom or a sulfur atom;
$X^2$ represents an oxygen atom, a sulfur atom, $NR^{12}$, or a direct bond; and
$R^{12}$ represents a C1-C3 alkyl group optionally having one or more halogen atoms, or a hydrogen atom.

2. The aromatic compound according to claim 1, wherein $R^1$ is a methyl group, $R^3$ is a hydrogen atom, $R^{11}$ is a hydroxyl group, and $X^1$ is an oxygen atom.

3. An aromatic compound represented by formula (2):

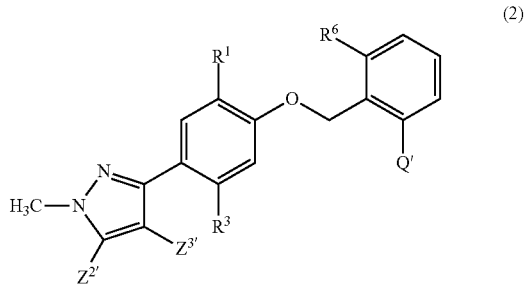

(2)

wherein $R^1$ represents a halogen atom or a C1-C4 alkyl group optionally having one or more halogen atoms;
$R^3$ represents a hydrogen atom or a C1-C4 alkyl group optionally having one or more halogen atoms;
$R^6$ represents a C1-C3 alkyl group optionally having one or more halogen atoms, a hydrogen atom, a halogen atom, a C1-C3 alkoxy group optionally having one or more halogen atoms, or a C3-C4 cycloalkyl group optionally having one or more halogen atoms;
$Z^{2'}$ represents a halogen atom or a C1-C3 alkoxy group;
$Z^{3'}$ represents a C1-C3 alkyl group or a halogen atom;
Q' represents the following group Q1', Q2', or Q3';

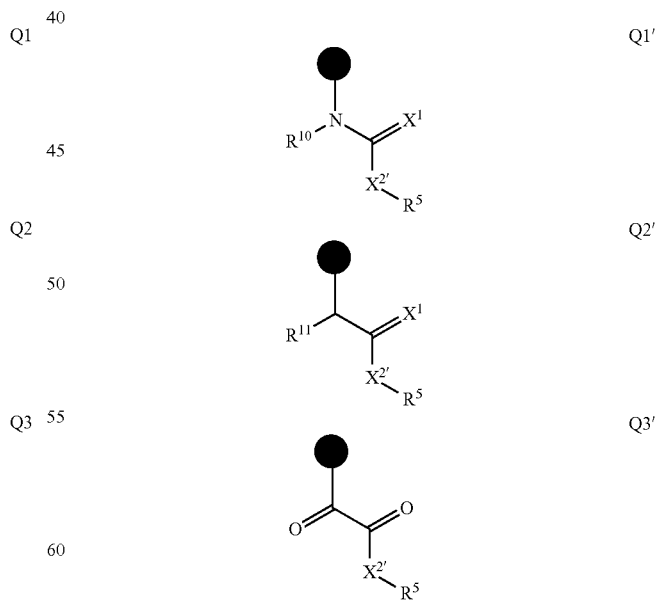

$R^5$ represents a C1-C3 alkyl group optionally having one or more halogen atoms;
$R^{10}$ represents a hydrogen atom, a hydroxyl group, or a methyl group;

$R^{11}$ represents a hydrogen atom, a hydroxyl group, a methyl group, or a methoxy group;

$X^1$ represents an oxygen atom or a sulfur atom;

$X^{2'}$ represents an oxygen atom, $NR^{12}$, or a direct bond;

$R^{12}$ represents a C1-C3 alkyl group optionally having one or more halogen atoms, or a hydrogen atom.

4. A pest control agent comprising the aromatic compound according to claim 1.

5. A method for controlling pests, which comprises treating plants or soil with an effective amount of the aromatic compound according to claim 1.

6. The aromatic compound according to claim 3, wherein $R^1$ is a methyl group, $R^3$ is a hydrogen atom, $R^{11}$ is a hydroxyl group, and $X^1$ is an oxygen atom.

7. A pest control agent comprising the aromatic compound according to claim 3.

8. A method for controlling pests, which comprises treating plants or soil with an effective amount of the aromatic compound according to claim 3.

* * * * *